United States Patent
Guse et al.

(10) Patent No.: US 11,740,241 B2
(45) Date of Patent: Aug. 29, 2023

(54) CONSTRUCT INCLUDING AN ANCHOR, AN ENZYME RECOGNITION SITE AND AN INDICATOR REGION FOR DETECTING MICROBIAL INFECTION IN WOUNDS

(71) Applicant: SYNOVO GMBH, Tübingen (DE)

(72) Inventors: Jan Hinrich Guse, Tübingen-Bühl (DE); Martin Reisser, Esslingen (DE); Nikolas Pietrzik, Tübingen (DE); Christiane Baeuerlein, Ofterdingen (DE); Kornelia Eitel, Tübingen (DE)

(73) Assignee: Synovo GmbH, Tübingen (DE)

( * ) Notice: Subject to any disclaimer, the term of this patent is extended or adjusted under 35 U.S.C. 154(b) by 995 days.

(21) Appl. No.: 16/090,075

(22) PCT Filed: Mar. 30, 2017

(86) PCT No.: PCT/IB2017/001182
§ 371 (c)(1),
(2) Date: Sep. 28, 2018

(87) PCT Pub. No.: WO2017/212345
PCT Pub. Date: Dec. 14, 2017

(65) Prior Publication Data
US 2021/0088518 A1   Mar. 25, 2021

Related U.S. Application Data

(60) Provisional application No. 62/315,546, filed on Mar. 30, 2016, provisional application No. 62/315,556, filed on Mar. 30, 2016.

(51) Int. Cl.
*C12N 9/10* (2006.01)
*G01N 33/573* (2006.01)
*G01N 33/58* (2006.01)

(52) U.S. Cl.
CPC ......... *G01N 33/573* (2013.01); *G01N 33/582* (2013.01); *G01N 2333/95* (2013.01); *G01N 2333/966* (2013.01); *G01N 2800/26* (2013.01)

(58) Field of Classification Search
CPC .......................... C12N 9/10; C12N 2501/734
See application file for complete search history.

(56) References Cited

U.S. PATENT DOCUMENTS

| 4,299,917 A * | 11/1981 | Berger | C12Q 1/37 436/63 |
| 8,685,890 B2 * | 4/2014 | Winter | A61K 47/64 506/9 |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke | |
| 10,143,784 B2 | 12/2018 | Walton et al. | |
| 10,426,670 B2 | 10/2019 | von Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |

(Continued)

FOREIGN PATENT DOCUMENTS

| CN | 1469758 A | 1/2004 |
| CN | 1838970 A | 3/2009 |

(Continued)

OTHER PUBLICATIONS

US 11,338,078 B2, 05/2022, Coulthard et al. (withdrawn)
Liu et al, Enzyme immobilization on cellulose matrixes. Journal of Bioactive and Compatible Polymers 2016, vol. 31(6) 553-567.*
Hasmann et al, Sensor materials for the detection of human neutrophil elastase and cathepsin G activity in wound fluid. Experimental Dermatology, 20, 508-513.*
Mendler et al, A new highly sensitive point of care screen for spontaneous bacterial peritonitis using the leukocyte esterase method. Journal of Hepatology 2010 vol. 53 j 477-483.*
Edwards et al, New Uses for Immobilized Enzymes and Substrates on Cotton and Cellulose Fibers. Industrial Application of Enzymes on Carbohydrate-Based Material Ed:Gillian Eggleston1John R. Vercellotti2 vol. 972, Aug. 30, 2007.*

(Continued)

*Primary Examiner* — Tekchand Saidha
(74) *Attorney, Agent, or Firm* — Taft Stettinius & Hollister LLP; Ryan O. White; Derek B. Lavender

(57) ABSTRACT

The disclosed technology relates to chemical entities for the detection of wounds, e.g., chronic wounds or infected wounds, including compositions, substrates, kits, dressing materials, and articles, and systems containing such compounds. The disclosed technology further relates to methods of using these compositions, kits and systems in diagnostic assays, and in the diagnosis and/or detection of chronic or infected wounds based on enzymatic action on specific moieties and/or reaction sites. The disclosed technology additionally relates to detection of pathogenic, e.g., bacterial and/or viral substances, such as enzymes and substrates, at the wound situs. Additional disclosure relates to methods of characterizing wounds based on expression of a plurality of markers and using such information to treat, manage, and follow-up patients suffering from chronic or infected wounds.

23 Claims, 16 Drawing Sheets

Specification includes a Sequence Listing.

(56) References Cited

U.S. PATENT DOCUMENTS

| | | |
|---|---|---|
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,026,847 B2 | 6/2021 | Piotrowski et al. |
| 11,083,629 B2 | 8/2021 | Locke et al. |
| 11,096,830 B2 | 8/2021 | Pratt et al. |
| 11,246,758 B2 | 2/2022 | Hardman et al. |
| 11,273,078 B2 | 3/2022 | Simmons |
| 11,291,587 B2 | 4/2022 | Kilpadi |
| 2003/0204070 A1 | 10/2003 | Chen et al. |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0104690 A1 | 4/2009 | Bayliff et al. |
| 2009/0234307 A1 | 9/2009 | Vitaris |

(56) References Cited

U.S. PATENT DOCUMENTS

| | | |
|---|---|---|
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2012/0258483 A1 | 10/2012 | Gubitz et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |

(56) References Cited

U.S. PATENT DOCUMENTS

| | | |
|---|---|---|
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0107964 A1 | 4/2020 | Locke et al. |
| 2020/0107965 A1 | 4/2020 | Greener |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121510 A1 | 4/2020 | Hartwell et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0155355 A1 | 5/2020 | Hill et al. |
| 2020/0155358 A1 | 5/2020 | Wheldrake |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179558 A1 | 6/2020 | Munro et al. |
| 2020/0179673 A1 | 6/2020 | Wan |

(56) References Cited

U.S. PATENT DOCUMENTS

| | | |
|---|---|---|
| 2020/0188180 A1 | 6/2020 | Akbari et al. |
| 2020/0188182 A1 | 6/2020 | Sanders et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0275693 A1 | 9/2021 | Ballamy |
| 2021/0290207 A1 | 9/2021 | Locke et al. |
| 2021/0338488 A1 | 11/2021 | Pratt et al. |
| 2021/0361822 A1 | 11/2021 | Kettel et al. |
| 2021/0378565 A1 | 12/2021 | Kettel et al. |
| 2021/0379241 A1 | 12/2021 | Kettel et al. |
| 2022/0031520 A1 | 2/2022 | Kilpadi |
| 2022/0079509 A1 | 3/2022 | Gellman et al. |
| 2022/0151834 A1 | 5/2022 | Simmons |

FOREIGN PATENT DOCUMENTS

| | | |
|---|---|---|
| CN | 1902494 B | 10/2010 |
| CN | 102341105 B | 9/2014 |
| EP | 3187204 A1 | 7/2017 |
| EP | 2323712 B1 | 8/2021 |
| EP | 3458004 B1 | 10/2021 |
| EP | 2544640 B1 | 11/2021 |
| EP | 3717626 B1 | 12/2021 |
| EP | 3936095 A1 | 1/2022 |
| EP | 3960137 A1 | 3/2022 |
| EP | 3421020 B1 | 5/2022 |
| EP | 2623137 B1 | 6/2022 |
| EP | 4003254 A1 | 6/2022 |
| EP | 4007551 A1 | 6/2022 |
| EP | 4007552 A1 | 6/2022 |
| EP | 4009929 A1 | 6/2022 |
| WO | 2005018543 A2 | 3/2005 |
| WO | 2008047095 A1 | 4/2008 |
| WO | 2010133589 A1 | 11/2010 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016018798 A1 | 2/2016 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |

(56) References Cited

FOREIGN PATENT DOCUMENTS

| WO | 2019234365 A1 | 12/2019 |
|---|---|---|
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |

OTHER PUBLICATIONS

Kiernan et al., Indigogenic substrates for detection and localization of enzymes. Biotechnic & Histochemistry, 82:2, 73-103.*

Miyachi et al, Peptide Nanofibers Modified with a Protein by Using Designed Anchor Molecules Bearing Hydrophobic and Functional Moieties. Chem. Eur. J. 2010, 16, 6644-6650.*

Geiger et al, Amine Protecting Groups. In: The Peptides: Analysis, Synthesis, Biology 1981, pp. 1-99. Elsevier Inc. Ed: Gross, E. and Meienhofer, J.*

Turner et al., "Evaluation of 3,4-dinitrophenyl tetra-N-acetyl-beta-chitotetraoside as a substrate for the measurement of lysozyme in normal and pathological sera", Ann. Clin. Biochem., 1979, vol. 16, pp. 51-53.

Inaba et al., "Synthesis of 4-Methylcoumarin-7-yloxy Tetra-N-acetyl-beta-chitotetraside, a Novel Synthetic Substrate for the Flouorometric Assay of Lysozyme", Chem. Pharm. Bull., 1984, vol. 32, pp. 1597-1603.

Japanese Office Action, Japan Patent Office, Japanese Patent Application No. 2019-502283, dated Apr. 27, 2021, 2 pages.

European Examination Report; European Patent Office; European Patent Application No. 17723752.6; dated Feb. 28, 2020; 6 pages.

Viir-Morteza Sadat Ebrahimi et al.; Rapid Detection of *Escherichia coli* via Enzymatically Triggered Reactions n Self-Reporting Chitosan Hydrogels; Applied Materials & Interfaces; 2015; 11 pages; vol. 7, No. 36; Copyright 2015 okmerican Chemical Society.

Viir-Morteza Sadat Ebrahimi et al.; Rapid Remote Detection of *Escherichia coli* via a Reporter-Hydrogel Soated Glass Fiber Tip; European Polymer Journal; 2015; 10 pages; vol. 72; Copyright 2015 Elsevier Ltd.

Francois P. Douillard et al.; Expanding the Molecular Toolbox for Lactococcus Lactis: Construction of an nducible Thioredoxin Gene Fusion Expression System; Microbial Cell Factories; 2011; 10 pages; vol. 10, No. 1; Sopyright 2011 Douillard et al.

Communication Pursuant to Article 94(3) EPC; European Patent Application No. 17787245.4; European Patent Office; dated Jul. 3, 2020; 6 pages.

Andrea Hasmann et al.; Sensor Materials for the Detection of Human Neutrophil Elastase and Cathepsin G Activity in Wound Fluid; Experimental Dermatology; Apr. 13, 2011; 6 pages; vol. 20, No. 6.

J.V. Edwards et al.; Detection of Human Neutrophil Elastase with Peptide-Bound Cross-Linked Ethoxylate Acrylate Resin Analogs; Journal of Peptide Research; Oct. 1, 2006; 9 pages; vol. 55, No. 4.

J. Vincent Edwards et al.; A Bio-Sensor for Human Neutrophil Elastase Employs Peptide-p-Nitroanilide Cellulose Conjugates; Sensor Letters; Aug. 1, 2008; 6 pages; vol. 6, No. 4.

Stephan J. Wirth et al.; Dye-Labelled Substrates for the Assay and Detection of Chitinase and Lysozyme Activity; Journal of Microbiological Methods; 1990; 9 pages; vol. 12.

Mir Morteza Sadat Ebrahimi et al.; Enzyme-Sensing Chitosan Hydrogels; Langmuir; Jun. 10, 2014; 9 pages.

Chinese Office Action; Application No. 201780034020.2; dated Apr. 28, 2022; 14 pages.

Chinese Office Action; Chinese Application No. 201780034018.5; dated Feb. 7, 2022; 11 pages.

Alex A. Aimetti et al.; Human Neutrophil Elastase Responsive Delivery from Poly(ethylene glycol) Hydrogels; Biomacromolecules; 2009; 6 pages; vol. 10 No. 6.

Sonia K. Brady et al.; Cellobiohydrolase 1 from Trichoderma Reesei Degrades Cellulose in Single Cellobiose Steps; Nature Communications; Dec. 10, 2015; 9 pages.

A. Hasmann et al.; Analysis of Myeloperoxidase Activity in Wound Fluids as a Marker of Infection; Annals of Clinical Biochemistry; May 2013; vol. 50.

Andrea Hasmann et al.; Novel Peptidoglycan-based Diagnostic Devices for Detection of Wound Infection; Elsevier ScienceDirect; Diagnostic Microbiology and Infectious Disease; 2011; 12 pages; vol. 71.

Doris Ribitsch et al.; Fusion of Binding Domains to Thermobifida Cellulosilytica Cutinase to Tune Sorption Characteristics and Enhancing PET Hydrolysis; 2013; 8 pages; vol. 14.

Doris Schiffer et al.; Enzyme-Responsive Polymers for Microbial Infection Detection; Expert Review of Molecular Diagnostics; 2015; 8 pages.

* cited by examiner

| Anchor Region or Function | Enzyme-Recognition, -Labile or -Reactive Function | Moiety Generating Visible Change, also termed Indicator Region |

FIG. 6 Esterase and lipase substrates with indoxyl as the chromophore
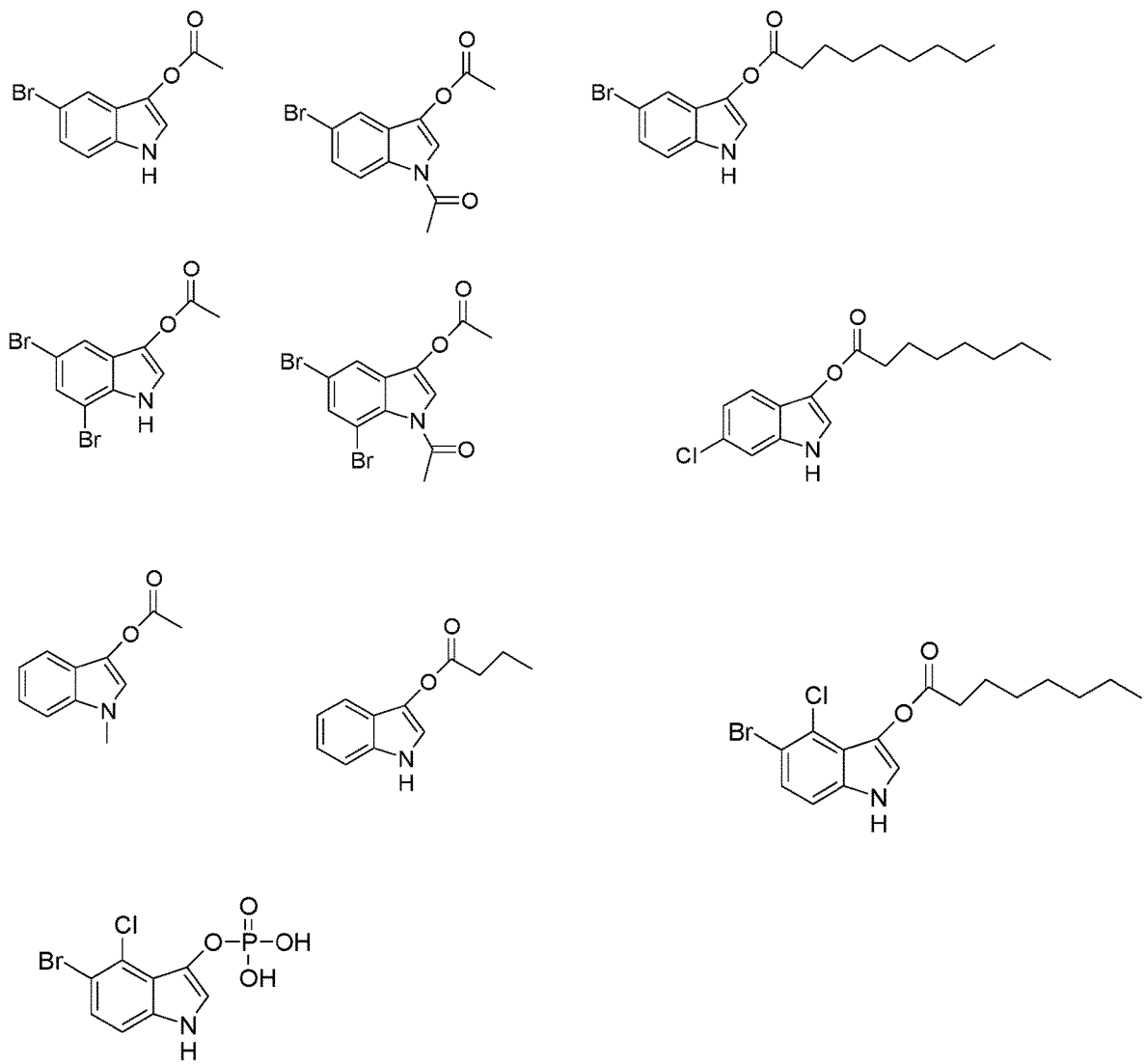
Akaline phosphatase substrate (hydrolysis of phosphate esters)

Examples X-Gal and X-Glc adducts to peptidoglycan (example 104) or chitosan via the Suzuki reaction product of example 103 (generic for all bromo containing systems). . Cleavage of the backbone polymer by lysozyme results in the mobilisation of PG or chitosan fragments whihc may become substrates for a galactosidase or a glucosidase.

X-Manosyl derivatives related to the products of examples 103 and 104. .
Cleavage of the backbone polymer by lysozyme results in the mobilisation of PG or
chitosan fragments which may become substrates for a manosidase.

FIG. 7C
Indoxyl based esterase substrate coupled to peptidogylcan or chitosan. Cleavage of the backbone polymer by lysozyme results in the mobilisation of PG or chitosan fragments which may become substrates for an esterase.
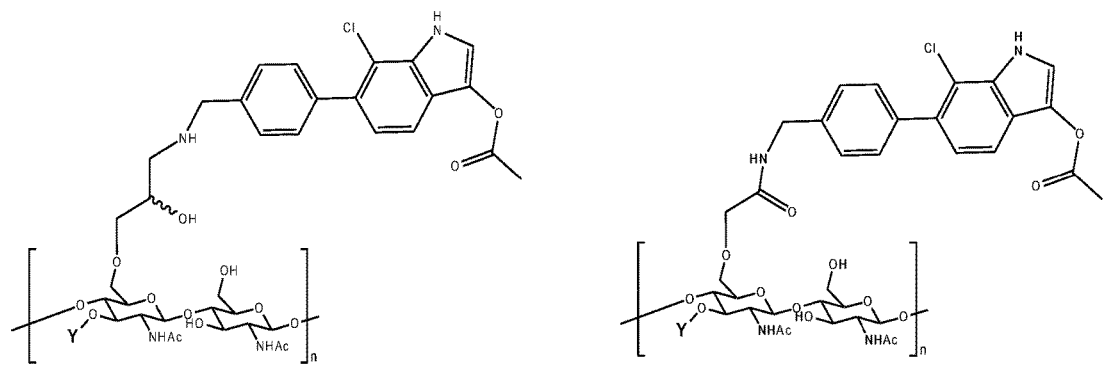
The Suzuki product of example 103 can be used as a terminal amide for peptide substrates of proteases
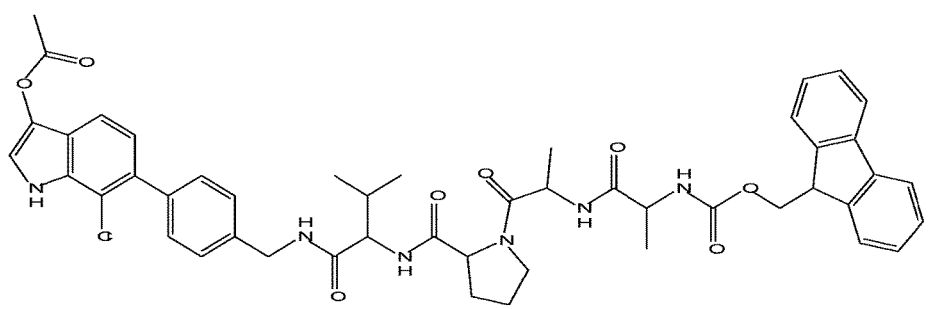

FIG. 8

Novel X-Gal conjugates of

Modification with chloroacetic acid forming
carboxymethyl-PG leads to a reactive
centre for amidation to the Suzuki
product of Example 103

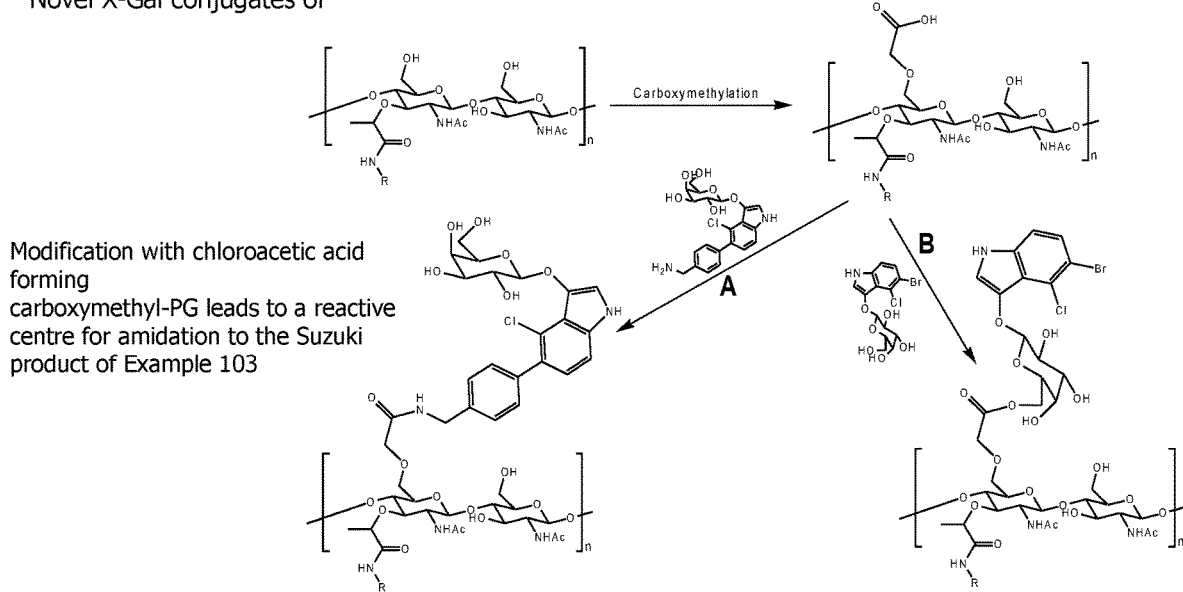

Product A employing benzylamino X-Gal (Example 103) leading to
amide that is a direct substrate for B-galactosidase mobilised by Lysozyme.    Product B directly using X-Gal
with no prior derivatization following a Steglich esterification protocol provides for a product that is labile to
esterases and B-galactosidase once lysozme has mobilised the backbone

FIG. 9A

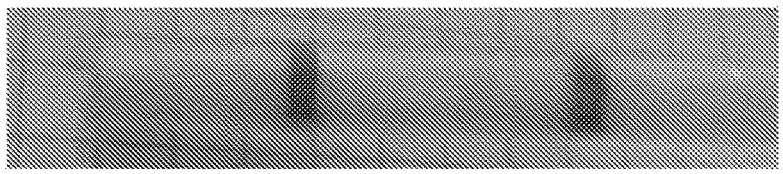

Feasibility of fast and slow reacting tubing inserts has been demonstrated Here the reaction is toward Elastase

FIG. 9B

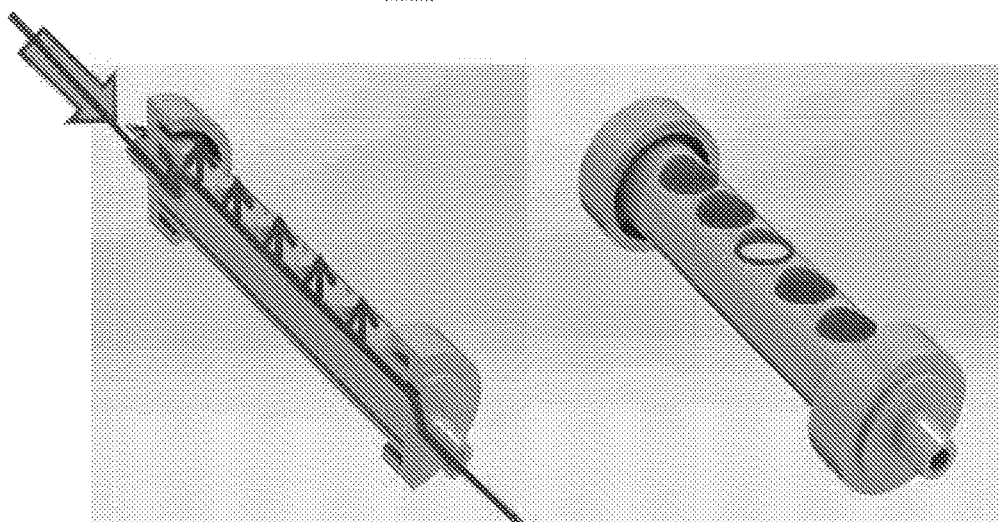

During aspiration, sputum or other fluids are transferred to indicator discs where the enzymes, if present, cause a reaction to form a blue colour if the fluid derives from an infected tissue

FIG. 9C

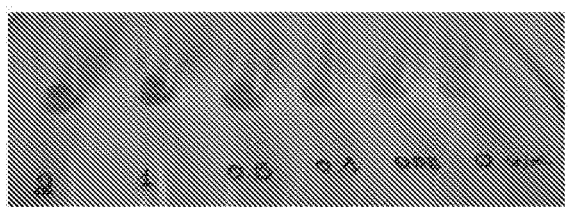 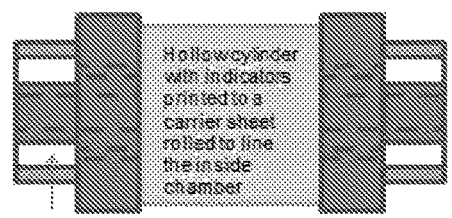

Sensitivity to elastase U/mL

Tubing attachment with collar

FIG. 9D

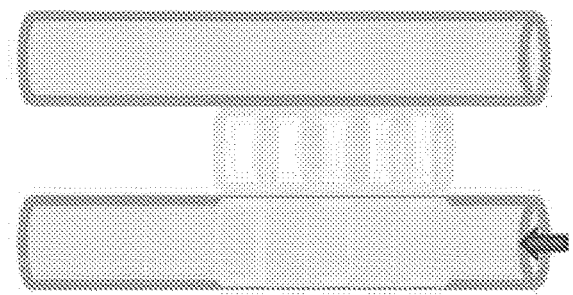

Tubing

Coated hollow insert flow

FIG. 13
ESI-MS Analysis of MPO reaction product
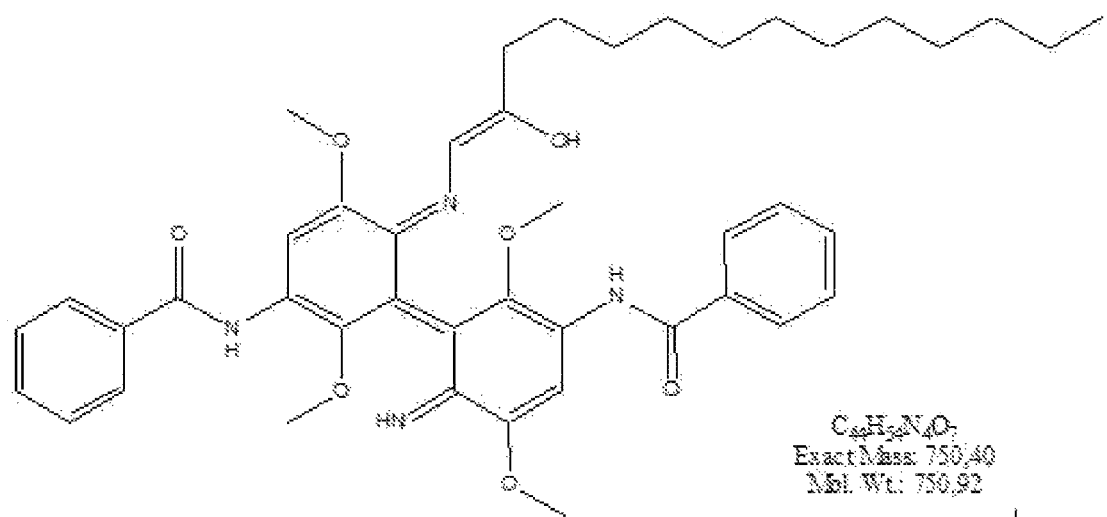
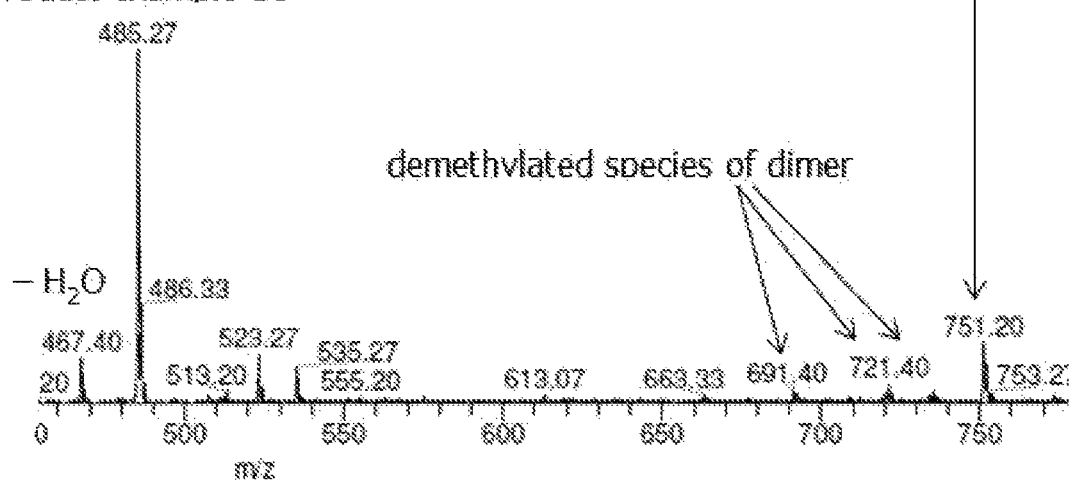

SEQUENCE LISTING

```
<160> NUMBER OF SEQ ID NOS: 46

<210> SEQ ID NO 1
<211> LENGTH: 104
<212> TYPE: PRT
<213> ORGANISM: Artificial Sequence
<220> FEATURE:
<223> OTHER INFORMATION: Protease substrate
<220> FEATURE:
<221> NAME/KEY: VARIANT
<222> LOCATION: (1)..(50)
<223> OTHER INFORMATION: each Xaa is independently any amino acid or
      absent
<220> FEATURE:
<221> NAME/KEY: VARIANT
<222> LOCATION: (54)..(54)
<223> OTHER INFORMATION: either the amino acid at position 54 is an
      unmodified valine residue or, if each Xaa at positions 55-104 is
      absent, the amino acid at position 54 is a valine residue linked
      to a moiety capable of causing a visible color change or a
      detectable
<220> FEATURE:
<221> NAME/KEY: VARIANT
<222> LOCATION: (55)..(104)
<223> OTHER INFORMATION: each Xaa is independently any amino acid or
      absent
<220> FEATURE:
<221> NAME/KEY: MOD_RES
<222> LOCATION: (55)..(104)
<223> OTHER INFORMATION: if the Xaa at the identified position is
      present and if no amino acid is positioned in the 3' direction, it
      is linked to a moiety capable of causing a visible color change or
      a detectable electronic change via a linking moiety

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45
```

```
Xaa Xaa Ala Ala Pro Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa
            100

<210> SEQ ID NO 2
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (4)..(4)
<223> OTHER INFORMATION: the Xaa at position 4 is a valine residue
      linked to a moiety capable of causing a visible color change or a
      detectable electronic change, optionally via a linking moiety

<400> SEQUENCE: 2

Xaa Ala Pro Xaa
1

<210> SEQ ID NO 3
<211> LENGTH: 4
<212> TYPE: PRT
<213> ORGANISM: Artificial Sequence
<220> FEATURE:
<223> OTHER INFORMATION: Cathepsin G-specific substrate

<400> SEQUENCE: 3

Ala Ala Pro Phe
1

<210> SEQ ID NO 4
<211> LENGTH: 4
<212> TYPE: PRT
<213> ORGANISM: Artificial Sequence
<220> FEATURE:
<223> OTHER INFORMATION: Cathepsin G-specific substrate

<400> SEQUENCE: 4

Ala Ala Pro Met
1

<210> SEQ ID NO 5
<211> LENGTH: 4
<212> TYPE: PRT
<213> ORGANISM: Artificial Sequence
<220> FEATURE:
<223> OTHER INFORMATION: Elastase substrate

<400> SEQUENCE: 5

Ala Ala Pro Val
1

<210> SEQ ID NO 6
<211> LENGTH: 5
<212> TYPE: PRT
```

```
<213> ORGANISM: Artificial Sequence
<220> FEATURE:
<223> OTHER INFORMATION: Protease substrate

<400> SEQUENCE: 6

Ala Pro Gly Gly Ile
1               5

<210> SEQ ID NO 7
<211> LENGTH: 4
<212> TYPE: PRT
<213> ORGANISM: Artificial Sequence
<220> FEATURE:
<223> OTHER INFORMATION: Protease substrate

<400> SEQUENCE: 7

Met Arg Arg Gln
1

<210> SEQ ID NO 8
<211> LENGTH: 4
<212> TYPE: PRT
<213> ORGANISM: Artificial Sequence
<220> FEATURE:
<223> OTHER INFORMATION: Protease substrate

<400> SEQUENCE: 8

Ala Ala Ala Ala
1

<210> SEQ ID NO 9
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 9

Xaa Ala Pro Val
1

<210> SEQ ID NO 10
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (5)..(5)
<223> OTHER INFORMATION: the Xaa at position 5 is a valine residue
      linked to a moiety capable of causing a visible color change or a
      detectable electronic change, optionally via a linking moiety

<400> SEQUENCE: 10

Xaa Ala Ala Pro Xaa
1               5

<210> SEQ ID NO 11
```

```
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 11

Xaa Ala Ala Pro Val
1               5

<210> SEQ ID NO 12
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(2)
<223> OTHER INFORMATION: the Xaa at position 1 is an alanine residue
      linked to an anchor moiety
<220> FEATURE:
<221> NAME/KEY: MOD_RES
<222> LOCATION: (4)..(4)
<223> OTHER INFORMATION: the Xaa at position 4 is a phenylalanine
      residue linked to a moiety capable of causing a visible color
      change or a detectable electronic change, optionally via a linking
      moiety

<400> SEQUENCE: 12

Xaa Ala Pro Xaa
1

<210> SEQ ID NO 13
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 13

Xaa Ala Pro Phe
1

<210> SEQ ID NO 14
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (4)..(4)
<223> OTHER INFORMATION: the Xaa at position 4 is an alanine residue
      linked to a moiety capable of causing a visible color change or a
      detectable electronic change, optionally via a linking moiety

<400> SEQUENCE: 14
```

```
Xaa Ala Pro Xaa
1

<210> SEQ ID NO 15
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 15

Xaa Ala Pro Ala
1

<210> SEQ ID NO 16
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (4)..(4)
<223> OTHER INFORMATION: the Xaa at position 4 is an alanine residue
      linked to a moiety capable of causing a visible color change or a
      detectable electronic change, optionally via a linking moiety

<400> SEQUENCE: 16

Xaa Ala Ala Xaa
1

<210> SEQ ID NO 17
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 17

Xaa Ala Ala Ala
1

<210> SEQ ID NO 18
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (6)..(6)
```

```
<223> OTHER INFORMATION: the Xaa at position 6 is a valine residue
      linked to a moiety capable of causing a visible color change or a
      detectable electronic change, optionally via a linking moiety

<400> SEQUENCE: 18

Xaa Ala Pro Val Ala Xaa
1               5

<210> SEQ ID NO 19
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 19

Xaa Ala Pro Val Ala
1               5

<210> SEQ ID NO 20
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (6)..(6)
<223> OTHER INFORMATION: the Xaa at position 6 is a valine residue
      linked to a moiety capable of causing a visible color change or a
      detectable electronic change, optionally via a linking moiety

<400> SEQUENCE: 20

Ala Ala Pro Val Ala Xaa
1               5

<210> SEQ ID NO 21
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (4)..(4)
<223> OTHER INFORMATION: the Xaa at position 4 is a valine residue
      linked to a moiety capable of causing a visible color change or a
      detectable electronic change, optionally via a linking moiety

<400> SEQUENCE: 21

Ala Ala Pro Xaa
1

<210> SEQ ID NO 22
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
```

```
<222> LOCATION: (6)..(6)
<223> OTHER INFORMATION: the Xaa at position 6 is an alanine residue
      linked to a moiety capable of causing a visible color change or a
      detectable electronic change, optionally via a linking moiety

<400> SEQUENCE: 22

Xaa Ala Pro Val Ala Xaa
1               5

<210> SEQ ID NO 23
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (6)..(6)
<223> OTHER INFORMATION: the Xaa at position 6 is an alanine residue
      linked to a moiety capable of causing a visible color change or a
      detectable electronic change, optionally via a linking moiety

<400> SEQUENCE: 23

Ala Ala Pro Val Ala Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (5)..(5)
<223> OTHER INFORMATION: the Xaa at position 5 is an alanine residue
      linked to a moiety capable of causing a visible color change or a
      detectable electronic change, optionally via a linking moiety

<400> SEQUENCE: 24

Xaa Ala Pro Phe Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (5)..(5)
<223> OTHER INFORMATION: the Xaa at position 5 is an alanine residue
      linked to a moiety capable of causing a visible color change or a
      detectable electronic change, optionally via a linking moiety

<400> SEQUENCE: 25

Ala Ala Pro Phe Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Protease substrate
```

```
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (5)..(5)
<223> OTHER INFORMATION: the Xaa at position 5 is an alanine residue
      linked to a moiety capable of causing a visible color change or a
      detectable electronic change, optionally via a linking moiety

<400> SEQUENCE: 26

Xaa Ala Pro Val Xaa
1               5

<210> SEQ ID NO 27
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 27

Xaa Ala Pro Val Ala
1               5

<210> SEQ ID NO 28
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (5)..(5)
<223> OTHER INFORMATION: the Xaa at position 5 is an alanine residue
      linked to a moiety capable of causing a visible color change or a
      detectable electronic change, optionally via a linking moiety

<400> SEQUENCE: 28

Ala Ala Pro Val Xaa
1               5

<210> SEQ ID NO 29
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (4)..(4)
<223> OTHER INFORMATION: the Xaa at position 4 is a valine residue
      linked to a moiety capable of causing a visible color change or a
      detectable electronic change, optionally via a linking moiety

<400> SEQUENCE: 29

Ala Ala Pro Xaa
1

<210> SEQ ID NO 30
<211> LENGTH: 4
<212> TYPE: PRT
<213> ORGANISM: Artificial Sequence
<220> FEATURE:
```

```
<223> OTHER INFORMATION: Protease substrate
<220> FEATURE:
<221> NAME/KEY: MOD_RES
<222> LOCATION: (4)..(4)
<223> OTHER INFORMATION: the Xaa at position 4 is a phenylalanine
      residue linked to a moiety capable of causing a visible color
      change or a detectable electronic change, optionally via a linking
      moiety

<400> SEQUENCE: 30

Ala Ala Pro Xaa
1

<210> SEQ ID NO 31
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (5)..(5)
<223> OTHER INFORMATION: the Xaa at position 5 is a methionine residue
      linked to a moiety capable of causing a visible color change or a
      detectable electronic change, optionally via a linking moiety

<400> SEQUENCE: 31

Xaa Ala Ala Pro Xaa
1               5

<210> SEQ ID NO 32
<211> LENGTH: 4
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 32

Xaa Ala Ala Pro
1

<210> SEQ ID NO 33
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (5)..(5)
<223> OTHER INFORMATION: the Xaa at position 5 is a methionine residue
      linked to a moiety capable of causing a visible color change or a
      detectable electronic change, optionally via a linking moiety

<400> SEQUENCE: 33

Ala Ala Ala Pro Xaa
1               5

<210> SEQ ID NO 34
<211> LENGTH: 5
<212> TYPE: PRT
```

```
<213> ORGANISM: Artificial Sequence
<220> FEATURE:
<223> OTHER INFORMATION: Protease substrate
<220> FEATURE:
<221> NAME/KEY: MOD_RES
<222> LOCATION: (5)..(5)
<223> OTHER INFORMATION: the Xaa at position 5 is a valine residue
      linked to a moiety capable of causing a visible color change or a
      detectable electronic change, optionally via a linking moiety

<400> SEQUENCE: 34

Ala Ala Ala Pro Xaa
1               5

<210> SEQ ID NO 35
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (6)..(6)
<223> OTHER INFORMATION: the Xaa at position 6 is a valine residue
      linked to a moiety capable of causing a visible color change or a
      detectable electronic change, optionally via a linking moiety

<400> SEQUENCE: 35

Ala Ala Ala Pro Val Xaa
1               5

<210> SEQ ID NO 36
<211> LENGTH: 5
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (5)..(5)
<223> OTHER INFORMATION: the Xaa at position 5 is a valine residue
      linked to a moiety capable of causing a visible color change or a
      detectable electronic change, optionally via a linking moiety

<400> SEQUENCE: 36

Xaa Ala Ala Pro Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety
<220> FEATURE:
<221> NAME/KEY: MOD_RES
<222> LOCATION: (6)..(6)
<223> OTHER INFORMATION: the Xaa at position 6 is a valine residue
      linked to a moiety capable of causing a visible color change or a
      detectable electronic change, optionally via a linking moiety

<400> SEQUENCE: 37
```

```
Xaa Ala Ala Pro Val Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: Protease substrate
<220> FEATURE:
<221> NAME/KEY: MOD_RES
<222> LOCATION: (1)..(1)
<223> OTHER INFORMATION: the Xaa at position 1 is an alanine residue
      linked to an anchor moiety

<400> SEQUENCE: 38

Xaa Ala Ala Pro Val Val
1               5

<210> SEQ ID NO 39
<211> LENGTH: 4
<212> TYPE: PRT
<213> ORGANISM: Artificial Sequence
<220> FEATURE:
<223> OTHER INFORMATION: Protease substrate

<400> SEQUENCE: 39

Ala Ala Pro Ala
1

<210> SEQ ID NO 40
<211> LENGTH: 6
<212> TYPE: PRT
<213> ORGANISM: Artificial Sequence
<220> FEATURE:
<223> OTHER INFORMATION: Consensus recognition motif for 3C protease

<400> SEQUENCE: 40

Leu Glu Val Leu Phe Gln
1               5

<210> SEQ ID NO 41
<211> LENGTH: 4
<212> TYPE: PRT
<213> ORGANISM: Artificial Sequence
<220> FEATURE:
<223> OTHER INFORMATION: Consensus furin cleavage site

<400> SEQUENCE: 41

Arg Arg Arg Arg
1

<210> SEQ ID NO 42
<211> LENGTH: 4
<212> TYPE: PRT
<213> ORGANISM: Artificial Sequence
<220> FEATURE:
<223> OTHER INFORMATION: Consensus furin cleavage site

<400> SEQUENCE: 42

Arg Arg Lys Arg
1

<210> SEQ ID NO 43
<211> LENGTH: 4
<212> TYPE: PRT
<213> ORGANISM: Artificial Sequence
<220> FEATURE:
```

```
<223> OTHER INFORMATION: Consensus furin cleavage site

<400> SEQUENCE: 43

Arg Leu Gly Arg
1

<210> SEQ ID NO 44
<211> LENGTH: 4
<212> TYPE: PRT
<213> ORGANISM: Artificial Sequence
<220> FEATURE:
<223> OTHER INFORMATION: Consensus furin cleavage site

<400> SEQUENCE: 44

Leu Leu Gly Arg
1

<210> SEQ ID NO 45
<211> LENGTH: 4
<212> TYPE: PRT
<213> ORGANISM: Artificial Sequence
<220> FEATURE:
<223> OTHER INFORMATION: Consensus furin cleavage site

<400> SEQUENCE: 45

Leu Leu Ala Arg
1

<210> SEQ ID NO 46
<211> LENGTH: 4
<212> TYPE: PRT
<213> ORGANISM: Artificial Sequence
<220> FEATURE:
<223> OTHER INFORMATION: Consensus furin cleavage site

<400> SEQUENCE: 46

Leu Leu Ala Leu
1
```

CONSTRUCT INCLUDING AN ANCHOR, AN ENZYME RECOGNITION SITE AND AN INDICATOR REGION FOR DETECTING MICROBIAL INFECTION IN WOUNDS

CROSS-REFERENCE TO RELATED APPLICATIONS AND DISCLOSURE

This application claims the benefit of United States Provisional Application Nos. 62/315,546, filed Mar. 30, 2016, and U.S. 62/315,556, filed Mar. 30, 2016, which disclosures are incorporated herein by reference in their entireties and made a part hereof.

SEQUENCE LISTING

The Sequence Listing associated with this application, which is separate part of the disclosure, includes the nucleotide and/or amino acid sequences and associated information using the symbols and format in accordance with the requirements of 37 CFR 1.821-1.825. The Sequence Listing in the ASCII text file titled CVT05-40138 Sequence_Listing.txt, which was created on Jan. 6, 2023 and is 17,494 bytes is incorporated herein by reference. This application also includes a PDF file that is identical to the ASCII text file titled CVT05-40138 Sequence_Listing.txt.

TECHNICAL FIELD

Embodiments described herein generally relate to wound healing, and in particular to compositions and methods for the detection and treatment of wounds.

BACKGROUND

In mammals, dermal injury triggers an organized complex cascade of cellular and biochemical events that result in a healed wound. Wound healing is a complex dynamic process that results in the restoration of anatomic continuity and function: an ideally healed wound is one that has returned to normal anatomic structure, function, and appearance. A typical wound heals via a model consisting of four stages—"exudative" phase, proliferative phase, reparative phase and epithelial maturation (Hatz et al., Wound Healing and Wound Management, Springer-Verlag, Munich, 1994) or hemostatic, inflammatory, proliferative and remodeling phase (Nwomeh et al., Clin. Plast. Surg. 1998, 25, 341). The inflammatory phase is particularly important to the wound healing process, wherein biochemical reactions at the wound situs facilitate healing but also cause tissue breakdown due to production of excess proteases.

Pathogenic infection is one of the most common impediments to wound healing. A progressive worsening of a clean wound to a colonized wound is often associated with increased bioburden imposed by pathogenic microorganisms. See, Ovington et al., Ostomy Wound Management, 49.7A: 8-12, 2003. An infected wound is an intermediate stage that is characterized by clinical signs of infection such as yellow appearance, soreness, redness, oozing pus, while a colonized wound is characterized by chronic pathogenic infection and is difficult to heal. Infection of the wound may also arrest the healing process. For example, pathogens in a wound can produce toxins (e.g., *Clostridium* species), generate noxious metabolites like ammonia that raise pH (e.g., *Proteus* species), activate or produce tissue lytic enzymes like proteases, or promote tissue invasion, thereby leading to an increase in the size or seriousness of the wound.

In order to keep the chronicity of wounds in check, a variety of assessment techniques and/or tools are employed in the clinical and veterinary setting. Current methods of assessing an infected wound are based primarily on assaying for a variety of parameters associated with the wound. For instance, a wound may be assessed visually, length and depth measurements may be taken, digital photography may be used where available to track the visual condition and size of a wound (Krasner et al., supra). In clinical practice, diagnosis of infection is based on measurement of secondary parameters, such as, odor, presence of local pain, heat, swelling, discharge, and redness. Many of these clinical indicators, such as inflammation and discharge have a low predictive value of infection in wounds. In other instances, the number(s) and type(s) of pathogenic flora at the wound situs may be determined using laboratory and/or clinical diagnostic procedures. Swabbing of a wound followed by microbiology testing in the hospital laboratory is an option for confirmation of bacterial colonization and identification of the strains associated with infection, thus allowing for the prescription of correct antibiotic course. However, this process is time consuming and labor intensive. Delay in diagnosis of infection can delay the administration of antibiotics and may increase the risk of developing sepsis.

One of the biggest drawbacks associated with existing clinical diagnostics is a lag associated with the onset of infection and the timing of detection. For instance, positive identification of infection using swabbing procedures often depends on attainment of a "critical mass" of microorganisms at the wound site and so early detection cannot be made until a detectable level is reached. Also, the swabs may be contaminated with the flora of the surrounding tissue, thereby complicating the diagnostic procedure. Other drawbacks include, e.g., sampling errors, delays in transport of the swabs, errors in analytical procedures, and/or errors in reporting. See, the review by Bowler et al., Clin Microbiol Rev. 14(2): 244-269, 2001.

There is therefore an imminent but unmet need for diagnostic reagents and methods that enable early diagnosis of clinical infection, preferably, which permit clinical diagnosis prior to manifestation of clinical symptoms of infection. There is also a need for compositions and methods that would assist in predicting clinical infection of a wound prior to the manifestation of clinical symptoms. Such a prognostic aid would allow early intervention with suitable treatment (e.g., antimicrobial treatment) before the wound is exacerbated and surgery or other drastic intervention is required to prevent further infection. Additionally, if clinicians could respond to wound infection as early as possible, the infection could also be treated with minimal antibiotic usage. This would reduce the need for hospitalization and would reduce the risk of secondary infections, e.g., as a result of contact with other diseased subjects.

SUMMARY

The technology disclosed herein provides for compositions and methods of detecting infected and/or chronic wounds. The disclosed technology improves upon exiting assays by: increasing the sensitivity, precision and specificity of detection of infected wounds; providing for the ability of qualitative and quantitative measurements; and, increasing the speed of detection of infected wounds in situ and in real-time. The assays and methods described herein are partly based on the use of specific reagents that detect biomarkers and/or probes which are present in infected or chronic wounds. The detection process may involve use of reagents that are specific to the markers present in infected wounds but not non-infected or non-chronic wounds and the detection step may involve qualitative or quantitative measurements of the signal(s) that are generated when the probe is acted upon by the marker. In embodiments wherein the detection method involves detection of enzymes present in wounds, the probes comprise modified enzyme substrates that are specific to the enzyme, which generate signals that may be optionally amplified. This greatly improves efficiency and specificity of detection. Moreover, a plurality of detection probes, each specific for one or more targets, e.g., enzymes that are specific to the wounds, may be employed. This greatly helps to maximize both efficiency and accuracy of diagnostic assays while minimizing the incidence of false positives {e.g., due non-specific interactions and/or target redundancy). Furthermore, the experimental results disclosed herein confirm that the novel probes and the assay techniques based thereon are capable of detecting and characterizing various types of wounds. Finally, the reagents of the disclosed technology may be used together with therapeutic molecules such as antibiotics, antifungal agents, etc. to monitor and evaluate treatment and management of chronic wounds.

Embodiments described herein are based, in part, on the discovery that cells of the immune system, including enzymes generated thereby, may serve as markers in the early diagnosis of wounds. These cells, e.g., neutrophils, are recruited at the wound situs to combat infection, do so by engulfing bacteria (and other pathogens) and/or neutralizing them with enzymes. Some enzymes are specific towards proteins (e.g., elastase, cathepsin G, lipase), others are specific towards cell wall components (e.g., lysozyme) and yet others mediate protein denaturation (e.g., NADPH oxidase, xanthine oxidase, myeloperoxidase (MPO) and other peroxidases). These cells, e.g., neutrophils, are generally only short-lived and when they lyse in the area of the infection, they release the contents of their lysosomes including the enzymes, which can then be detected to provide a reliable measurement of the status of the wound.

Accordingly, various embodiments described herein utilize the detection of enzyme markers, which are indicative of the presence of myeloid cells, and neutrophils in particular, in a biological sample of interest, for example, wound tissue. Increased level or activity of such enzymes in the wound fluid, therefore, corresponds to a heightened bacterial challenge and a manifestation of disturbed host/bacteria equilibrium in favor of the invasive bacteria.

In one aspect, provided herein is a chemical entity capable of detecting enzyme activity from a body fluid, the chemical entity comprising one or more of an anchor region, an enzyme recognition region, an enzyme-labile or enzyme-reactive region, and an indicator region.

In some embodiments, the chemical entity comprises at least three of an anchor region, an enzyme recognition region, an enzyme-labile or enzyme-reactive region and an indicator region. In some embodiments, the chemical entity comprises one of an anchor region, an enzyme-labile or enzyme-reactive region and an indicator region. In some embodiments, the chemical entity comprises one of an anchor region, one of an enzyme recognition region, one of an enzyme-labile or enzyme-reactive region and one of an indicator region. In some embodiments, the chemical entity binds to a support material via the anchor region. In some embodiments, the chemical entity comprises at least two indicator regions. In some embodiments, the enzyme recognition region partially or fully overlaps with the enzyme-labile or enzyme-reactive region. In some embodiments, the anchor region partially or fully overlaps with the enzyme-labile or enzyme-reactive region. In some embodiments, the anchor region partially or fully overlaps with the indicator region. In some embodiments, the indicator region partially or fully overlaps with the enzyme-labile or enzyme-reactive region. In some embodiments, the indicator region, once separated from the chemical entity by target enzyme activity, interacts with one or more accessory enzymes selected from a lipase, esterase, peroxidase, oxidase, glycosidase, glucuronidase, glucosidase, galactosidase, and a combination thereof. In some embodiments, the enzyme-labile or enzyme-reactive region interacts with one or more target enzymes selected from Napsin (aspartyl protease), Glucosylceramidase glucuronidase, palmitoyl protein thioesterase, Cathepsins A, B, D, G, L, S, Z, Acid ceramidase, lactoferrin (LF), lysozyme, myeloperoxidase (MPO), elastase, cathepsins, and proteinase-3 elastase, lysozyme, esterase, lipase and, and a combination thereof.

In some embodiments, the enzyme-labile or enzyme-reactive region comprises a moiety capable of producing a visible color or detectable electronic change upon interaction of the enzyme-labile or enzyme-reactive region with one or more target enzymes, the moiety being selected from a peroxidase substrate, arylamine, an amino phenol, a phenol, a quinone, a neutral dye, a charged dye, a nanoparticle, a quantum dot, a colloidal gold particle, or an analog thereof. In some embodiments, the peroxidase substrate is selected from p-aminophenol, ABTS (2,2inophenol, ABTS (rate is selected from gold acid) diammonium salt), 3,3'-diaminobenzidine, DCPIP, N,N-dimethyl-p-phenylenediamine, o-dianisidine, p-phenylenediamine, 4-chloro-1-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), indoxyl, indigo, Fast Blue RR, and 4-chloro-7-nitrobenzofurazan, and an analog thereof. In some embodiments, the peroxidase substrate an aniline analog. In some embodiments, the peroxidase substrate is an N-alkyl derivative of Fast Blue RR with more than 6 carbon units. In some embodiments, the indicator region comprises a moiety capable of producing a visible color or detectable electronic change upon interaction of the enzyme-labile or enzyme-reactive region with one or more target enzymes, the moiety being selected from an indoxyl analog, a neutral dye, a charged dye, a nanoparticle, and a colloidal gold particle. In some embodiments, the moiety capable of producing a visible color or detectable electronic change is a charged dye or a luminol derivative. In some embodiments, the charged dye is selected from toluidine blue, reactive black 5, remazol brilliant blue, reactive violet 5, and reactive orange 16. In some embodiments, the charged dye is selected from reactive blue 4, reactive red 120, reactive blue 2, reactive green 19, and reactive brown 10. In some embodiments, the enzyme-labile or enzyme-reactive region is labile to or reactive with lysozyme, and the enzyme-labile or enzyme reactive region comprises a polysaccharide, glucosamine, or peptidoglycan, and the polysaccharide, glucosamine, or peptidoglycan. In some embodiments, the enzyme-labile or enzyme-reactive region comprises a peptidoglycan, and peptidoglycan is labile to or reactive with lysozyme. In some embodiments, the enzyme-labile or enzyme-reactive region comprises a phenol, a napthol, an indoxyl, or a quinone, and the phenol, carboxyaminophenyl, indoxyl, or quinone is labile to or reactive with myeloperoxidase and not reactive to heme. In some embodiments, the enzyme-labile or enzyme-reactive region comprises a peptide, peptidomimetic, or protein, and the peptide, peptidomimetic, or protein is labile to or reactive with elastase. In some embodiments, the enzyme-labile or enzyme-reactive region comprises a peptide comprising an amino acid sequence of $X_y$AAPX$_y$-L-Z, wherein each X is independently any amino acid, each y is independently a number selected from 1 to 50, L is a linking moiety, and Z is a moiety capable of causing a visible color change or a detectable electronic change. In some embodiments, the enzyme-labile or enzyme-reactive region comprises a peptide comprising an amino acid sequence of $X_y$AAPVX$_y$-L-Z [SEQ ID NO: 1], wherein each X is independently any amino acid, each y is independently a number selected from 0 to 50, L is a linking moiety such as an ester or amide, and Z is a moiety capable of causing a visible color change or a detectable electronic change. In some embodiments, the enzyme-labile or enzyme-reactive region comprises a peptide, peptidomimetic, or protein, and the peptide, peptidomimetic, or protein is labile to or reactive with cathepsin G. In some embodiments, the enzyme-labile or enzyme-reactive region comprises a peptide comprising an amino acid sequence of $X_y N^4 N^3 N^2 N^1 X_y$-L-Z, wherein each X is independently any amino acid; each y is independently a number selected from 0 to 6; $N^4$ is selected from alanine, glycine, valine, and glutamine; $N^4$ is selected from alanine, glycine, proline, lysine, and serine; $N^2$ is selected from proline, alanine, and glycine; $N^1$ is selected from serine, lysine, phenylalanine, arginine, leucine, and methionine; L is a linking moiety, and Z is a moiety capable of causing a visible color change or a detectable electronic change. In some embodiments, the anchor region is selected from a polystyrene bead, silica gel bead, polysaccharide bead, polyacrylamide bead, cellulose bead, polysaccharide, derivatized cellulose, polyacrylate, polyethyleneimine, polyacrylamide, UV-activatable group, phenolic azide, epoxide, peptidoglycan, an aliphatic chain, an aliphatic alcohol chain, a multi-cyclic or multi-aromatic ring system, a lipophilic group, and a combination thereof. In some embodiments, the anchor region binds to a support material after a short period of UV irradiation. In some embodiments, the anchor region comprises an ionic chemical group for binding to a support material. In some embodiments, the anchor region comprises a reactive moiety for covalent attachment to the support material. In some embodiments, the anchor region and the enzyme labile region are polypeptides and the anchor region comprises a polymer binding domain. In some embodiments, the enzyme labile region is labile to a protease and the polymer binding domains are selected from hydrophobic binding domains. In some embodiments, the enzyme labile region is labile to cathepsin or elastase. In some embodiments, the chemical entity is selected from a small molecule entity or a modified polymer.

In one aspect, provided herein is a chemical entity for the detection of infection, the chemical entity comprising an indicator region comprising a pH-sensitive moiety that presents a visible color change. In some embodiments, the chemical entity further comprises a reactive group that allows the reaction to a solid phase. In some embodiments, the pH-sensitive moiety is bromothymol blue, phenol red, bromophenol red, chlorophenol red, thymol blue, bromocresol green, bromocresol purple; or other sulfophthalein dyes.

In some embodiments, the anchor region binds to a support material after a short period of UV irradiation. In some embodiments, the anchor region comprises an ionic chemical group for binding to a support material. In some embodiments, the anchor region comprises a reactive moiety for covalent attachment to the support material. In some embodiments, the anchor region comprises a hydrophobic moiety that causes little or no solubility in aqueous systems thus allowing the material to stay associated with a solid phase.

In some embodiments, the reactive region interacts with the bacterial enzyme β-lactamase. This is a bacterial enzyme that is capable of degrading common antibacterial drugs and its presence is of interest to treating physicians. A chromogenic β-lactamase substrate is generally useful in addition to reagents that report on other biomarkers.

In some embodiments, the reactive region is a substrate for viral proteases or the host furin protease. In some embodiments, the detection of the cleaved product requires a polycationic trap. In certain embodiments, these can be cross-linked. Depending on the degree and type of cross-linking they can also be superabsorbers. In some embodiments, the enzyme substrates are able to give rise to a redox active species that can be detected electronically. In other embodiments, the electronic detection of enzyme products in solid phase is made by means of reflected light. Disclosed herein are chemical entities, which can be of monomelic, oligomeric or polymeric nature. These are modified to serve as medium for detection of chosen marker for infection in a wound or in body fluids, before the infections are otherwise apparent. In some embodiments, the chemical entity is for detecting infection in a mammal. In some embodiments, the chemical entity detects one or more biomarkers of infection and produces a visible change in the presence of the one or more biomarkers. In some embodiments, the one or more biomarkers are leukocyte enzymes. In some embodiments, the one or more biomarkers are selected from elastase, lysozyme, myeloperoxidase, leukocyte peroxidase, esterase, lipase, napsin (aspartyl protease), glucosylceramidase glucuronidase, palmitoyl protein thioesterase, cathepsins A, B, D, G, L, S, Z, Acid ceramidase, lactoferrin (LF), and proteinase-3, β-lactamase, and other similar enzymes, or combination thereof. In some embodiments, the chemical entity detects a specific pH range. In some embodiments, the chemical entity detects one or more leukocyte enzymes and a specific pH range; and produces a visible change in the presence of the one or more leukocyte enzymes and the specific pH range. In some embodiments, the visible change is a color change that is easily distinguished from colors common in wounds or body fluids (e.g., red, yellow, pink, or brown). In some embodiments, the visible change is fluorescent, luminescent, or mediated via physical means such as refraction, gas evolution, or a change in polymer state. In some embodiments, the chemical entity comprises one or more components selected from the group consisting of: an anchor region, an enzyme recognition region, an enzyme-labile or enzyme-reactive region, and an indicator region. In some embodiments, the body fluid is blood, plasma, serum, cerebrospinal fluid, sputum, urine or wound exudate. In preferred embodiments, the body fluid is wound exudate.

In some embodiments, the chemical entity is incorporated into a wound dressing where the chemical entity reacts with wound exudates that come into contact with the wound dressing. In some embodiments, the chemical entity is incorporated into a wound dressing where the chemical entity reacts with wound exudates that are drawn up through the wound dressing to a reagent layer comprising the chemical entity. In some embodiments, the chemical entity is an indicator conjugate that gives rise to a color or other visible marker when infection biomarkers are present. In some embodiments, the chemical entity is used in methods to diagnose an infected wound in a mammal. In some embodiments, the chemical entity is used in methods to treat a wound in a mammal. In some embodiments, the chemical entity is used in methods to diagnose and treat a wound in a mammal.

In some embodiments, the chemical entity is incorporated into a vacume wound therapy system via tubing or other components where the chemical entity reacts with vacume exudates that come into contact with the insert in the device.

In some embodiments, the chemical entity is incorporated into a ventilator system via tubing or other components where the chemical entity reacts with aspirates, aerosols or sputum exudates that come into contact with the chemical entities.

In some embodiments, the chemical entity is incorporated into a dipstick where the chemical entity reacts after the fluids to be assess are applied using an external swab or similar. In some embodiments, the chemical entity gives rise to a change that can be detected electronically either via reflected light, amperometry or a similar electrochemical process.

In some embodiments, use of the chemical entity makes it feasible to detect changes in the infection status of a mammal or patient prior to these changes being otherwise apparent. In some embodiments, the methods are the basis for an improved or proactive therapy, wherein a subsequent change of treatment or an application of a more detailed diagnostic is subsequently used to select a therapy to prevent a worsening of the medical condition of a mammal or patient.

Chemical Entity

In some embodiments, the chemical entity is a small molecule chemical entity or a modified polymer comprising one or more components selected from the group consisting of: an anchor region, an enzyme recognition region, an enzyme-labile or enzyme-reactive region, and an indicator region.

In some embodiments, the enzyme-labile or enzyme-reactive region is a structure that is reacted by an enzyme. In some embodiments, the enzyme recognition site is a structure that allows binding to an enzyme.

In certain embodiments, the chemical entity is a modified polymer. In certain embodiments, the chemical entity is a small molecule chemical entity. Disclosed herein, are chemical entities comprising one or more components selected from the group consisting of: an anchor region, an enzyme-labile or enzyme-reactive region, an enzyme recognition region, and an indicator region. In some embodiments, the chemical entity comprises at least one anchor region, at least one enzyme recognition region, at least one enzyme-labile or enzyme-reactive region, and at least one indicator region. In some embodiments, the chemical entity binds to a support material through the anchor region. In some embodiments, the chemical entity is an indicator conjugate. In some embodiments, the chemical entity comprises at least one enzyme-labile or enzyme-reactive region, at least one enzyme recognition region and at least one indicator region. In some embodiments, the chemical entity comprises at least one anchor region, and at least one indicator region.

In some embodiments, the chemical entity comprises an anchor region, an enzyme recognition region, an enzyme-labile or enzyme-reactive region, and an indicator region. In some embodiments, the chemical entity comprises an enzyme recognition region, an enzyme-labile or enzyme-reactive region, and an indicator region. In some embodiments, the chemical entity comprises an anchor region, an enzyme recognition region, and an enzyme-labile or enzyme-reactive region. In some embodiments, the chemical entity comprises an enzyme recognition region, an anchor region and two enzyme-labile or enzyme-reactive regions. In some embodiments, the chemical entity comprises an enzyme recognition region, an anchor region, two enzyme-labile or enzyme-reactive regions, and two indicator regions. In some embodiments, the chemical entity comprises an enzyme recognition region, two enzyme-labile or enzyme-reactive regions, and two indicator regions.

In some embodiments, the one or more anchor regions and the one or more enzyme-labile or enzyme-reactive regions overlap partially with one another. In some embodiments, the anchor region and the enzyme recognition region or the enzyme-labile or enzyme-reactive region partially or fully overlap with one another. In some embodiments, the enzyme recognition region and the enzyme-labile or enzyme-reactive region partially or fully overlap with one another. In some embodiments, the one or more anchor regions are within the one or more enzyme-labile or enzyme-reactive regions. In some embodiments, the anchor region is within the enzyme-labile or enzyme-reactive region. In some embodiments, the one or more enzyme-labile or enzyme-reactive regions are within the one or more anchor regions. In some embodiments, the enzyme-labile or enzyme-reactive region is within the anchor region.

In some embodiments, the anchor region of the chemical entity binds the chemical entity to a support material. In some embodiments, the anchor region comprises an ionic chemical group. In some embodiments, the ionic chemical group forms an ionic bond with the support material. In some embodiments, the anchor region comprises a hydrophobic moiety. In some embodiments, the hydrophobic moiety interacts with the support material to bind the chemical entity to the support material. In some embodiments, the anchor region comprises a hydrophilic moiety. In some embodiments, the hydrophilic moiety interacts with the support material to bind the chemical entity to the support material.

In some embodiments, the anchor region is a bead, a polymer, a material with an ionic chemical group, a material with a hydrophilic moiety, or a material with a hydrophobic moiety. In some embodiments, the anchor region is a bead. In some embodiments, the anchor region is a polymer. In some embodiments, the anchor region is a material with an ionic chemical group, wherein the ionic chemical group is positively charged. In some embodiments, the anchor region is a material with an ionic chemical group, wherein the ionic chemical group is negatively charged. In some embodiments, the anchor region is a material with a hydrophilic moiety. In some embodiments, the anchor region is a material with a hydrophobic moiety such as an aliphatic chain or an aliphatic alcohol. In some embodiments, the anchor region comprises a reactive moiety for covalent attachment to a support material such as a photoactive phenylazide or an epoxide group.

In some embodiments, the anchor region is a polystyrene bead, silica gel bead, polysaccharide bead, polyacrylamide bead, cellulose bead, polysaccharide, derivatized cellulose, polyacrylate, polyethyleneimine, polyacrylamide, UV-activatable reactive group or peptidoglycan derivative, or a combination thereof. In some embodiments, the anchor region binds to a support material after a short period of UV irradiation.

In some embodiments, the enzyme-labile or enzyme-reactive region reacts with one or more target enzymes selected from elastase, lysozyme, myeloperoxidase, leukocyte peroxidase, esterase, lipase, napsin (aspartyl protease), glucosylceramidase glucuronidase, palmitoyl protein thioesterase, cathepsins A, B, D, G, L, S, Z, Acid ceramidase, lactoferrin (LF), and proteinase-3,□-lactamase and other similar enzymes, or a combination thereof. In some embodiments, the enzyme-labile or enzyme-reactive region reacts with elastase. In some embodiments, the enzyme-labile or enzyme-reactive region reacts with lysozyme. In some embodiments, the enzyme-labile or enzyme-reactive region reacts with cathepsin G. In some embodiments, the enzyme-labile or enzyme-reactive region reacts with myeloperoxidase.

In some embodiments, the enzyme-labile or enzyme-reactive region comprises a peptide, peptidomimetic, or protein that is labile to elastase or cathepsin G, or a combination thereof. In some embodiments, the enzyme-labile or enzyme-reactive region comprises a peptide, peptidomimetic, or protein that is labile to elastase. In some embodiments, the enzyme-labile or enzyme-reactive region comprises a peptide, peptidomimetic, or protein that is labile to cathepsin G.

In some embodiments, the enzyme-labile or enzyme-reactive region comprises a peptide that is labile to elastase. In some embodiments, the enzyme-labile or enzyme-reactive region comprises a peptide comprising an amino acid sequence of $X_yAAP(V/F/A)X_y$-L-Z, wherein each X is independently any amino acid, each y is independently an integer greater than 0, or each y is independently an integer from 1 to 50, or each y is independently an integer from 1 to 10, or each y is independently an integer from 1 to 6, L is a linking moiety, and Z is a moiety capable of causing a visible color change or a detectable electronic change; and the peptide is labile to elastase. In some embodiments, one or more of the amino acids in the amino acid sequence is protected. In some embodiments, one or more of the amino acids in the amino acid sequence is protected with an fmoc group. In some embodiments, one of the amino acid in the amino acid sequence is protected with an fmoc group.

In some embodiments, the enzyme-labile or enzyme-reactive region comprises a peptide comprising an amino acid sequence of $X_yAAP(V/F/A)X_y$-Z, wherein each X is independently any amino acid, each y is independently an integer greater than 0, or each y is independently an integer from 1 to 50, or each y is independently an integer from 1 to 10, or each y is independently an integer from 1 to 6, and Z is a moiety capable of causing a visible color change or a detectable electronic change; and the peptide is labile to elastase. In some embodiments, one or more of the amino acids in the amino acid sequence is protected. In some embodiments, one or more of the amino acids in the amino acid sequence is protected with an fmoc group. In some embodiments, one of the amino acid in the amino acid sequence is protected with an fmoc group.

In some embodiments, the enzyme-labile or enzyme-reactive region comprises a peptide comprising an amino acid sequence of $X_yAAPX_y$-L-Z, wherein each X is independently any amino acid, each y is independently a number selected from 1 to 50, or each y is independently an integer from 1 to 10, or each y is independently an integer from 1 to 6, L is a linking moiety, and Z is a moiety capable of causing a visible color change or a detectable electronic change; and the peptide is labile to elastase. In some embodiments, one or more of the amino acids in the amino acid sequence is protected. In some embodiments, one or more of the amino acids in the amino acid sequence is protected with an fmoc group. In some embodiments, one of the amino acid in the amino acid sequence is protected with an fmoc group.

In some embodiments, the enzyme-labile or enzyme-reactive region comprises a peptide comprising an amino acid sequence of $X_yAAPX_y$-Z, wherein each X is independently any amino acid, each y is independently a number selected from 1 to 50, or each y is independently an integer from 1 to 10, or each y is independently an integer from 1 to 6, and Z is a moiety capable of causing a visible color change or a detectable electronic change; and the peptide is labile to elastase. In some embodiments, one or more of the amino acids in the amino acid sequence is protected. In some embodiments, one or more of the amino acids in the amino acid sequence is protected with an fmoc group. In some embodiments, one of the amino acid in the amino acid sequence is protected with an fmoc group.

In some embodiments, the enzyme-labile or enzyme-reactive region comprises a peptide comprising an amino acid sequence of $X_yUUUU_y$-Z, wherein each X is independently any amino acid, each y is independently a number selected from 1 to 50, or each y is independently an integer from 1 to 10, or each y is independently an integer from 1 to 6, U represents an amino acid selected from arginine, lysine, glycine or alanine, and Z is a moiety capable of causing a visible color change or a detectable electronic change In some embodiments, the enzyme-labile or enzyme-reactive region comprises a peptide comprising an amino acid sequence of $X_yUUUUUU_y$-Z, wherein each X is independently any amino acid, each y is independently a number selected from 1 to 50, or each y is independently an integer from 1 to 10, or each y is independently an integer from 1 to 6, U represents an amino acid selected from LEVLFQ, and Z is a moiety capable of causing a visible color change or a detectable electronic change In some embodiments, the enzyme-labile or enzyme-reactive region comprises a peptide that is labile to cathepsin G.

In some embodiments, the enzyme-labile or enzyme-reactive region comprises a peptide comprising an amino acid sequence of $X_yN^4N^3N^2N^1X_y$-L-Z, wherein each X is independently any amino acid; each y is independently a number selected from 0 to 6; $N^4$ is selected from alanine, glycine, valine, and glutamine; $N^3$ is selected from alanine, glycine, proline, lysine, and serine: $N^2$ is selected from proline, alanine, and glycine; $N^1$ is selected from serine, lysine, phenylalanine, arginine, leucine, and methionine; L is a linking moiety, and Z is a moiety capable of causing a visible color change or a detectable electronic change; and the peptide is labile to cathepsin G. In some embodiments, one or more of the amino acids in the amino acid sequence is protected. In some embodiments, one or more of the amino acids in the amino acid sequence is protected with an fmoc group. In some embodiments, one of the amino acid in the amino acid sequence is protected with an fmoc group.

In some embodiments, the enzyme-labile or enzyme-reactive region comprises a peptide comprising an amino acid sequence of $X_yN^4N^3N^2N^1X_y$-Z, wherein each X is independently any amino acid; each y is independently a number selected from 0 to 6; $N^4$ is selected from alanine, glycine, valine, and glutamine; $N^3$ is selected from alanine, glycine, proline, lysine, and serine. $N^2$ is selected from proline, alanine, and glycine; $N^1$ is selected from serine, lysine, phenylalanine, arginine, leucine, and methionine; and Z is a moiety capable of causing a visible color change or a detectable electronic change; and the peptide is labile to cathepsin G. In some embodiments, one or more of the amino acids in the amino acid sequence is protected. In some embodiments, one or more of the amino acids in the amino acid sequence is protected with an fmoc group. In some embodiments, one of the amino acid in the amino acid sequence is protected with an fmoc group.

In some embodiments, Z is a peroxidase substrate, an arylamine, an amino phenol, an aminophenyl ether, an indoxyl, a neutral dye, a charged dye, a nanoparticle, or a colloidal gold particle. In some embodiments, Z is a peroxidase substrate. In some embodiments, the peroxidase substrate is selected from p-aminophenol, ABTS (2,2'-Azino-bis(3-ethylbenzothiazoline-6-sulfonic acid) diammonium salt), 3,3'-diaminobenzidine, DCPIP, N,N-dimethyl-p-phenylenediamine, o-dianisidine, p-phenylenediamine, 4-chloro-I-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), indoxyl, indigo, Fast Blue RR, 4-chloro-7-nitrobenzofurazan. In some embodiments, Z is an arylamine. In some embodiments, Z is an amino phenol. In some embodiments, Z is an aminophenol ether. In some embodiments, Z is an indoxyl. In some embodiments, Z is a neutral dye. In some embodiments, Z is a charged dye. In some embodiments, the charged dye is selected from remazole brilliant blue, toluidine blue, reactive black 5, remazol brilliant blue, reactive violet 5, and reactive orange 16, or a hydrolytic or ammonolytic derivatives thereof. In some embodiments, the charged dye is remazole brilliant blue, or a hydrolytic or ammonolytic derivatives thereof. In some embodiments, the charged dye is toluidine blue. In some embodiments, the charged dye is reactive black 5, or ahydrolytic or ammonolytic derivatives thereof. In some embodiments, the charged dye is reactive violet 5, or hydrolytic or ammonolytic derivatives thereof. In some embodiments, the charged dye is reactive orange 16, or hydrolytic or ammonolytic derivatives thereof.

In some embodiments, Z is a dichlorotriazine-based reactive dye such as reactive blue 4, reactive red 120, reactive blue 2, reactive green 19 and reactive brown 10. In some embodiments, the dichlorotriazine-based reactive dye appears black.

In some embodiments, Z is a reactive dye containing a sulfonylethyl-hydrogensulphate-reactive-group. In some embodiments, the reactive dye is reactive black 5, remazol brilliant blue, reactive violet 5 or reactive orange 16. In some embodiments, the reactive dye is reactive black 5. In some embodiments, the reactive dye is remazol brilliant blue. In some embodiments, the reactive dye is reactive violet 5. In some embodiments, the reactive dye is reactive orange 16. In some embodiments, the reactive dye is reactive black 5, remazol brilliant blue, or reactive violet 5. In some embodiments, the reactive dye is reactive black 5 or remazol brilliant blue.

In some embodiments, Z is a nanoparticle. In some embodiments, Z is a colloidal gold particle.

In some embodiments, Z is a charged dye, an indole derivative, or a luminol derivative. In some embodiments, Z is an indole derivative. In some embodiments, Z is a luminol derivative.

In some embodiments, the enzyme-labile or enzyme-reactive region reacts with lysozyme. In some embodiments, the enzyme-labile or enzyme-reactive region comprises peptidoglycan.

In some embodiments, the enzyme-labile or enzyme-reactive region is a beta lactam.

In some embodiments, the enzyme-labile or enzyme-reactive region comprises a phenol, an amino phenol, an aminophenyl ether, an indoxyl, or a quinone. In some embodiments, the enzyme-labile or enzyme-reactive region comprises a phenol. In some embodiments, the enzyme-labile or enzyme-reactive region comprises an amino phenol. In some embodiments, the enzyme-labile or enzyme-reactive region comprises an amino phenol ether. In some embodiments, the enzyme-label or enzyme-reactive region comprises an indoxyl. In some embodiments, the enzyme-labile or enzyme-reactive region comprises a quinone. In some embodiments, the enzyme-labile or enzyme-reactive region reacts with myeloperoxidase but does not react with heme.

In some embodiments, the enzyme-labile or enzyme-reactive region comprises a peroxidase substrate, an arylamine, an amino phenol, a neutral dye, a charged dye, a nanoparticle, or a colloidal gold particle. In some embodiments, the enzyme-labile or enzyme-reactive region comprises a peroxidase substrate. In some embodiments, the peroxidase substrate is selected from p-aminophenol, ABTS (2,2-Azino-bis(3-ethylbenzothiazoline-6-sulfonic acid) diammonium salt), 3,3'-diaminobenzidine, DCPIP, N,N-dimethyl-p-phenylenediamine, o-dianisidine, p-phenylenediamine, 4-chloro-1-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), and 4-chloro-7-nitrobenzofurazan, Fast Blue RR, N-(2-hydroxy)tetradecyl-Fast Blue RR. In some embodiments, the enzyme-labile or enzyme-reactive region comprises an arylamine. In some embodiments, the enzyme-labile or enzyme-reactive region comprises an amino phenol. In some embodiments, the enzyme-labile or enzyme-reactive region comprises a neutral dye. In some embodiments, the enzyme-labile or enzyme-reactive region comprises a charged dye. In some embodiments, the charged dye is selected from remazole brilliant blue, toluidine blue, reactive black 5, remazol brilliant blue, reactive violet 5, and reactive orange 16, or hydrolytic or ammonolytic derivatives of each of these. In some embodiments, the charged dye is remazole brilliant blue, or hydrolytic or ammonolytic derivatives thereof. In some embodiments, the charged dye is toluidine blue. In some embodiments, the charged dye is reactive black 5, or hydrolytic or ammonolytic derivatives thereof. In some embodiments, the charged dye is reactive violet 5, or hydrolytic or ammonolytic derivatives thereof. In some embodiments, the charged dye is reactive orange 16, or hydrolytic or ammonolytic derivatives thereof.

In some embodiments, the enzyme-labile or enzyme-reactive region comprises a dichlorotriazine-based reactive dye such as reactive blue 4, reactive red 120, reactive blue 2, reactive green 19 and reactive brown 10.

In some embodiments, the enzyme-labile or enzyme-reactive region comprises a nanoparticle. In some embodiments, Z is a colloidal gold particle.

In some embodiments, the enzyme-labile or enzyme-reactive region comprises a charged dye, an indole derivative, or a luminol derivative. In some embodiments, the enzyme-labile or enzyme-reactive region comprises an indole derivative. In some embodiments, the enzyme-labile or enzyme-reactive region comprises a luminol derivative.

In some embodiments, the indicator region comprises a dye that presents a visible color change in normal ambient lighting. In some embodiments, the dye has a contrasting color to wound products, which are commonly red, yellow, or brown. In further embodiments, the dye is violet, blue or dark green. In some embodiments, the dye is violet. In some embodiments, the dye is blue. In some embodiments, the dye is dark green. In some embodiments, the dye has low molecular weight, is charged, contains reactive or linkable groups, is stable to gamma irradiation, and is deeply colored. In some embodiments, the dye is selected from cibracron series dyes, azo dyes, and remazol dyes, or hydrolytic or ammonolytic derivatives thereof. In some embodiments, the dye is selected from cibracron series dyes. In some embodiments, the dye is selected from azo dyes. In some embodiments, the dye is selected from remazol dyes, or hydrolytic or ammonolytic derivatives thereof. In some embodiments, the dye is selected from rhodamine, coumarin, cyanine, xanthene, polymethine, pyrene, dipyrromethene borondifluoride, napthalimide, a phycobiliprotein, peridinium chlorophyll proteins, fluorescein, 6-FAM, rhodamine, Texas Red, California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®, Cy3.5®, Cy5®, Cy5.5®, Cy7®, CyChrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 630/650, BODIPY® 650/665, BODIPY® R6G, BODIPY® TMR, BODIPY® TR, and dimethylaminoazobenzenesulfonic acid (dabsyl), or conjugates thereof, or combinations thereof.

In some embodiments, the indicator region comprises a dichlorotriazine-based reactive dye such as reactive blue 4, reactive red 120, reactive blue 2, reactive green 19 and reactive brown 10. In some embodiments, the dichlorotriazine-based reactive dye appears black.

In some embodiments, the indicator region comprises the reaction product of a reactive dye containing a sulfonyl-ethyl-hydrogensulphate-reactive-group. In some embodiments, the reactive dye is reactive black 5, remazol brilliant blue, reactive violet 5 or reactive orange 16. In some embodiments, the reactive dye is reactive black 5. In some embodiments, the reactive dye is remazol brilliant blue. In some embodiments, the reactive dye is reactive violet 5. In some embodiments, the reactive dye is reactive orange 16. In some embodiments, the reactive dye is reactive black 5, remazol brilliant blue, or reactive violet 5. In some embodiments, the reactive dye is reactive black 5 or remazol brilliant blue.

In some embodiments, the indicator region comprises a particle (e.g., colloidal metal or quantum dots) that present color changes in normal ambient lighting. In some embodiments, the indicator region comprises a nanoparticle. In some embodiments, the indicator region comprises a colloidal gold particle.

In some embodiments, the indicator region comprises a dye that presents a visible color change under UV light. In some embodiments, the indicator region comprises a dye that is fluorescent. In some embodiments, the indicator region comprises a dye that is luminescent.

In some embodiments, the indicator region comprises an enzyme-reactive moiety. In some embodiments, the enzyme-reactive moiety interacts with an accessory enzyme to produce a product that is visible to the naked eye or detectable by electronic means. In some embodiments, the enzyme-reactive moiety interacts with an accessory enzyme to produce a product that is visible to the naked eye. In some embodiments, the enzyme-reactive moiety interacts with an accessory enzyme to produce a product that is detectable by electronic means. In some embodiments, the indicator region comprises an indoxyl glycoside or galactoside that is cleaved by glucuronidase, glucosidase or galactosidase depending on the terminal sugar used, to produce indigo. In some embodiments, the indicator region comprises a phenol or napthol that is oxidized by an accessory enzyme to produce a visible product. In some embodiments, the indicator region comprises a phenol that is oxidized by peroxidase to produce a visible product. In some embodiments, the indicator region comprises a metallo motif that is detectable by electronic means. In some embodiments, the indicator region comprises a ferrocene or ferrocene analog that is detectable by electronic means. In some embodiments, the accessory enzyme is selected from lipase, esterase, peroxidase, oxidase, glycosidase, and glucosidase. In some embodiments, the accessory enzyme is not present in the wound fluid. In some embodiments, the accessory enzyme is present in the wound fluid. In some embodiments, the enzyme-reactive moiety interacts with an accessory enzyme to produce a product that is visible under UV light.

In some embodiments, the chemical entity consists essentially of at least one anchor region, at least one enzyme-labile or enzyme-reactive region, and at least one indicator region. In some embodiments, the chemical entity consists essentially of at least one enzyme-labile or enzyme-reactive region, and at least one indicator region. In some embodiments, the chemical entity consists essentially of at least one anchor region and at least one enzyme-labile or enzyme-reactive region. In some embodiments, the chemical entity is capable of being bound to a support material without an anchor region.

In some embodiments, the chemical entity is printed on or in a support material such as filter paper or a woven or non-woven material that is capable of being wet by a wound fluid and which displays capillary action. In some embodiments, the reporting entity or chemical entity is chemically bonded onto or into a support material such as filter paper or a woven or non-woven material that is capable of being wet by a wound fluid and which displays capillary action that is similar in all dimensions. In some embodiments, the chemical entity is ionically bound onto or into a support material such as filter paper or a woven or non-woven material that is capable of being wet by a wound fluid and which displays capillary action. In some embodiments, the chemical entity is covalently bound onto or into a support material such as filter paper or a woven or non-woven material that is capable of being wet by a wound fluid and which displays capillary action. Support material includes, but is not limited to, cellulose, polyamide, polyester, polyacrylate and other similar polymers that are useful as fibers. In some embodiments, the support material is cellulose. In some embodiments, the support material is polyamide. In some embodiments, the support material is polyester. In some embodiments, the support material is polyacrylate.

In some instances, the pH of a wound can influence many factors of wound healing, such as angiogenesis, protease activity, oxygen release, and bacterial toxicity. Chronic nonhealing wounds may have an elevated alkaline environment. As the wound progresses towards healing, the pH of the wound moves to neutral and then becomes acidic. Monitoring of the pH of the wound may provide a method to assess the condition of the wound (e.g., infection or no infection) and aid in determining a wound's response to treatment.

In some embodiments, the pH-sensitive moiety is bromothymol blue, phenol red, bromophenol red, chlorophenol red, thymol blue, bromocresol green, bromocresol purple; or other sulfophthalein dyes.

In some embodiments, the MPO responsive indicator incorporates an alkyl aniline amide with a molecular weight greater than 459 Da. In preferred embodiments, this indicator has the following structure:

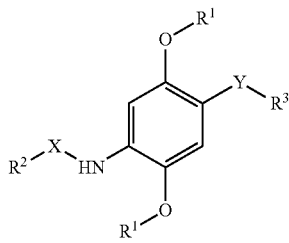

Wherein,
$R^1$ =—CH$_3$, —CH$_2$CH$_3$; —CH$_2$CH$_2$CH$_2$CH$_3$
X=—C(=O)—, —S(=O)$_2$—
$R^2$= can be but is not limited to:
-C$_1$-C$_{10}$ alkyl, alkenyl, alkynyl, aryl, heteroaryl, alkylaryl, alkylheteroaryl
wherein alkyl, alkenyl, alkynyl, aryl, heteroaryl, alkylaryl and alkylheteroaryl groups are optionally substituted by one to five substituents selected independently from: ferrocene, halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, —NR$^4$R$^5$, R$^4$C(=O)—, R$^4$C(=O)O—, R$^4$OC(=O)O—, R$^4$ HC(=O)—, R$^4$C(=O) H—, R$^4$R$^5$NC(=O)—, R$^4$OC(=O)—

$R^4$ and $R^5$ can independently be, but are not limited to:
—(C$_1$-C$_{12}$)alkyl
—(C$_1$-C$_{12}$)alkenyl
—(C$_1$-C$_{12}$)akynyl
—(C$_1$-C$_5$)[(C$_1$-C$_4$)alkoxy]alkyl
—(C$_1$-C$_5$)[(C$_1$-C$_4$)alkoxy]alkenyl
—(C$_6$-C$_{10}$)aryl-(C$_1$-C$_5$)alkyl
—(C$_2$-C$_9$)heteroaiyl-(C$_1$-C$_5$)alkyl
wherein alkyl, alkenyl, alkynyl, aryl and heteroaryl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy,
or N(R$^4$R$^5$) is an aziridine, azetidine, pyrrolidine, piped dine, azepane or azocane, 1-substituted piperazine, or morpholine moiety
Y=—NH—CH2-CH(OH)—, —NH—, —NH—C(=O)—NH—, —NH—C(=S)—NH—
$R^3$ can be but is not limited to:
—C$_6$-C$_{30}$ alkyl, alkenyl, alkynyl, aryl, heteroaryl, alkylaryl, alkylheteroaryl
wherein alkyl, alkenyl, alkynyl, aryl, heteroaryl, alkylaryl and alkylheteroaryl groups are optionally substituted by one to five substituents selected independently from: ferrocene, halogen (as can be F, Cl, Br, I), (C$_1$-C$_4$)alkyl, (C$_1$-C$_4$) alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, cyano (—CN), azido (—N$_3$), —NR$^4$R$^5$, R$^4$C(=O)—, R$^4$C(=O)O—, R$^4$OC(=O)O—, R$^4$NHC(=O)—, R$^4$C(=O)H—, R$^4$R$^5$NC(=O)—, R$^4$OC(=O)—

In some embodiments, it is desired that the indicator substrates stay in place and react in place. Thus, limited solubility in aqueous systems is preferred. The ability to stay in place on a solid phase is defined as the water resistance and the means by which it is measured is recorded in example 114. In preferred embodiments, the water resistance of a substrate is greater than one, and in still more preferred embodiments, it is greater than 2.

In some embodiments, disclosed herein are compounds of the following formula (Formula D):

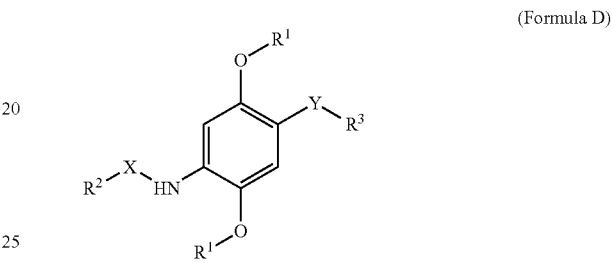

(Formula D)

wherein,
$R^1$=—CH$_3$, —CH$_2$CH$_3$; —CH$_2$CH$_2$CH$_2$CH$_3$
X=—C(=O)—, —S(=O)$_2$—
$R^2$= can be but is not limited to: —C$_1$-C$_{10}$ alkyl, alkenyl, alkynyl, aryl, heteroaryl, alkylaryl, alkylheteroaryl wherein alkyl, alkenyl, alkynyl, aryl, heteroaryl, alkylaryl and alkylheteroaryl groups are optionally substituted by one to five substituents selected independently from: ferrocene, halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, —NR$^4$R$^5$, R$^4$C(=O)—, R$^4$C(=O)O—, R$^4$OC(=O)O—, R$^4$NHC(=O)—, R$^4$C(=O)NH—, R$^4$R$^5$NC(=O)—, R$^4$OC(=O)—

$R^4$ and $R^5$ can independently be, but are not limited to:
—(C$_1$-C$_{12}$)alkyl —(C$_1$-C$_{12}$)alkenyl —(C$_1$-C$_{12}$)akynyl
—(C$_1$-C$_8$)[(C$_1$-C$_4$)alkoxy]alkyl —(C$_1$-C$_8$)[(C$_1$-C$_4$)alkoxy]alkenyl —(C$_6$-C$_{10}$)aryl-(C$_1$-C$_5$)alkyl —(C$_2$-C$_9$)heteroaryl-(C$_1$-C$_5$)alkyl; wherein alkyl, alkenyl, alkynyl, aryl and heteroaryl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, or N(R$^4$R$^5$) is an aziridine, azetidine, pyrrolidine, piped dine, azepane or azocane, 1-substituted piperazine, or morpholine moiety;
Y=—NH—CH2-CH(OH)—, —NH—, —NH—C(=O)—NH—, —NH—C(=S)—NH—
$R^3$ can be but is not limited to: —C$_6$-C$_{30}$ alkyl, alkenyl, alkynyl, aryl, heteroaryl, alkylaryl, alkylheteroaryl, wherein alkyl, alkenyl, alkynyl, aryl, heteroaryl, alkylaryl and alkylheteroaryl groups are optionally substituted by one to five substituents selected independently from: ferrocene, halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, cyano (—CN), azido (—N$_3$), —R$^4$R$^5$, R$^4$C(=O)—, R$^4$C(=O)O—, R$^4$OC(=O)O—, R$^4$ HC(=O)—, R$^4$C(=O) H—, R$^4$R$^5$NC(=O)—, R$^4$OC(=O)—.

In some embodiments, disclosed herein are compounds of the following formula (Formula A)

$$\text{(Formula A)}$$

PG—HN—X-φ-ε-δ-γ-β-α—C(=O)—Y—Ar wherein
Y is O, or N
Ar is

[structures of substituted indoles: indol-3-yl; 5-bromoindol-3-yl; 6-chloro-5-bromoindol-3-yl; 5-chloroindol-3-yl; 6-chloroindol-3-yl; 7-bromo-5-bromoindol-3-yl; 4-chloro-5-bromoindol-3-yl; substituted phenyl (R); substituted naphthyl (R); substituted naphthyl (R); substituted quinolinyl (R); substituted isoquinolinyl (R)]

or ferrocene;
R is a —$C_1$-$C_{10}$ alkyl, alkenyl, alkynyl, aryl, heteroaryl, alkylaryl, or alkylheteroaryl;
α is A, V, F, G, M, R, or L;
β is a bond, or independently, P, F, A, R, L, or G;
γ is a bond, or independently, P, A, R, L, or G;
δ is a bond, or independently, P, A, R, L, G, or V;
ε is a bond, or independently, P, A, R, L, G, V, or E;
φ is a bond, or independently, P, A, R, L, or G;
wherein, if β, γ, δ, ε, and φ, are each bonds, then the N-terminal of α is bonded to X;

X is a peptide chain comprising from 0 to 14 amino acids;
PG is —C(=O)—O—$R^1$ wherein $R^1$ is $C_1$-$C_{30}$ alkyl, t-butyl, or methylfluorenyl, or —C(=O)—$R^2$ wherein $R^2$ is —$C_1$-$C_{30}$ alkyl, alkenyl, alkynyl, aryl, heteroaryl, alkylaryl, or alkylheteroaryl.

In some embodiments, disclosed herein are compounds of the following formula (Formula B)

$$\text{(Formula B)}$$

PG—HN—X-φ-ε-δ-γ-β-α—C(=O)—L—Z wherein
L is A, AA, V, or triazolyl,
Z is ferrocene, crystal violet, malachite green, toluidine blue, reactive black 5, remazol brilliant blue, reactive violet 5, and reactive orange 16, reactive blue 4, reactive red 120, reactive blue 2, reactive green 19, or reactive brown 10
α is selected from: A, V, F, G, M, R, or L
β is a bond, or independently, P, F, A, R, L, or G
γ is a bond, or independently, P, A, R, L, or G
δ is a bond, or independently, P, A, R, L, G, or V
ε is a bond, or independently, P, A, R, L, G, V, or E
φ is a bond, or independently, P, A, R, L, or G,
wherein, if β, γ, δ, ε, and φ, are each bonds, then the N-terminal of α is bonded to X;
X is a peptide chain comprising from 0 to 14 AA, wherein AA is an amino acid, a polyamine, or a polyoxyalkylene;
PG is polystyrene bead, silica gel bead, polysaccharide bead, polyacrylamide bead, cellulose bead, polysaccharide, derivatized cellulose, polyacrylate, polyethyleneimine, polyacrylamide, UV-activatable group, phenolic azide, epoxide, peptidoglycan, an aliphatic chain, an aliphatic alcohol chain, an aliphatic amine, mercaptoethyl, a multi-cyclic or multi-aromatic ring system, a lipophilic group, or a combination thereof, —C(=O)—O—$R^1$ wherein $R^1$ is $C_1$-$C_{30}$ alkyl, t-butyl, methylfluorenyl, —C(=O)—$R^2$ wherein $R^2$ is —$C_1$-$C_{ao}$ alkyl, alkenyl, alkynyl, aryl, heteroaryl, alkylaryl, or alkylheteroaryl.

In general, the elastase substrates have the formula a-b-c-d-e-f, wherein
In one embodiment,
a is selected from: A, V, F, G, M, R, L
b is selected from: no amino acid, or independently, P, F, A, R, L, G
g is selected from: no amino acid, or independently, P, A, R, L, G
d is selected from: no amino acid, or independently, P, A, R, L, G, V
e is selected from: no amino acid, or independently, P, A, R, L, G, V, E
f is selected from: no amino acid, or independently, P, A, R, L, G.

In another embodiment, elastase substrates have the formula a-b-c-d-e-f, wherein
a is selected from: A, V, F, G, M, R, L
b is selected from: no amino acid, or independently, P, F, A, G
g is selected from: no amino acid, or independently, P, A, R, L, G
d is selected from: no amino acid, or independently, P, A, R, L, G, V e is selected from: no amino acid, or independently, P, A, G, V, E f is selected from: no amino acid, or independently, P, A, G.

In another embodiment, elastase substrates have the formula a-b-c-d-e-f, wherein a is selected from: A, V, F, G, M, R, L b is selected from: no amino acid, or independently, P, F, A, G g is selected from: no amino acid, or independently, P, A, L, G d is selected from: no amino acid, or independently, P, A, L, G, V e is selected from: no amino acid, or independently, P, A, G, V, E f is selected from: no amino acid, or independently, P, A, G.

In another embodiment, elastase substrates have the formula a-b-c-d-e-f, wherein a is selected from: A, V, F, G b is selected from: no amino acid, or independently, P, F, A, G g is selected from: no amino acid, or independently, P, A, G d is selected from: no amino acid, or independently, P, A, G, e is selected from: no amino acid, or independently, A, G, V, f is selected from: no amino acid, or independently, A, G.

Especially, in another embodiment, elastase substrates have the formula a-b-c-d-e-f, wherein a is selected from: A, V, F b is selected from: no amino acid, or independently, P, F, A, g is selected from: no amino acid, or independently, A, G d is selected from: no amino acid, or independently, A, G, e is selected from: no amino acid, or independently, A, G, f is selected from: no amino acid, or independently, A, G.

Preferably, elastase substrates have the formula a-b-c-d-e-f, wherein a is selected from: A, V, F b is selected from: no amino acid, or independently, P, F, A, g is selected from: no amino acid, or independently, A, d is selected from: no amino acid, or independently, A, e is selected from: no amino acid, or independently, A, f is selected from: no amino acid, or independently, A.

DESCRIPTION OF THE FIGURES

FIG. 6: Esterase and lipase substrates containing an indoxyl chromophore.

FIG. 7C: Esterase substrates containing an indoxyl chromophore coupled to Peptidoglycan, chitosan or a peptide via the Suzuki product of example 103.

FIG. 8: A scheme for the carboxymethylation of peptidoglycan and subsequent derivatisation.

FIG. 9A: A tube containing an indicator substrate for use in detecting infection in tissues or body fluids emanating from an organ of interest (airway, blood, urine etc.). The tube is a PVC material into which a nonwoven printed with the substrate from example 18 has been inserted.

FIG. 9B: A tubing insert designed to accommodate a flat filter paper series containing one or more substrates such as those from examples 10 or 18 with that of example 95 serving as a positive control (center).

FIG. 9C: Tubing containing a polyolefin inner cylinder serving as the carrier for the substrate of example 11. This material serves as the lining in the hollow cylinder (right).

FIG. 9D: Adaptation of the hollow lining to the PVC tubing in exemplary form.

FIG. 13: An example of the reaction product of MPO and the product of example 10 and Fast Blue RR.

DETAILED DESCRIPTION

Figure 1:
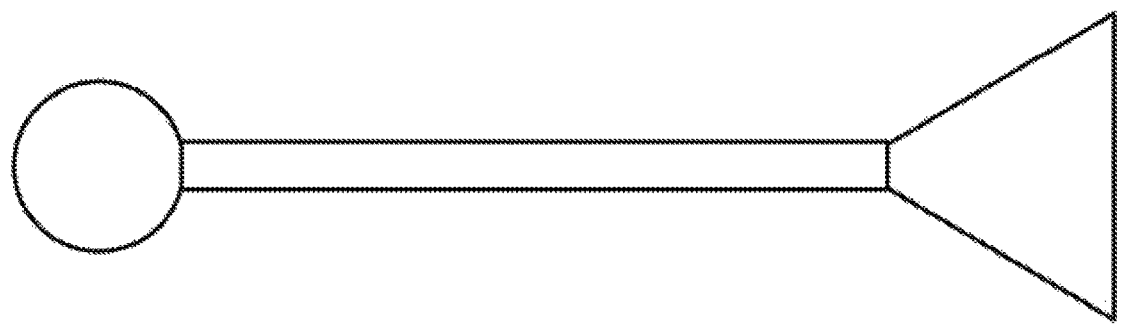
FIG. 1: Exemplary embodiment of compounds disclosed herein.
Figure 2:
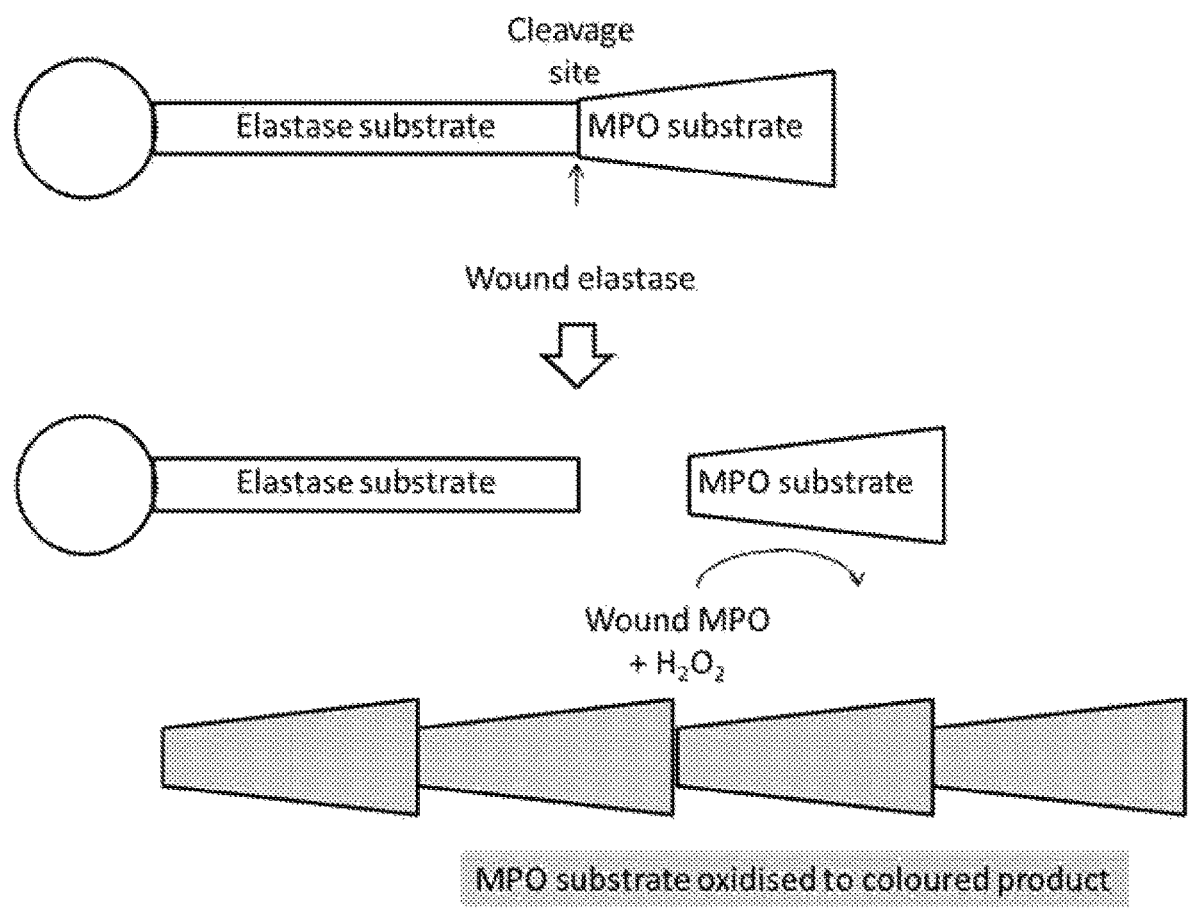
FIG. 2: Exemplary embodiment of compounds disclosed herein with multiple reaction requirement toward MPO and elastase (e.g. example 9, Methyl-3-Fmoc-AAPV-amide-4-aminophenol or Methyl-3-amino-4-Fmoc-AAPV-amidebenzoate) [SEQ ID NO: 2].
Figure 3A:
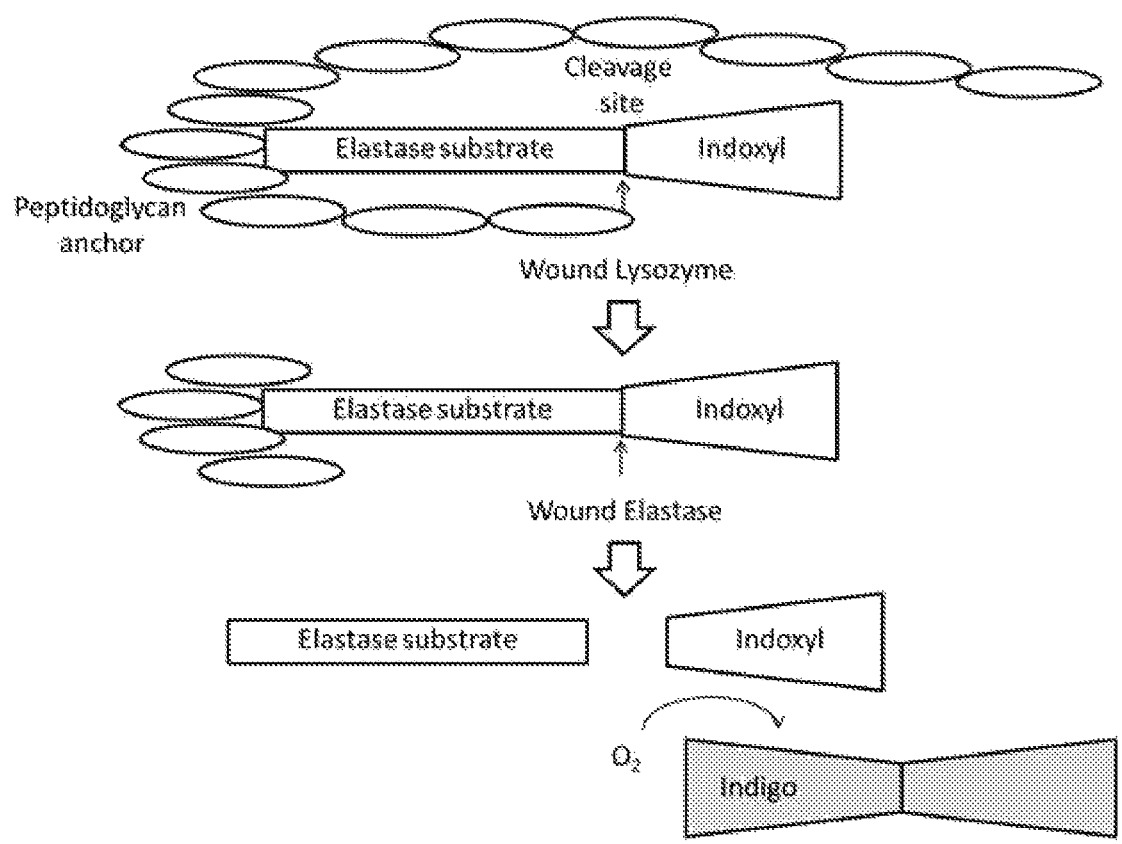
FIG. 3A: Exemplary embodiment of compounds disclosed herein with multiple reaction requirement toward elastase.
Figure 3B:
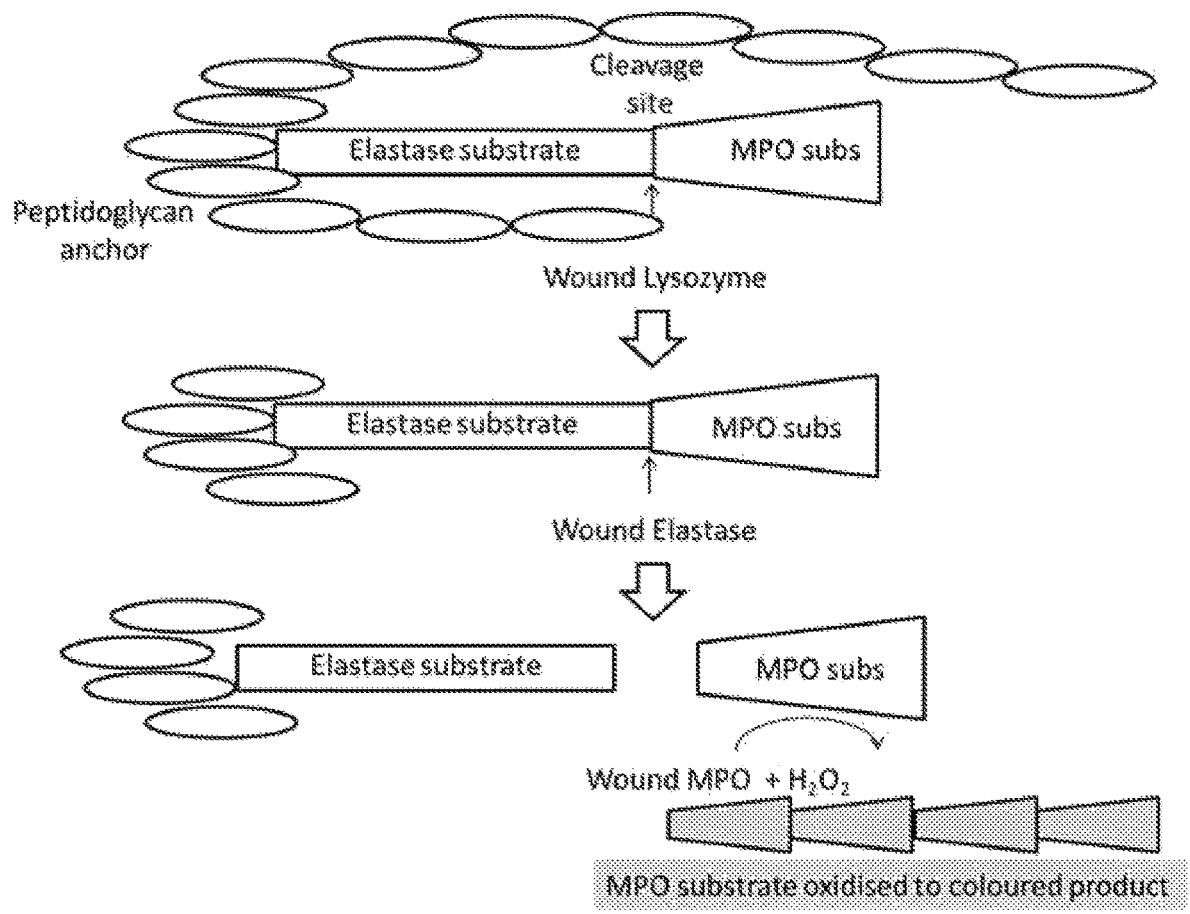
FIG. 3B: Exemplary embodiment of compounds disclosed herein with multiple reaction requirement toward elastase.
Figure 4A:
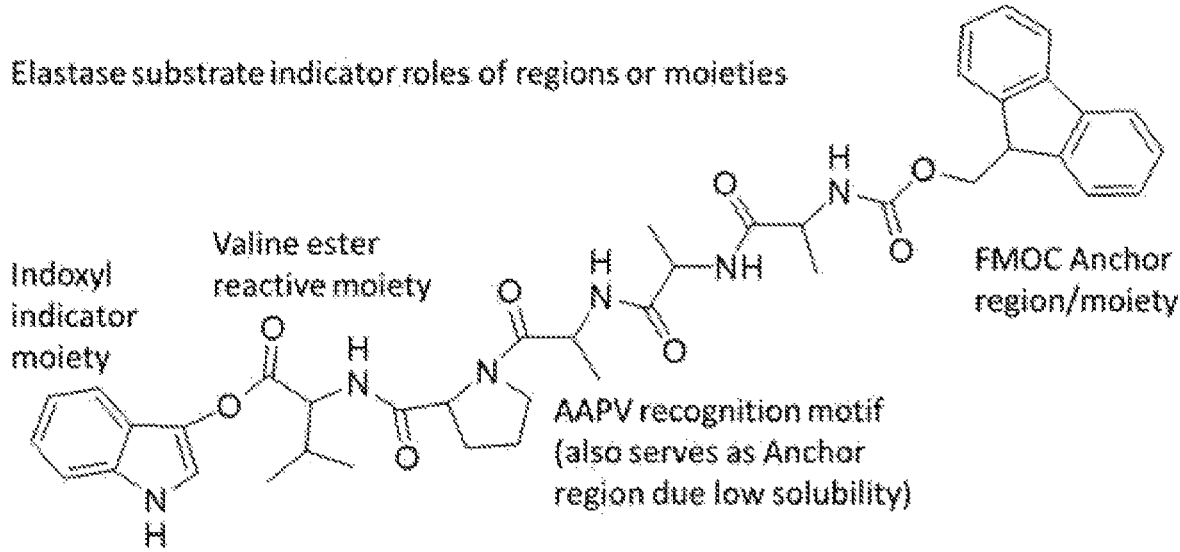
FIG. 4A: Exemplary embodiment of compounds disclosed herein with reaction toward elastase in which overlapping function for the anchor is shown for an elastase substrate.
Figure 4B:
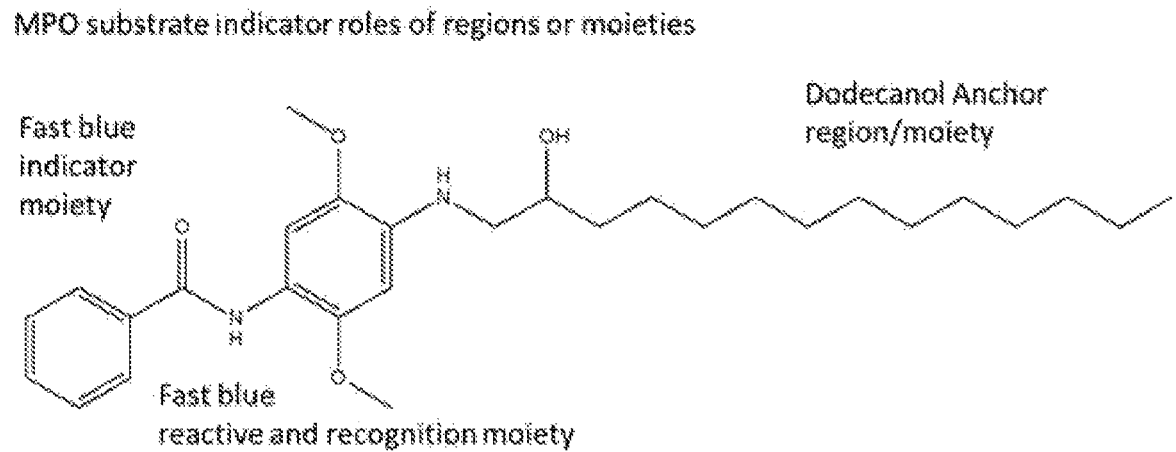
FIG. 4B: Exemplary embodiment of compounds disclosed herein with reaction toward MPO in which overlapping function for an indicator and reactive region is shown for an MPO substrate.
Figure 5:
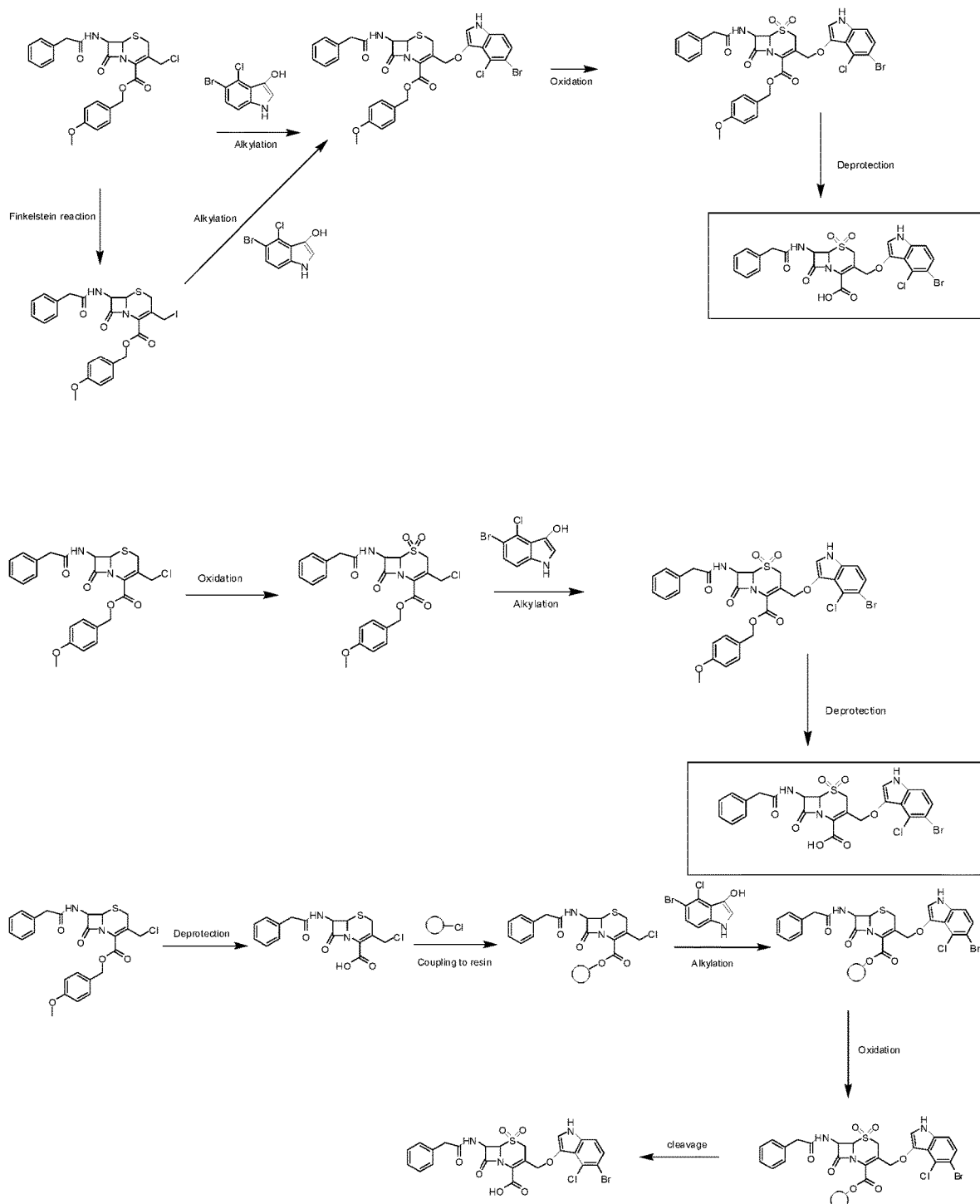
FIG. 5: Synthetic routes toward p-lactamase substrates containing an indoxyl ether.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any

I. Definitions

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

"Substantially" or "essentially" means nearly totally or completely, for instance, 80%-95% or greater of some given quantity, e.g., at least 85%, at least 87%, at least 88%, at least 89%, at least 90%, at least 91%, at least 92%, at least 93%, at least 94%, at least 95%, at least 96%, at least 97%, at least 98%, at least 99%, at least 99.9%, or more % by weight or volume or any other parameter being measured. "Substantially free" means nearly totally or completely absent of some given quantity such as being present at a level of less than about 1% to about 20% of some given quantity, e.g., less than 10%, less than 9%, less than 8%, less than 7%), less than 6%, less than 5%, less than 4%, less than 3%, less than 2%, less than 1%, less than 0.5%), less than 0.1%, or less % by weight or volume or any other parameter being measured. In some embodiments, "substantially free" means presence at a level of less than or equal to 1-5% by weight of the pharmaceutical composition.

II. Overview

Provided herein are compositions and systems for the therapy and diagnosis of wounds and wound management, wherein the compositions, when in use, indicate the presence of elevated enzyme levels in a wound in situ.

As used herein, a "wound" refers to physical disruption of the continuity or integrity of tissue structure. "Wound healing" refers to the restoration of tissue integrity. It will be understood that this can refer to a partial or a full restoration of tissue integrity. Treatment of a wound thus refers to the promotion, improvement, progression, acceleration, or otherwise advancement of one or more stages or processes associated with the wound healing process.

The wound may be acute or chronic. Chronic wounds, including pressure sores, venous leg ulcers and diabetic foot ulcers, can simply be described as wounds that fail to heal. Whilst the exact molecular pathogenesis of chronic wounds is not fully understood, it is acknowledged to be multifactorial. As the normal responses of resident and migratory cells during acute injury become impaired, these wounds are characterized by a prolonged inflammatory response, defective wound extracellular matrix (ECM) remodeling and a failure of re-epithelialization.

The wound may be any internal wound, e.g., where the external structural integrity of the skin is maintained, such as in bruising or internal ulceration, or external wounds, particularly cutaneous wounds, and consequently the tissue may be any internal or external bodily tissue. In one embodiment the tissue is skin (such as human skin), i.e. the wound is a cutaneous wound, such as a dermal or epidermal wound.

The human skin is composed of two distinct layers, the epidermis and the dermis, below which lies the subcutaneous tissue. The primary functions of the skin are to provide protection to the internal organs and tissues from external trauma and pathogenic infection, sensation and thermoregulation. The skin tissue of most mammals is structured similarly.

The outermost layer of skin, the epidermis, is approximately 0.04 mm thick, is avascular, is comprised of four cell types (keratinocytes, melanocytes, Langerhans cells, and Merkel cells), and is stratified into several epithelial cell layers. The inner-most epithelial layer of the epidermis is the basement membrane, which is in direct contact with, and anchors the epidermis to, the dermis. All epithelial cell division occurring in skin takes place at the basement membrane. After cell division, the epithelial cells migrate towards the outer surface of the epidermis. During this migration, the cells undergo a process known as keratinization, whereby nuclei are lost and the cells are transformed into tough, flat, resistant non-living cells. Migration is completed when the cells reach the outermost epidermal structure, the stratum corneum, a dry, waterproof squamous cell layer which helps to prevent desiccation of the underlying tissue. This layer of dead epithelial cells is continuously being sloughed off and replaced by keratinized cells moving to the surface from the basement membrane. Because the epidermal epithelium is avascular, the basement membrane is dependent upon the dermis for its nutrient supply.

The dermis is a highly vascularized tissue layer supplying nutrients to the epidermis. In addition, the dermis contains nerve endings, lymphatics, collagen protein, and connective tissue. The dermis is approximately 0.5 mm thick and is composed predominantly of fibroblasts and macrophages. These cell types are largely responsible for the production and maintenance of collagen, the protein found in all animal connective tissue, including the skin. Collagen is primarily responsible for the skin's resilient, elastic nature. The subcutaneous tissue, found beneath the collagen-rich dermis, provides for skin mobility, insulation, calorie storage, and blood to the tissues above it.

Wounds can be classified in one of two general categories, partial thickness wounds or full thickness wounds. A partial thickness wound is limited to the epidermis and superficial dermis with no damage to the dermal blood vessels. A full thickness wound involves disruption of the dermis and extends to deeper tissue layers, involving disruption of the dermal blood vessels. The healing of the partial thickness wound occurs by simple regeneration of epithelial tissue. Wound healing in full thickness wounds is more complex. Cutaneous wounds contemplated herein may be either partial thickness or full thickness wounds.

Wounds contemplated herein include cuts and lacerations, surgical incisions or wounds, punctures, grazes, scratches, compression wounds, abrasions, friction wounds (e.g., nappy rash, friction blisters), decubitus ulcers (e.g., pressure or bed sores); thermal effect wounds (burns from cold and heat sources, either directly or through conduction, convection, or radiation, and electrical sources), chemical wounds (e.g. acid or alkali burns) or pathogenic infections (e.g., viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g., psoriasis and eczema, stomach or intestinal ulcers, oral wounds, including a ulcers of the mouth, damaged cartilage or bone, amputation wounds and corneal lesions.

Chemical Entities and Compositions Thereof

Embodiments described herein provide chemical entities, which may be used to diagnose and/or treat chronic wounds. The chemical entities and compositions thereof, as described herein, are used in methods to detect the level of one or more enzymes in a mammalian wound. In some embodiments, the chemical entities and compositions thereof, as described herein, are used in methods to diagnose a chronic wound in a mammal. In some embodiments, the chemical entities and compositions thereof described herein are used in methods to diagnose an infected wound in a mammal. In other embodiments, the chemical entities and compositions thereof described herein are used in methods to treat a wound in a mammal. In further embodiments, the chemical entities and compositions thereof described herein are used in methods to treat an infected or a chronic wound in a mammal.

In other embodiments, the chemical entities and compositions thereof described herein may be used to diagnose one or more pathogenic microorganisms, e.g., bacteria or viruses, based on the detection of one or more biomarkers that are specific for the microorganisms.

In one embodiment, provided herein is a chemical entity capable of detecting enzyme activity from a body fluid, the chemical entity comprising: an anchor region (A); an enzyme-recognition site (R) and an indicator region (I). Under this embodiment, the chemical entity has a basic chemical structure A-R-I (Formula I), wherein A is an anchor region; R is an enzyme recognition site and I is an indicator region.

In some embodiments, the anchor region (A) is associated with the indicator region (I) via an enzyme recognition site (R). Under this embodiment, the enzyme recognition site is a structure or a motif that allows binding to an enzyme.

In one embodiment, the enzyme recognition site (R) is naturally present in the anchor region. Cleavage of the backbone of the anchor region by enzymes results in the mobilisation of fragments, which in turn may become substrates for the enzyme.

In another embodiment, the enzyme recognition site (R) is introduced in the anchor region (A) via chemical modification. Alternately, the enzyme recognition site (R) may be naturally present in the indicator region (I) or synthetically introduced in the indicator region (I) via one or more chemical modifications.

In one embodiment, the chemical entity of Formula I comprises an anchor (A) which is associated with the indicator (I), either covalently or non-covalently, in which case, the recognition site (R) may be located in the associating moiety (e.g., via a covalent bond). As is understood in the art, covalent bonds involve sharing of electrons between the bonded atoms. In contrast, non-covalent bonds may include, for example, ionic interactions, electrostatic interactions, hydrogen bonding interactions, physiochemical interactions, van der Waal forces, Lewis-acid/Lewis-base interactions, or combinations thereof.

In one embodiment, the anchor A is associated with the indicator I via a covalent interaction to form the recognition site R. In another embodiment, the anchor A is associated with the indicator I via a covalent interaction that is not a part of the recognition site R. Under the second embodiment, the R may wholly constitute a part of the indicator molecule or constitute a separate motif or moiety to which the indicator region is associated.

In some embodiments, the chemical entity further comprises an enzyme-labile or enzyme-reactive region.

In one embodiment, the recognition site (R) interacts with one or more target enzymes selected from the group consisting of selected from lipase, esterase, peroxidase, oxidase, glycosidase, glucuronidase, glucosidase, galactosidase, and a combination thereof. In some embodiments, the enzyme-labile or enzyme-reactive region interacts with one or more target enzymes selected from Napsin (aspartyl protease), Glucosylceramidase glucuronidase, palmitoyl protein thioesterase, Cathepsins A, B, D, G, L, S, Z; acid ceramidase, lactoferrin (LF), lysozyme, myeloperoxidase (MPO), elastase, cathepsins, and proteinase-3 elastase, lysozyme, esterase, lipase and a combination thereof.

Anchor Region (A)

In some embodiments of the chemical entity of Formula I, the anchor region comprises a compound which is a polysaccharide, a cellulose, a polyacrylate, a polyethyleneimine, a polyacrylamide, a peptidoglycan, or a chitosan, or a monomer thereof, an oligomer thereof, a derivative thereof, a mixture or a combination thereof.

In one embodiment, the anchor A comprises a polysaccharide selected from hydroxypropyl methylcellulose (UPMC), hydroxyethyl cellulose, hydroxymethyl cellulose, D-galactopyranoside, or a derivative thereof.

In one embodiment, the anchor A comprises peptidoglycan or a monomer thereof, an oligomer thereof, a derivative thereof, a mixture or a combination thereof. As is understood in the art, peptidoglycan, also known as murein, is a polymer consisting of sugars and amino acids that forms a mesh-like layer outside the plasma membrane of most bacteria, forming the cell wall, e.g., of a bacterium. The sugar component consists of alternating residues of $\beta$-(1,4) linked N-acetylglucosamine and N-acetylmuramic acid. Attached to the N-acetylmuramic acid is a peptide chain of three to five amino acids. The peptide chain can be cross-linked to the peptide chain of another strand forming the 3D mesh-like layer.

Accordingly, in one embodiment, the peptidoglycan may comprise at least 2, at least 3, at least 4, at least 5, or more units of alternating amino sugars selected from N-acetylglucosamine (GlcNAc or NAG) and N-acetylmuramic acid (MurNAc or NAM) or a combination thereof. Peptidoglycan, including, shorter fragments thereof, may be generated from natural or synthetic sources. See, Lee et al., *Chembiochem.*, 11(18):2525-9, 2010.

In another embodiment, the anchor A comprises a peptidoglycan or a polysaccharide derivative. Example peptidoglycan include peptidoglycan salts, water-soluble peptidoglycan, carboxylated peptidoglycan, etc. Representative examples of such derivatives include, e.g., peptidoglycans containing carboxymethyl, carboxyethyl, carboxypropyl group(s), optionally comprising one or more halogen, alcohol, ester or amide groups. Other particular examples include, halogenated peptidoglycans comprising one or more chlorine groups. Soluble peptidoglycans and fractions containing soluble fragments of peptidoglycans originating from the bacterium or bacterial wall of Nocardiae have been described in U.S. Pat. No. 5,017,359.

Polysaccharide derivatives include, e.g., hydroxyethyl cellulose (HEC), hydroxypropyl cellulose (HPC), ethyl hydroxyethyl cellulose (EHEC), carboxymethyl cellulose, carboxymethyl hydroxyethyl cellulose (CMHEC), hydroxypropyl hydroxyethyl cellulose (HPHEC), methyl cellulose (MC), methyl hydroxypropyl cellulose (MHPC), methyl hydroxyethyl cellulose (MHEC), carboxymethyl cellulose (CMC), hydroxypropyl methylcellulose acetate succinate (HPMC-AS), hydrophobically modified hydroxyethyl cellulose (hmHEC), hydrophobically modified hydroxypropyl cellulose (hmHPC), hydrophobically modified ethyl hydroxyethyl cellulose (hmEHEC), hydrophobically modified carboxymethyl hydroxyethyl cellulose (hmCMHEC), hydrophobically modified hydroxypropyl hydroxyethyl cellulose (hmHPHEC), hydrophobically modified methyl cellulose (hmMC), hydrophobically modified methyl hydroxypropyl cellulose (hmMHPC), hydrophobically modified methyl hydroxyethyl cellulose (hmMHEC), hydrophobically modified carboxymethyl methyl cellulose (hmCMMC), sulfoethyl cellulose (SEC), hydroxyethyl sulfoethyl cellulose (HESEC), hydroxypropyl sulfoethyl cellulose (HPSEC), methyl hydroxyethyl sulfoethylcellulose (MHESEC), methyl hydroxypropyl sulfoethyl cellulose (MHPSEC), hydroxyethyl hydroxypropyl sulfoethyl cellulose (HEHPSEC), carboxymethyl sulfoethyl cellulose (CM-SEC), hydrophobically modified sulfoethyl cellulose (hmSEC), hydrophobically modified hydroxyethyl sulfoethyl cellulose (hmHESEC), hydrophobically modified hydroxypropyl sulfoethyl cellulose (hmHPSEC) or hydrophobically modified hydroxyethyl hydroxypropyl sulfoethyl cellulose (hmHEHPSEC). Particularly preferred cellulose derivatives are cellulose ethers having a thermal flocculation point in water, such as, for example, methyl cellulose, methyl hydroxyethyl cellulose, methyl hydroxypropyl cellulose and hydroxypropyl cellulose. See, U.S. Pat. No. 8,465,586.

In one embodiment, "peptidoglycan derivative" and "polysaccharide derivative" as used herein includes salts, amides, esters, enol ethers, enol esters, acetals, ketals, orthoesters, hemiacetals, hemiketals, acids, bases, solvates, hydrates or prodrugs of the peptidoglycan or polysaccharide. Such derivatives may be readily prepared by those of skill in this art using known methods for such derivatization. In certain embodiments, the derivatives may be administered to animals or humans without substantial toxic effects and either are pharmaceutically active or are prodrugs.

In another embodiment, the derivative is a salt of the peptidoglycan or polysaccharide compound, e.g., salts of Li, Na, K, Rb, Mg, Ca, Sr, or Ba, preferably $Na^+$, $K^+$, $Mg^{2+}$, $Ca^{2+}$. Salts of charged peptidoglycan or polysaccharides, such as sodium or calcium salts, are included by this definition.

In some embodiments, the derivative anchor compound is a halogenated anchor compound, e.g., halogenated polysaccharide, halogenated peptidoglycan, halogenated polyacrylate, halogenated polyethyleneimine, halogenated polyacrylamide, halogenated peptidoglycan, or halogenated chitosan, or a monomer thereof, e.g., halogenated N-acetylglucosamine (GlcNAc or NAG) and/or halogenated N-acetylmuramic acid (MurNAc or NAM). The halogen is selected from the group consisting of Cl, Br, I; particularly, the halogen is Cl.

In some embodiments, the derivative compound is an isomer of the anchor compound, term "isomer" includes compounds with the same formula but a different arrangement of atoms in the molecule. In embodiments, isomers of the compounds are "tautomers" or "stereoisomers" of the compounds. The term "stereoisomer" refers to compounds that differ in the chirality of one or more stereocenters. Stereoisomers include enantiomers and diastereomers. The term "tautomer" refers to alternate forms of a compound that differ in the position of a proton, such as enol-keto and imine-enamine tautomers, or the tautomeric forms of the anchor compound.

In some embodiments, the anchor compound may contain a combination or mixture of one or more of the aforementioned compounds. The term "combination" includes compounds containing more than one component, which may be conjugated or non-conjugated to one another. In one embodiment, the anchor compound comprises a combination of one or more of the aforementioned compounds which are conjugated to each other, e.g., via covalent or non-covalent interaction. As a particular example, the anchor may comprise a combination of chitosan and peptidoglycan. See, U.S. Patent Application Publication No. 2007/0167400. In another embodiment, the mixture may comprise commercially available preparation of peptidoglycan and polysaccharide mixture (PG/PS; Lee Labs Inc., Grayson, G A; see, U.S. Pat. No. 8,129,518).

In some embodiments, the compounds include mixtures of the aforementioned polymeric compounds. The term "mixture" refers to a mingling together of two or more substances without the occurrence of a reaction by which they would lose their individual properties. For instance, a mixture of compound A and compound B may contain any weight ratio of compound A and compound B, such that the total weight of the mixture would amount to 100%, e.g., 99:1 weight ratio of compound A/compound B or 1:99 weight ratio of compound A/compound B. A typical mixture may contain about 2, 3, 4, 5, or more of the aforementioned polymer compounds.

In some embodiments, the anchor A further comprises an ionic chemical group, a material with a hydrophilic moiety, or a material with a hydrophobic moiety, e.g., an aliphatic chain or an aliphatic alcohol. In embodiments wherein the anchor comprises an ionic chemical group, the ionic chemical group may be positively or negatively charged. In some embodiments, the anchor region comprises a reactive moiety for covalent attachment to a support material such as a photoactive phenylazide or an epoxide group. See, U.S. Patent Application Publication No. 2016/0159777.

Methods of introducing reactive groups into peptidoglycans and/or other glycosidic compounds such as polysaccharide, cellulose, glycans, etc., are known in the art. See US Patent Application Publication No. 2005/011261.

Indicators

In some embodiments, the chemical entities comprise one or more indicators, e.g., at least 1, at least 2, at least 3, at least 4, or more of indicators. Such compositions may include, for example, a plurality of substrates conjugated to the same gel polymer or different gel polymers.

In certain embodiments, the indicators are labeled. The term "label," as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, streptavidin, protein A, protein G, antibodies or fragments thereof, polyhistidine, Ni2+, Flag tags, myc tags, heavy metals, and enzymes (including alkaline phosphatase, peroxidase, and luciferase). Methods for attaching the labels to the anchor compounds are described in the Examples.

In certain embodiments, the indicators are labeled with a label which is a detectable label. A detectable label is a moiety, the presence of which can be ascertained directly or indirectly. Generally, detection of the label involves the creation of a detectable signal such as for example an emission of energy. The label may be of a chemical, peptide or nucleic acid nature although it is not so limited. The nature of label used will depend on a variety of factors, including the nature of the analysis being conducted, the type of the energy source and detector used and the type of polymer, analyte, probe and primary and secondary analyte-specific binding partners.

In a particular embodiment, the label is sterically and chemically compatible with the constituents to which it is bound, e.g., the anchor region. In particular, the label is of the shape and size that it does not hinder enzyme recognition site (S) and/or enzyme-reactive region (R).

In another embodiment, the indicator or a motif therein attached to the anchor is a substrate for a lipase, esterase, peroxidase, oxidase, glycosidase, glucuronidase, protease, lactamase, glucosidase, galactosidase, or a combination thereof.

In one embodiment, the indicator or a motif therein attached to the anchor is a substrate for a protease. Particularly, the indicator or motif therein attached to the anchor is a substrate for elastase.

In another embodiment, the indicator or a motif therein attached to the anchor is a substrate for a protease selected from the group consisting of elastase, cathepsin G, protease 3C or myeloperoxidase (MAO), or a combination thereof.

In another embodiment, the indicator or a motif therein attached to the anchor is a substrate for a glycosidase which is lysozyme and a protease selected from the group consisting of elastase, cathepsin G or myeloperoxidase (MAO), or a combination thereof.

In some embodiments, the enzyme-labile or enzyme-reactive region interacts with one or more target enzymes selected from napsin (aspartyl protease), glucosylceramidase glucuronidase, palmitoyl protein thioesterase, Cathepsins A, B, D, G, L, S, Z; acid ceramidase, lactoferrin (LF), lysozyme, myeloperoxidase (MPO), elastase, cathepsins, and proteinase-3C.

In one embodiment, the indicator (I) or a motif therein attached to the anchor is a peroxidase substrate, an arylamine, an amino phenol, an aminophenyl ether, an indoxyl, a neutral dye, a charged dye, a nanoparticle, or a colloidal gold particle.

In some embodiments, the indicator (I) or a motif therein attached to the anchor is a peroxidase substrate. In some embodiments, the peroxidase substrate is selected from p-aminophenol, ABTS (2,2inophenol, ABTS (strate. In some embodiments, acid) diammonium salt), 3,3'-diaminobenzidine, 3,4 diaminobenzoic acid, DCPIP, N,N-dimethyl-p-phenylenediamine, o-dianisidine, p-phenylenediamine, 4-chloro-1-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), indoxyl, indigo, Fast Blue RR, 4-chloro-7-nitrobenzofurazan. In some embodiments, the indicator (I) or a label attached thereto is an arylamine. In some embodiments, the indicator (I) or a label attached thereto is an amino phenol. In some embodiments, the indicator (I) or a label attached thereto is an aminophenol ether. In some embodiments, the indicator (I) or a label attached thereto is an indoxyl. In some embodiments, the indicator (I) or a label attached thereto is a neutral dye. In some embodiments, the indicator (I) or a label attached thereto is a charged dye. In some embodiments, the charged dye is selected from remazole brilliant blue, toluidine blue, reactive black 5, remazol brilliant blue, reactive violet 5, and reactive orange 16, or a hydrolytic or ammonolytic derivatives thereof. In some embodiments, the charged dye is remazole brilliant blue, or a hydrolytic or ammonolytic derivatives thereof. In some embodiments, the charged dye is toluidine blue. In some embodiments, the charged dye is reactive black 5, or ahydrolytic or ammonolytic derivatives thereof. In some embodiments, the charged dye is reactive violet 5, or hydrolytic or ammonolytic derivatives thereof. In some embodiments, the charged dye is reactive orange 16, or hydrolytic or ammonolytic derivatives thereof. In some embodiments, the indicator (I) or a label attached thereto is a dichlorotriazine-based reactive dye such as reactive blue 4, reactive red 120, reactive blue 2, reactive green 19 and reactive brown 10. In some embodiments, the dichlorotriazine-based reactive dye appears black.

In some embodiments, the indicator (I) or a label attached thereto is a reactive dye containing a sulfonyl ethyl-hydrogensulphate-reactive-group. In some embodiments, the reactive dye is reactive black 5, remazol brilliant blue, reactive violet 5 or reactive orange 16. In some embodiments, the reactive dye is reactive black 5. In some embodiments, the reactive dye is remazol brilliant blue. In some embodiments, the reactive dye is reactive violet 5. In some embodiments, the reactive dye is reactive orange 16. In some embodiments, the reactive dye is reactive black 5, remazol brilliant blue, or reactive violet 5. In some embodiments, the reactive dye is reactive black 5 or remazol brilliant blue.

In some embodiments, the indicator (I) or a label attached thereto is a nanoparticle. In some embodiments, the indicator (I) or a label attached thereto is a colloidal gold particle. In some embodiments, the indicator (I) or a label attached thereto is a charged dye, an indole derivative, or a luminol derivative.

Particularly, the indicator or a motif therein attached to the anchor comprises a dye containing a sulfonyl ethyl-hydrogensulphate-reactive-group, e.g., reactive black 5, remazol brilliant blue, reactive violet 5 or reactive orange 16, or a combination thereof; or a dye containing a dichlortriazine reactive-group, e.g., reactive blue 4, reactive red 120, reactive blue 2, reactive green 19 and reactive brown 10, or a combination thereof.

Anchor-Indicator Conjugates

In various enzymes an anchor A is conjugated with the indicator I directly, e.g., via an glycosidic linkage. The anchor portion of the conjugate is selected from the group consisting of, e.g., peptidoglycan or chitosan or a polysaccharide and the indicator I is selected from the group consisting of a dye containing a sulfonylethyl-hydrogensulphate-reactive-group or a dye containing a dichlortriazine reactive-group.

Markers

Embodiments described herein may utilize chemical moieties that assay for various biological markers present in a chronic or infected wound. In one embodiment, the marker is a wound-specific marker, which is an enzyme selected from the group consisting of hydrolases, proteases, esterases, and peroxidases.

As used herein, a "wound specific enzyme" is an enzyme that is differentially expressed in a wound. By "differential expression" it is meant that the level or the activity of the enzyme is higher or lower in the wound microenvironment compared to other sites, e.g., normal tissue or surrounding tissue. Particularly, differential expression implies higher level of expression or activity of the enzyme in the wound microenvironment compared to normal or unwounded tissue. Differential expression of enzyme may be analyzed by routine means. For example, levels of enzyme in a sample may be analyzed by ELISA assays or other immunoassays. Activities of the enzyme may be analyzed by measuring rates of loss of a substrate and/or rates of formation of the product, e.g., using mass spectroscopy or HPLC. Such techniques are known in the art and are described in the Examples section.

In one embodiment, the marker is a hydrolase. As used herein, a "hydrolase" or "hydrolytic enzyme" is an enzyme that catalyzes the hydrolysis of a chemical bond, e.g., esterases and nucleases (break ester bonds); glycolases (break glycosidic linkers); peptidases (break peptide bonds), etc.

In one specific embodiment, the wound-specific glycoside hydrolase is lysozyme. Lysozyme (UNIPROT accession Nos. P61626 [human] and P08905 [mouse]) is a glycoside hydrolase and its main function is to destroy the cell walls of bacteria. It hydrolyses the (1→4)-β-linkages between N-acetylmuramic acid and N-acetyl-D-glucosamine residues in peptidoglycan and also between N-acetyl-D glucosamine residues in chitodextrin. The natural substrate for lysozyme is the peptidoglycan layer of bacterial cell walls. However, a variety of low molecular mass substrates including murein degradation products as well as synthetic compounds have been used for various photometric, isotopic, and immunological lysozyme assays. Holtje et al., EXS, 75: 105-10, 1996. See also Sigma Catalog Number M5639 and Sigma Catalog Number N8638.

In one embodiment, the individual components of the chemical moiety have been adapted for recognition by wound-specific hydrolase, e.g., a wound-specific lysozyme.

Alternately or additionally, the individual components of the chemical moiety can be modified for recognition by other wound specific enzymes. In one embodiment, the additional wound specific enzyme is a protease. As used herein, a "wound specific protease" is a protease that is differentially expressed in a wound. By "differential expression" it is meant that the level or the activity of the protease is higher or lower in the wound microenvironment compared to other sites, e.g., normal tissue or surrounding tissue. Particularly, differential expression implies higher level of expression or activity of the protease in the wound microenvironment compared to unwounded tissue. Differential expression of proteases may be analyzed by routine means. For example, levels of proteases in a sample may be analyzed by ELISA assays or other immunoassays. Activities of the proteases may be analyzed by measuring rates of loss of a peptide substrate and/or rates of formation of the product, e.g., using mass spectroscopy or HPLC. Such techniques are known in the art and are described in the Examples section.

In one embodiment, the wound-specific protease is cathepsin G (UNIPROT accession Nos. P08311 [human] and P28293 [mouse]), which is one of the three serine proteases of the chymotrypsin family that are stored in the azurophil granules. Cathepsin G-specific substrates have the sequence Ala-Ala-Pro-Phe [SEQ ID NO: 3] or Ala-Ala-Pro-Met [SEQ ID NO: 4] (Sigma Aldrich Catalog Nos. S7388 and M7771).

In another embodiment, the wound specific protease is elastase (e.g., human neutrophil elastase or HNE) (UNIPROT accession Nos. P08246 [human] and Q3UP87 [mouse]). HNE is a serine proteinase in the same family as chymotrypsin and has broad substrate specificity. Secreted by neutrophils and macrophages during inflammation, it destroys bacteria and host tissue. In one embodiment, the substrate for detecting HNE has a core sequence Alanine-Alanine-Proline-Valine (AAPV) [SEQ ID NO: 5]. In another embodiment, the substrate for HNE is Ala-Pro-Glu-Glu-Ile [SEQ ID NO: 6]/Met-Arg-Arg-Gln [SEQ ID NO: 7] (APEEI/MRRQ) (Kasperkiewicz et al., $PNAS$ $USA$, 111(7): 2518-2523, 2014; Korkmaz et al., $Methods$ $Mol$ $Biol$, 844: 125-138, 2012).

In one embodiment, the enzyme-labile region comprises a peptide that is liable to elastase. Under this embodiment, the chromogenic indicator for elastase would be high contrast and thus serve as a clear indicator when used in situ in medicinal products.

The ideal substrate would make a blue, violet or deep green color. It would also be fixed in a sterically permissible position with high turnover. The state of the art is the opposite. Available substrates contain a p-nitrophenol group, which is low molecular weight but gives rise to a yellow soluble chromophore. Most skilled investigators regard that the substrate should be soluble in water, reasoning that this is the most likely way that the substrate will find its way to the active site.

In contrast the embodiments described herein depart from that general rationale. It was contemplated that elastase digests a solid phase substrate, namely structural proteins, which are, by definition, not soluble, that a substrate specific to it would have to be adapted accordingly. As such, both the color of the indicator and the systems that they could be employed with, e.g., electronically detection, were adapted to the wound environment.

Therefore, contrary to the art teachings to employ soluble substrates, embodiments described herein contemplate use of a low water soluble, elastase substrates that give rise to Blue, violet or Green colors.

Still in a further embodiment, the wound-specific enzyme is peroxidase, more specifically, a myeloperoxidase (MPO). MPO (UNIPROT accession Nos. P05164 [human] and PI 1247 [mouse]) is a peroxidase found in neutrophil granulocytes. In the presence of hydrogen peroxide (H2O2) and a halide (most commonly chloride) it produces the antimicrobial substances hypochlorite, singlet oxygen (102), chlorine ($C_{12}$) and hydroxyl radicals (OH·). MPO can be detected using tetramethylbenzidine or 4-Benzoylamino-2,5-dimethoxyaniline. See, Andrews et al., $Anal$ $Biochem$, 127(2): 346-50, 1982; Klebanoff et al., $J.$ $Leukocyte$ $Biol$, 77, 598-625, 2005.

Still in a further embodiment, the wound-specific enzyme is a bacterial enzyme, more specifically, beta-lactamases (β-lactamases). β-lactamases (AccessionGO:0008800) are hydrolase enzymes (EC 3.5.2.6) produced by bacteria (also known as penicillinase) that provide multi-resistance to β-lactam antibiotics such as penicillins, cephamycins, and carbapenems (ertapenem). Through hydrolysis, the lactamase enzyme breaks the β-lactam ring open.

Still in a further embodiment, the wound-specific enzyme is a viral enzyme, more specifically, protease 3C. These proteases are encoded by enteroviruses, rhinoviruses, aphtoviruses and cardioviruses, which genera all cause a wide range of infections for humans and other mammals. Accordingly, protease 3C can be employed as a marker for wound infection.

Still in a further embodiment, the wound-specific enzyme is MPO (UNIPROT accession Nos. P05164 [human] and PI 1247 [mouse]) is a peroxidase found in neutrophil granulocytes. In the presence of hydrogen peroxide (H2O2) and a halide (most commonly chloride) it produces the antimicrobial substances hypochlorite, singlet oxygen (1O2), chlorine ($C_{12}$) and hydroxyl radicals (OH·). MPO can be detected using tetramethylbenzidine or 4-Benzoylamino-2,5-dimethoxyaniline. See, Andrews et al., *Anal Biochem,* 127(2): 346-50, 1982; Klebanoff et al., *J. Leukocyte Biol,* 77, 598-625, 2005

Enzyme Recognition Site (R)

Insofar as embodiments disclosed herein relate to the specific detection of wound-specific markers, disclosed herein are substrates containing enzyme recognition sites (R) for the wound-specific markers. Thus, in one embodiment, the chemical moiety comprises an anchor region A or an indicator (I) comprising a recognition site for a wound-specific enzyme, e.g., an enzyme cleavage site.

In one embodiment, the enzyme recognition site comprises glycosidic bonds. As used herein, a "glycosidic bond" is formed between the hemiacetal or hemiketal group of a saccharide (or a molecule derived from a saccharide) and the hydroxyl group of some compound such as an alcohol. A substance containing a glycosidic bond is a glycoside. The term "glycoside" is now extended to also cover compounds with bonds formed between hemiacetal (or hemiketal) groups of sugars and several chemical groups other than hydroxyls, such as —SR (thioglycosides), —SeR (selenoglycosides), —$R^1R^2$ (N-glycosides), or even —CR1R2R3 (C-glycosides).

In one embodiment, the chemical moieties disclosed herein contain one or more glycosidic bonds which are cleaved by glycolases. In one specific embodiment, the chemical moieties comprise a glycosidic bond linking anchor A and the indicator I, either directly or via another group. Particularly, the anchor A and the indicator I are directly linked via one or more glycosidic bonds, in which case, the chemical entity is cleaved by the glycolase and therefore can be used in detecting the glycolase.

In one embodiment, the indicator molecule comprises an enzymatically-cleavable peptide comprising a peptide bond. As used herein, a "peptide bond" is formed by the condensation reaction between two amino acids, wherein the acid moiety of one reacts with the amino moiety of the other to produce a peptide bond (—CO—NH—) between the two amino acids. The individual peptides provide a motif for the recognition by a sequence-specific protease. As used herein, the term "sequence-specific protease" means a protease recognizing a specific sequence of a peptide for its digesting (for example, caspase), and is distinguished from a generic protease (for example, trypsin) that sequentially decomposes a peptide from one end thereof or digest a peptide in a sequence-nonspecific manner. For sequence specificity, the amino acid sequence of the peptide substrate may comprise four or more amino acid (a.a.) residues.

As used herein, the term "peptide" includes a natural peptide comprising a linear chain or branched amino acids, peptidomimetics, as well as pharmaceutically acceptable salts thereof. Typically, a peptide comprises a plurality of amino acid residues, e.g., 2, 3, 4, 5, 6, 8, 10, or more amino acid residues which are bonded to each other via covalent bonds, e.g., a peptide bond. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids. Included by this definition are natural amino acids such as: (1) histidine (His) (2) isoleucine (He) (3) leucine (Leu) (4) lysine (Lys) (5) methionine (Met) (6) phenylalanine (Phe) (7) threonine (Thr) (8) tryptophan (Trp) (9) valine (Val) (10) arginine (Arg) (11) cysteine (Cys) (12) glutamine (Gin) (13) glycine (Gly) (14) proline (Pro) (15) serine (Ser) (16) tyrosine (Tyr) (17) alanine (Ala) (18) asparagine (Asn) (19) aspartic acid (Asp) (20) glutamic acid (Glu) (21) selenocysteine (Sec); including unnatural amino acids: (a) citrulline; (b) cystine; (c) gama-amino butyric acid (GAB A); (d) omithine; (f) theanine and amino acid derivatives such as betaine; carnitine; carnosine creatine; hydroxytryptophan; hydroxyproline; N-acetyl cysteine; S-Adenosyl methionine (SAM-e); taurine; tyramine. Among these, amino acids containing reactive side chains, e.g., cysteine, serine, threonine, lysine, arginine, aspartate/asparagine, glutamate/glutamine, glycine, alanine, etc. are particularly employed for modification of the substrate.

In some embodiments, the chemical entities contain one or more enzyme-labile or enzyme-reactive regions (R) for the detection of wound-specific enzymes.

In one embodiment, wherein the enzyme is a glycosidase such as lysozyme, the enzyme-labile or enzyme-reactive region comprises an acyl chitosan of at least 3 glucosamine or N-acetylglucosamine or peptidoglycan units, which are optionally acetylated. The enzyme reactive site may contain, for example, 3, 4, 5, 6, 7, 8, 9, 10, 11, 12, 15, 20 or more units of glucosamine or N-acetyl glucosamine or peptidoglycan units. In one embodiment, the R comprises at least 3 glucosamine or N-acetylglucosamine or a combination thereof, wherein the glucosamine and/or N-acetyl glucosamine are optionally acetylated. In another embodiment, the enzyme-labile or enzyme-reactive region comprises peptidoglycan, wherein the peptidoglycan is optionally acetylated.

In some embodiments, the chemical moieties comprise enzyme reactive sites (R) for one or more wound-specific protease disclosed above, e.g., cathepsin G, and myeloperoxidase, elastase or a combination thereof. As used herein, the term "reactive site for a protease" means a peptide comprising an amino acid sequence of a protein, which is recognized by the protease as a substrate for its protease activity, e.g., as a substrate that can be cleaved into one or more products. In some embodiments, the chemical entities comprise a peptide region comprising a peptide sequence comprising a plurality of amino acids. The term "plurality" means two or more units, e.g., amino acids, although the individual units need not be structurally and/or functionally different. Typically, the indicator region (I) of the chemical entity comprises the peptide which serves as the enzyme reactive site for the wound-specific protease.

In one embodiment, the enzyme-labile or enzyme-reactive region comprises a peptide that is labile to elastase, cathepsin G, myeloperoxidase or a combination thereof.

In one embodiment, the enzyme-labile region comprises a peptide that is liable to elastase. Under this embodiment, the chromogenic indicator for elastase would be high contrast and thus serve as a clear indicator when used in situ in medicinal products.

The ideal substrate would make a blue, violet or deep green color. It would also be fixed in a sterically permissible position with high turnover. The state of the art is the opposite. Available substrates contain a p-nitrophenol group, which is low molecular weight but gives rise to a yellow soluble chromophore. Most skilled investigators regard that the substrate should be soluble in water, reasoning that this is the most likely way that the substrate will find its way to the active site.

In contrast the embodiments described herein depart from that general rationale. It was contemplated that elastase digests a solid phase substrate, namely structural proteins, which are, by definition, not soluble, that a substrate specific to it would have to be adapted accordingly. As such, both the color of the indicator and the systems that they could be employed with, e.g., electronically detection, were adapted to the wound environment.

Therefore, contrary to the art teachings to employ soluble substrates, embodiments described herein contemplate use of a low water soluble, elastase substrates that give rise to Blue, violet or Green colors.

The peptide sequence is often considered to be important for protease substrates, however, Elastase has a very general hydrolytic potential and accepts very many substrates. This is because it is also involved in anti-microbial defense and immune cell translocation in many tissues. In this regard, it can cut many different peptides. It Cuts well between A, F, V or M, and a simple amino acid with limited side chain complexity. AAPV [SEQ ID NO: 5], AAPF [SEQ ID NO: 3], AAAA [SEQ ID NO: 8] are all examples of well recognized targets. What is apparent is that with increasing distance on the N-terminus, the amino acids play a less important role. On the C-terminus of the cut site, there is no obvious consensus, however, less complexity appears to be preferred.

More important in this case are two factors:
Distance from the anchor
Nature of the chromophore If the Anchor site is too close, the action of the enzyme is inhibited. Therefore, ideally, there are 4 or more aminoacids between the cut site and the anchor.

The chromophore, and notably its charge are important. Neutral chromophores are preferred to positively charged moieties, and these are preferred vs. negatively charged chromophores or dyes. A high density of negative charge near the cut site inhibits the enzyme. Thus, where negative dyes are used, they are preferably spaced 2 or more aminoacids C-terminal form the cut site.

Longer amino acid sequences are generally less hindered but they are also less economical In one embodiment, the enzyme-labile or enzyme-reactive region comprises a peptide comprising an amino acid sequence of:

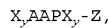

wherein each X is independently any amino acid,
y is each, independently, an integer between 0 and 200, and
Z comprises a detectable label.

In one embodiment, the enzyme-labile or enzyme-reactive region comprises a peptide comprising an amino acid sequence of:

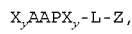

wherein each X is independently any amino acid,
y is each, independently, an integer between 0 and 200, and
Z comprises a detectable label.

In another embodiment, the enzyme-labile or enzyme-reactive region comprises a peptide comprising an amino acid sequence of:

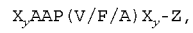

wherein each X is independently any amino acid,
y is each, independently, an integer between 0 and 200, and
Z comprises a detectable label.

In yet another embodiment, the enzyme-labile or enzyme-reactive region comprises a peptide comprising an amino acid sequence of:

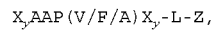

wherein each X is independently any amino acid,
y is each, independently, an integer between 0 and 200,
L is a linking moiety, and
Z comprises a detectable label.

In another specific embodiment, the reactive region R comprises the peptide sequence $X_yAAPX_y$-Z, $X_yAAPX_y$-L-Z, $X_yAAP(V/F/A)X_y$-Z or $X_yAAP(V/F/A)X_y$-L-Z, wherein X, L and Z are each, as described above, and y is, each, independently an integer from 1 to 50.

Still in a further embodiment, the reactive region R comprises the peptide sequence $X_yAAPX_y$-Z, $X_yAAPX_y$-L-Z, $X_yAAP(V/F/A)X_y$-Z or $X_yAAP(V/F/A)X_y$-L-Z, wherein X, L and Z are each, as described above, and y is, each, independently an integer from 1 to 10.

Particularly, the reactive region R comprises the peptide sequence $X_yAAPX_y$-Z, $X_yAAPX_y$-L-Z, $X_yAAP(V/F/A)X_y$-Z or $X_yAAP(V/F/A)X_y$-L-Z, wherein X, L and Z are each, as described above, and y is, each, independently an integer from 1 to 6.

In one embodiment, each of the aforementioned peptides comprising the sequence $X_yAAPX_y$-Z, $X_yAAPX_y$-L-Z, $X_yAAP(V/F/A)X_y$-Z or $X_yAAP(V/F/A)X_y$-L-Z, are each, individually, labile to elastase.

In some embodiments, one or more of the amino acids in the amino acid sequence $X_yAAPX_y$-Z, $X_yAAPX_y$-L-Z, $X_yAAP(V/F/A)X_y$-Z or $X_yAAP(V/F/A)X_y$-L-Z is protected, e.g., with an amine protection group, for example, fluorenylmethyloxycarbonyl (Fmoc).

In some embodiments, the enzyme-labile or enzyme-reactive region comprises a peptide that is labile to cathepsin G.

In one embodiment, the enzyme-labile or enzyme-reactive region comprises a peptide comprising an amino acid sequence of:
$X_yN^4N^3N^2N^1X_y$-Z, wherein
X is each, independently, any amino acid;
y is each independently a number selected from 0 to 6;
$N^4$ is selected from alanine, glycine, valine, and glutamine;
$N^3$ is selected from alanine, glycine, proline, lysine, and serine;
$N^2$ is selected from proline, alanine, and glycine;
$N^1$ is selected from serine, lysine, phenylalanine, arginine, leucine, and methionine; and
Z comprises a detectable label; and the peptide is labile to cathepsin G.

In some embodiments, one or more of the amino acids in the amino acid sequence is protected. In some embodiments, one or more of the amino acids in the amino acid sequence is protected with a t-boc group. In some embodiments, one of the amino acid in the amino acid sequence is protected with an fmoc group.

In some embodiments, the enzyme-labile or enzyme-reactive region comprises a peptide comprising an amino acid sequence of $X_y N^4 N^3 N^2 N^1 X_y$-L-Z, wherein X is each, independently, any amino acid;

y is each, independently, a number selected from 0 to 6;

$N^4$ is selected from alanine, glycine, valine, and glutamine;

$N^3$ is selected from alanine, glycine, proline, lysine, and serine;

$N^2$ is selected from proline, alanine, and glycine;

$N^1$ is selected from serine, lysine, phenylalanine, arginine, leucine, and methionine; and L is a linking moiety; and Z comprises a detectable label.

In one embodiment, each of the aforementioned peptides comprising the sequence $X_y N^4 N^3 N^2 N^1 X_y$-Z and $X_y N^4 N^3 N^2 N^1 X_y$-L-Z, are each, individually, labile to cathepsin G.

In some embodiments, one or more of the amino acids in the amino acid sequence $X_y N^4 N^3 N^2 N^1 X_y$-Z and $X_y N^4 N^3 N^2 N^1 X_y$-L-Z is protected, e.g., with an amine protection group, for example, fluorenylmethyloxycarbonyl (Fmoc).

In some embodiments, the enzyme-labile or enzyme-reactive region comprises a peptide comprising an amino acid sequence of (a) $X_y UUUU_y$-Z, wherein X is, each, independently any amino acid; y is, each, independently, a number selected from 1 to 50; U is an amino acid selected from LEVLFQ, and Z is a label. Particularly under this embodiment, y is a number selected from 1 to 10.

In some embodiments, one or more of the amino acids in the amino acid sequence (a) XyUUUUy-Z is protected, e.g., with a t-boc group or an fmoc group.

In some embodiments, the amino acid sequence $X_y UUUU_y$-Z is liable to a viral 3C protease.

Detectable Label Z

In some embodiments, Z is a peroxidase substrate, an arylamine, an amino phenol, an aminophenyl ether, an indoxyl, a neutral dye, a charged dye, a nanoparticle, or a colloidal gold particle.

In some embodiments, Z is a peroxidase substrate selected from p-aminophenol, ABTS (2,2inophenol, ABTS (s, the peroxidase substrate acid) diammonium salt), 3,3'-diaminobenzidine, 3,4 diaminobenzoic acid, DCPIP, N,N-dimethyl-p-phenylenediamine, o-dianisidine, p-phenylenediamine, 4-chloro-1-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), indoxyl, indigo, Fast Blue RR, 4-chloro-7-nitrobenzofurazan.

In some embodiments, Z is an arylamine, an amino phenol, an aminophenol ether, an indoxyl, a neutral dye, a charged dye selected from remazole brilliant blue, toluidine blue, reactive black 5, remazol brilliant blue, reactive violet 5, and reactive orange 16, or a hydrolytic or ammonolytic derivatives thereof. Particularly, Z is a charged dye selected from remazole brilliant blue; toluidine blue; reactive black 5 or a hydrolytic or an ammonolytic derivative thereof.

In some embodiments, Z is a dichlorotriazine-based reactive dye such as reactive blue 4, reactive red 120, reactive blue 2, reactive green 19 and reactive brown 10. In some embodiments, the dichlorotriazine-based reactive dye appears black. In some embodiments, Z is a reactive dye containing a sulfonyl ethyl-hydrogensulphate-reactive-group.

In some embodiments, Z is a nanoparticle. In some embodiments, Z is a colloidal gold particle.

In some embodiments, Z is a charged dye, an indole derivative, or a luminol derivative.

In some embodiments, the enzyme-labile or enzyme-reactive region comprises a phenol, an amino phenol, an aminophenyl ether, an indoxyl, or a quinone. In some embodiments, the enzyme-labile or enzyme-reactive region comprises a phenol. In some embodiments, the enzyme-labile or enzyme-reactive region comprises an amino phenol. In some embodiments, the enzyme-labile or enzyme-reactive region comprises an amino phenol ether. In some embodiments, the enzyme-label or enzyme-reactive region comprises an indoxyl. In some embodiments, the enzyme-labile or enzyme-reactive region comprises a quinone. In some embodiments, the enzyme-labile or enzyme-reactive region reacts with myeloperoxidase but does not react with heme.

In some embodiments, the enzyme-labile or enzyme-reactive region comprises a peroxidase substrate, an arylamine, an amino phenol, a neutral dye, a charged dye, a nanoparticle, or a colloidal gold particle. In some embodiments, the enzyme-labile or enzyme-reactive region comprises a peroxidase substrate. In some embodiments, the peroxidase substrate is selected from p-aminophenol, ABTS (2,2-Azino-bis(3-ethylbenzothiazoline-6-sulfonic acid) diammonium salt), 3,3'-diaminobenzidine, 3,4 diaminobenzoic acid, DCPIP, N,N-dimethyl-p-phenylenediamine, o-dianisidine, p-phenylenediamine, 4-chloro-1-naphthol, o-phenylenediamine N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), and 4-chloro-7-nitrobenzofurazan, Fast Blue RR, N-(2-hydroxy)tetradecyl-Fast Blue RR. In some embodiments, the enzyme-labile or enzyme-reactive region comprises an arylamine. In some embodiments, the enzyme-labile or enzyme-reactive region comprises an amino phenol. In some embodiments, the enzyme-labile or enzyme-reactive region comprises a neutral dye. In some embodiments, the enzyme-labile or enzyme-reactive region comprises a charged dye. In some embodiments, the charged dye is selected from remazole brilliant blue, toluidine blue, reactive black 5, remazol brilliant blue, reactive violet 5, and reactive orange 16, or hydrolytic or ammonolytic derivatives of each of these. In some embodiments, the charged dye is remazole brilliant blue, or hydrolytic or ammonolytic derivatives thereof. In some embodiments, the charged dye is toluidine blue. In some embodiments, the charged dye is reactive black 5, or hydrolytic or ammonolytic derivatives thereof. In some embodiments, the charged dye is reactive violet 5, or hydrolytic or ammonolytic derivatives thereof. In some embodiments, the charged dye is reactive orange 16, or hydrolytic or ammonolytic derivatives thereof.

In some embodiments, the enzyme-labile or enzyme-reactive region comprises a dichlorotriazine-based reactive dye such as reactive blue 4, reactive red 120, reactive blue 2, reactive green 19 and reactive brown 10.

In some embodiments, the enzyme-labile or enzyme-reactive region comprises a nanoparticle. In some embodiments, Z is a colloidal gold particle.

In some embodiments, the enzyme-labile or enzyme-reactive region comprises a charged dye, an indole derivative, or a luminol derivative. In some embodiments, the enzyme-labile or enzyme-reactive region comprises an indole derivative. In some embodiments, the enzyme-labile or enzyme-reactive region comprises a luminol derivative.

In some embodiments, the indicator region comprises a dye that presents a visible color change in normal ambient lighting. In some embodiments, the dye has a contrasting color to wound products, which are commonly red, yellow, or brown. In further embodiments, the dye is violet, blue or dark green. In some embodiments, the dye is violet. In some embodiments, the dye is blue. In some embodiments, the dye is dark green. In some embodiments, the dye has low molecular weight, is charged, contains reactive or linkable groups, is stable to gamma irradiation, and is deeply colored. In some embodiments, the dye is selected from cibracron series dyes, azo dyes, and remazol dyes, or hydrolytic or ammonolytic derivatives thereof. In some embodiments, the dye is selected from cibracron series dyes. In some embodiments, the dye is selected from azo dyes. In some embodiments, the dye is selected from remazol dyes, or hydrolytic or ammonolytic derivatives thereof. In some embodiments, the dye is selected from rhodamine, coumarin, cyanine, xanthene, polymethine, pyrene, dipyrromethene borondifluoride, napthalimide, a phycobiliprotein, peridinium chlorophyll proteins, fluorescein, 6-FAM, rhodamine, Texas Red, California Red, iFluor594, tetramethylrhodamine, a carboxyrhodamine, carboxyrtiodamine 6F, carboxyrtiodol, carboxyrhodamine 110, Cascade Blue, Cascade Yellow, coumarin, Cy2®, Cy34®), Cy3.5®, Cy5®, Cy5.5®, Cy7®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 630/650, BODIPY® 650/665, BODIPY® R6G, BODIPY® TMR, BODIPY® TR, and dimethylaminoazobenzenesulfonic acid (dabsyl), or conjugates thereof, or combinations thereof.

In some embodiments, the indicator region comprises a dichlorotriazine-based reactive dye such as reactive blue 4, reactive red 120, reactive blue 2, reactive green 19 and reactive brown 10. In some embodiments, the dichlorotriazine-based reactive dye appears black.

In some embodiments, the indicator region comprises the reaction product of a reactive dye containing a sulfonylethyl-hydrogensulphate-reactive-group. In some embodiments, the reactive dye is reactive black 5, remazol brilliant blue, reactive violet 5 or reactive orange 16. In some embodiments, the reactive dye is reactive black 5. In some embodiments, the reactive dye is remazol brilliant blue. In some embodiments, the reactive dye is reactive violet 5. In some embodiments, the reactive dye is reactive orange 16. In some embodiments, the reactive dye is reactive black 5, remazol brilliant blue, or reactive violet 5. In some embodiments, the reactive dye is reactive black 5 or remazol brilliant blue.

In some embodiments, the indicator region comprises a particle (e.g., colloidal metal or quantum dots) that present color changes in normal ambient lighting. In some embodiments, the indicator region comprises a nanoparticle. In some embodiments, the indicator region comprises a colloidal gold particle.

In some embodiments, the indicator region comprises a dye that presents a visible color change under UV light. In some embodiments, the indicator region comprises a dye that is fluorescent. In some embodiments, the indicator region comprises a dye that is luminescent.

In some embodiments, the indicator region comprises an enzyme-reactive moiety. In some embodiments, the enzyme-reactive moiety interacts with an accessory enzyme to produce a product that is visible to the naked eye or detectable by electronic means. In some embodiments, the enzyme-reactive moiety interacts with an accessory enzyme to produce a product that is visible to the naked eye. In some embodiments, the enzyme-reactive moiety interacts with an accessory enzyme to produce a product that is detectable by electronic means. In some embodiments, the indicator region comprises an indoxyl glycoside that is cleaved by hexaminidase, glucuronidase, glucosidase or galactosidase depending on the terminal sugar used, to produce indigo. In some embodiments, the indicator region comprises a phenol that is oxidized by an accessory enzyme to produce a visible product. In some embodiments, the indicator region comprises a phenol that is oxidized by laccase to produce a visible product. In some embodiments, the indicator region comprises a metallo motif that is detectable by electronic means. In some embodiments, the indicator region comprises a ferrocene or ferrocene analog that is detectable by electronic means. In some embodiments, the accessory enzyme is selected from lipase, esterase, hexosaminidase, peroxidase, oxidase, glycosidase, glucosidase, and laccase. In some embodiments, the accessory enzyme is not present in the wound fluid. In some embodiments, the accessory enzyme is present in the wound fluid. In some embodiments, the enzyme-reactive moiety interacts with an accessory enzyme to produce a product that is visible under UV light.

Chemical Entities Containing a Plurality of Enzyme Recognition Sites (R)

In further embodiments, disclosed herein are chemical entities containing the anchor A, the indicator I, which individually or together comprise a plurality of enzyme recognition sites (R). Typically, such chemical entities are employed to assay for a plurality of enzymes, e.g., a combination comprising at least one protease and at least one glycosidase.

In one embodiment, disclosed herein are chemical entities containing the anchor A, the indicator I, which individually or together comprise a plurality of enzyme recognition sites (R), wherein at least one reactive site is specific for a glycosidase, e.g., lysozyme; and at least one enzyme reaction site is specific for a protease selected from the group consisting of lipase, esterase, peroxidase, oxidase, glycosidase, glucuronidase, glucosidase, galactosidase, Napsin (aspartyl protease), Glucosylceramidase glucuronidase, palmitoyl protein thioesterase, cathepsins A, B, D, G, L, S, Z; acid ceramidase, lactoferrin (LF), lysozyme, myeloperoxidase (MPO), elastase, lactamase, cathepsins, and proteinase-3C or a combination thereof. The individual reaction sites and recognition sites for these enzymes have been described previously.

In one embodiment, disclosed herein are chemical entities containing the anchor A, the indicator I, which individually or together comprise a plurality of enzyme recognition sites (R), wherein at least one reactive site is specific for a protease elastase; and at least one enzyme reaction site is specific for a protease selected from the group consisting of myeloperoxidase (MPO), cathepsins, and proteinase-3C. The individual reaction sites and recognition sites for these enzymes have been described previously.

In one embodiment, disclosed herein are chemical entities containing the anchor A, the indicator I, which individually or together comprise a plurality of enzyme recognition sites (R), wherein at least one reactive site is specific for a protease elastase; and at least one enzyme reaction site is specific for a microbial enzyme selected from the group consisting of beta-lactamase and proteinase-3C. The individual reaction sites and recognition sites for these enzymes have been described previously In one embodiment, disclosed herein are chemical entities containing the anchor A, the indicator I, which individually or together comprise a plurality of enzyme recognition sites (R), wherein at least one reactive site is specific for an elastase; and at least one enzyme reaction site is specific for a protease selected from the group consisting of MPO. The individual reaction sites and recognition sites for these enzymes have been described previously.

In one embodiment, disclosed herein are chemical entities containing the anchor A, the indicator I, which individually or together comprise a plurality of enzyme recognition sites (S) and enzyme reaction sites (R), wherein at least one reactive site is specific for a protease elastase; and at least one enzyme reaction site is specific for a protease selected from the group consisting of proteinase 3C. The individual reaction sites and recognition sites for these enzymes have been described previously.

Owing to the greater predictive power of employing a combination of enzyme substrates, it is contemplated that the diagnostic utility of chemical entities comprising a plurality of reaction and recognition sites, as outlined above, will be greatly enhanced compared to entities comprising unitary (e.g., single type) of reaction and recognition sites. At the very least, entities comprising a plurality of reaction/recognition sites will permit diagnosis of at least 2, at least 3, at least 4 or more markers simultaneously. By the way of example, host elastase and/or MPO activity at the wound situs may be detected and monitored simultaneously with pathogen-derived markers (e.g., beta-lactamase or viral protease 3C-specific reaction sites) using the multiplex chemical entities disclosed herein.

Support Material

In some embodiments, the anchor region (A) of the chemical entity binds the chemical entity to a support material, e.g., via covalent interaction, ionic interaction, hydrophobic interaction, electrostatic interactions, hydrogen bonding interactions, physiochemical interactions, van der Waal forces, Lewis-acid/Lewis-base interactions, or combinations thereof.

In some embodiments, the support matrix comprises dextran, agarose, silica, synthetic polymer, or dextran, agarose, silica, or synthetic polymer covalently coupled to an antibody, ligand, or epitope tag.

In some embodiments, the anchor region is a polystyrene bead, silica gel bead, polysaccharide bead, polyacrylamide bead, cellulose bead, polysaccharide, derivatized cellulose, polyacrylate, polyethyleneimine, polyacrylamide, UV-activatable reactive group, peptidoglycan, or chitosan derivative, or a combination thereof. In some embodiments, the anchor region binds to a support material after a short period of UV irradiation.

In some embodiments, the chemical entity is printed on or in a support material such as filter paper or a woven or non-woven material that is capable of being wet by a wound fluid and which displays capillary action. In some embodiments, the reporting entity or chemical entity is chemically bonded onto or into a support material such as filter paper or a woven or non-woven material that is capable of being wet by a wound fluid and which displays capillary action that is similar in all dimensions. In some embodiments, the chemical entity is ionically bound onto or into a support material such as filter paper or a woven or non-woven material that is capable of being wet by a wound fluid and which displays capillary action. In some embodiments, the chemical entity is covalently bound onto or into a support material such as filter paper or a woven or non-woven material that is capable of being wet by a wound fluid and which displays capillary action. Support material includes, but is not limited to, cellulose, polyamide, polyester, polyacrylate and other similar polymers that are useful as fibers. In some embodiments, the support material is cellulose. In some embodiments, the support material is polyamide. In some embodiments, the support material is polyester. In some embodiments, the support material is polyacrylate.

Additional Moieties

In some instances, the pH of a wound can influence many factors of wound healing, such as angiogenesis, protease activity, oxygen release, and bacterial toxicity. Chronic nonhealing wounds may have an elevated alkaline environment. As the wound progresses towards healing, the pH of the wound moves to neutral and then becomes acidic. Monitoring of the pH of the wound may provide a method to assess the condition of the wound (e.g., infection or no infection) and aid in determining a wound's response to treatment.

Accordingly, in some embodiments, the chemical entity for the detection of infection in a wound comprises an indicator region comprising a pH-sensitive moiety that presents a visible color change. In one embodiment, the pH-sensitive moiety presents a visible color change at alkaline pH, e.g., a pH=7.2-9.5; pH=7.2-9.0; pH=7.2-8.5; pH=7.2-8.0; pH=7.5-8.5; pH=7.5-9.0; pH=8.0-9.0. In other embodiments, the pH-sensitive moiety presents a visible color change at pH=7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5, or 0.1 increments thereof.

In some embodiments, the pH-sensitive moiety presents a visible color change at neutral pH range, e.g., at pH=6.9, 7.0, or 7.1, or 0.05 increments thereof.

In some embodiments, the pH-sensitive moiety presents a visible color change at acidic pH, e.g., pH=4.5-6.8; pH=4.5-6.5; pH=5.0-6.8; pH=5.4-6.8; pH=5.4-6.5. In other embodiments, the pH-sensitive moiety presents a visible color change at pH=4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or 0.1 increments thereof.

In some embodiments, the pH-sensitive moiety is selected from the group consisting of bromothymol blue, phenol red, bromophenol red, chlorophenol red, thymol blue, bromocresol green, bromocresol purple; nitrazine yellow; and sulfophthalein dyes or a combination thereof.

Compositions:

Embodiments described herein further relate to compositions containing the compounds of Formula I. Such compositions may be prepared using conventional methods.

Once formulated, the resulting stock composition of compounds of Formula I may be further modified into desired form, e.g., gels, balms, lotions, cream, paste, ointments, etc. using conventional methods, e.g., using carriers, gelling agents, emollients, surfactants, humectants, viscosity enhancers, emulsifiers, etc. See, e.g., WO 2013/004953.

Carriers for use in the composition may include, but are not limited to, water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof. In one embodiment, the carrier is propylene glycol. Typically, the composition contains a carrier in an amount from about 1% by weight of the composition to about 99.9% by weight of the composition, more typically from about 2% by weight of the composition to about 95% by weight of the composition, and more typically from about 5% by weight of the composition to about 90% by weight of the composition.

Thermo-reversible gelling agents are defined as ingredients that are soluble, partially soluble, or miscible in a hydrophilic carrier at elevated temperatures, such as 50° C., wherein the agents have the ability to thicken the carrier when cooled to 25° C., but will be less viscous at 50° C. when application to a substrate is necessary. Suitable hydrophilic carriers include water, glycols, e.g., propylene glycol. Thermo-reversible gelling agents for use in the composition may include salts of fatty acids such as sodium stearate, sodium palmitate, potassium stearate. These salts can be added to the composition or can be created in-situ by addition of the fatty acid and neutralizing with appropriate base. An example of in-situ formation of the composition is to provide stearic acid and sodium hydroxide to produce sodium stearate. Other common hermos-reversible gelling agents could include, e.g., polyethylene glycols and derivatives such as PEG-20, PEG-150 distearate, PEG-150 pentaerythrityl tetrastearate, disteareth-75 IPDI, disteareth-100 IPDI, fatty alcohols, e.g., cetyl alcohol, fatty acids such as stearic acid, hydroxystearic acid and its derivatives, and combinations thereof.

In addition to the carrier and hermos-reversible gelling agent, the composition can contain various other ingredients and components. Examples of other ingredients that may be included within the composition are emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Pharmaceutical Compositions and/or Preparations:

Embodiments described herein further relate to pharmaceutical compositions and/or preparations comprising one or more of the aforementioned compounds of Formula I and a carrier. The phrase "pharmaceutically acceptable" is employed herein to refer to those compounds, salts, compositions, dosage forms, etc., which are—within the scope of sound medical judgment-suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

The pharmaceutical compositions may be prepared by any suitable means known in the art. Examples of such compositions include those adapted for (a) topical application, e.g., articles (e.g., gauzes, pads, swabs, dressings), creams, ointments, gels, lotions, etc.; (b) parenteral administration, e.g., subcutaneous, intramuscular or intravenous injection as a sterile solution or suspension; (c) oral administration, external application (e.g. drenches including aqueous and non-aqueous solutions or suspensions), tablets, boluses, powders, granules, pellets for admixture with feedstuffs, pastes for application to the tongue, etc.

In certain embodiments, the pharmaceutical compositions may comprise one or more antibiotic agents. As used herein, the term "antibiotic" or "antimicrobial agent" refers to a substance that inhibits the growth of or destroys microorganisms. Preferably, the antibiotic is useful in curbing the virulence of an infectious agent and/or treating an infectious disease. Antibiotic also refers to semi-synthetic substances wherein a natural form produced by a microorganism, e.g., yeast or fungus is structurally modified.

Preferably, the antibiotic is selected from the group consisting of β-lactams (including, β-lactamase inhibitors and cephalosporins), fluoroquinolones, aminoglycosides, tetracyclines and/or glycylcyclines and/or polymyxins. Any combination of antimicrobial agents may also be employed, e.g., at least one β-lactam and at least one fluoroquinolone; at least one aminoglycoside and one cephalosporin; at least one β-lactam and one β-lactamase inhibitor, optionally together with an aminoglycoside, etc.

As used herein, the term "p-lactam" inhibitor includes natural and semi-synthetic penicillins and penicillin derivatives, e.g., benzathine penicillin, benzylpenicillin (penicillin G), phenoxymethylpenicillin (penicillin V), procaine penicillin and oxacillin; methicillin, dicloxacillin and flucloxacillin; temocillin; amoxicillin and ampicillin; azlocillin, carbenicillin, ticarcillin, mezlocillin and piperacillin; biapenem, doripenem, ertapenem, imipenem, meropenem, panipenem and PZ-601; cephalexin, cephalothin, cefazolin, cefaclor, cefuroxime, cefamandole, cefotetan, cefoxitin, cefotaxime, and cefpodoxime; cefepime and cefpirome; cefadroxil, cefixime, cefprozil, cephalexin, cephalothin, cefuroxime, cefamandole, cefepime and cefpirome; cefoxitin, cefotetan, cefmetazole and flomoxef; tigemonam, nocardicin A and tabtoxin; clavulanic acid, moxalactam and flomoxef. Fluoroquinolones include, ciprofloxacin, garenoxacin, gatifloxacin, gemifloxacin, levofloxacin, and moxifloxacin. Aminoglycosides include, for e.g., kanamycin, amikacin, tobramycin, dibekacin, gentamicin, sisomicin, netilmicin, neomycin B, neomycin C, neomycin E (paromomycin) and streptomycin, including, synthetic derivatives clarithromycin and azithromycin. Tetracyclines include naturally-occurring compounds (e.g., tetracycline, chlortetracycline, oxytetracycline, demeclocycline) or semi-synthetic agents (e.g., lymecycline, meclocycline, methacycline, minocycline, rolitetracycline). Glycylcyclines (e.g., minocycline/tigecycline) are derived from tetracyclines. Polymyxins include, e.g., polymyxin B and polymyxin E (colistin).

In certain embodiments, the compositions may contain an antibiotic at a concentration of 0.1 mg/mL, 0.5 mg/L, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL 44 mg/mL, 45 mg/mL, 50 mg/mL, 60 mg/mL, 70 mg/mL, 80 mg/m, 90 mg/mL, 100 mg/mL, 150 mg/mL, 200 mg/mL, 250 mg/mL, 300 mg/mL, 400 mg/mL, 500 mg/mL, or more. For example, imipenem and ertapenem may be used in the concentrations of 50, 30, 20, 15, 10, 5 and 1 mg/mL.

Wound Dressings:

Disclosed herein, in certain embodiments, are wound dressings comprising wound dressing materials as described herein, e.g., compounds of Formula I. In some embodiments, the wound dressings consist essentially of the wound dressing materials as described herein, e.g., a compound of Formula I.

In one embodiment, the wound dressing disclosed herein are biocompatible, biodegradable, non-immunogenic and readily commercially available.

In one embodiment, the compounds of Formula I are provided in the form of particles, such as fiber particles or powder particles, optionally containing a medicament. In particular, the materials preferably contain PG fibers.

The compositions may preferably comprise an intimate mixture of the dressing material and other compounds. For instance, in one embodiment, the intimate mixture comprises a mixed solution or dispersion of the dressing material and a suitable vehicle, such as a solvent, or a solid composition produced by removing solvent from such a solution or dispersion. Under this embodiment, the dressing material makes up at least 5%, more preferably at least 10%, 20%, 30%, 50%, 75%, 90% or greater % by weight of the material. In certain preferred embodiments, the material consists essentially of the dressing material.

Other components of the material may include 0-25% by weight, for example from about 1 to about 20% by weight, of one or more other biocompatible polysaccharides, for example alginates such as sodium alginate or calcium alginate, starch derivatives such as sodium starch glycolate, cellulose derivatives such as methyl cellulose or carboxymethyl cellulose, or glycosaminoglycans such as hyaluronic acid or its salts, chondroitin sulfate or heparan sulfate. The materials may also comprise up to about 25% by weight, for example from about 1 to about 20% by weight, of one or more structural proteins selected from the group consisting of fibronectin, fibrin, laminin, elastin, collagen and mixtures thereof. Preferably the protein comprises collagen, and more preferably it consists essentially of collagen. The materials may also comprise up to about 20% by weight, preferably from about 2% to about 10% by weight of water. The materials may also contain 0-40% by weight, for example from about 5 to about 25% by weight, of a plasticizer, preferably a polyhydric alcohol such as glycerol or sorbitol.

In certain embodiments, the materials may also comprise up to about 10% by weight, for example from about 0.01 to about 5% by weight, typically from about 0.1 to about 2% by weight of one or more therapeutic wound healing agents, such as non-steroidal anti-inflammatory drugs (e.g., acetaminophen), steroids, local anesthetics, antimicrobial agents, or growth factors (e.g., fibroblast growth factor or platelet derived growth factor). The antimicrobial agent may, for example, comprise an antiseptic, an antibiotic, or mixtures thereof. Preferred antibiotics include tetracycline, penicillins, terramycins, erythromycin, bacitracin, neomycin, polymycin B, mupirocin, clindamycin and mixtures thereof. Preferred antiseptics include silver, including colloidal silver, silver salts including salts of one or more of the anionic polymers making up the material, silver sulfadiazine, chlorhexidine, povidone iodine, triclosan, sucralfate, quaternary ammonium salts and mixtures thereof. These medicated wound dressing materials according to the disclosed technology provide sustained release of the therapeutic agents as the wound dressing material breaks down in use.

All of the above percentages are on a dry weight basis. Preferably, the weight ratio of the wound dressing material to other auxiliary agents and materials is from about 1:99 to about 99:1. More preferably, the weight ratio is in the range about 1:9 to about 9:1, more preferably it is in the range about 4:1 to about 1:4, still more preferably in the range about 2:1 to about 1:2.

The material may be in any convenient form, such as a powder, microspheres, flakes, a mat or a film.

In certain embodiments, the material is in the form of a semisolid or gel ointment for topical application.

In certain embodiments, the material is in the form of a freeze-dried or solvent-dried bioabsorbable sponge for application to a chronic wound. Preferably, the average pore size of the sponge is in the region of 10-500 µm, more preferably about 100-300 µm. A suitable sponge has been made by freeze-drying or solvent drying an aqueous dispersion comprising compounds of Formula I, together with suitable therapeutic agents.

In yet other embodiments, the material is in the form of a flexible film, which may be continuous or interrupted (e.g. perforated). The flexible film preferably comprises a plasticizer to render it flexible, such as glycerol.

The ready availability of both gel forming polymers, e.g., cellulose derivatives, having a range of controllable properties means that the properties of the compositions the disclosed technology can be controlled to an exceptional degree. In particular, the rate of biological absorption, porosity and density of the materials can be controlled.

In one embodiment, provided herein are wound dressing materials in sheet form, comprising an active layer of a composition comprising compounds of Formula I. The active layer would normally be the wound contacting layer in use, but in some embodiments it could be separated from the wound by a liquid-permeable top sheet. In one embodiment, the area of the active layer is from about 1 cm$^2$ to about 400 cm$^2$, particularly from about 4 cm$^2$ to about 100 cm$^2$.

In another embodiment, the wound dressing material further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

In embodiments wherein the dressing material comprises a backing sheet, the back sheet is substantially liquid-impermeable. In another embodiment, the backing sheet is semipermeable, e.g., the backing sheet is preferably permeable to water vapor, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 g/m$^2$/24 hrs, preferably 500 to 2000 g/m$^2$/24 hrs at 37.5° C. at 100% to 10% relative humidity difference. The backing sheet thickness is preferably in the range of 10 to 1000 micrometers, more preferably 100 to 500 micrometers.

Suitable polymers for forming the backing sheet include polyurethanes and poly alkoxyalkyl acrylates and methacrylates. Preferably, the backing sheet comprises a continuous layer of a high density blocked polyurethane foam that is predominantly closed-cell. A suitable backing sheet material is a polyurethane film.

In wound dressings comprising a backing layer comprising an adhesive, the adhesive layer should be moisture vapor transmitting and/or patterned to allow passage of water vapor. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane. Polyurethane-based pressure sensitive adhesives may be selectively used.

In another embodiment, the dressing may comprise further layers of a multilayer absorbent article may be built up between the active layer and the protective sheet. For example, these layers may comprise an apertured plastic film to provide support for the active layer in use, in which case the apertures in the film are preferably aligned in register with the apertures in the hydrogel layer.

Still further, in other embodiments, the dressing may comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam. In other embodiments, the absorbent layer may be a nonwoven fibrous web, for example a carded web of viscose staple fibers.

In certain embodiments, the wound dressing may be protected by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the hydrogel layer from the cover sheet. For example, the cover sheet may be formed from a non-adherent plastic such as a fluoropolymer, or it may be provided with a release coating such as a silicone or fluoropolymer release coating.

In one embodiment, the wound dressing is sterile and packaged in a microorganism-impermeable container.

Kits:

In certain embodiments, the disclosed technology provides kits comprising, in one or separate compartments, the compounds of Formula I, optionally together with an excipient, carrier or oil. The kits may further comprise additional ingredients, e.g., gelling agents, emollients, surfactants, humectants, viscosity enhancers, emulsifiers, etc., in one or more compartments. The kits may optionally comprise instructions for formulating an article for diagnosing, detecting or treating wounds, e.g., chronic or infected wounds. The kits may also comprise instructions for using the components, either individually or together, in the treatment of wounds.

In a related embodiment, the disclosed technology provides kits comprising a package and at least one absorbent article (described above) comprising the aforementioned compositions. Alternately, the kits may comprise the individual components separately, optionally together with secondary information, useable in or with the package.

Other embodiments disclosed herein relate to the use of the composition for the preparation of a dressing for the treatment of a wound. Preferably, the wound is a chronic wound, for example a wound selected from the group consisting of venous ulcers, decubitis ulcers and diabetic ulcers.

Surfaces:

Embodiments of the disclosed technology further provide for surfaces comprising the aforementioned compounds of Formula I, wherein the reporter or peptide is oriented to permit binding to a partner, e.g., an enzyme. Preferably, the surface is a surface of a solid support. Numerous and varied solid supports are known to those in the art. Useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as days, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

In one embodiment, the support is a well of an array plate, e.g., a microarray. Methods for constructing such arrays are known in the art, e.g., Cao et al., *Appl Environ Microbiol.*, 77(23): 8219-8225, 2011. Each compound of Formula I (or the peptide indicators alone) may be spotted in triplicate to eliminate irregular data due to physical defects in the array.

Systems:

Embodiments of the disclosed technology further provide for diagnostic systems comprising the aforementioned compositions and/or kits.

The various components of the diagnostic systems may be provided in a variety of forms. For example, the compounds of Formula I {e.g., compounds containing peptide reporters) may be provided as a lyophilized reagent. These lyophilized reagents may be pre-mixed before lyophilization so that when reconstituted they form a complete mixture with the proper ratio of each of the components ready for use in the assay. In addition, the diagnostic systems of the disclosed technology may contain a reconstitution reagent for reconstituting the lyophilized reagents of the kit.

Nucleic Acids

In one embodiment, included herein are nucleic acids encoding the following peptides:

$X_y AAPX_y$-Z, $X_y AAPX_y$-L-Z, $X_y AAP(V/F/A)X_y$-Z or $X_y AAP(V/F/A)X_y$-L-Z; $X_y N^4 N^3 N^2 N^1 X_y$-Z or $X_y N^4 N^3 N^2 N^1 X_y$-L-Z, wherein X, y, N1, N2, N3, N4, L and Z are each, as described above.

In one embodiment, included herein are nucleic acids encoding the following peptide $X_y UUUU_y$-Z, wherein X, y, U and Z are each described above.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 10 nucleotides in length, and most preferably are at least about 40 nucleotides, at least about 100 nucleotides, or at least about 300 nucleotides in length.

Embodiments disclosed herein further relate to variants of the aforementioned polynucleotides.

In one embodiment, included herein are variants of aforementioned nucleic acids which comprise, or alternatively consist of, a nucleotide sequence which is at least 80%, 85%, 90%, 95%, 96%, 97%, 98% or 99%, or greater % identity to, for example, the nucleic acids encoding the following peptides: $X_y AAPX_y$-Z, $X_y AAPX_y$-L-Z, $X_y AAP(V/F/A)X_y$-Z or $X_y AAP(V/F/A)X_y$-L-Z; $X_y N^4 N^3 N^2 N^1 X_y$-Z or $X_y N^4 N^3 N^2 N^1 X_y$-L-Z, wherein X, y, NI, N2, N3, N4, L and Z are each, as described above.

In one embodiment, included herein are variants of aforementioned nucleic acids which comprise, or alternatively consist of, a nucleotide sequence which is at least 80%, 85%, 90%, 95%, 96%, 97%, 98% or 99%, or greater % identity to, for example, the nucleic acids encoding the following peptide $X_y UUUU_y$-Z, wherein X, y, U and Z are each described above.

One skilled in the art can use routine software, e.g., Three-to-One Sequence Manipulation Suite (which generates three potential nucleic acid sequences for each inputted polypeptide sequence), to arrive at the encoding nucleic acid sequences. The Three-to-One software is available freely from bioinformatics(dot)org.

The phrases "percent identity" or "% identity" refer to the percentage of sequence similarity found in a comparison of two or more amino acid or nucleic acid sequences. Percent identity can be determined electronically, e.g., by using the MEGALIGN program (LASERGENE software package, DNASTAR). The MEGALIGN program can create alignments between two or more sequences according to different methods, e.g., the Clustal Method. (Higgins et al., *Gene* 73:237-244, 1988). The CLUSTAL algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein et al. (1990) *Methods Enzymol.* 183:626-645.) Identity between sequences can also be determined by other methods known in the art, e.g., by varying hybridization conditions.

In another embodiment, included herein are variant polynucleotides which hybridize to one or more nucleic acid molecules under stringent hybridization conditions or lower stringency conditions. "Hybridization," as the term is used herein, refers to any process by which a strand of nucleic acid bonds with a complementary strand through base pairing. For example, hybridization under high stringency conditions could occur in about 50% formamide at about 37° C. to 42° C. Hybridization could occur under reduced stringency conditions in about 35% to 25%) formamide at about 30° C. to 35° C. In particular, hybridization could occur under high stringency conditions at 42° C. in 50% formamide, 5 SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "hybridization complex" as used herein, refers to a complex formed between two nucleic acid sequences by virtue of the formation of hydrogen bonds between complementary bases. A hybridization complex may be formed in solution or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

In another embodiment, included herein are variants which are polynucleotide fragments of the aforementioned nucleic acids.

Also included herein are oligonucleotides, e.g., PCR primers, which hybridize to one or more nucleic acids. The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

Also included herein are modified nucleic acids such as PNA. "Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen et al. (1993) *Anticancer Drug Des.* 8:53-63).

Vectors

Also included herein are vectors which contain one or more of the aforementioned nucleic acids. In one embodiment, the vector comprises at least one protein encoding nucleic acid, e.g., nucleic acids encoding the polypeptide sequences for $X_y AAPX_y$-Z, $X_y AAPX_y$-L-Z, $X_y AAP(V/F/A)X_y$-Z or $X_y AAP(V/F/A)X_y$-L-Z; $X_y N^4 N^3 N^2 N^1 X_y$-Z or $X_y N^4 N^3 N^2 N^1 X_y$-L-Z or $X_y UUUU_y$-Z [wherein X, y, N1-N4, L, Z, and U have been described previously] or an enzyme-cleavable fragment thereof and/or an immunogenic fragment thereof, in operable linkage with one or more additional sequences. The additional sequences may be synthetic in nature. The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

Codon Optimized Sequences

Included herein are codon-optimized sequences of the aforementioned nucleic acid sequences and vectors. Codon optimization for expression in a host cell, e.g., bacteria such as E. coli or insect Hi5 cells, may be routinely performed using Codon Optimization Tool (CodonOpt), available freely from Integrated DNA Technologies, Inc., Coralville, Iowa.

Host Cells

Included herein are host cells containing the aforementioned nucleic acid sequences and vectors. In one embodiment, the host cell is capable of recombinantly expressing the gene sequence contained in the vector under standard culture conditions to generate the polypeptide product, e.g., polypeptide sequences for $X_yAAPX_y$-Z, $X_yAAPX_y$-L-Z, $X_yAAP(V/F/A)X_y$-Z or $X_yAAP(V/F/A)X_y$-L-Z; $X_yN^4N^3N^2N^1X_y$-Z or $X_yN^4N^3N^2N^1X_y$-L-Z or $X_yUUUU_y$-Z [wherein X, y, N1-N4, L, Z, and U have been described previously] or an enzyme-cleavable fragment thereof and/or an immunogenic fragment thereof. In one specific embodiment, the host cell is E. coli.

Polypeptides

In one embodiment, included herein are polypeptides comprising the following amino acid sequences: $X_yAAPX_y$-Z, $X_yAAPX_y$-L-Z, $X_yAAP(V/F/A)X_y$-Z or $X_yAAP(V/F/A)X_y$-L-Z; $X_yN^4N^3N^2N^1X_y$-Z or $X_yN^4N^3N^2N^1X_y$-L-Z or $X_yUUUU_y$-Z [wherein X, y, N1-N4, L, Z, and U have been described previously].

In another embodiment, included herein are variants of aforementioned polypeptides which comprise, or alternatively consist of, an amino acid sequence which is at least 80%, 85%, 90%, 95%, 96%, 97%, 98% or 99%, or greater % identity to, for example, the following polypeptide sequences: $X_yAAPX_y$-Z, $X_yAAPX_y$-L-Z, $X_yAAP(V/F/A)X_y$-Z or $X_yAAP(V/F/A)X_y$-L-Z; $X_yN^4N^3N^2N^1X_y$-Z or $X_yN^4N^3N^2N^1X_y$-L-Z or $X_yUUUU_y$-Z [wherein X, y, N1-N4, L, Z, and U have been described previously]. Particularly, the fragment comprises a minimal structural motif for the enzyme recognition site (R) for the enzymes described herein, e.g., lysozyme, elastase, cathepsin G, MAO, proteinase 3C or a combination thereof. Alternately or additionally, the fragment peptides are immunogenic molecules that can be recognized by antibodies or antigen-binding domains thereof.

Homologs

In another embodiment, included herein are homologs to the aforementioned peptides and polynucleotides. The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that nonspecific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of nonspecific binding, the substantially homologous sequence or probe will not hybridize to the second non-complementary target sequence.

Mutants

In another embodiment, included herein are variant peptides comprising a mutation in the core polypeptide sequence for $X_yAAPX_y$-Z, $X_yAAPX_y$-L-Z, $X_yAAP(V/F/A)X_y$-Z or $X_yAAP(V/F/A)X_y$-L-Z; $X_yN^4N^3N^2N^1X_y$-Z or $X_yN^4N^3N^2N^1X_y$-L-Z or $X_yUUUU_y$-Z [wherein X, y, N1-N4, L, Z, and U have been described previously] or an enzyme-cleavable fragment thereof.

In one embodiment, the mutation is a substitution, deletion, addition of 1-3 amino acids. Preferably, the mutation does not change the enzyme recognition sites in the mutant peptides so formed. If the mutation results in a change in the composition of the recognition site or cleavage site, then it is contemplated that the mutation is due to a conserved amino acid substitution, The words "insertion" or "addition," as used herein, refer to changes in an amino acid or nucleotide sequence resulting in the addition of one or more amino acid residues or nucleotides, respectively, to the sequence found in the naturally occurring molecule. A "substitution," as used herein, refers to the replacement of one or more amino acids or nucleotides by different amino acids or nucleotides, respectively.

Antibodies

Embodiments disclosed herein further include antibodies which bind specifically to one or more of the aforementioned immunogenic peptides.

In one embodiment, the antibodies bind to polypeptides comprising the following amino acid sequences: $X_yAAPX_y$-Z, $X_yAAPX_y$-L-Z, $X_yAAP(V/F/A)X_y$-Z or $X_yAAP(V/F/A)X_y$-L-Z; $X_yN^4N^3N^2N^1X_y$-Z or $X_yN^4N^3N^2N^1X_y$-L-Z or $X_yUUUU_y$-Z [wherein X, y, N1-N4, L, Z, and U have been described previously]. In another embodiment, the antibodies bind to fragment of these polypeptides. Contemplated herein are antigen-binding fragments of such antibodies, e.g., F(ab) domain, $F(ab)_2$ domains, scFv domains, including synthetically generated antibodies (using, e.g., phase display technology).

In one embodiment, the antibodies bind to polypeptide sequences for $X_yAAPX_y$-Z, $X_yAAPX_y$-L-Z, $X_yAAP(V/F/A)X_y$-Z or $X_yAAP(V/F/A)X_y$-L-Z; $X_yN^4N^3N^2N^XX_y$-Z or $X_yN^4N^3N^2N^XX_y$-L-Z or $X_yUUUU_y$-Z [wherein X, y, N1-N4, L, Z, and U have been described previously] or an enzyme-cleavable fragment thereof and/or an immunogenic fragment thereof. Contemplated herein are antigen-binding fragments of such antibodies, e.g., F(ab) domain, $F(ab)_2$ domains, scFv domains, including synthetically generated antibodies (using, e.g., phase display technology).

Purified Molecules

Included herein are purified biomolecules, e.g., nucleic acids, proteins, peptides, and/or antibody molecules, including, conjugates thereof. The term "substantially purified," as used herein, refers to nucleic acids, amino acids or antibodies that are removed from their natural environment and are isolated or separated, and are at least about 60% free, preferably about 75% free, and most preferably about 90% free from other components with which they are naturally associated.

In embodiments described herein, the biomolecules may be altered by combining with various components of the chemical entities, e.g., anchor region and/or indicator region, such that their form and/or functionality is significantly changed compared to any natural counterparts.

Methods of Making Compounds of Formula I:

Embodiments provided herein further relate to methods of making compounds of Formula I, including precursors thereof. The term "precursor" includes any compound which is employed as a reactant to generate an intermediary or a final product.

In one embodiment, provided herein is a method of making a compound of Formula I comprising the structure A-R-I, wherein, A is an anchor as described above and I is an indicator as described above, comprising, conjugating the anchor with the indicator molecule, e.g., via covalent bond. In one embodiment, the anchor or the indicator may comprise a recognition site (R) for a wound-specific marker, e.g., a wound-specific enzyme such as a hydrolase, and more specifically a protease or glycosidase, as described before. Under this embodiment, the substrate for the wound-specific marker comprises, for example, a hydrolysable substrate, e.g., an amino acid, a sugar, a peptide, a polysaccharide, a nucleic acid, a lipid, a lactam or a combination thereof.

In one embodiment, the anchor is conjugated to the reporter molecule via a peptide linkage, a glycosidic linkage, an amide linkage, an ester linkage, an ether linkage, an anhydride linkage or a similar linkage. As used herein, a "peptide bond" is formed by the condensation reaction between two amino acids, wherein the acid moiety of one reacts with the amino moiety of the other to produce a peptide bond (—CO—H—) between the two amino acids. In one embodiment, the peptide bond is cleaved with a wound-specific protease, e.g., elastase, cathepsin G, proteinase C, or MAO, or a combination thereof. As used herein, a "glycosidic bond" is formed between the hemiacetal or hemiketal group of a saccharide (or a molecule derived from a saccharide) and the hydroxyl group of some compound such as an alcohol. In one embodiment, the peptide bond is cleaved with a wound-specific glycosidase, e.g., lysozyme. A lactam bond is formed between an amide and a lactone and is found in the core structure of many antibiotics. In one embodiment, the lactam bond is cleaved by a beta-lactamase.

Methods for conjugating reactive moieties to generate glycosidic, peptide, ester, oxyester, amide, amido, oxyamido, ether, sulfonyl, sulfinyl, sulfonamide, or other linkages such as alkoxy, alkylthio, alkylamino, etc. are known in the art and are further described in the examples.

In another embodiment, provided herein is a method of making a compound of Formula I comprising the structure A-I, wherein, A and I are each, as described previously.

In one embodiment, the A is conjugated to the I via a glycosidic linkage or a peptide linkage.

In another embodiment, the A is conjugated to the I via a hydrophilic or hydrophobic linkage.

In one embodiment, the compound of Formula I having the structure A-I is synthesized by first conjugating the anchor region A with the indicator region I to generate the compound of Formula I.

In another embodiment, the indicator is first synthesized via genetic recombinant technology, e.g., expressing a nucleic acid encoding the indicator region in a suitable host cell, and combining the indicator with the anchor region. Under this embodiment, in one instance, the indicator region is designed to contain nucleic acid sequences which bind to the anchor region, e.g., hydrophilically or hydrophobically. One representative example of a hydrophilic interaction comprises use of an anchor containing polar groups, e.g., partially carboxylated sugar or peptidoglycan, which interacts with polar amino acids in the indicator molecule. Another representative example of a hydrophobic interaction comprises use of an anchor containing non-polar groups, e.g., amidated or esterified side chains (or a derivative thereof), which interacts with hydrophobic amino acid residues in the indicator molecule.

In one embodiment, peptide indicators, e.g., polypeptides comprising the following amino acid sequences: $X_y AAPX_y$-Z, $X_y AAPX_y$-L-Z, $X_y AAP(V/F/A)X_y$-Z or $X_y AAP(V/F/A)X_y$-L-Z; $X_y N^4 N^3 N^2 N^1 X_y$-Z or $X_y N^4 N^3 N^2 N^1 X_y$-L-Z or $X_y UUUU_y$-Z [wherein X, y, N1-N4, L, Z, and U have been described previously], (including variant polypeptides) may be synthesized via host-cell expression systems. Such a method may comprise, for example, generating a construct encoding one or more of the aforementioned polypeptides or variants, placing said construct in a suitable vector, e.g., plasmid vector or baculovirus vector, transfecting a host cell, e.g., E coli or insect Hi5 cells, with the vector; culturing the host cells under suitable conditions to allow expression of said vector; and optionally purifying the expressed polypeptide from the culture.

In another embodiment, peptide indicators, e.g., polypeptides comprising the following amino acid sequences: $X_y AAPX_y$-Z, $X_y AAPX_y$-L-Z, $X_y AAP(V/F/A)X_y$-Z or $X_y AAP(V/F/A)X_y$-L-Z; $X_y N^4 N^3 N^2 N^1 X_y$-Z or $X_y N^4 N^3 N^2 N^1 X_y$-L-Z or $X_y UUUU_y$-Z [wherein X, y, N1-N4, L, Z, and U have been described previously] (including variant polypeptides) may be synthesized using solid-phase peptide synthesis (see, Merrifield et al., *J. Am. Chem. Soc.* 85 (14): 2149-2154).

Still further, the compound of Formula I having the structure A-R-I may be synthesized in a single reaction chamber or multiple reaction chambers.

Diagnostic and Therapeutic Methods:

In one embodiment, the compositions, dressing materials, articles, kits and systems described herein are useful in diagnosing or treating wounds, particularly chronic or infected wounds. Although any type of wound may be diagnosed and/or treated, the embodiments are particularly suitable for diagnosing and treating wounds that exude wound fluid. For example, the wound may be a chronic or acute wound. Representative examples of chronic wounds include, e.g., venous ulcers, pressure sores, decubitis ulcers, diabetic ulcers and chronic ulcers of unknown aetiology. Representative examples of acute wounds include, e.g., acute traumatic laceration, perhaps resulting from an intentional operative incision.

As used herein, the term "a wound fluid" refers to any wound exudate or other fluid (suitably substantially not including blood) that is present at the surface of the wound, or that is removed from the wound surface by aspiration, absorption or washing. The determining, measuring or quantifying is suitably carried out on wound fluid that has been removed from the body of the patient, but can also be performed on wound fluid in situ. The term "Wound fluid" does not normally refer to blood or tissue plasma remote from the wound site. The wound fluid is mammalian wound fluid, suitably human wound fluid.

In one embodiment, the diagnostic method comprises contacting a wound with at least one composition comprising a compound of Formula I or Formula II, a dressing material comprising such compounds, article comprising such materials or compounds, kits comprising such materials or compounds, or a system comprising such materials or compounds described herein; and measuring a parameter associated with the wound. In a specific embodiment, the parameter being measured is a level or activity of a wound-specific hydrolase. Particularly, the parameter being measured is the activity of the hydrolase.

In the aforementioned embodiments, the measurement may either be made in situ or ex situ. As used herein, the term "in situ" refers to processes, events, objects, or components that are present or take place within the context of the system or device, including, the surrounding environment, for example, the biological material with which the composition, article, system or device is in contact with. As an example, an in situ reaction may refer to the reaction of the various components present in the device (e.g., compound of Formula I or Formula II), including, components provided by the human skin tissue (e.g., wound exudate containing the enzyme). The term is contrasted with ex situ, which refers to outside of the environment.

In a second embodiment, the measurement is performed ex situ, e.g., removing the fluid from the wound for analysis in the apparatus or device of the disclosed technology.

Suitably, the measurement is made in situ.

In one diagnostic embodiment, the method comprising determining a level of a reporter, e.g., a product of a substrate acted upon by a wound-specific enzyme. More specifically, the method comprises determining a level of a hydrolase enzyme product. As used herein, the term "determining" includes measuring a numerical value of the activity or level of said hydrolase; establishing if the activity or level falls above or below a predetermined range; and/or comparing the numerical value of activity or level with a control standard. The control standard may comprise determining a level or activity of the hydrolase in a biopsy material obtained from an unwounded site or from a healthy subject.

In one specific embodiment, the term "determining" comprises measuring the parameter {e.g., activity or level) of at least one wound specific enzyme selected from lipase, esterase, peroxidase, oxidase, glycosidase, glucuronidase, glucosidase, galactosidase, napsin (aspartyl protease), glucosylceramidase glucuronidase, palmitoyl protein thioesterase, Cathepsins A, B, D, G, L, S, Z; acid ceramidase, lactoferrin (LF), lysozyme, myeloperoxidase (MPO), elastase, cathepsins, and proteinase-3 or a combination thereof; establishing if said parameter exceeds a first predetermined threshold; and/or comparing the numerical value of parameter with a control standard. The control standard may comprise determining a parameter of the protease in a biopsy material obtained from an unwounded site or from a healthy subject. In related embodiments, the term "determining" comprises establishing whether a weighted average (weighted sum) of the parameters associated with a plurality of the aforementioned proteases exceeds a predetermined threshold value for said weighted average.

In one particular embodiment, the parameter is activity level of the analyte {e.g. a protease) in a wound fluid. Typically, the activity of an individual analyte is expressed in terms units/mL.

In another embodiment, the parameter is the level of the analyte {e.g., protease) in a wound fluid. Typically, the term amount is also indicative of the activity of a particular analyte.

When used herein, the term "combined amount" or "combined activity" refers to a single numerical value that results from the application of a mathematical function to a plurality of values, for example those amounts obtained for a number of individual analytes. For example, the term "combined amount" or "combined activity" may refer to the sum or product of a group of individual values. Typically, the term "combined amount" or "combined activity" relates to the sum of a group of individual values. For example, in suitable embodiments, the amount of elastase refers to elastase-like activity (e.g., U/mL) and the amount of metalloproteinase (MMP) refers to total concentration of the respective analyte (e.g., in ng/mL).

When used herein, the term "quantifying" refers to measuring an absolute numerical quantity of a particular analyte(s) or substrate(s) in a sample, within the margins of experimental error.

The term "marker" or "analyte" refers to any chemical entity that is identified or determined using the apparatus, devices, kits or methods defined herein. The markers or analytes determined or identified by the apparatus, devices, kits or methods of the disclosed technology are cleaved products of the aforementioned enzymes.

When used herein, the term "predetermined range" refers to a data range or profile that the skilled person would understand is indicative of a particular sub-class of patient. For instance, the predetermined range may be a data range or profile that is typical of a wound that would respond well to a particular wound treatment, such as antibiotic therapy. Alternatively, the predetermined range may suitably refer to a data range that is typical of a wound that would not respond well to a particular wound treatment, such as antibiotic therapy.

When used herein, the term "predetermined threshold" refers to a minimum level that the skilled person would determine is indicative of a non-healing wound based on statistical analysis of levels determined for known healing and non-healing wounds, for example as explained further above. For the test to be clinically useful, the threshold should be set at an appropriate level so that non-healing wounds with high protease activity are correctly identified. Increasing the threshold will increase the chance of only non-healing wounds being over the threshold. However, if the threshold is too high, wounds that are non-healing due to a high level of proteases would not be identified and clinically this would mean they would not receive the required protease modulating treatment.

When used herein, the term "control standard" or "control" refers to a data set or profile that can be used as a reference or comparison in order to define or normalize another data point or set of data. For instance, the term "control" or "control standard" may be data set or profile that is indicative of a particular sub-class of patient. Suitably, the control standard may be a data set or profile indicative of healing or non-healing wound status.

Suitably, in other aspects or embodiments of the disclosed technology, the "control" or "control standard" can be a data set or profile that can be used as a comparative tool to allow a skilled person to determine whether a wound is likely to be responsive or non-responsive to a wound treatment, such as antibiotic therapy. In one embodiment, the control standard is a data set or profile indicative of a patient that does not respond well to wound treatment. Typically, the control standard is a data set or profile indicative of a patient that responds well to wound treatment. Patients that tend to respond well to wound treatment as disclosed herein exhibit lower combined amount or activity of hydrolases than patients that tend not to respond well to the treatment. For example, patients that tend to respond well to wound treatment as disclosed herein exhibit lower combined amounts of at least one wound-specific hydrolase.

In one embodiment, the threshold human neutrophil elastase activity is about 5 U/mL to about 30 U/mL, including all values in between, e.g., about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL, about 21 U/mL, about 22 U/mL, about 23 U/mL, about 24 U/mL, about 25 U/mL, or more, indicate chronic wound infection.

In one specific embodiment, the threshold human neutrophil elastase activity levels of at least 9.6 indicate chronic wound infection. In some embodiments, human neutrophil elastase activity levels of at least 22.9 U/mL indicate chronic wound infection.

In one embodiment, the threshold lysozyme activity levels of about 1000 U/mL to about 10000 U/mL, including all values in between, e.g., about 1100 U/mL, about 1200 U/mL, about 1300 U/mL, about 1400 U/mL, about 1500 U/mL, about 1600 U/mL, about 1700 U/mL, about 1800 U/mL, about 1900 U/mL, about 2000 U/mL, about 2100 U/mL, about 2200 U/mL, about 2300 U/mL, about 2400 U/mL, about 2500 U/mL, about 2600 U/mL, about 2700 U/mL, about 2800 U/mL, about 2900 U/mL, about 3000 U/mL, about 3250 U/mL, about 3500 U/mL, about 3750 U/mL, about 4000 U/mL, about 4250 U/mL, about 4500 U/mL, about 4750 U/mL, about 5000 U/mL, about 5250 U/mL, about 5500 U/mL, about 5750 U/mL, about 6000 U/mL, or more, indicate chronic wound infection. In one specific embodiment, lysozyme activity levels of at least 4800 U/mL indicate chronic wound infection.

In one embodiment, the threshold cathepsin G activity levels of about 10 U/mL to about 100 U/mL, including all values in between, e.g., about 15 U/mL, about 20 U/mL, about 25 U/mL, about 30 U/mL, about 35 U/mL, about 40 U/mL, about 45 U/mL, about 50 U/mL, about 55 U/mL, about 60 U/mL, about 65 U/mL, about 70 U/mL, about 75 U/mL, about 80 U/mL, about 85 U/mL, about 90 U/mL, about 95 U/mL, about 100 U/mL, about 110 U/mL, about 120 U/mL, or more, indicate chronic wound infection. In some embodiments, cathepsin G activity levels of at least 50 U/mL, at least 40 U/mL, at least 30 U/mL, at least 20 U/mL, at least 15 U/mL or at least 10 U/mL indicates chronic wound infection.

Embodiments disclosed herein further relate to treatment of chronic or infected wounds using the compositions, materials, articles, dressings, kits and/or systems described herein. The therapeutic embodiment includes, contacting a composition, material, article, dressing, kit, system or devices of the disclosed technology with a subject in need thereof. Optionally, the method may include determination of whether the subject is responding to the treatment.

The skilled person would be able to easily identify whether wounds are "responsive to treatment" or not. In particular, the skilled person will readily be able to determine the levels of the proteases identified in the present claims that are predictive or indicative of a good response or poor response to wound treatment, particularly to treatment with wound dressings comprising oxidized cellulose. The terms "responsive" and "responder(s)" as used herein refer to wounds that are considered to respond well to wound treatment, particularly to treatment with a pharmacological agent, e.g., antibiotics. Similarly, "non-responsive" and "non-responder(s)" refers to wounds that are not considered to respond well to wound treatment, particularly to treatment with the pharmacological agent, e.g., antibiotics. For instance, patients who exhibit better than 50% wound closure after 4 weeks of wound treatment are considered to be responsive to said treatment.

In certain embodiments, a patient may be simultaneously diagnosed and treated with the compositions, articles, systems, or devices described herein. When used herein, the term "simultaneously" means performing the stated objectives, e.g., diagnosis and treatment, together.

In certain embodiments, a patient may be sequentially diagnosed and treated with the compositions, articles, systems, or devices described herein. When used herein, the term "sequentially" means the stated objectives, e.g., diagnosis and treatment, are temporally or spatially separated, e.g., diagnosis prior to treatment or diagnosis following treatment or a combination thereof, e.g., $1^{st}$ diagnosis==>treatment==>$2^{nd}$ diagnosis.

Embodiments described herein further enable a care giver or a patient to determine quickly and reliably whether a wound is likely to be non-healing, and to select an appropriate therapy based on this determination. For example, non-healing wounds may require the application of special wound dressings such as wound dressings comprising specific therapeutic agents, to promote healing. Accordingly, embodiments described herein further provide methods of treatment of a wound, e.g., chronic or infected wounds, comprising determining whether a wound is healing or non-healing, followed by applying a wound dressing comprising a therapeutic agent to the wound if it is non-healing.

Embodiments described herein provide methods and assays for diagnosis or detection of infected wounds. The methods are suitable for the detection of bacterial infectious agents. In one embodiment, the wounds are infected with gram-negative bacteria. Typical gram-negative bacteria include proteobacteria such as *E. coli*, *Salmonella*, *Pseudomonas*, and *Helicobacter*, and cyanobacteria. When classified in connection with medicine, they include *Pseudomonas aeruginosa* and Hemophilus *influenzae* causing the disturbance of the respiratory system, *Escherichia coli* and *Proteus mirabilis* causing the disturbance of the urinary system, and *Helicobacter pylori* and *Bacillus gaertner* causing the disturbance of the alimentary system and micrococci such as *Neisseria meningitidis*, *Moraxella catarrhalis*, and *Neisseria gonorrhea*.

In another embodiment, the wounds are infected with gram-positive bacteria. By "gram-positive bacteria" is meant a bacterium or bacteria that contain(s) teichoic acid {e.g., lipoteichoic acid and/or wall teichoic acid), or a functionally equivalent glycopolymer {e.g., a rhamnopolysaccharide, teichuronic acid, arabinogalactan, lipomannan, and lipoarabinomannan) in its cell wall. Non-limiting examples of functionally equivalent glycopolymers are described in Weidenmaier et al, *Nature*, 6:276-287, 2008.

The bacteria include pathogenic bacteria that infect mammalian hosts {e.g., bovine, murine, equine, primate, feline, canine, and human hosts). Examples of such pathogenic bacteria include, e.g., members of a bacterial species such as *Bacteroides*, *Clostrdium*, *Streptococcus*, *Staphylococcus*, *Pseudomonas*, *Haemophilus*, *Legionella*, *Mycobacterium*, *Escherichia*, *Salmonella*, *Shigella*, *Vibrio*, or *Listeria*. Some clinically relevant examples of pathogenic bacteria that cause disease in a human host include, but are not limited to, *Bacillus anthracis*, *Bacillus cereus*, *Bordetella pertussis*, *Borrelia burgdorfen*, *Brucella aborus*, *Brucella canis*, *Brucella melitensis*, *Brucella suis*, *Campylobacter jejuni*, *Chlamydia pneumoniae*, *Chlamydia psittaci*, *Chlamydia trachomatis*, *Clostridium botulinum*, *Clostridium difficile*, *Clostridium perfringens*, *Clostridium tetani*, *Coryne bacterium diphtheriae*, *Enterococcus faecalis*, vancomycin-resistant *Enterococcus faecalis*, *Enterococcus faecium*, *Escherichia coli*, enterotoxigenic *Eschenchia coli* (ETEC), enteropathogenic *Escherichia coli*, *E. coli* 0157.H7, *Francisella tularensis*, *Haemophilus infuenzae*, *Helicobacter pylori*, *Legionella pneumophila*, *Leptospira interrogans*, *Listeria monocytogenes*, *Mycobacterium leprae*, *Mycobacterium tuberculosis*, *Mycoplasma pneumoniae*, *Neisseria* gonorrhoeae, Neisseria meningitidis, Proteus, Pseudomonas aeruginosa, Rickettsia rickettsii, Salmonella typhi, Salmonella typhimurium, Shigella sonnei, Staphylococcus aureus, Staphylococcus epidermis, Staphylococcus saprophyticus, methicillin-resistant Staphylococcus aureus (MRSA), vancomycin-resistant Staphylococcus aureus (VSA), Streptococcus agalactiae, Streptococcus pneumoniae, Streptococcus pyogenes, Treponema pallidum, Vibrio cholerae, and Yersinia pestis.

In another embodiment, the infectious bacteria is selected from the group consisting of Clostridium difficile, Carbapenem-Resistant Enterobacteriaceae (CR-Klebsiella spp; CR-E. coli), and Neisseria gonorrhoeae. In another embodiment, the infectious bacteria is selected from the group consisting of multidrug-resistant Acinetobacter, drug-resistant Campylobacter, extended spectrum β-Lactamase (ESBL)-producing enterobacteriaceae, vancomycin-resistant enterococcus, multidrug-resistant Pseudomonas aeruginosa, drug-resistant non-typhoidal Salmonella, drug-resistant Salmonella enterica serovar Typhi, drug-resistant Shigella, methicillin-resistant Staphylococcus aureus (MRSA), drug-resistant Streptococcus pneumoniae, and drug-resistant Tuberculosis. In another embodiment, the infectious bacteria is selected from the group consisting of vancomycin-resistant Staphylococcus aureus, erythromycin-resistant Group A Streptococcus, clindamycin-Resistant Group B Streptococcus.

In certain embodiments, the chronic or infected wounds are found in host subjects. Preferably, the hosts are mammals, e.g., a rodent, a human, a livestock animal, a companion animal, or a non-domesticated or wild animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoo animal. As used herein, a "zoo animal" refers to an animal that may be found in a zoo. Such animals may include non-human primates, large cats, wolves, and bears. In an exemplary embodiment, the subject is a human.

In one aspect, provided herein are methods of detecting levels of one or more enzymes in a mammalian wound, the method comprising the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

Preferably, the diagnosis and treatment is conducted in situ. Embodiments described herein therefore allow diagnosis and treatment of wounds in an easy, non-invasive manner. For instance, the diagnosis may be made in real time and the treatment may be applied to the infected wound or to the patient (systemically) and the progress of wound treatment be monitored over real-time, e.g., dissipation of the signal generated by the reporter molecule due to wound-healing.

In another aspect, provided herein are methods of detecting protease activity in wounds using a chemical entity, wherein the chemical entity comprises one or more components selected from the group consisting of: an anchor region, an enzyme-labile or enzyme-reactive region, and an indicator region. In another aspect, the method compromises placing substrates for MPO, elastase, lysozyme, phospholipase, and catalase on a solid surface such that any reaction is visible to the eye. In another aspect, the method serves to assess a variety of body fluids including wound, tear, vitreal, CSF, airway aspirates or sputum, synovial, blood, plasma, serum, urine, peritoneal, interstitial, subcutaneous, bile, intestinal or similar fluids, via contacting them with a material containing the substrates and assessing the change of the substrates thereafter.

In another aspect, provided herein are methods of detecting infection in an airway, comprising contacting the chemical entities with the fluid from the infected organ either via specific sampling or via long-term contact with a ventilation device.

EXAMPLES

The structures, materials, compositions, and methods described herein are intended to be representative examples, and it will be understood that the scope of the disclosure is not limited by the scope of the examples. Those skilled in the art will recognize that the embodiments and disclosed technology may be practiced with variations on the disclosed structures, materials, compositions and methods, and such variations are regarded as within the ambit of the disclosure.

All ionic compounds were handled and isolated as salts with various counter ions, depending on the last step and not further specified.

The "molecular weight" of poly-p-nitrophenylacrylates was determined as virtual molecular mass by reaction with ethanolamine in DMF and quantitation of the released nitrophenol in IN NaOH at 405 nm. Virtual molecular mass=g of material/reactive site. "H-RBB" refers to the reaction product of Remazol Brilliant Blue R® with ammonia (see example 29), "RBB" to the respective radical the terminus, "H—" in compound names refers to hydrogen, not histidine; "normal conditions" means room temperature, atmospheric pressure, no protective means against humidity or oxygen; Peptide fragments are synthesized by conventional methods known to those skilled in the art; any peptides are described via the one-letter code; nevertheless single letters may also refer to hetero atoms; "CV" means Bis-(4-dimethylaminophenyl)-(4-[N-piperazino]phenyl)-carbenium ion, a derivative of crystal violet.

Example 1. Fmoc-AAPV-Indoxyl ester [SEQ ID NO: 2]

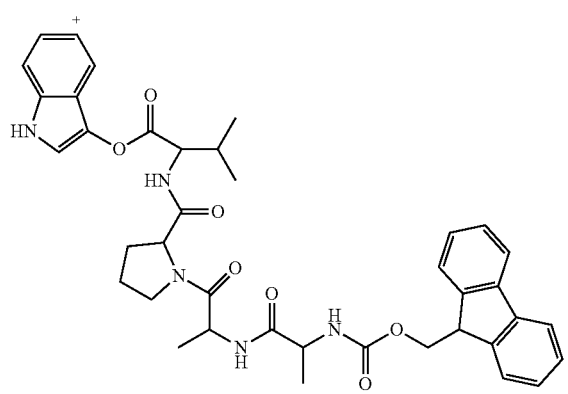 [SMILES: CC(NC(=O)OCC1c2ccccc2-c2ccccc21)C(=O)NC(C)C(=O)N1CCCC1C(=O)NC(C(=O)Oc1c[nH]c2c1=C[C+]=CC=2)C(C)C]

Fmoc-AAPV-OH [SEQ ID NO: 9] (43.47 g, 75.12 mmol) and CDI (14.62 g, 90.19 mmol) were weighed directly into a 500 mL round bottom flask via powder funnel. DCM (dry, 120 mL) was added directly to the flask, additional DCM (dry, 30 mL) was used to wash the powder funnel and was added to the flask as well. The mixture was stirred at RT under argon atmosphere for 15 min and then additional 45 min while passing argon through the mixture. Then the indoxyl was added in one portion using a powder funnel; funnel was washed with DCM (dry 10 mL) which was added to the reaction mixture as well. Stirring at RT while passing argon through the reaction mixture was continued for 1 h, then additional DCM (dry, 20 mL) was added and stirring at RT while passing argon through the mixture was continued for 10 min. Afterwards the mixture was stirred at RT under argon atmosphere overnight. The reaction mixture was filtered via Buchner-funnel with filter paper and filled into a separation funnel. The reaction flask was washed with DCM (30 mL), the wash-DCM was filtered via the Buchner funnel as well and filled into the separation funnel, too. Water (350 mL) was added to the separation funnel; after extraction the organic phase was collected. The separation funnel was washes with acetone until no more colour was washed out, then it was filled with water completely and emptied again. The organic phase was refilled into the separation funnel and washed with water (350 mL) once more. After phase separation the organic phase was collected in a clean Erlenmeyer flask, dried (Na2SO4, 40.56 g), and concentrated to dryness. The crude product was suspended in diethy ether (600 mL) and stirred at RT for 2 h. The solid was filtered off via glass frit. Some solid stuck to the flask; it was dissolved in DCM (50 mL), concentrated to dryness and added to the rest of the solid. All the solid was resuspend in diethy ether (600 mL) and stirred at RT overnight. Afterwards the solid was filtered off via glass frit again. Solid sticking to the flask was dissolved in DCM (50 mL), concentrated to dryness and combined with the rest of the solid. The product was kept at RT covered with a filter paper with holes for 7 days and was then dried at the oil pump (RT, 2 h, 0.008 mbar) to yield 41.4 g (79.4%) of the product.

Example 2.
Fmoc-AAPV-5-Bromo-4-Chloro-Indoxyl ester
[SEQ ID NO: 2]

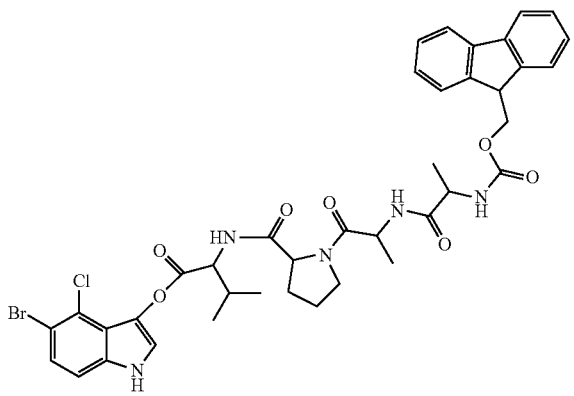 [SMILES: CC(NC(=O)OCC1c2ccccc2-c2ccccc21)C(=O)NC(C)C(=O)N1CCCC1C(=O)NC(C(=O)Oc1c[nH]c2ccc(Br)c(Cl)c12)C(C)C]

Fmoc-AAPV-OH [SEQ ID NO: 9] (117 mg, 0.20 mmol) and CDI (39 mg, 0.24 mmol) were dissolved in DCM (dry, 3 mL) and stirred at RT under argon atmosphere for 5 min. Then the mixture was stirred at RT for 5 min while passing argon through the mixture before 5-bromo-4-chloro-indoxyl (50 mg, 0.20 mmol) was added in one portion. Passing argon through the mixture was continued for 5 min, additional DCM (dry, 2 mL) was added and the mixture was stirred at RT under argon atmosphere for 3.5 h. Afterwards the reaction mixture was concentrated to dryness and stored in the freezer under argon atmosphere for 18 d. The crude product was chromatographied: 15.8 g silica gel, eluent: 2% MeOH in DCM. A blue solid (42 mg), still contaminated, was obtained. The product was chromatographed a second time: 13.7 g silica gel, eluent: starting eluent EtOAc/cyclohexane (3:1, 200 mL) the change to pure EtOAc. An almost colorless solid (32 mg) was obtained. ESI-MS (positive): $[M+H]^+$: 805, $[M+Na]^+$: 828, $[M+K]^+$: 844

Example 3 Fmoc-AAAPV-Indoxyl ester [SEQ ID NO: 10]

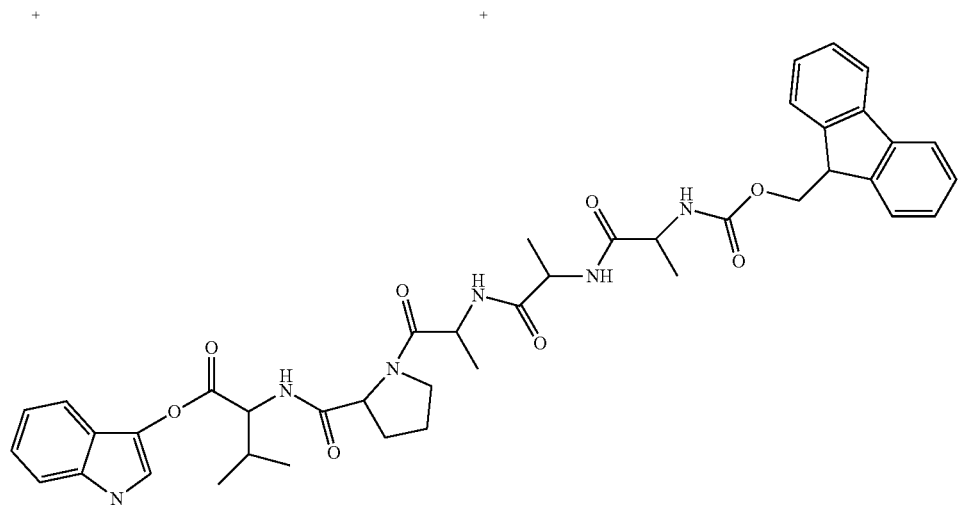 [SMILES: CC(NC(=O)OCC1c2ccccc2-c2ccccc21)C(=O)NC(C)C(=O)NC(C)C(=O)N1CCCC1C(=O)NC(C(=O)Oc1c[nH]c2ccccc12)C(C)C]

Fmoc-AAAPV-OH [SEQ ID NO: 11] (361 mg, 0.56 mmol) and HOBt »H₂O (127 mg, 0.94 mmol) were dissolved in DCM (3 mL) at room temperature under argon atmosphere. DIPEA (190 µE, 0.90 mmol) and EDCMTCI (179 mg, 0.93 mmol) were added. The mixture was stirred under argon atmosphere at room temperature for 2 h. Then indoxyl (55 mg, 0.41 mmol) was added in one portion while argon was passed through the moxture. passing argon through the reaction mixture was continued for 5 min more minutes; then additional DCM (2 mL) was added and the mixture was stirred under argon atmosphere at room temperature overnight. DCM (20 mL) was added and the mixture was extracted with aq. sat. $NaHCO_3$ (for an acceleration of the phase separation, brine (5 mL) was added). The organic phase was washed with brine (15 mL), dried ($Na_2SO_4$) and concentrated to dryness. The crude product was purified by column chromatography (15.0 g silica gel, 40-63 πI) starting with DCM as the solvent. The column was eluted with DCM until all blue and pink color was washed down the column. Then eluent was changed to 5% MeOH in DCM. A colorless product (88 mg) and a slightly pink (contaminated) solid (49 mg) were collected.

Example 4. Fmoc-AAAPV-(N-acetyl)-indoxyl ester
[SEQ ID NO: 10]

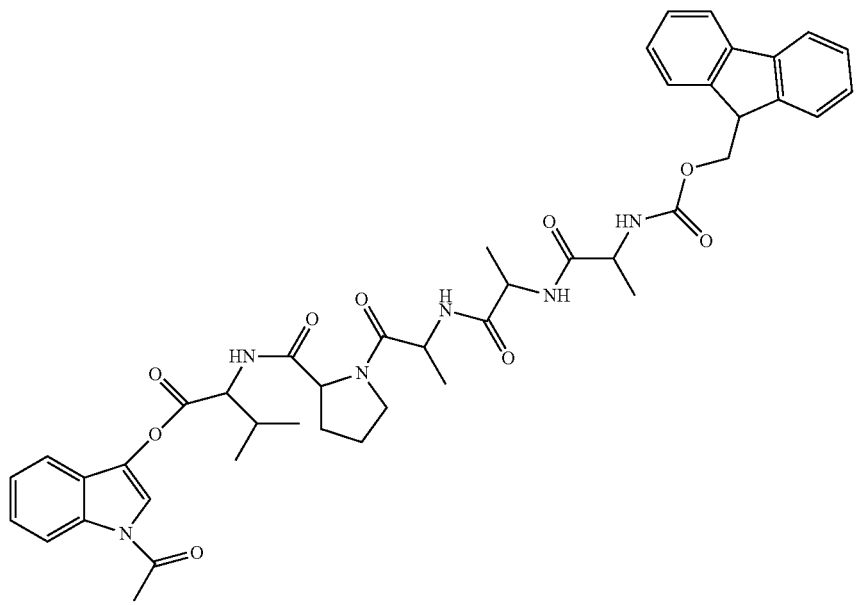 [SMILES: CC(=O)n1cc(OC(=O)C(NC(=O)C2CCCN2C(=O)C(C)NC(=O)C(C)NC(=O)C(C)NC(=O)OCC2c3ccccc3-c3ccccc32)C(C)C)c2ccccc21]

Fmoc-AAAPV-OH (305 mg, 0.428 mmol) [SEQ ID NO: 11] and $HOB_t·H_2O$ (97.5 mg, 0.47 mmol) were dissolved in DMF (2 mL) at room temperature under argon atmosphere. After 5 min, DIPEA (145.6 µL, 0.86 mmol) and EDCl·HCl (138 mg, 0.72 mmol) were added. The mixture was stirred at room temperature under argon atmosphere for 1 h (Mixture 1). In parallel indoxylacetate (50 mg, 0.285 mmol) was dissolved in DMF (2 mL) at room temperature under argon atmosphere. Argon was passed through the solution for 5 min before NaOMe (15 mg, 0.270 mmol) was added. Passing argon through the mixture was continued for additional 20 min (Mixture 2). Mixture 1 was added to Mixture 2 within a few seconds. A stream of argon was purged through the reaction mixture for 2 h then the mixture was stirred under argon atmosphere overnight. The mixture was concentrated to dryness, re-dissolved in EtOAc (50 mL), washed with aq. sat. $NaHCO_3$ (2×30 mL), water (1×20 mL) and brine (1×30 mL). The organic phase was dried ($Na_2SO_4$) and concentrated to dryness. The crude product was purified by column chromatography (15.0 g silica gel, 40-63 πI, eluent: DCM) to yield 33 mg of the solid product. ESI-MS (positive): $[M+H]^+$: 807; $[M+Na]^+$: 829.

Example 5: Fmoc-AAAPV-3-Indolamide [SEQ ID NO: 10]

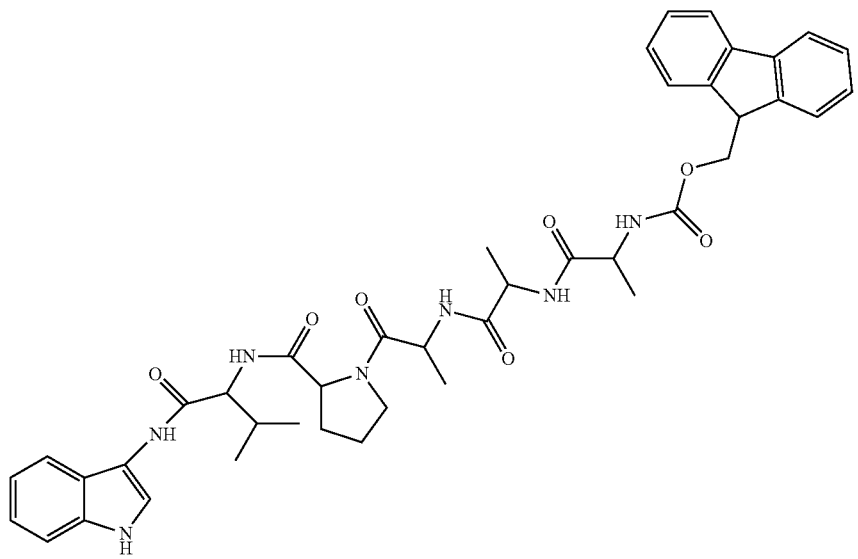 [SMILES: CC(NC(=O)OCC1c2ccccc2-c2ccccc21)C(=O)NC(C)C(=O)NC(C)C(=O)N1CCCC1C(=O)NC(C(=O)Nc1c[nH]c2ccccc12)C(C)C]

Fmoc-AAAPV-OH [SEQ ID NO: 11] and HOBt*H₂O were dissolved in DCM (dry.) in a 25 mL two necked round bottom flask at room temperature under argon atmosphere. DIPEA and EDCI*HCl were added. The mixture was stirred under argon atmosphere at room temperature for 1 h; then argon was passed through the mixture for 5 min. IH-Indol-3-amine was added in one portion and passing argon through the mixture is continued for 5 min. Then additional DCM (dry, 2 mL).) was added and the mixture was stirred under argon atmosphere at room temperature for 2 h. DCM (25 mL) was added and the mixture was extracted with sat. NaHCO₃-sol. (sat); after extraction the organic phase was washed with brine (20 mL). The combined aqueous phases were extracted with EtOAc (30 ml). (TLC of EtOAc and DCM phases with 5% MeOH in DCM: EtOAc: one spot; DCM. 3 spots). Both organic phases were dried (Na₂SO₄) and concentrated to dryness separately. The crude product from the DCM phase was purified by column chromatography starting with DCM as the solvent. The column was flushed with DCM until all blue and pink color was washed down the column. Then eluent was changed to 5% MeOH in DCM. Collected: 34 mg of a brown solid ESI-MS (positive): [M+H]⁺: 764; [M+Na]⁺:

Example 6: Fmoc-AAPV-4-methoxy-I-naphthol ester [SEQ ID NO: 2]

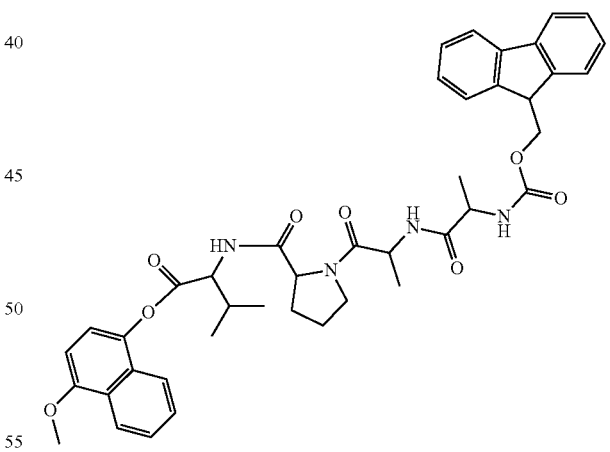

Fmoc-AAPV-OH [SEQ ID NO: 9] (169 mg, 0.29 mmol) and CDI (59 mg, 0.36 mmol) were dissolved in DCM (dry, 3 mL) under argon atmosphere in at RT. After 10 min 4-methoxy-1-naphthol (50 mg, 0.29 mmol) was added and the solution was stirred at RT for 45 min. DCM (30 mL) and water (20 ml) were added; after extraction the organic phase was dried with Na₂SO₄ and concentrated to dryness. The crude product was purified by column chromatography (eluent: 5% MeOH in DCM) to yield 58 mg of a beige solid. ESI-MS (positive): [M+H]⁺: 735; [M+Na]⁺: 757.

Example 7: Fmoc-AAPV-1-naphthol ester [SEQ ID NO: 2]

Example 8. Fmoc-AAPV-(2-Napthol) [SEQ ID NO: 2]

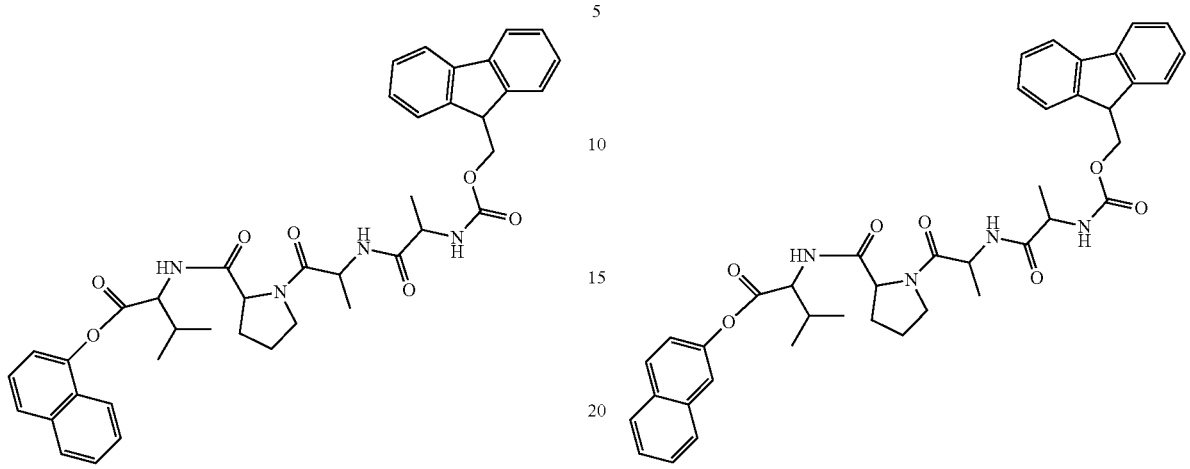

Fmoc-AAPV-OH [SEQ ID NO: 9] (241 mg, 0.42 mmol) and HOBt*H$_2$O (107 mg, 0.70 mmol) were suspended in DCM (dry, 4 mL). After 5 min DIPEA (119 μL, 0.70 mol) and EDCI*HCl (134 mg, 0.7 mmol) were added. Then the 1-Naphthol (50 mg, 0.35 mmol) was added in one portion, and the mixture was stirred at RT under argon atmosphere over the weekend. DCM (20 mL) and water (20 mL) were added and the mixture was extracted. Since phase separation was very slow a brine solution. (10 mL) was added and the mixture was extracted again. The organic phase was dried (Na$_2$SO$_4$) and concentrated to dryness. The crude product was purified by column chromatography (eluent: 5% MeOH in DCM) to yield 106 mg of the product. ESI-MS (positive): [M+H]$^+$: 705; [M+Na]$^+$: 727.

Synthesis: Fmoc-AAPV-OH [SEQ ID NO: 9] (241 mg, 0.42 mmol) and HOBt*H$_2$O (107 mg, 0.42 mmol) were suspended in dry DCM (3 mL) under argon atmosphere at RT. After 5 min DIPEA (119 μE, 0.7 mmol) and EDCPHC1 (134 mg, 0.7 mmol) were added and the solution was stirred at RT for 45 min. Then the 2-Naphthol (50 mg, 0.35 mmol) was added in one portion, and the mixture was stirred at RT under argon atmosphere for 2 h. DCM (30 mL) and water (30 ml) were added; after extraction the organic phase was washed with a brine (30 mL), dried with Na$_2$SO$_4$ and concentrated to dryness to yield 250 mg of an almost colorless solid. For purification the crude product was flashed over a short column of silica gel, eluent: 5% MeOH in DCM. Yield: 168 mg of a colorless solid (68%). ESI-MS (positive) [M+H]$^+$: 853.

Example 9: Methyl-3-Fmoc-AAPV-amide-4-aminobenzoate [SEQ ID NO: 2] and Methyl-3-amino-Fmoc-AAPV-amidobenzoate [SEQ ID NO: 2]

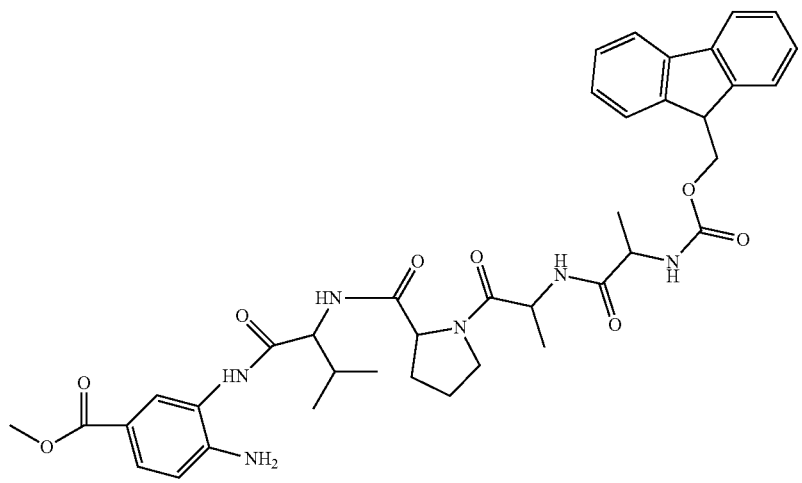

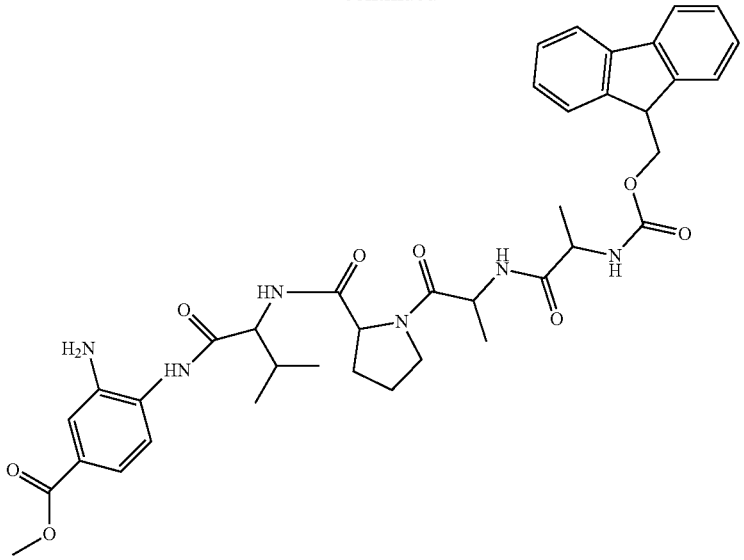

Fmoc-AAPV-OH [SEQ ID NO: 9] (214 mg, 0.37 mmol) and HOBt*H$_2$O (91 mg, 0.6 mmol) were suspended in dry DCM (dry, 2 mL) under argon atmosphere at RT. After 5 min DIPEA (105 µL, 0.6 mmol) and EDCl*HCl (115 mg, 0.6 mmol) were added and the solution was stirred at RT for 45 min. Then methyl-3,4-diaminobenzoate (50 mg, 0.3 mmol) was added in one portion, followed by additional DCM (dry, 1 mL), and the mixture was stirred at RT under argon atmosphere overnight. DCM (20 mL) and water (10 ml) were added; after extraction the organic phase is washed with sat. NaCl-sol. (10 mL), dried with Na$_2$SO$_4$ and concentrated to dryness. The crude product was purified by column chromatography on silica gel. Eluent: started with 2% MeOH/DCM (approx. 120 mL) then changed to 5% MeOH in DCM. Yield: 97 mg containing a mixture of both isomers and 10 mg of only one of the isomers. ESI-MS (positive): [M+H]$^+$: 727; [M+Na]$^+$: 749.

Example 10. N-(I-[2-hydroxy]tetradecanyl) Fast blue RR (N-4-(I,3-Dimethoxy-2-N-benzoylamidophenyl)-N'-rac-(2-hydroxy-n-tetradecyl)-amine)

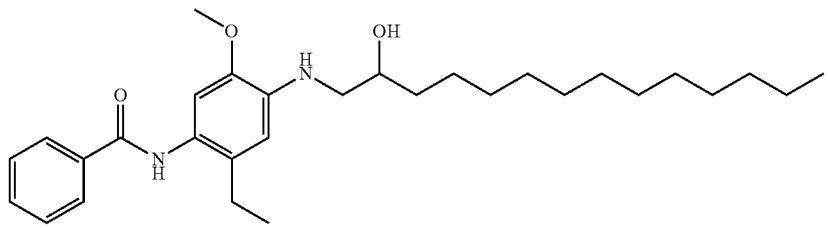 [SMILES: CCCCCCCCCCCCC(O)CNc1cc(CC)c(NC(=O)c2ccccc2)cc1OC]

Fast Blue RR dye (7.3 mmol) was placed in a 3 necked round bottom flask and was dissolved in chloroform (30 ml) at ambient temperature while stirring (magnetic stirrer, 500 rpm). After 30 min. stirring 1,2-epoxytetradecane (1 1 mmol) was added, followed by treatment with sulfuric acid (catalytic). Temperature was raised to reflux and stirring was continued for 12 h. When in process control (ESI-MS (+p)) indicated full consumption of starting materials any solids were filtered off and dried in air stream. Several recrystallization steps (ethanol) were necessary to obtain desired product in sufficiently pure form. Yield: 600 mg. ESI-MS (positive mode) [M+H]$^+$: 485.

Example 11. Fmoc-AAAPV-diaminobenzoic acid) [SEQ ID NO: 10]

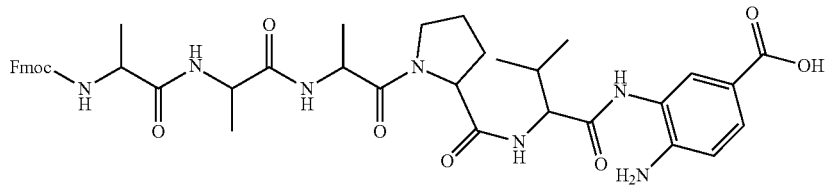

Fmoc-AAAPV-OH [SEQ ID NO: 11] (710 mg) was dissolved with DMF (5 mL). HOBt (210 mg) and DCC (240 mg) were added subsequently, and the mixture was stirred for 15 min at RT. 3,4-Diaminobenzoic acid (160 mg) and pyridine (100 μL) were dissolved with DMF (1 mL) and added to reaction mixture with stirring. After 14 h, the solvent was evaporated, and the residue was purified by silica gel chromatography with cyclohexane/DCM/methanol (4/2/1), containing 0.5% of formic acid, to yield 400 mg of product. ESI-MS (positive) [M+H]=784.

Example 12. Fmoc-AAPF-Indoxyl ester [SEQ ID NO: 12]

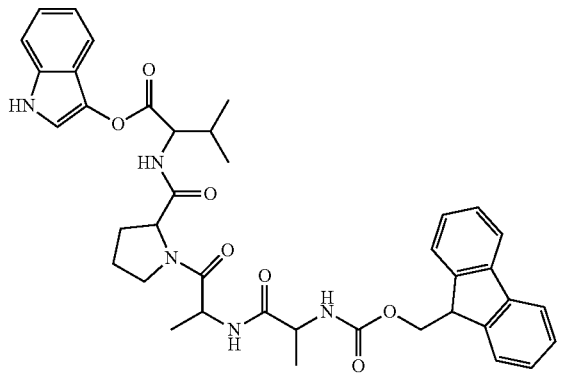 [SMILES: CC(NC(=O)OCC1c2ccccc2-c2ccccc21)C(=O)NC(C)C(=O)N1CCCC1C(=O)NC(C(=O)Oc1c[nH]c2ccccc12)C(C)C]

Fmoc-AAPF-OH [SEQ ID NO: 13] (994 mg, 1.59 mmol) and CDI (308 mg, 1.90 mmol) were dissolved in dry DCM (4 mL). The mixture was stirred at RT under argon atmosphere for 10 min and additional 20 min while passing argon through the mixture, followed by an add-on of additional DCM (dry, 2 mL). Stirring while passing argon through the reaction mixture was continued for 2 min, then indoxyl (208 mg, 1.56 mmol) was added in one portion. Stirring while passing argon through the solution was continued for 15 min, afterwards additional DCM (dry, 2 mL) was added and the mixture was stirred at RT under argon atmosphere overnight. Reaction mixture was filled into a separation funnel, flask was washed with DCM (20 mL) and wash-DCM was added to separation funnel as well. The mixture was washes with water (30 ml) and organic phase was collected together with some slurry between organic and aqueous phase. Organic phase was washed with water (30 mL) again, dried with Na$_2$SO$_4$ and concentrated to dryness. The crude product was suspended in Et$_2$O (50 mL) and is stirred at RT for 90 min. Then the solid was filtered off and re-suspended in fresh Et$_2$O (40 mL) and stirred at RT overnight. The solid was filtered off and dried at oil pump to yield 444 mg (38%) of the product.

ESI-MS (positive): [M+H]$^+$: 742; [M+Na]$^+$: 764

Example 13: Fmoc-AAA-Indoxyl ester

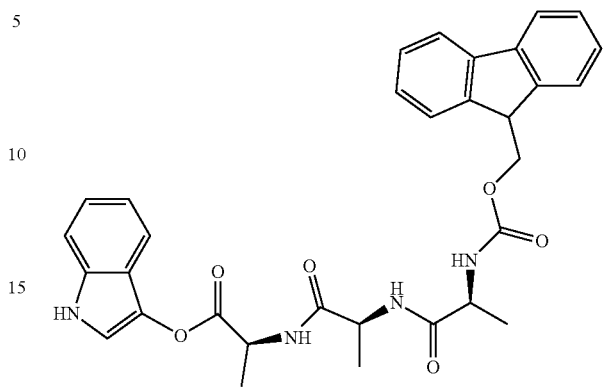

Fmoc-AAA-OH (103 mg, 0.52 mmol) and CDI (102 mg, 0.23 mmol) were dissolved in DCM (dry, 6 mL). The mixture was stirred at RT under argon atmosphere for 15 min and additional 10 min while passing argon through it. Then indoxyl (30 mg, 0.23 mmol) was added in one portion. Stirring while passing argon through the mixture was continued for 10 min, afterwards additional DCM (dry, 2 mL) was added and the mixture was stirred at RT under argon atmosphere overnight. Reaction mixture was washed with water (a lot of solid sat between organic and aqueous phase). Organic phase was collected, washed with water once again, dried with Na$_2$SO$_4$, and concentrated to dryness (only 33 mg).

The crude product was taken up in Et$_2$O (5 mL) and was shaken for 2 min. The liquid was decanted and 7 mg (5%) of the desired product could be obtained.

[M+Na]$^+$: 591

Example 14: Fmoc-AAPA-Indoxyl ester [SEQ ID NO: 14]

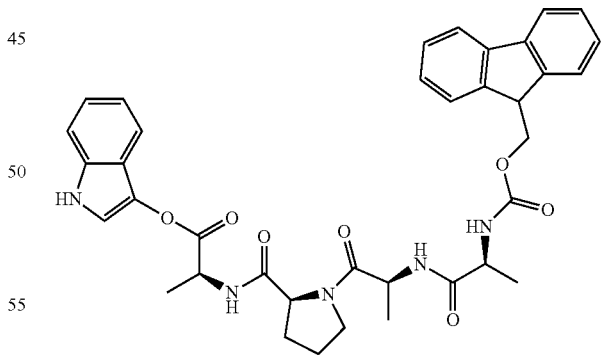

Fmoc-AAPA-OH [SEQ ID NO: 15] (285 mg, 0.52 mmol) and CDI (102 mg, 0.63 mmol) were dissolved in DCM (dry, 5 mL) in a 25 mL two-necked round bottom flask (heated with heat gun while evacuated and cooled down under argon atmosphere) The mixture was stirred at RT under argon atmosphere for 5 min and additional 10 min while passing argon through the mixture. Then indoxyl (71 mg, 0.53 mmol) was added in one portion. Stirring while passing argon through the mixture was continued for 15 min, afterwards additional DCM (dry, 2 mL) was added and it was stirred at RT under argon atmosphere for two days. The mixture was transferred into a separation funnel and washed with water twice. The organic phase is dried with $Na_2SO_4$ and concentrated to dryness. The crude product was taken up in $Et_2O$ (20 mL) and stirred at RT for 30 min. Then it is purified by column chromatography on silica gel (eluent: 2% MeOH in DCM) to give 25 mg (7%) of the desired product.

ESI-MS (positive): $[M+Na]^+$: 688

Example 15. Fmoc-V-Indoxyl ester

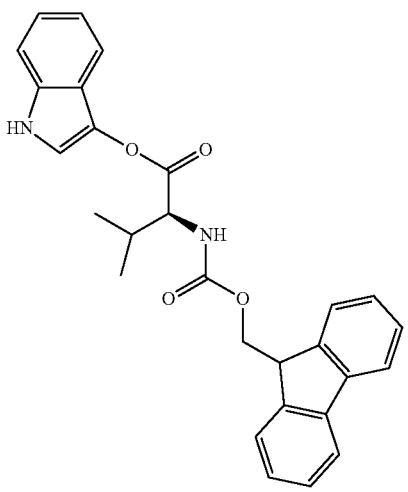 [SMILES: CC(C)[C@H](NC(=O)OCC1c2ccccc2-c2ccccc21)C(=O)Oc1c[nH]c2ccccc12]

Fmoc-V—OH (501 mg, 1.48 mmol) and CDI (291 mg, 1.79 mmol) were dissolved in DCM (dry, 6 mL). The mixture was stirred at RT under argon atmosphere for 10 min and additional 10 min while passing argon through the mixture. Then additional DCM (dry, 2 ml) was added, followed by indoxyl (199 mg, 1.49 mmol) in one portion. Starring the mixture while passing argon through it was continued for 10 min, afterwards additional DCM (dry, 2 mL) was added and the mixture was stirred at RT under argon atmosphere overnight. Reaction mixture was washes with water twice, dried with $Na_2SO_4$, and concentrated to dryness. Crude product was purified by column chromatography with silica gel.

Eluent: started with DCM (Column is washed with DCM under pressure until all blue and pink color was washed down the column), then eluent was changed to 5% MeOH in DCM.

The product came down the column with the first colored fractions.

Product was chromatographed a second time with DCM as the eluent.

Collected were fractions: 25-35 (130 mg)

36-44 (92 mg)

45-52 (81 mg)

Overall yield: 222 mg (33%)

Since only fractions 36-44 gave a weighable solid these fractions were used for testing.

$[M+Na]^+$: 477

Example 16: Fmoc-AAAA-Indoxyl ester [SEQ ID NO: 16]

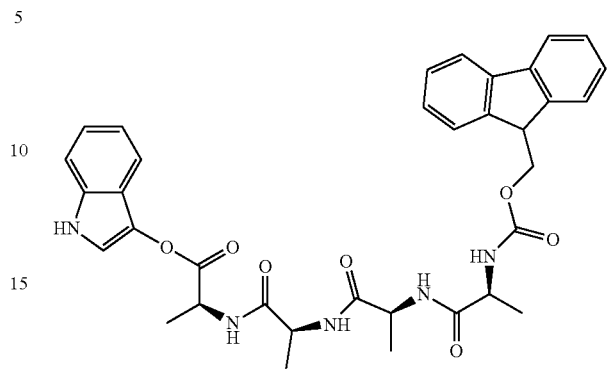

Fmoc-AAAA-OH [SEQ ID NO: 17] (503 mg, 0.95 mmol) and CDI (191 mg, 1.18 mmol) were suspended in DCM (dry, 10 mL). The mixture was stirred at RT under argon atmosphere for 10 min and additional 10 min while passing argon through the mixture. Then indoxyl (125 mg, 0.94 mmol) was added in one portion, followed by additional DCM (dry, 5 mL). Stirring at Rt while passing argon through the mixture was continued for 15 min, afterwards again additional DCM (dry, 5 mL) was added, and stirring while passing argon through the mixture was continued for two more minutes. Then the reaction mixture was stirred at RT under argon atmosphere overnight. Since all the solvent was evaporated overnight DCM (25 mL) was added and the mixture was stirred at RT for 5 min before it was washed with water (2×25 mL). Organic phase was dried with $Na_2SO_4$ and concentrated to dryness. Only 57 mg of crude product were obtained. Since a lot of solid was hold in the aqueous phase this solid was filtered off and dried. This solid was combined with the 57 mg obtained above. The combined solids were suspended in $Et_2O$ (20 mL) and stirred at RT overnight. The solid was filtered off and gave 229 mg (39%) of a solid containing product and starting material (FmocA-A-A-A-OH)

$[M+H]^+$: 640; $[M+Na]^+$: 662

Example 17: Fmoc-APV-Indoxyl ester

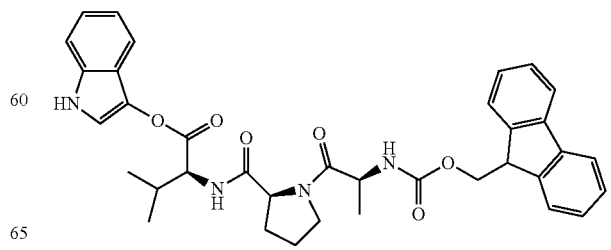

Fmoc-APV-OH (482 mg, 0.92 mmol) and CDI (191 mg, 1.18 mmol) were dissolved in DCM (dry, 10 mL). The mixture was stirred at RT under argon atmosphere for 10 min and additional 10 min while passing argon through the mixture. Then indoxyl (125 mg, 0.94 mmol) was added in one portion, followed by additional DCM (dry, 5 mL). Stirring at RT while passing argon through the mixture was continued for 15 min, afterwards again additional DCM (dry, 5 mL) was added, and stirring while passing argon through the reaction mixture was continued for 2 min and then the reaction mixture was stirred at RT under argon atmosphere overnight. Reaction mixture was washes with water (2×20 mL), organic phase was dried with Na$_2$SO$_4$ and concentrated to dryness. The crude product was suspended in Et$_2$O (20 mL) and stirred at RT for 2 h. Only little solid remained which sticked to the flask. Liquid was decanted and solid collected (76 mg, 17%)

[M+Na]$^+$: 645

Example 18: Fmoc-Phe-Indoxyl ester

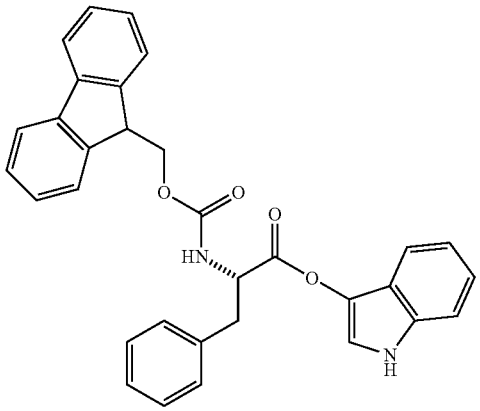

Fmoc-Phe-OH (2.9 g, 7.5 mmol) and CDI (1.47 g, 9.0 mmol) are directly weighed into a 100 mL three-necked round bottom flask. DCM (dry, 50 mL) was added and the mixture was stirred at RT for 5 min, then it was stirred 10 min at RT while passing argon through it. Afterwards additional DCM (dry, 4 mL) was added, followed by indoxyl (1.00 g, 7.6 mmol). Stirring at RT while passing an argon stream through the mixture was continued for 30 min. Then additional DCM (dry, 10 mL) was added, and again the mixture was stirred at RT (with argon stream) for 20 min. Finally it is stirred at RT under argon atmosphere overnight. Reaction mixture was filled into a separation funnel, flask was washed with DCM (30 mL), and wash-DCM was filled into separation funnel as well. Water (100 mL) was added, after extraction the organic phase was collected and refilled into a clean separation funnel. Organic phase was washed with water (100 mL) again, dried (Na$_2$SO$_4$) and concentrated to dryness. Crude product was taken up in diethyl ether (100 mL) for purification. Since it dissolved completely it was concentrated to dryness again and purified by column chromatography on silica gel (eluent: DCM). Collected fractions:
28 and 29: 152 mg
22-27
30-48

Fractions 22-27 were concentrated to dryness. Then DCM (20 mL) was added to dissolve some of the blue colour. Solid was filtered off, re-dissolved and concentrated to dryness again to yield 132 mg of the product.

The filtrate was combined with fractions 30-48, yielding 1.00 g of the impure product. Overall yield: 1.284 g (26.5%).

[M+Na]$^+$: 525

Example 19: Ac-Phe-Indoxyl ester

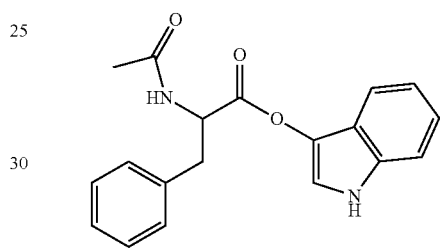

Ac-Phe-OH (1.55 g, 7.5 mmol) and CDI are weighed directly into a 100 mL three necked round bottom flask. DCM8dry, 50 mL) was added and the mixture was stirred at RT for 5 min. Then it was stirred at RT whole passing argon through it for 15 min. After the 15 min indoxyl was added (1.01 g, 7.6 mmol). Stirring while passing argon through the mixture was continued for 20 min. At that point more DCM (dry, 5 mL) was added and stirring (with argon stream) was continued for 23 min. Once more DCM (dry, 8 mL) was and stirring at RT (with argon stream) was continued for 5 min. The mixture was stirred at RT under argon atmosphere overnight. Mixture was filled into separation funnel, flask was washed with DCM (20 mL) which were filled into separation funnel as well. After washing with water (80 mL) organic phase was collected and refilled into a clean separation funnel. Mixture was again washed with water, organic phase was collected, dried (Na$_2$SO$_4$) and concentrated to dryness. Crude product was purified by column chromatography on silica gel. Eluent: started with DCM (under pressure) until most of blue and pink color was washed down, then solvent was changed to 2% MeOH in DCM and chromatography was continued without pressure. Only the almost pure fractions were collected: 196 mg (8%).

[M+Na]$^+$: 345

Example 20: Fmoc-F-V-T(Bzl)-F-

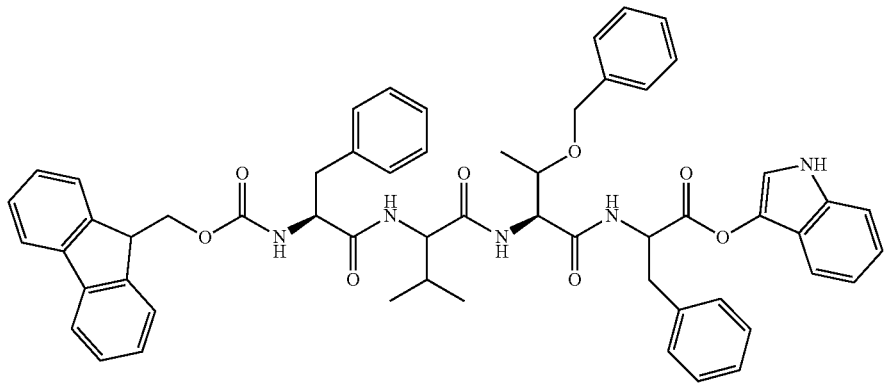 [SMILES: CC(C)C(NC(=O)[C@H](Cc1ccccc1)NC(=O)OCC1c2ccccc2-c2ccccc21)C(=O)N[C@H](C(=O)NC(Cc1ccccc1)C(=O)Oc1c[nH]c2ccccc12)C(C)OCc1ccccc1]

Fmoc-F-V-T(Bzl)-F-OH (1.228 mg, 1.49 mmol) was suspended in DCM (dry, 10 mL). CDI (291 mg, 1.79 mmol) was added, the mixture was stirred at RT for 10 min and additional 15 min at RT while passing argon through it. DCM (dry, 3 ml) was added and the mixture was stirred at RT (with argon stream) for two more minutes before indoxyl (200 mg, 1.50 mmol) was added in one portion. The mixture was stirred at RT (with argon stream) for 45 min. Afterwards additional DCM (dry, 8 mL) was added and the mixture was stirred at RT for 5 more minutes before the argon line was removed and the mixture was stirred at RT under argon atmosphere overnight. DCM (20 mL) was added, the remaining blue solid was filtered off and washed with DCM (20 mL). The filtrate was filled into a separation funnel and washed with water twice. The organic phase was dried (Na$_2$SO$_4$) and concentrated to dryness. The crude product was taken up in DCM (7 mL) and diethyl ether was added (20 mL). The mixture was stirred for 2 h at RT, then the precipitate (58 mg, 5%) was filtered off and washed with diethyl ether (20 mL).

[M+Na]$^+$: 962

Example 21: β-Lactam indoxyl ether

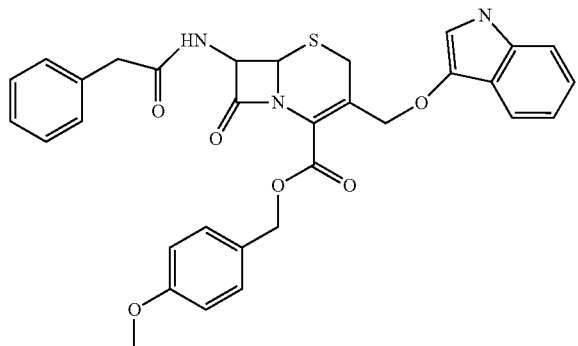 [SMILES: COc1ccc(COC(=O)C2=C(COc3c[nH]c4ccccc34)CSC3C(NC(=O)Cc4ccccc4)C(=O)N23)cc1]

Indoxyl (327 mg, 2.46 mmol) was weighed into a 25 mL three-necked round bottom flask (flask was heated in vacuo with heat gun and cooled down under argon atmosphere). THF (dry, 6 mL) was added and the mixture was stirred at RT while streaming argon through the mixture for 10 min. Then potassium tert-butoxide (228 mg, 2.03 mmol) was added in one portion and stirring at RT with a permanent argon stream was continued for 15 min. At this point 4-methoxybenzyl 3-Chloromethyl-7-(2-phenylacetamido)-3-cephem-4-carboxylate (1.01 g, 2.05 mmol) was added in one portion. Stirring the mixture at RT with a steady argon stream was continued for additional 30 min. The product was detected via ESI-MS. ESI-MS (positive): [M+Na]+= 606; [M+K]+=622.

Example 22. N-(Propargyl)-(RBB)

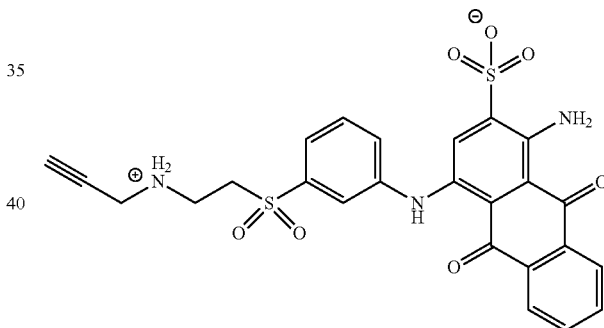

Class: Dye conjugate based on Remazol Brilliant Blue R, 1,3-dipolar [3+2] cycloaddition ("click chemistry")

Synthesis: Reaction of Remazol Brilliant Blue R with propargylamine hydrochloride was performed under normal conditions in saturated aq. NaHCO$_3$. Reaction monitoring was done with ESI-MS (–p). The product was extracted with ethyl acetate from the aqueous phase and precipitated with adequate purity for use in the subsequent reaction (1,3-dipolar [2+3]-cycloaddition). ESI-MS (negative) [M–H]$^+$: 538.

Example 23. Fmoc Protected Reagent (Fmoc-V-{2-hydroxy-3-[1-(5-(N-RBB-methyl)1,2,3-triazolyl)}propylamide) (Fmoc-V-triazol-RBB)

Example 22 was reacted with FMOC-valine-N-(2-hydroxy-3-azidopropyl, amide using click chemistry conditions (Hunig's base, copper catalysis). The reaction product is used in further examples below.

Example 24. H—V-{2-hydroxy-3-[I-(5-(N-RBB-methyl)I,2,3-triazolyl)}propylamide (H—V-triazol-RBB)

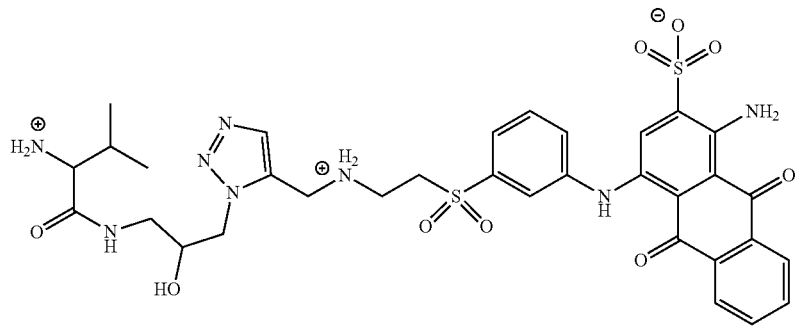

Class: Dye conjugate based on Remazol Brilliant Blue R, amino acid building block for peptide synthesis.

Synthesis: Reaction of Fmoc protected reagent (Fmoc-V-Triazole-RBB, Example 23) with piperidine in methanol was performed under normal conditions. Reaction monitoring was done with ESI-MS (–p). The product precipitated after drying in vacuo with adequate purity for use in the subsequent reaction (amidation). Yield: quantitative (crude product). ESI-MS (negative) [M–H]": 753.

Example 25. Fmoc-AAPVAV-{2-hydroxy-3-[I-(5-(N-RBB-methyl)1,2,3-triazolyl)}propylamide (Fmoc-AAPVAV-triazol-RBB) [SEQ ID NO: 18]

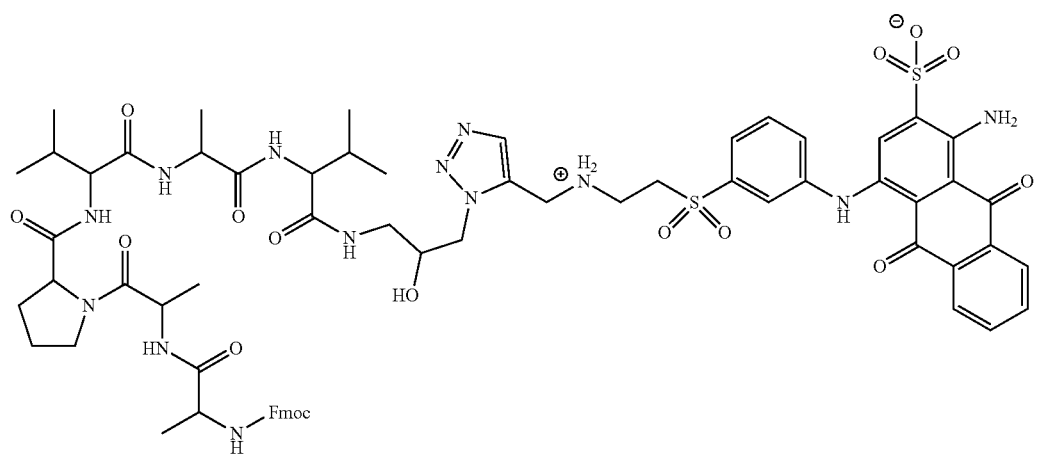

Class: Dye-peptide conjugate based on Remazol Brilliant Blue R.

Synthesis: A stirred mixture of pentapeptide Fmoc-AAPVA-OH [SEQ ID NO: 19] (1 equiv) and HOBt»H$_2$O (1.2 equiv) in DCM was treated with DCC (1.2 equiv) at ambient temperature for 15 min. H—V-{2-hydroxy-3-[I-(5-(TSr-RBB-methylo)I,2,3-triazolyl)}propylamide (1 equiv; Example 24) was added in one portion and the reaction mixture was stirred at room temperature until reaction monitoring via ESI-MS (–p) indicated consumption of starting materials. Simple removal of volatiles in vacuo yielded a crude product as blue amorphous solid. Yield: ~83% (crude product). ESI-MS (negative) [M–H]$^+$: 1385.

Example 26. Fmoc-AAPV-{2-hydroxy-3-[I-(5-(N-RBB-methyl)1,2,3-triazolyl)}propylamide (Fmoc-AAPV-triazol-RBB) [SEQ ID NO: 2]

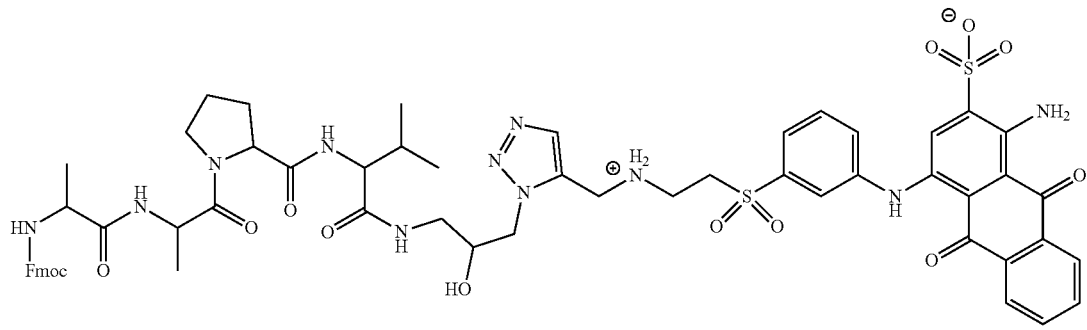

Class: Dye-peptide conjugate based on Remazol Brilliant Blue R.

Synthesis: A stirred mixture of tripeptide Fmoc-AAP-OH (1 equiv) and HOBt·H$_2$O (1.2 equiv) in DCM was treated with DCC (1.2 equiv) at ambient temperature for 15 min. H—V-{2-hydroxy-3-[I-(5-(N-RBB-methylo)I,2,3-triazolyl)}propylamide (1 equiv; Example 24) was added in one portion and the reaction mixture was stirred at room temperature until reaction monitoring via ESI-MS (-p) indicated consumption of starting materials. Aqueous work-up yielded a crude product as blue amorphous solid. Yield: ~90% (crude product). ESI-MS (negative) [M–H]$^+$: 1214.

Example 27. H-AAPVAV-{2-hydroxy-3-[I-(5-(N-RBB-methyl)1,2,3-triazolyl)}propylamide (H-AAPVAV-triazol-RBB) [SEQ ID NO: 20]

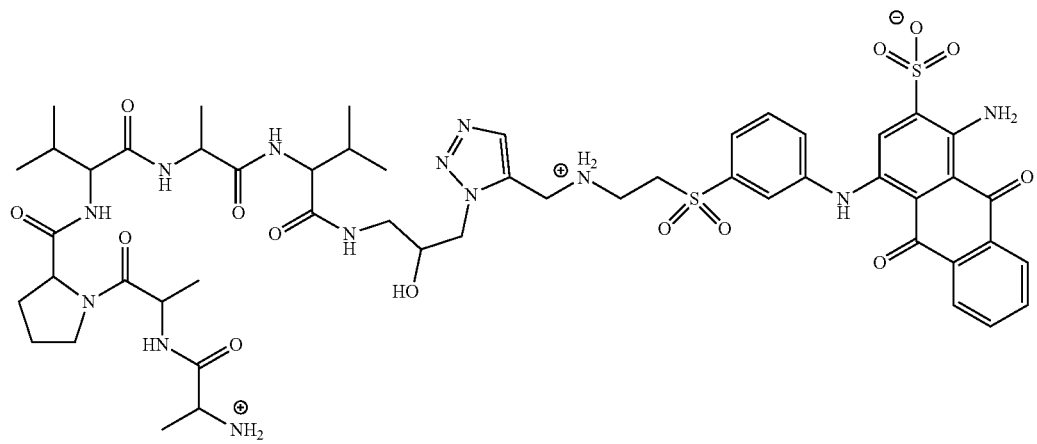

Dye-peptide conjugate based on Remazol Brilliant Blue R. Synthesis: Fmoc-AAPVAV-{2-hydroxy-3-[I-(5-(N-RBB-methylo)I,2,3-triazolyl)}propylamide [SEQ ID NO: 18] (1 equiv; Example 25) was treated with a mixture of methanol/piperidine (2:1) at ambient temperature for 45 min while stirring. Reaction monitoring via ESI-MS (-p) indicated consumption of starting materials. Simple evaporation of volatiles in vacuo yielded a crude product as blue amorphous solid. Yield: quantitative (crude product). ESI-MS (negative) [M–H]$^+$: 1162.

Example 28. H-AAPV-{2-hydroxy-3-[I-(5-(N-RBB-methyl)I,2,3-triazolyl)}propylamide) (H-AAPV-triazol-RBB) [SEQ ID NO: 21]

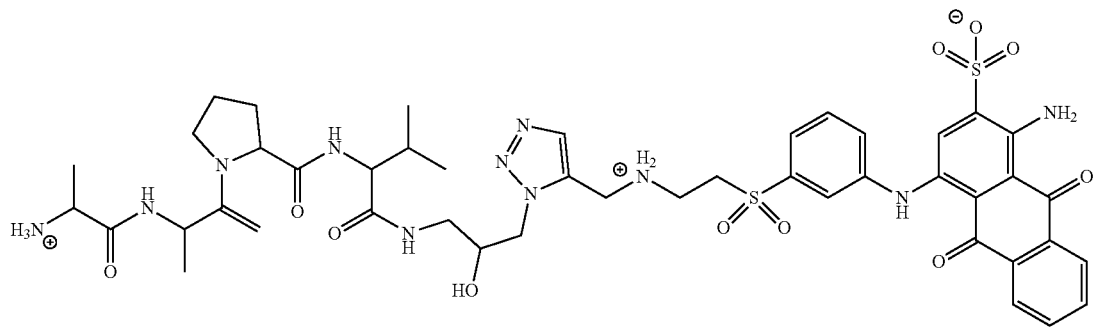

Class: Dye-peptide conjugate based on Remazol Brilliant Blue R.

Synthesis: Fmoc-AAPV-{2-hydroxy-3-[I-(5-(N-RBB-methylo)I,2,3-triazolyl)}propylamide (1 equiv [SEQ ID NO: 2]; Example 26) was treated with a mixture of methanol/piperidine (2:1) at ambient temperature for 45 min while stirring. Reaction monitoring via ESI-MS (–p) indicated consumption of starting materials. Simple evaporation of volatiles in vacuo yielded a crude product as blue amorphous solid. Yield: quantitative (crude product). ESI-MS (negative) [M–H]'': 992.

Example 29. RB-Amine (H-RBB)

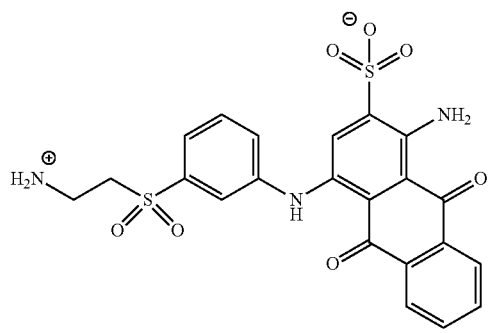 [SMILES: Nc1c(S(=O)(=O)[O-])cc(Nc2cccc(S(=O)(=O)CC[NH3+])c2)c2c1C(=O)c1ccccc1C2=O]

Class: Dye conjugate based on Remazol Brilliant Blue R, Starting material for Amination/Amidation Synthesis: Reaction of Remazol Brilliant Blue R with ammonium hydroxide solution was performed under normal conditions, with initial cooling in an ice bath. Reaction was monitored via ESI-MS (–p). The product was filtered from the aqueous phase and precipitated with adequate purity for use in the subsequent reaction (amidation). Yield: >64% (crude product). ESI-MS (negative) [M–H]$^+$: 500.

Example 30—amido-Fmoc-Alanine (Fmoc-A-RBB)

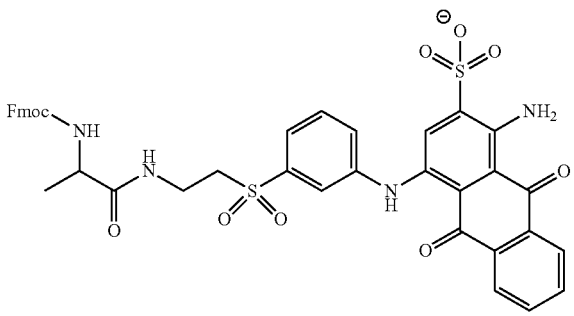

Class: Dye conjugate based on Remazol Brilliant Blue R, amino acid building block for peptide synthesis.

Synthesis: Reaction of H-RBB (Example 29) with Fmoc-alanine pentafluorophenyl ester was performed under normal conditions in ethanol. Reaction monitoring was done with ESI-MS (–p). The product was extracted from the aqueous phase with dichloromethane (DCM) and precipitated after drying in vacuo with adequate purity for use in the subsequent reaction (deprotection/amidation). Yield: >90% (crude product). ESI-MS (negative) [M–H]$^+$: 793.

Example 31. RB-amido-Alanine-NH$_2$ (H-A-RBB)

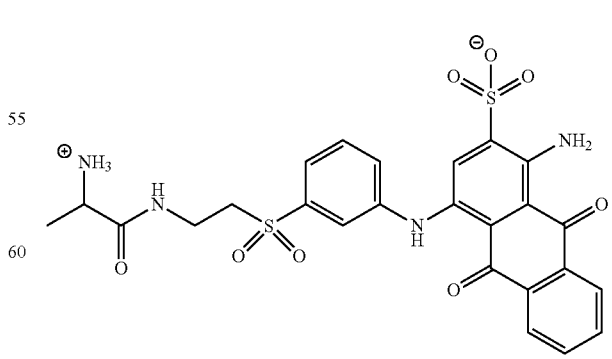

Class: Dye conjugate based on Remazol Brilliant Blue R, amino acid building block peptide synthesis.

Synthesis: Reaction of Fmoc-A-RBB (Example 30) with piperidine in methanol was performed under normal conditions. Reaction monitoring was done with ESI-MS (−p). The product precipitated after drying in vacuo with adequate purity for use in the subsequent reaction (amidation). Yield: quantitative (crude product). ESI-MS (negative) [M−H]⁺: 571.

Example 32. Fmoc-AAPVAA-RBB [SEQ ID NO: 22]

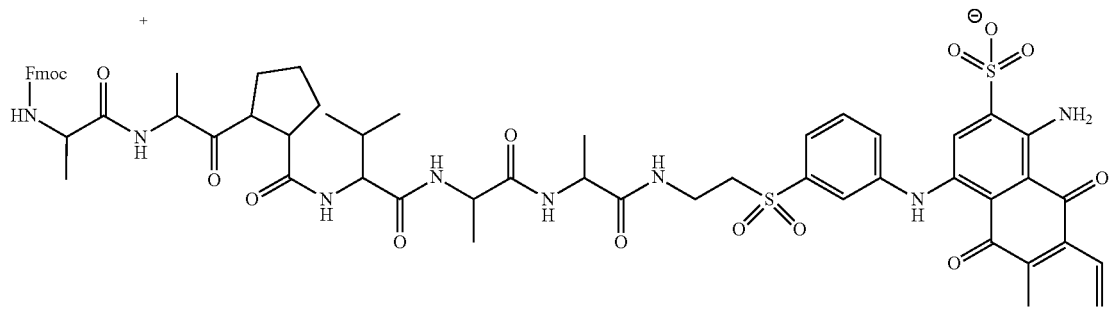

Class: Dye-peptideconjugate conjugate based on Remazol Brilliant Blue R

Synthesis: A stirred mixture of pentapeptide Fmoc-AAPVA-OH [SEQ ID NO: 19] (1 equiv) and HOBt·H₂O (1.2 equiv) in DCM was treated with DCC (1.2 equiv) at ambient temperature for 15 min. H-A-RBB (1 equiv, Example 31) was added in one portion and the reaction mixture was stirred at room temperature until reaction monitoring via ESI-MS (−p) indicated consumption of starting materials. Aqueous work-up yielded a crude product as blue amorphous solid. Yield: ~58% (crude product). ESI-MS (negative) [M−H]⁺: 1202.

H-AAPVAA-RBB SEQ ID NO: 23

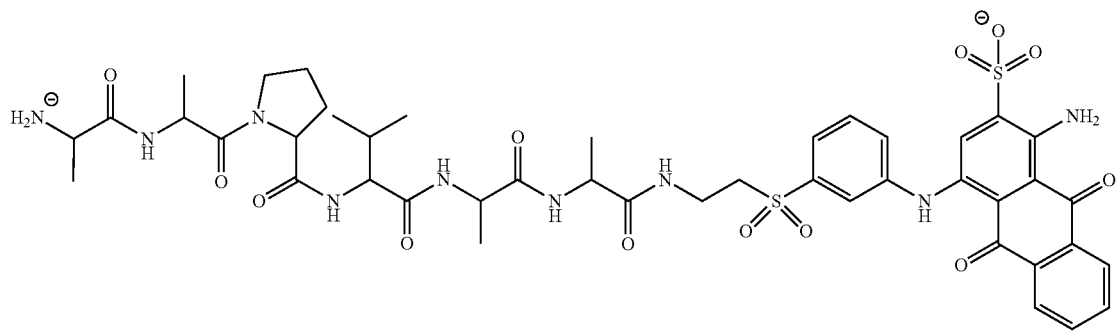 [SMILES: CC([NH-])C(=O)NC(C)C(=O)N1CCCC1C(=O)NC(C(=O)NC(C)C(=O)NC(C)C(=O)NCCS(=O)(=O)c1cccc(Nc2cc(S(=O)(=O)[O-])c(N)c3c2C(=O)c2ccccc2C3=O)c1)C(C)C]

Class: Dye-peptide conjugate based on Remazol Brilliant Blue R.

Synthesis: Fmoc-AAPVAA-RBB [SEQ ID NO: 22] (1 equiv, Example 32) was treated with a mixture of methanol/piperidine (2:1) at ambient temperature for 45 min while stirring. Reaction monitoring via ESI-MS (−p) indicated consumption of starting materials. Simple evaporation of volatiles in vacuo yielded a crude product as blue amorphous solid. Yield: quantitative (crude product). ESI-MS (negative) [M−H]⁺: 980.

Example 34. Acrylamido-AAPVAA-RBB [SEQ ID NO: 22]

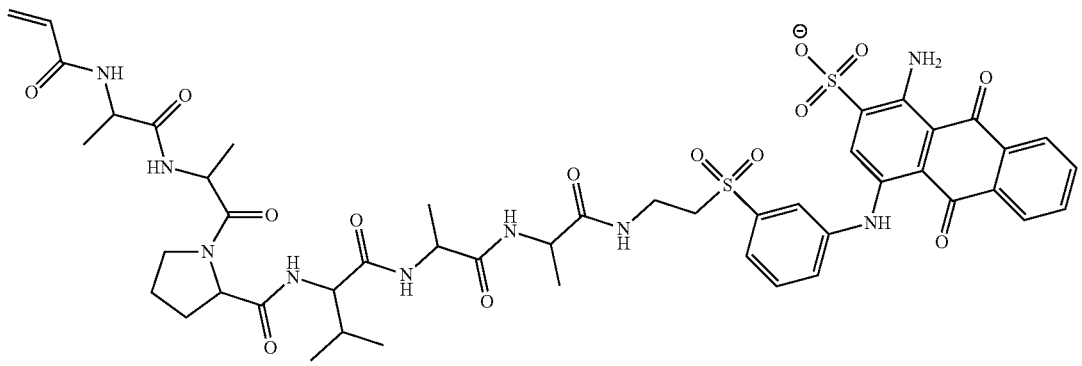 [SMILES: C=CC(=O)NC(C)C(=O)NC(C)C(=O)N1CCCC1C(=O)NC(C(=O)NC(C)C(=O)NC(C)C(=O)NCCS(=O)(=O)c1cccc(Nc2cc(S(=O)(=O)[O-])c(N)c3c2C(=O)c2ccccc2C3=O)c1)C(C)C]

Class: Dye-peptide conjugate based on Remazol Brilliant Blue R.

Synthesis: H-AAPVAA-RBB [SEQ ID NO: 23] (1 equiv; Example 33) was dissolved in methanol and treated with acrylic acid pentafluorophenyl ester (1.2 equiv) at ambient temperature while stirring. Reaction monitoring via ESI-MS (-p) indicated consumption of starting materials after ~12 h (overnight). Simple evaporation of volatiles in vacuo yielded crude product as blue amorphous solid adequately pure for the next step. Yield: >95% (crude product). ESI-MS (negative) [M−H]$^+$: 599.

Example 35. Fmoc-VA-RBB

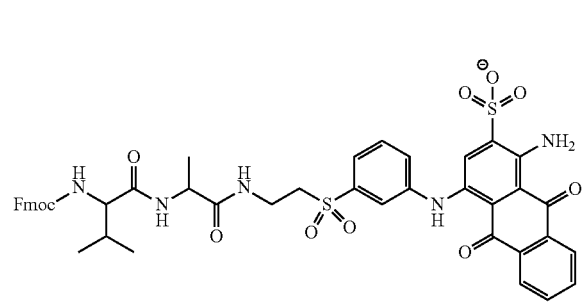

Class: Dye conjugate based on Remazol Brilliant Blue R, amino acid building block for peptide synthesis.

Synthesis: A solution of H-A-RBB (1 equiv; Example 31) in methanol was treated with Fmoc-Valine-OPfp ester at ambient temperature while stirring. After reaction monitoring via ESI-MS (-p) indicated consumption of starting materials, the reaction mixture was subjected to aqueous work-up and extracted with DCM. Evaporation of DCM in vacuo yielded a crude product as blue amorphous solid. Yield: ~48% (crude product). ESI-MS (negative) [M−H]$^+$: 892.

Example 36. H-VA-RBB

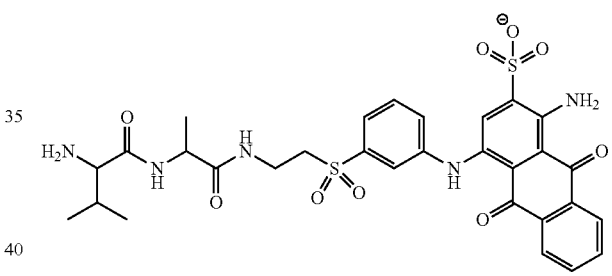

Class: Dye conjugate based on Remazol Brilliant Blue R, amino acid building block for peptide synthesis;

Synthesis: Fmoc-VA-RBB (1 equiv; Example 35) was treated with a mixture of methanol/piperidine (2:1) at ambient temperature for 45 min while stirring. Reaction monitoring via ESI-MS (-p) indicated consumption of starting materials. Simple evaporation of volatiles in vacuo yielded a crude product as blue amorphous solid. Yield: quantitative (crude product). ESI-MS (negative) [M−H]$^+$: 670.

Example 37. Fmoc-AAPFA-RBB [SEQ ID NO: 24]

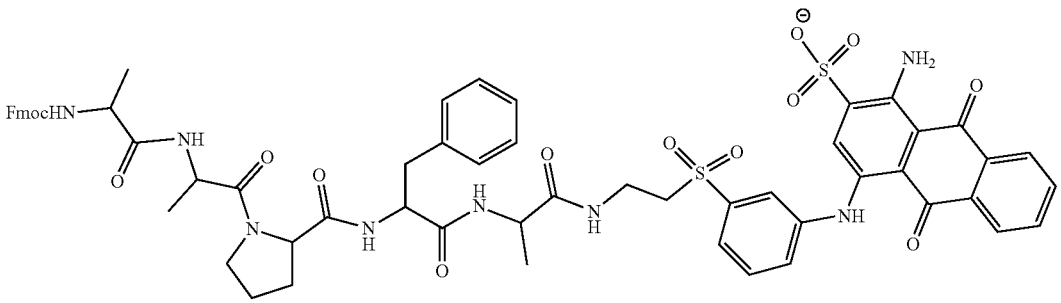

Class: Dye-peptide conjugate based on Remazol Brilliant Blue R.

Synthesis: A stirred mixture of tetrapeptide Fmoc-AAPF-OH [SEQ ID NO: 13] (1 equiv) and HOB$_t$·H$_2$O (1 equiv) in DCM was treated with DCC (1 equiv) at ambient temperature for 15 min. H-A-RBB (0.8 equiv; Example 31) was added in one portion and the reaction mixture was stirred at room temperature until reaction monitoring via ESI-MS (–p) indicated consumption of starting materials. Aqueous work-up and evaporation of volatiles in vacuo yielded a crude product as blue amorphous solid. Yield: ~98% (crude product). ESI-MS (negative) [M–H]": 1179.

Class: Dye-peptide conjugate based on Remazol Brilliant Blue R.

Synthesis: A stirred mixture of pentapeptide Fmoc-AAPVA-OH [SEQ ID NO: 27] (1 equiv) and HOB$_t$·H$_2$O (1.2 equiv) in DCM was treated with DCC (1.2 equiv) at ambient temperature for 15 min. H-RBB (1 equiv, Example 29) was added in one portion and the mixture was stirred at room temperature until reaction monitoring via ESI-MS (–p) indicated consumption of starting materials. Aqueous work-up yielded a crude product as blue amorphous solid. Yield: ~23% (crude product). ESI-MS (negative) [M–H]": 1131.

Alternate Synthesis 1: A stirred mixture of tripeptide Fmoc-AAP-OH (1 equiv) and HOB$_t$·H$_2$O (1 equiv) in DCM was treated with DCC (1 equiv) at ambient temperature for 15 min. H-VA-RBB (0.8 equiv; Example 36) was added in one portion and the reaction mixture was stirred at room temperature until reaction monitoring via ESI-MS (–p) indicated consumption of starting materials (~15 h, over- Example 38. H-AAPFA-RBB [SEQ ID NO: 25]

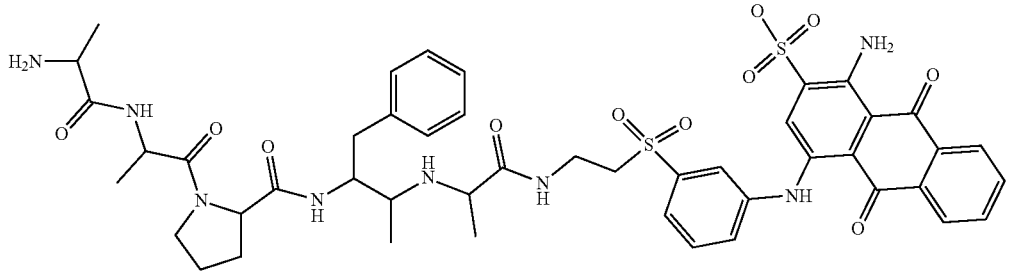

Class: Dye-peptide conjugate based on Remazol Brilliant Blue R.

Synthesis: Fmoc-AAPFA-RBB [SEQ ID NO: 24] (1 equiv) (example 37) was treated with a mixture of methanol/piperidine (2:1) at ambient temperature for 45 min while stirring. Reaction monitoring via ESI-MS (–p) indicated consumption of starting materials. Simple evaporation of volatiles in vacuo yielded a crude product as blue amorphous solid. Yield: quantitative (crude product). ESI-MS (negative) [M–H]$^+$: 957.

Example 39. Fmoc-AAPVA-RBB [SEQ ID NO: 26]

night). Aqueous work-up and evaporation of volatiles in vacuo yielded adequately pure crude product as blue amorphous solid. Yield: ~70% (crude product). ESI-MS (negative) [M–H]$^+$: 1131.

Alternate synthesis 2: Fmoc-AAPVA-OH [SEQ ID NO: 27] (110 mg) and HOB$_t$ (50 mg) were suspended in DMF (10 mL). DCC (50 mg) was added. After stirring for 5 min, H-RBB (100 mg; Example 29) dissolved in DMF (3 mL) was added. After stirring for 2 h, the reaction was complete as indicated by MS. The crude mixture was taken forward for Fmoc deprotection (see Alternate Synthesis in Example 40). ESI-MS (negative) [M–H]$^+$: 1131.

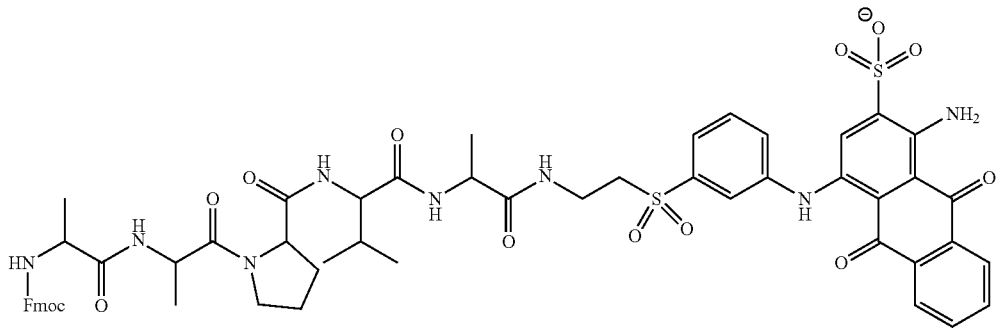

Example 40. H-AAPVA-RBB [SEQ ID NO: 28]

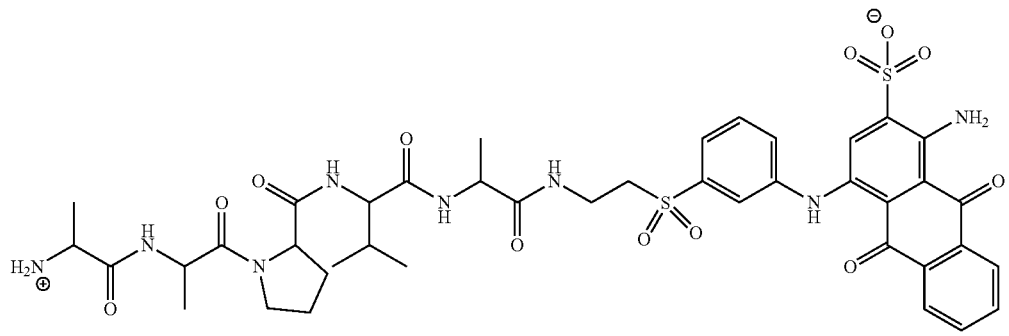 [SMILES: CC([NH3+])C(=O)NC(C)C(=O)N1CCCC1C(=O)NC(C(=O)NC(C)C(=O)NCCS(=O)(=O)c1cccc(Nc2cc(S(=O)(=O)[O-])c(N)c3c2C(=O)c2ccccc2C3=O)c1)C(C)C]

Class: Dye-peptide conjugate based on Remazol Brilliant Blue R.

Synthesis: Fmoc-AAPVA-RBB [SEQ ID NO: 26] (1 equiv; Example 39) was treated with a mixture of methanol/piperidine (2:1) at ambient temperature for 45 min while stirring. Reaction monitoring via ESI-MS (-p) indicated consumption of starting materials. Simple evaporation of volatiles in vacuo yielded a crude product as blue amorphous solid. Yield: quantitative (crude product). ESI-MS (negative) [M–H]–: 909.

Alternate synthesis: Using the crude DMF mixture of Fmoc-AAPVA-RBB [SEQ ID NO: 26](from Alternate Synthesis 2 in Example 39), piperidine (200 μE) was added and the mixture was stirred overnight. The solvent was evaporated, and the residue was re-dissolved in methanol (~50 mL). After concentration to 10 ml, the deep blue supernatant was poured into diethyl ether (200 mL). The precipitate was isolated and dried to yield 145 mg of a fine blue powder (H-AAPVA-RBB) [SEQ ID NO: 28]. ESI-MS (negative) [M–H]+: 909.

Example 41. Fmoc-V-RBB

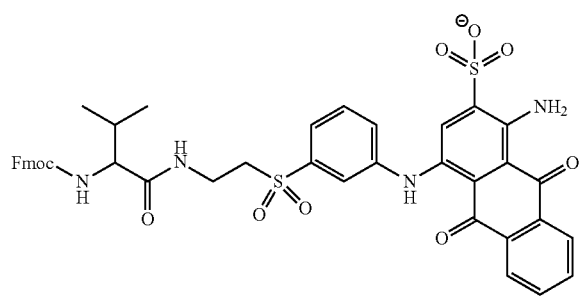

Class: Dye conjugate based on Remazol Brilliant Blue R, amino acid building block for peptide synthesis.

Synthesis: A solution of H-RBB (1 equiv; Example 29) in methanol was treated with Fmoc-Valine-OPfp ester at ambient temperature while stirring. After reaction monitoring via ESI-MS (-p) indicated consumption of starting materials, the reaction mixture was subjected to aqueous work-up and extracted with DCM. Evaporation of DCM in vacuo yielded a crude product as white amorphous solid. Yield: ~31% (crude product). ESI-MS (negative) [M–H]": 821.

Example 42. H—V-RBB

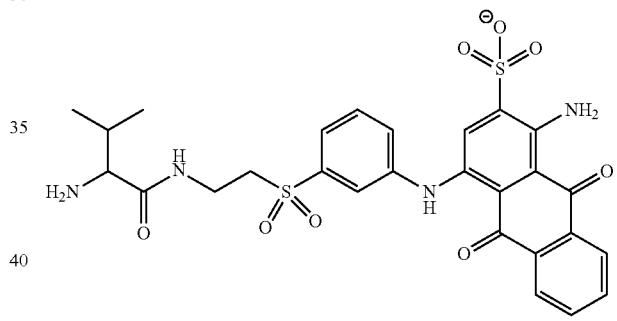

Class: Dye conjugate based on Remazol Brilliant Blue R, amino acid building block for peptide synthesis.

Synthesis: Fmoc-V-RBB (1 equiv; Example 41) was treated with a mixture of methanol/piperidine (2:1) at ambient temperature for 45 min while stirring. Reaction monitoring via ESI-MS (-p) indicated consumption of starting materials. Simple evaporation of volatiles in vacuo yielded a crude product as blue amorphous solid. Yield: quantitative (crude product). ESI-MS (negative) [M–H]+: 599.

Example 43. Fmoc-AAPV-RBB [SEQ ID NO: 2]

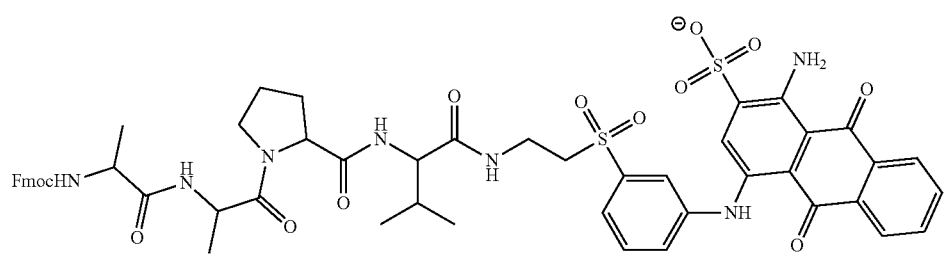

Class: Dye-peptide conjugate based on Remazol Brilliant Blue R.

Synthesis: A stirred mixture of tripeptide Fmoc-AAP-OH (1 equiv) and HOBt·H₂O (1 equiv) in DCM was treated with DCC (1 equiv) at ambient temperature for 15 min. H—V-RBB (0.8 equiv; Example 42) was added in one portion and the reaction mixture was stirred at room temperature until reaction monitoring via ESI-MS (-p) indicated consumption of starting materials (~15 h, overnight). Aqueous work-up and evaporation of volatiles in vacuo yielded adequately pure crude product as blue amorphous solid. Yield: ~70% (crude product). ESI-MS (negative) [M−H]⁺: 1060.

Example 44. H-AAPV-RBB [SEQ ID NO: 29]

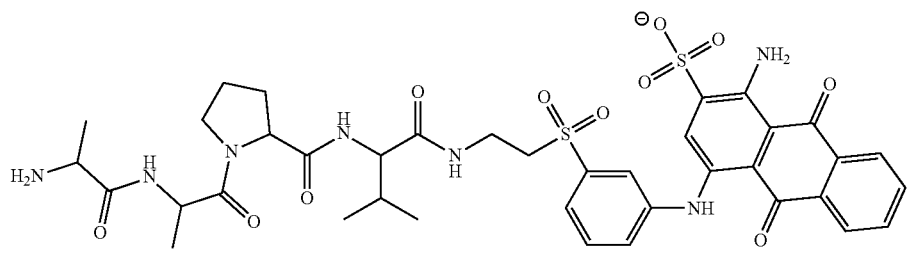 [SMILES: CC(N)C(=O)NC(C)C(=O)N1CCCC1C(=O)NC(C(=O)NCCS(=O)(=O)c1cccc(Nc2cc(S(=O)(=O)[O-])c(N)c3c2C(=O)c2ccccc2C3=O)c1)C(C)C]

Class: Dye-peptide conjugate based on Remazol Brilliant Blue R.

Synthesis: Fmoc-AAPV-RBB [SEQ ID NO: 2] (1 equiv; Example 43) was treated with a mixture of methanol/piperidine (2:1) at ambient temperature for 45 min while stirring. Reaction monitoring via ESI-MS (-p) indicated consumption of starting materials. Simple evaporation of volatiles in vacuo yielded adequately pure crude product as blue amorphous solid. Yield: quantitative (crude product). ESI-MS (negative) [M−H]'': 838.

Example 45. Fmoc-AAPF-RBB [SEQ ID NO: 12]

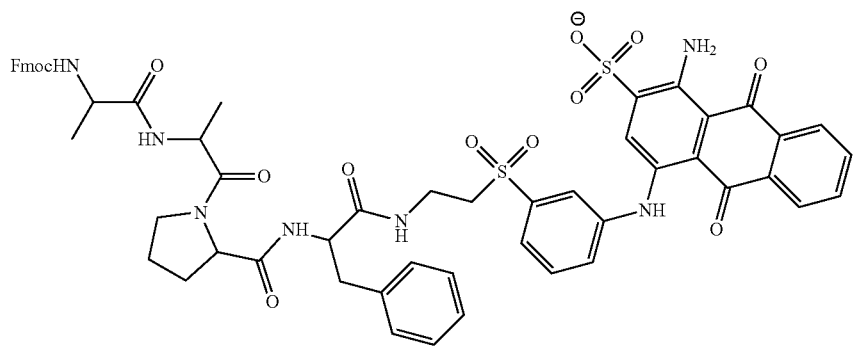

Class: Dye-peptide conjugate based on Remazol Brilliant Blue R.

Synthesis: A stirred mixture of tetrapeptide Fmoc-AAPF-OH [SEQ ID NO: 4] (1 equiv) and HOBt·H₂O (1 equiv) in DCM were treated with DCC (1 equiv) at ambient temperature for 15 min. H-RBB (0.8 equiv; Example 29) was added in one portion and the reaction mixture was stirred at room temperature until reaction monitoring via ESI-MS (-p) indicated consumption of starting materials. Aqueous work-up and evaporation of volatiles in vacuo yielded a crude product as blue amorphous solid. Yield: ~98% (crude product). ESI-MS (negative) [M−H]⁺: 1108.

Example 46. H-AAPF-RBB [SEQ ID NO: 30]

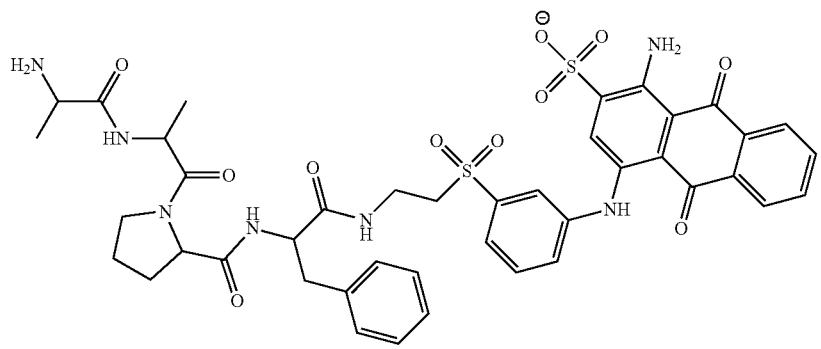 [SMILES: CC(N)C(=O)NC(C)C(=O)N1CCCC1C(=O)NC(Cc1ccccc1)C(=O)NCCS(=O)(=O)c1cccc(Nc2cc(S(=O)(=O)[O-])c(N)c3c2C(=O)c2ccccc2C3=O)c1]

Class: Dye-peptide conjugate based on Remazol Brilliant Blue R.

Synthesis: Fmoc-AAPF-RBB [SEQ ID NO: 12] (1 equiv) (example 45) was treated with a mixture of methanol/piperidine (2:1) at ambient temperature for 45 min while stirring. Reaction monitoring via ESI-MS (−p) indicated consumption of starting materials. Simple evaporation of volatiles in vacuo yielded a crude product as blue amorphous solid. Yield: quantitative (crude product). ESI-MS (negative) [M−H]$^+$: 886.

Example 47. Acrylamido-AAPF-RBB [SEQ ID NO: 12]

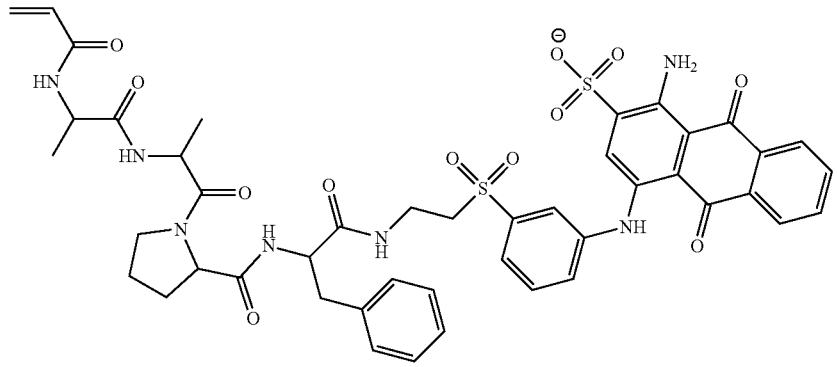 [SMILES: C=CC(=O)NC(C)C(=O)NC(C)C(=O)N1CCCC1C(=O)NC(Cc1ccccc1)C(=O)NCCS(=O)(=O)c1cccc(Nc2cc(S(=O)(=O)[O-])c(N)c3c2C(=O)c2ccccc2C3=O)c1]

Class: Dye-peptide conjugate based on Remazol Brilliant Blue R.

Synthesis: H-AAPF-RBB [SEQ ID NO: 30] (1 equiv; Example 46) was dissolved in methanol and treated with acrylic acid pentafluorophenyl ester (3 equiv) at ambient temperature while stirring. Reaction monitoring via ESI-MS (−p) indicated consumption of starting materials after ~12 h (overnight). Simple evaporation of volatiles in vacuo yielded crude product which was again dissolved in DCM leaving insoluble white byproducts behind. Subsequent evaporation in vacuo upon filtration yielded the product as blue amorphous solid adequately pure for the next step. Yield: ~98% (crude product). ESI-MS (negative) [M−H]$^+$: 94

Example 48. Fm-Valin-(3-Azido-2-hydroxy)-propylamide

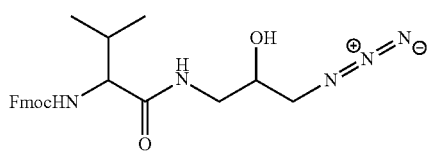

Class: Amino acid building block for Peptide synthesis, substrate for 1,3-dipolar [3+2]-cycloaddition.

Synthesis: Fmoc-N-(2-epoxypropyl-1-amido)-valine (1 equiv) was dissolved in DCM. Sodium azide (excess) was dissolved in water and the aqueous phase was added to the organic solution at ambient temperature while stirring (>1000 rpm). Catalytic amount of phase transfer catalyst tetra-«-butyl ammonium hydrogen sulfate was added followed by subsequent additions of catalytic amounts of sulfuric acid. The latter was consumed by time and needed to be refreshed on a regular basis until reaction monitoring via ESI-MS (+p) indicated full conversion of starting materials. Aqueous work-up and evaporation of volatiles in vacuo yielded crude colorless to beige product as amorphous solid. Yield: 66% (crude product). ESI-MS (positive) [M+Na]$^+$: 460.

Example 49. Acrylamido-AAPVA-RBB [SEQ ID NO: 26]

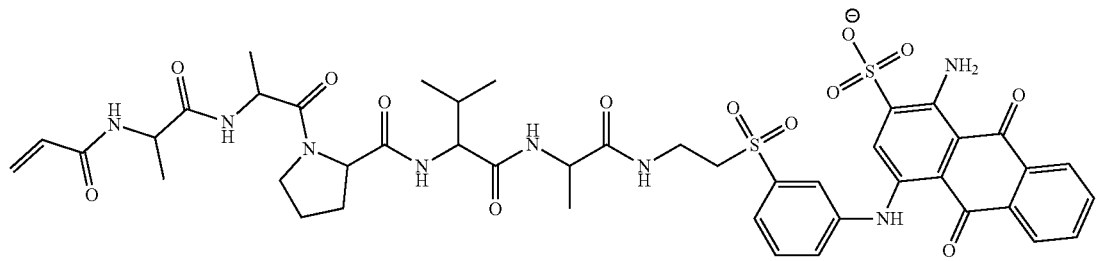 [SMILES: C=CC(=O)NC(C)C(=O)NC(C)C(=O)N1CCCC1C(=O)NC(C(=O)NC(C)C(=O)NCCS(=O)(=O)c1cccc(Nc2cc(S(=O)(=O)[O-])c(N)c3c2C(=O)c2ccccc2C3=O)c1)C(C)C]

Class: Dye-peptide conjugate based on Remazol Brilliant Blue R.

Synthesis: H-AAPVA-RBB [SEQ ID NO: 28] (1 equiv; Example 40) was dissolved in methanol and treated with acrylic acid pentafluorophenyl active ester (1.2 equiv) at ambient temperature while stirring. Reaction monitoring via ESI-MS (–p) indicated consumption of starting materials after ~12 h (overnight). Simple evaporation of volatiles in vacuo yielded crude product as blue amorphous solid adequately pure for the next step. Yield: >95% (crude product). ESI-MS (negative) [M–H]$^+$: 963.

Example 50. Bis-Aminoethyl-(Remazol Black B)

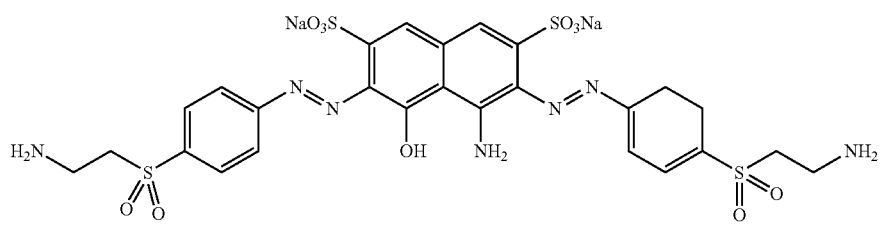

Class: Dye conjugate based on Remazol Black B, Amination/Amidation substrate

Synthesis: Remazol Black B (1 equiv) was dissolved in water and treated with aqueous ammonia (28-30%, excess) at ambient temperature while stirring. Reaction monitoring via ESI-MS (–p) indicated full conversion of starting materials after ~20 h (overnight). Simple evaporation of volatiles in vacuo yielded crude product as black amorphous solid with slight violet gloss adequately pure for the next step. Yield: quantitative (crude product). ESI-MS (negative) [M–H]$^+$: 740.

Example 51. Aminoethyl-Remazol Brilliant Violet

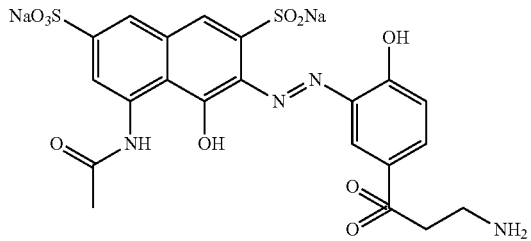

Class: Azo-Dye conjugate based on Remazol Brilliant Violet 5R, Amination/Amidation substrate.

Synthesis: Remazol Brilliant Violet 5R (1 equiv) was dissolved in water and treated with aqueous ammonia (28-30%, excess) at ambient temperature while stirring. Reaction monitoring via ESI-MS (−p) was not possible due to the fact that neither starting materials nor products were detectable in ESI-MS ionization. After prolonged period of reaction time (9 d) to ensure full conversion simple evaporation of volatiles in vacuo yielded crude product as dark violet amorphous solid. Yield: ~82% (crude product).

Example 52. Fmoc-AAPF-aminoethyl-(Remazol Black B) [SEQ ID NO: 12]

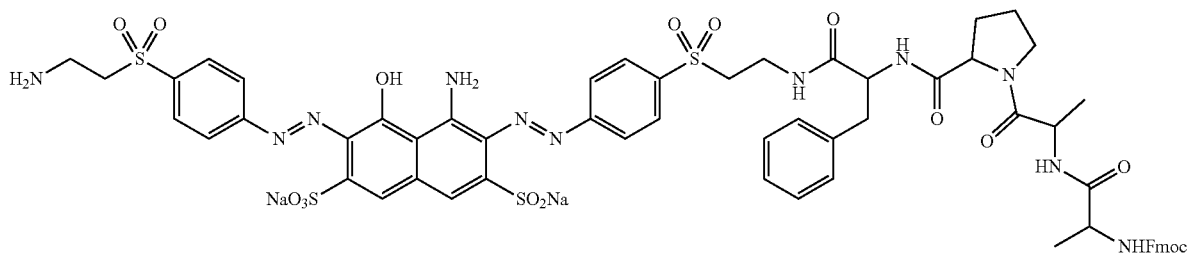

Class: Dye conjugate based on Remazol Black B, Tetrapeptide building block, Cathepsin substrate.

Synthesis: A stirred mixture of tetrapeptide Fmoc-AAPF-OH [SEQ ID NO: 13] (1 equiv) and HOBt·H$_2$O (1 equiv) in DCM was treated with DCC (1 equiv) at ambient temperature for 15 min. Bis-Aminoethyl-(Remazol Black B) (0.8 equiv; Example 50) was added in one portion and the reaction mixture was stirred at room temperature until reaction monitoring via ESI-MS (−p) indicated consumption of starting materials. Used in next step without further purification.

Example 53. Fmoc-AAPF-aminoethyl-(Remazol Black B)-(N-acetyl)-ethylamide [SEQ ID NO: 12]

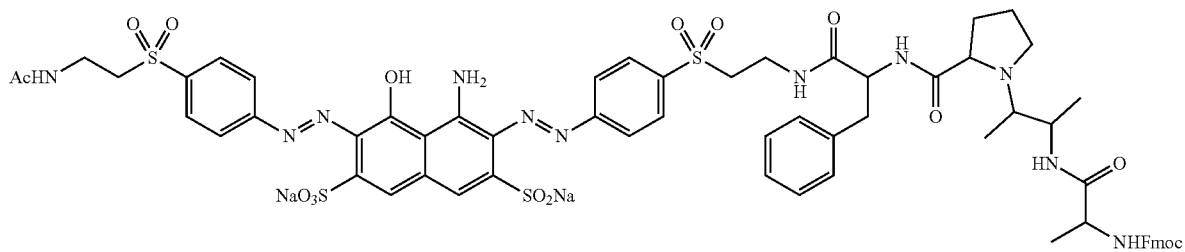

Class: Dye-peptide conjugate based on Remazol Black B, Cathepsin substrate.

Synthesis: The stirred reaction mixture for Fmoc-AAPF-aminoethyl-(Remazol Black B) [SEQ ID NO: 12] (Example 52) was treated with excess acetic anhydride at ambient temperature for 4 h. When reaction monitoring by ESI-MS (−p/+p) indicated consumption of starting materials, the reaction mixture was filtered and the filtrate was evaporated in vacuo yielding black amorphous powder as a crude product. The crude product was subsequently used without additional purification. Identity was imputed through reaction with elastase to yield the mono-acetylated-Remazol Black B-amino derivative.

Example 54. CMC 9M31F-AAPFA-RBB [SEQ ID NO: 24]

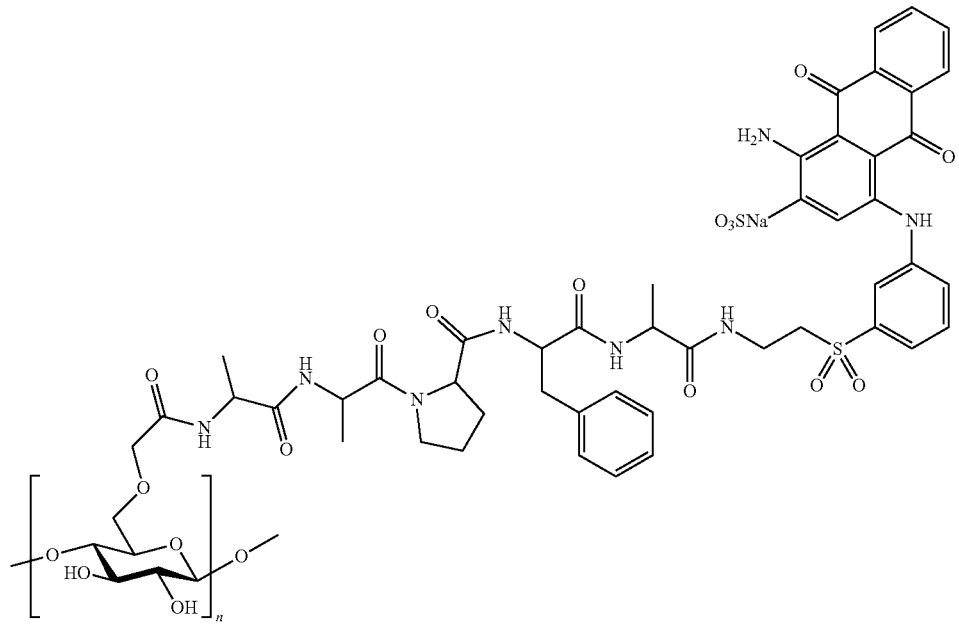

Class: Full prototype assembly (Back bone/cutting unit/Dye), Cathepsin substrate.

Synthesis: Blanose CMC 9M3 IF (1 equiv) was dissolved in water and was treated with HOBt (1.2 equiv) followed by EDC»HCl (1.2 equiv) for 0.5 h while stirring at ambient temperature. H-AAPFA-RBB [SEQ ID NO: 25] (0.1 equiv; Example 38) was added and stirring was continued overnight (>14 h). The following day, the reaction mixture was purified by dialysis yielding a blue jelly as crude product. Yield: depends on degree of substitution; 1 g Blanose provides ca. 1 g product. The resulting product was a polymer and was not easily characterised by spectroscopy. It was, however, blue, and the blue color is associated with the high MW fraction following dialysis in a 10 kDa membrane. Reaction with elastase was detected using ESI MS to detect the release of the dye.

Example 55. CMC 9M31F-AAPF-RBB [SEQ ID NO: 12]

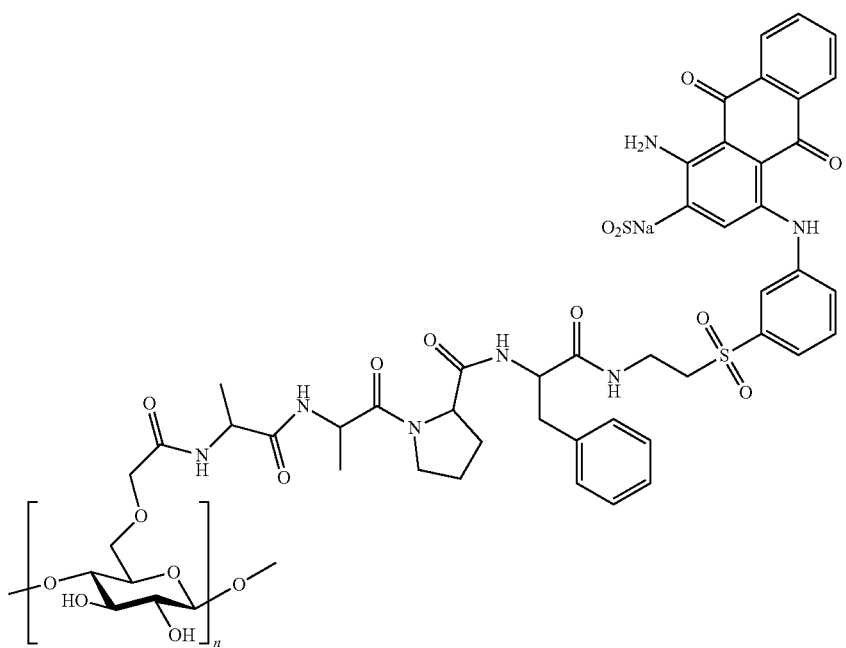

Class: Full prototype assembly (Back bone/cutting unit/Dye), Cathepsin substrate.

Synthesis: Blanose CMC 9M3 IF (1 equiv) was dissolved in water and was treated with $HOB_t$ (1.2 equiv) followed by EDC·HCl (1.2 equiv) for 0.5 h while stirring at ambient temperature. H-AAPF-RBB [SEQ ID NO: 30] (0.1 equiv; Example 46) was added and stirring was continued overnight (>14 h). The following day, the reaction mixture was purified by dialysis yielding a blue jelly as crude product. Yield: depends on degree of substitution; 1 g Blanose provides ca. 1 g product. The resulting product was a polymer and was not easily characterised by spectroscopy. It was, however, blue, and the blue color is associated with the high MW fraction following dialysis in a 10 kDa membrane. Reaction with elastase is detected using ESI MS to detect the release of the dye.

Example 56. AAPVA-RBB Bound to Paper Membrane [SEQ ID NO: 26]

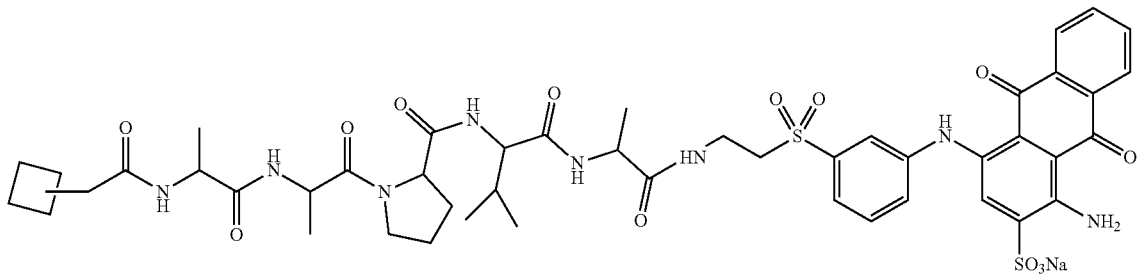

Class: Full prototype assembly on a surface or solid phase "6651" (anchor region/enzyme-labile or enzyme-reactive region/indicator region), Elastase substrate.

Synthesis: Paper membrane (1 equiv) was soaked in DMF and subsequently treated with HOBi·H$_2$O (~1.2 equiv), DCC (~1.2 equiv) and H-AAPVA-RBB [SEQ ID NO: 28] (~1 equiv; Example 40) at ambient temperature while stirring. After two days of reaction time, paper membranes were filtered off, washed with water, saturated aq. NaHCO$_3$, ethanol, ethyl acetate, and dried with diethyl ether. After treatment, the membranes kept a slight greenish color, indicating a very low degree of loading. Yield: n.a. The resulting product was a polymer and was not easily characterised by spectroscopy.

Example 57. Fmoc-M-RBB

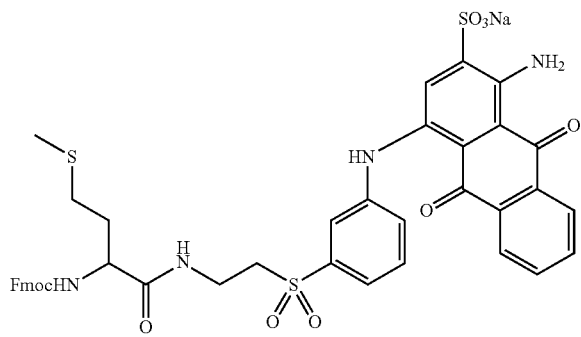

Class: Methionine-Dye conjugate based on Remazol Brilliant Blue, Educt for Amination/Amidation substrate.

Synthesis: H-RBB (1 equiv; Example 29) was dissolved in methanol and Fmoc-methionine pentafluorophenyl ester (3 equiv) was added at ambient temperature while stirring. Reaction monitoring via ESI-MS (-p) indicated consumption of starting materials and the reaction was stopped by evaporation of any volatiles in vacuo. A blue amorphous solid was obtained as crude product, sufficiently pure for the next step. Yield: quantitative (based on Dye). ESI-MS (negative) [M−H]$^+$: 853.

Example 58. H-M-RBB

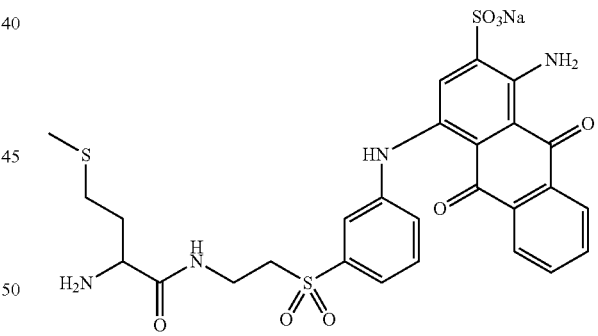

Class: Methionine-Dye conjugate based on Remazol Brilliant Blue, Amination/Amidation substrate.

Synthesis: Fmoc-M-RBB (1 equiv; Example 57) was dissolved in a mixture of methanol and piperidine (2:1 v/v) at ambient temperature while stirring. After a short time (<1 h), reaction monitoring via ESI-MS (-p) indicated consumption of starting materials, and the reaction was stopped by evaporation of any volatiles in vacuo. A blue amorphous solid remained as crude product which was taken up in acetonitrile. Insoluble white byproducts were filtered off and again volatiles were removed in vacuo. The blue amorphous product obtained was sufficiently pure for the next step. Yield: quantitative. ESI-MS (positive) [M+H]$^+$: 633.

Example 59. Fmoc-AAAPM-RBB [SEQ ID NO: 31]

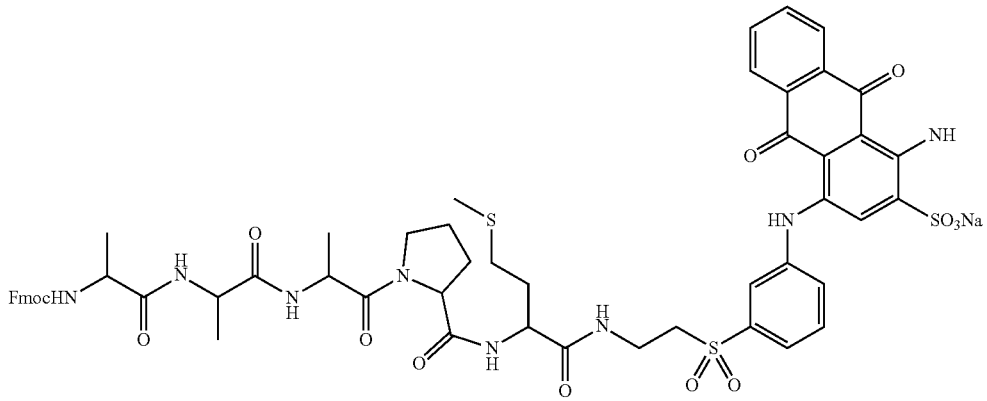

Class: Dye conjugate based on Remazol Brilliant Blue, Pentapeptide building block, Cathepsin substrate.

Synthesis: A stirred mixture of tetrapeptide Fmoc-AAAP-OH [SEQ ID NO: 32] (1 equiv) and HOBt·H$_2$O (1.2 equiv) in DCM was treated with DCC (1.2 equiv) at ambient temperature for 15 min. H-M-RBB (1 equiv; Example 58) was added in one portion and the reaction mixture was stirred at room temperature until reaction monitoring via ESI-MS (−p) indicated consumption of starting materials. Reaction mixture was further diluted with DCM, urea species filtered off, and the filtrate was subjected to aqueous work-up. After drying over sodium sulfate evaporation of volatiles in vacuo yielded blue amorphous solid as crude product sufficiently pure for the next step. Yield: >85%. ESI-MS (negative) [M−H]$^+$: 1163.

Example 60. H-AAAPM-RBB [SEQ ID NO: 33]

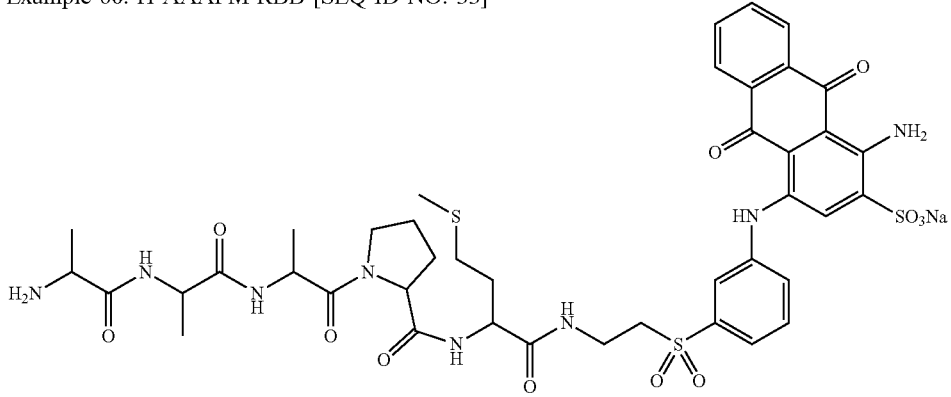

Class: Dye conjugate based on Remazol Brilliant Blue, Pentapeptide building block, Cathepsin substrate.

Synthesis: Fmoc-AAAPM-RBB [SEQ ID NO: 31] (1 equiv; Example 59) was dissolved in a mixture of methanol and piperidine (2:1 v/v) at ambient temperature while stirring. After a short time (<1 h), reaction monitoring via ESI-MS (−p) indicated consumption of starting materials, and the reaction was stopped by evaporation of any volatiles in vacuo. A blue amorphous solid remained as crude product which was taken up in acetonitrile. Insoluble white byproducts were filtered off and again volatiles were removed in vacuo. A blue amorphous product was obtained, sufficiently pure for further investigations. Yield: quantitative. ESI-MS (negative) [M−H]$^+$: 941.

Example 61. Poly-N-acroyl-S-tritylcysteine

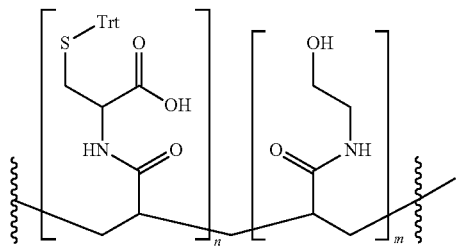

To a solution of poly-N-nitrophenyl acrylate (PAA) (722 mg) in dry DMF (6 mL) was added H-Cys(Trt)-OH (1030 mg) and triethylamine (450 µL). The reaction mixture was carefully moved {i.e., rolled), with occasional ultrasonication, until all solid was dissolved. Then the mixture was warmed to 54° C. for 1 5 h with occasional shaking. When reaction monitoring by MS indicated disappearance of H-Cyst(Trt)-OH, ethanolamine (250 µL.) was added to quench unreacted sites and warming was continued for an additional 30 min. The mixture was poured into methanol (80 mL). All precipitates were isolated, re-dissolved with DMF (5 mL) and re-precipitated with methanol (100 mL) by addition of formic acid (100 µL.) or saturated aq. calcium chloride solution (100µ). The precipitate was isolated, stirred for 2 h with methanol (100 mL) and filtered. After washing with methanol and diethyl ether, 540 mg of the product was isolated.

Combination of the supernatants, addition of formic acid until the color of nitrophenol disappeared and re-precipitation of the precipitate as described above yielded an additional 405 mg of product. Total yield: approx. 70%. (Due to the polymeric nature of the material, no specific characterization was possible. However, the disappearance of tritylcysteine is a strong support for the proposed structure.)

Using this procedure, other amines were loaded to the activated polyacrylate (see Table 1). When performed on a small scale, gel chromatography of the crude reaction mixture in DMF proved to be a suitable purification method. (Due to the polymeric nature of the materials, no specific characterization was possible. However, material passed through Sephadex is of high molecular weight and blue, thus proving attachment of the dye to the polymer).

TABLE 1

| Entry | PAA (mg) | amine | amine for quench | Purification method |
|---|---|---|---|---|
| 1 | 579 | H-AAPVA-CV, SEQ ID NO: 28 (as mixture in DMF, 15 mg) (example 71) | ethanolamine | chromatography over Sephadex LH 20 ® |
| 2 | 500 | tris-hydroxymethylmethylamine ("TRIS") (60 mg) | di-n-octylamine | Precipitation |
| 3 | 450 | S-Tritylcysteine (240 mg) | butlyamine | Precipitation |
| 4 | 620 | S-Tritylcysteine (52 mg) | N$_a$-Boc-Lysine | Precipitation |

Example 62. Linking of a Peptide-Dye Conjugate to a polymer (poly-(N-acroyl-Boc-Lys-OH)-co-(acroyl-Cys(Trt)-OH)

Step A:

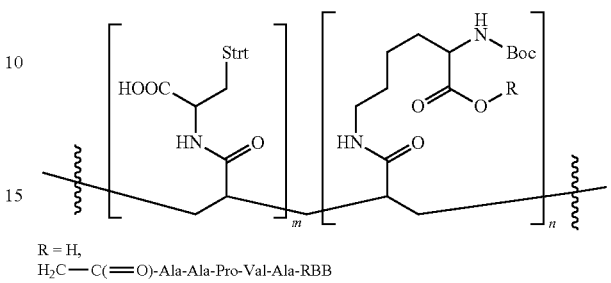

R = H,
H$_2$C—C(═O)-Ala-Ala-Pro-Val-Ala-RBB

H-AAPVA-RBB [SEQ ID NO: 28] (52 mg; Example 40) was dissolved in DMF (1 mL) and combined with ethyl diisopropylamine (10 µL). Chloroacetic acid anhydride (10.8 mg) was added. The mixture was stirred for 1 h, then additional chloroacetic acid anhydride (8.5 mg) was added. After stirring for further 2 h, MS indicated predominant conversion. 500 NL of this solution was combined with poly-(N-acroyl-Boc-Lys-OH)-co-(acroyl-Cys(Trt)-OH) (104 mg; entry 4 in Table 1) and ethyl diisopropylamine (70 µL). The mixture was heated to 60° C. overnight, then to 80° C. for 40 min. The reaction mixture was applied to a Sephadex LH 20® column for purification; the front-eluting blue zone was isolated to yield 85 mg of product. (Due to the polymeric nature of the materials, no specific characterization was possible. However, material passed through Sephadex is of high molecular weight and blue, thus proving attachment of the dye to the polymer). Treatment with elastase released Ala-RBB, as found by MS-analysis (m/z=571, negative mode).

Step B:

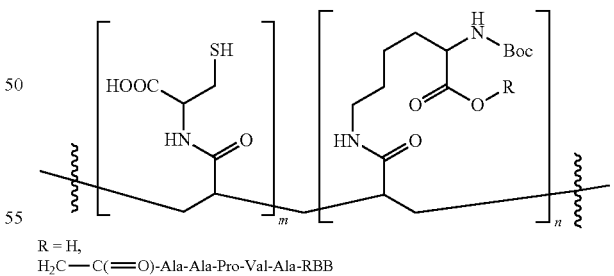

R = H,
H$_2$C—C(═O)-Ala-Ala-Pro-Val-Ala-RBB

The product of Step A was dissolved with DCM (1 mL) and methanol (0.5 mL) and treated for 40 min with trifluoroacetic acid (0.5 mL). All volatiles were removed in vacuo and the product was precipitated by addition of diethylether (100 mL). The product is a blue polymeric solid, with no observable mass in the negative mode below m/z=1200. Treatment with elastase released A-RBB, as found by MS-analysis (m/z=571, negative mode).

Step C:

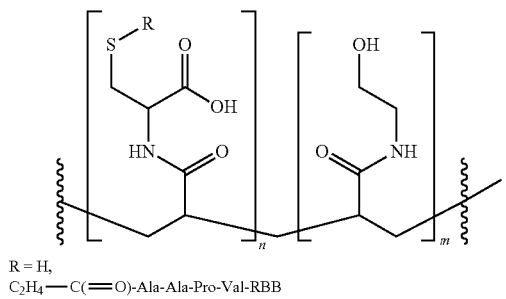

R = H,
C₂H₄—C(═O)-Ala-Ala-Pro-Val-RBB

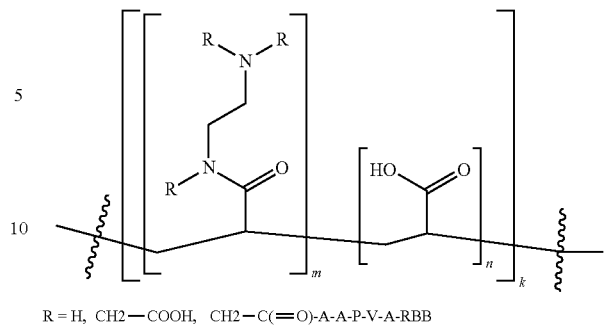

R = H, CH2—COOH, CH2—C(═O)-A-A-P-V-A-RBB

Poly-N-acroylcystein and 530 mg of Poly-N-acroyl-S-tritylcystein were dissolved with a mixture of 18 mL of dichloromethane, 1 mL of triisopropylsilane, and 2 mL of trifluoroacetic acid. 0.5 mL of water was added and the mixture was stirred overnight. The mixture was evaporated and washed with water and diethylether. (Due to the polymeric nature of the materials, no specific characterization was possible).

Example 63. Exemplary Construction of a High-Load Amino-Peptide-Dye Conjugate Linked to a Polymer b) 500 μL, of a 58 mM solution of Chloroacetamido-AAPVA-RBB [SEQ ID NO: 31] (prepared in Step A) and 4 μL of ethyl enediamine are combined, heated to 60° C. overnight and to 80° C. for 1 h. 72 mg of poly-(4-nitrophenyl)acrylate are dissolved in 500 μL of DMF and 70 μL of triethylamine are added and the mixture is stirred overnight. 300 μL of a 1M aq. solution of KOH are added, and the mixture is rolled for additional 45 min. A precipitate was isolated by centrifugation, subsequently dissolved with 0.1M KOH and precipitated with formic acid. The precipitate was dissolved with 1 ml of saturated aq. NaHCO3 and passed through a column of 6 g of Sephadex LH20. Drying in vacuo yields 84 mg of a bluish solid.

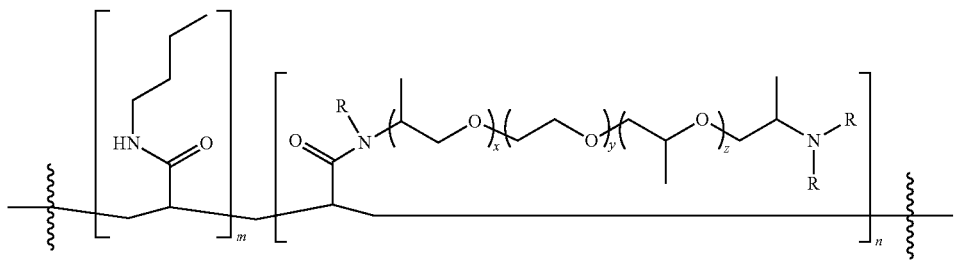

R = H, H₂C—C(═O)-Ala-Ala-Pro-Val-Ala-RBB
y = 12-13,
(x + z) = 6 a) H-AAPVA-RBB [SEQ ID NO: 28] (68 mg; Example 40) was dissolved with DMF (1 mL). Chloroacetic anhydride (16 mg) was added followed by ethyl diisopropylamine (100 μL). After stirring for 1 h, Jeffamine® 900 (80 mg) was added, and the mixture was warmed to 70° C. for 4 h. Poly-p-nitrophenylacrylate (75 mg) and diisopropylamine (100μï,) were added. After stirring for 2 h, residual reactive sites of the polymer were quenched with «-butylamine. (150 μL) The blue polymeric product was isolated by gel chromatography over Sephadex LH 20® to yield 105 mg. (Due to the polymeric nature of the materials, no specific characterization was possible. However, the material passed through Sephadex is of high molecular weight and blue, thus proving attachment of the dye to the polymer).

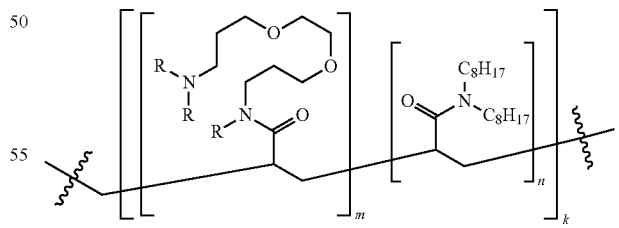

c) R═H, CH₂C(═O)-AAAPV-RBB [SEQ ID NO: 34]. 190 mg of H-AAAPV-RBB [SEQ ID NO: 34] (example 68c) are dissolved in 3 mL of DMF and 40 mg of chloroacetic anhydride are added. 40 μL of diisopropyl ethyl amine are added, and the mixture was stirred for 15 min at RT. A 2$^{nd}$ batch of chloroacetic anhydride (17 mg) and of diisopropyl ethylamine (20 μL), each, was added, and stirring is continued for 1 h. The reaction mixture was applied to silica gel and chromatographed with a gradient of cyclohexane-methanol-dichloromethan from 16-3-3 to 3-1-1, containing 0.2% of formic acid. The product fraction contained 69 mg, which are dissolved with 1 mL of DMF. 20 µL of diisopropyl ethyl amine are added, then 12 µL of Jeffamine EDR 176. The reaction mixture was agitated for 72 h at RT. Analysis with a mass spectrometer reveals a mixture of alkylation products with the peptide being added 1, 2, or 3 times to the amine (negative mode, m/z=1125=monoalkyl, single charge; m/z=1038=double alkyl, double charge; m/z=1513=triple alkyl, double charge; and m/z=1009=triple alkyl, triple charge). The reaction mixture was supplied with 38 mg of poly-p-nitrophenylacrylate, agitated for 1 h at RT and then kept 90 min at 54° C. 250 µL of N,N-dioctyl amine are added, and the mixture is kept at 54° C. for further 3 h with occasional shaking. The product was isolated by precipitation with acetone and chromatography of the precipitate after solution in methanol through a column of 6 g of Sephadex LH 20 with water-methanol 3-1 (highest molecular weight fraction is collected) to yield 31 mg of a water soluble material. The same procedure can be applied to H-AAAPVV-RBB [SEQ ID NO: 35] (example 68c).

Example 64. Fmoc-AAAPV-(diaminobenzoic acid) [SEQ ID NO: 36]

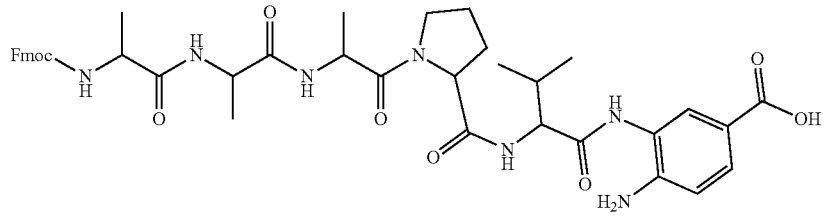

Fmoc-AAAPV-OH [SEQ ID NO: 11] (710 mg) was dissolved with DMF (5 mL). HOBt (210 mg) and DCC (240 mg) were added subsequently, and the mixture was stirred for 15 min at RT. 3,4-Diaminobenzoic acid (160 mg) and pyridine (100 µL) were dissolved with DMF (1 mL) and added to reaction mixture with stirring. After 14 h, the solvent was evaporated, and the residue was purified by silica gel chromatography with cyclohexane/DCM/methanol (4/2/1), containing 0.5% of formic acid, to yield 400 mg of product. ESI-MS (positive) [M+H]=784.

Example Fmoc-AAAPV-(diaminobenzoic acid) [SEQ ID NO: 36]

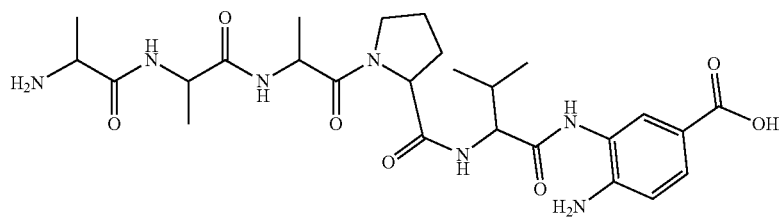 [SMILES: CC(N)C(=O)NC(C)C(=O)NC(C)C(=O)N1CCCC1C(=O)NC(C(=O)Nc1cc(C(=O)O)ccc1N)C(C)C]

To a solution of Fmoc-AAAPV-(diaminobenzoic acid) [SEQ ID NO: 36] (400 mg; Example 64) in DMF (3 mL) was added piperidine (0.5 mL). The mixture was stirred overnight, and concentrated by evaporation (1 mbar, 55° C.). The residue was stirred 2× with diethylether (25 mL) and intermediate filtration. The product formed was sufficiently pure for subsequent use. ESI-MS (positive) [M+H]=562.

Example 66 Poly(AAAPV-{diaminobenzoic acidjacrylamide) [SEQ ID NO: 36]

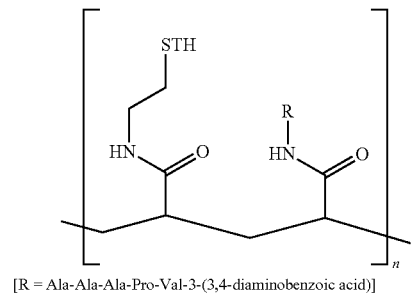

[R = Ala-Ala-Ala-Pro-Val-3-(3,4-diaminobenzoic acid)]

Cysteamine hydrochloride (11 mg) was dissolved in DMF (5 mL) pre-treated with argon. Poly-4-nitrophenyl acrylate (120 mg) and triethylamine (200 µL) were added. Care was taken to exclude oxygen during the entire process. The mixture was stirred for 1 h at 55° C. H-AAAPV-(diaminobenzoic acid) [SEQ ID NO: 34] (230 mg; Example 65) was dissolved with DMF (3 mL), treated with argon and added to the reaction mixture. The mixture was stirred overnight at 65° C. The product was precipitated under a stream of argon with methanol (100 mL), containing 0.5% formic acid. (Due to the polymeric nature of the materials, no specific characterization was possible. However, material passed through Sephadex is of high molecular weight and blue, thus proving attachment of the dye to the polymer.)

Example 67. Poly-co-[(N-mercaptoethyl acrylamide)-(AAAPV-{RBB}-acrylamide)] [SEQ ID NO: 36]

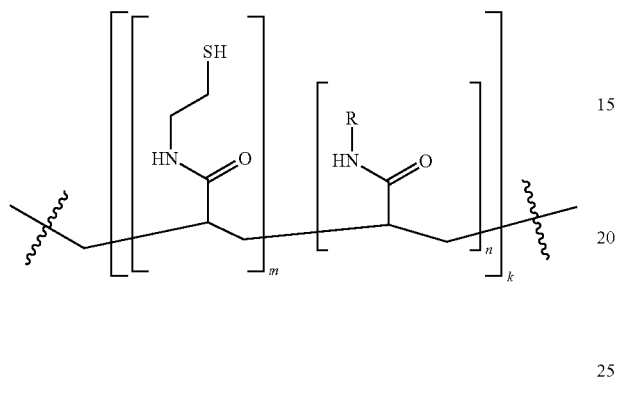

a) Cysteamine hydrochloride (2 mg) was dissolved in DMF (5 mL) pre-treated with argon. Poly-4-nitrophenyl acrylate (36 mg) and triethylamine (50 µL) were added. Care was taken to exclude oxygen during the entire process. The mixture was stirred for 1 h at 55° C. H-AAAPV-RBB [SEQ ID NO: 34] (125 mg, Example 68c) was dissolved with DMF (2 mL), treated with argon, and added to the reaction mixture. The mixture was stirred overnight at 65° C. The product was eluted by passing 1 ml of the reaction mixture with a mixture of water and methanol (4/1; pre-treated with argon) through a column of Sephadex LH 20® (6 g); the blue eluate at the very front was collected and concentrated in vacuo. (Due to the polymeric nature of the materials, no specific characterization was possible. However, material passed through Sephadex is of high molecular weight and blue colored, thus proving attachment of the dye to the polymer).

b) 2.2 mL of a solution of 95 mg of poly-p-nitrophenylacrylate in 9.5 mL of DMF was flushed with argon and combined with 46 µL of a solution of 32 mg of mercaptoethylamine hydrochloride and 45 µL of trimethylamine in 739 µL of argon flushed DMF. After stirring for 30 min, 45 mg of H-AAAPV-RBB [SEQ ID NO: 34] (example 68c) and 100 µL of triethylamine were added, and the mixture was agitated for 16 h at room temperature. After keeping the mixture at 54° C. for 90 min, 100 µL of ethanolamine were added and the reaction was kept for further 90 min at 54° C. The product was isolated by passing the mixture through a column of 6 g of Sepahdex LH 20 with water-methanol 3-1. (Due to the polymeric nature of the materials, no specific characterization was possible. However, material passed through Sephadex is of high molecular weight and blue colored, thus proving attachment of the dye to the polymer).

The same procedure can be applied to H-AAAPVV-RBB [SEQ ID NO: 35] (example 68c).

Poly-co-[(N-2-{3-(4-azidophenyl)propionyl)acrylamide-(AAAPV-{RBB}-acrylamide)][SEQ ID NO: 36]

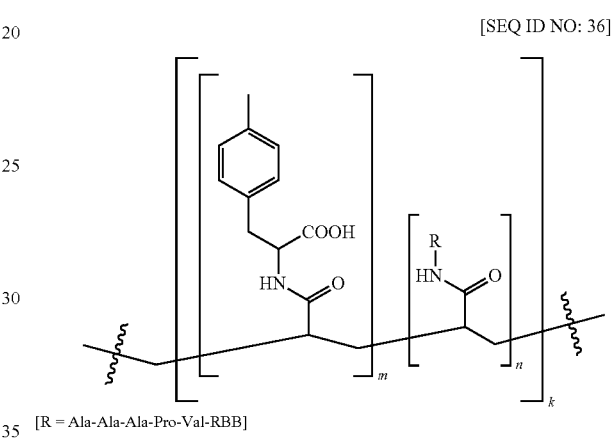

[R = Ala-Ala-Ala-Pro-Val-RBB]

c) 2.2 mL of a solution of 95 mg of poly-p-nitrophenylacrylate in 9.5 mL of DMF was combined with 2.2 mg of 4-azido phenylalanine and 5.8 µL of trimethylamine. After agitating for 30 min at RT, 43 mg of H-AAAPV-RBB [SEQ ID NO: 34] was added together with 100 µL of triethylamine, and the mixture was agitated for 16 h at RT. After keeping the mixture at 54° C. for 90 min, 100 µL of ethanolamine were added and the reaction was kept for further 90 min at 54° C. The product was isolated by passing the mixture through a column of 6 g of Sephadex LH 20 with water-methanol 3-1. (Due to the polymeric nature of the materials, no specific characterization was possible. However, material passed through Sephadex is of high molecular weight and blue, thus proving attachment of the dye to the polymer).

The same procedure can be applied to H-AAAPVV-RBB. [SEQ ID NO: 35] (Structure as above with R=Ala-Ala-Ala-Pro-Val-Val-RBB).

AAAPV-RBB Bound to Beads [SEQ ID NO: 34]

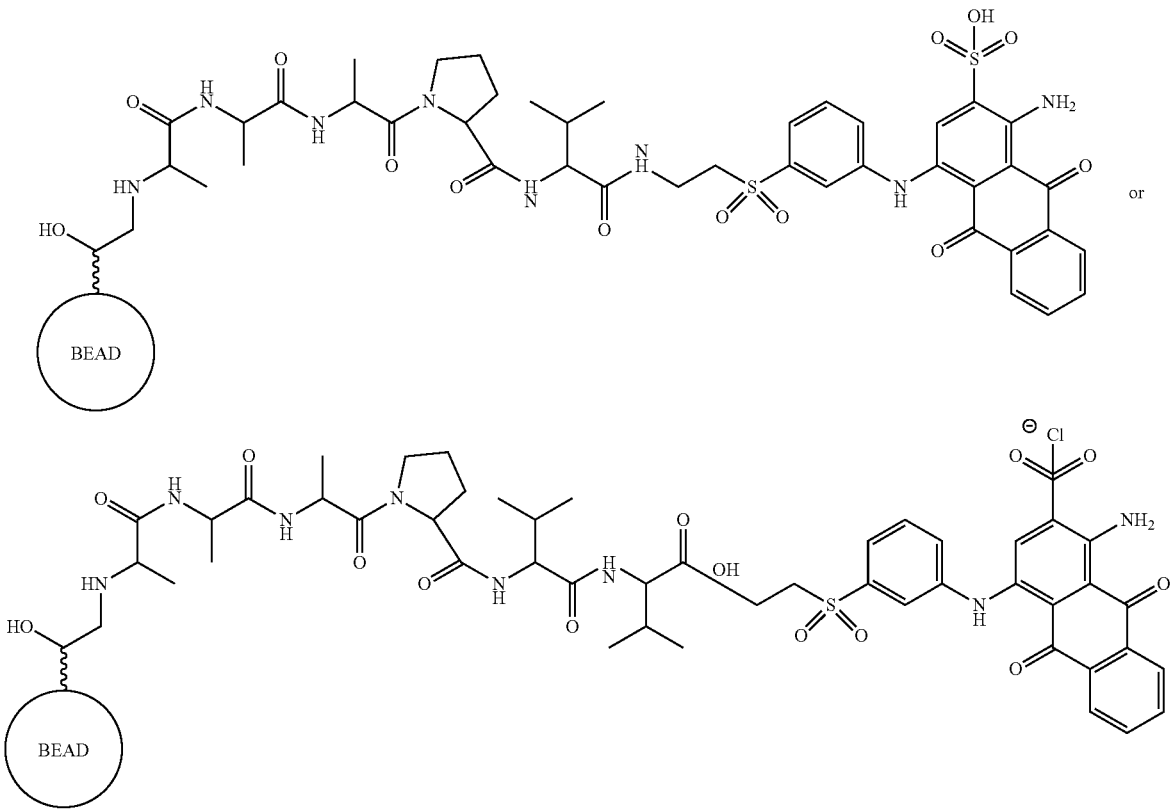

d) 30 mg of H-AAAPV-RBB [SEQ ID NO: 34] was combined with 93 mg of Sephabeads ECEP (epoxy activated) and 50 µL of DMF. The mixture was kept at 54° C. for 72 and washed with dichloromethane-methanol mixture (3-1) and then with DMF, until no more blue eluted.

The same procedure can be applied to H-AAAPVV-RBB [SEQ ID NO: 35] instead of H-AAAPV-RBB [SEQ ID NO: 34] IDC-1033

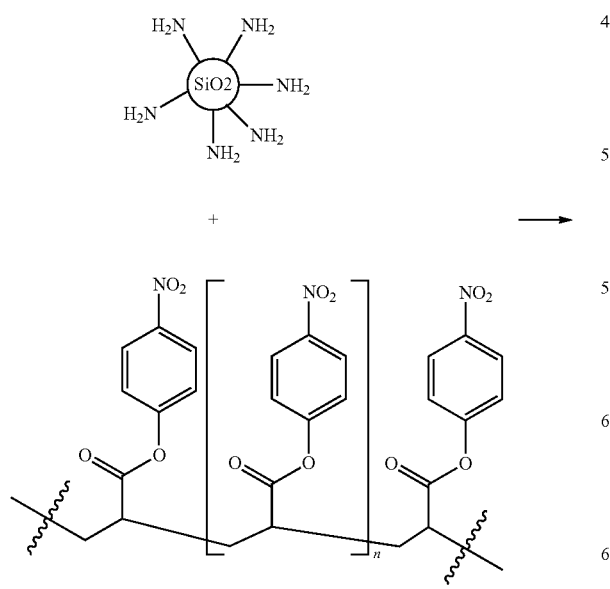

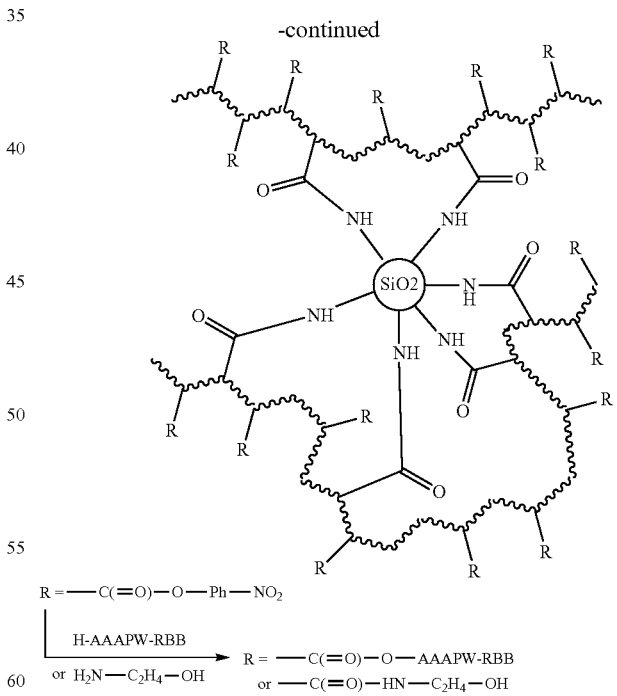

e) 50 mg of Chemicell SiCore Amin beads were washed with DMF 4 times and suspended in 800 µL of DMF. 90 mg of poly-p-nitrophenylacrylate was added, and the mixture was shaken at 60° C. for 3 h. 32 mg of H-AAAPVV-RBB [SEQ ID NO: 35] (example 68c) and 50 µL of triethylamine were added. Shaking at 60° C. was continued for 16 h. The beads were centrifuged off, the supernatant was decanted and used for example 67 g, and the beads ware treated with 10 μL of ethanolamine in 100 μL of DMF. After washing 5 times with 1.5 mL of DMF, the beads were washed 2 times with 1.5 mL of water. The beads have acquired a blue color, that can't be washed off.

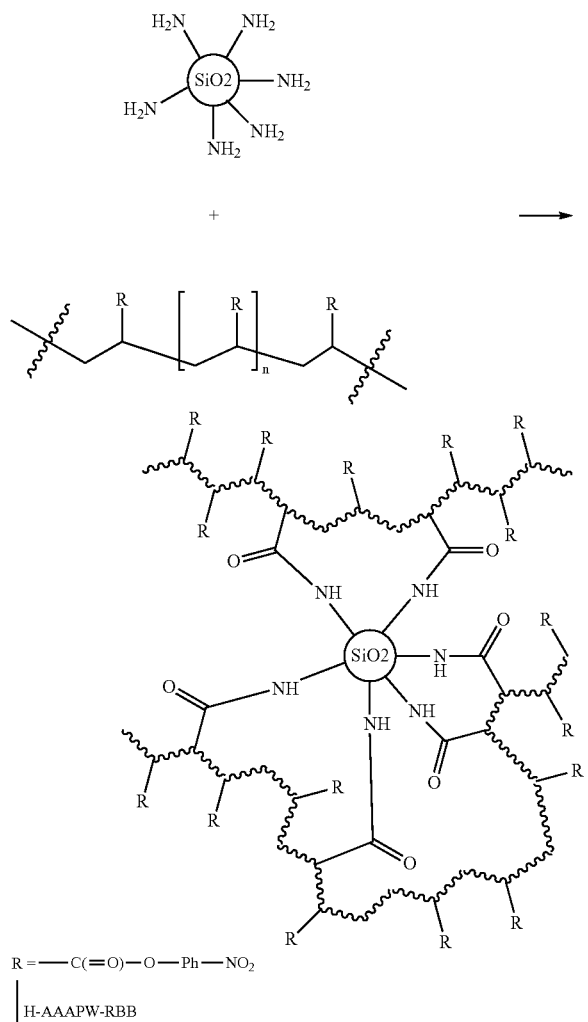

R = —C(═O)—O—Ph—NO₂

H-AAAPW-RBB ⟶ R = —C(═O)—AAAPW-RBB

R = —C(═O)—AAAPW-RBB
or —C(═O)—NH—C₂H₄—OH

) f) 33 mg f AAAPVV-RBB [SEQ ID NO: 35] and 19 mg of poly-p-nitrophenylacrylate were combined in 0.5 mL of DMF with 50 μL of triethylamine and agitated at 60° C. for 3 h. Beads prepared as in e) (50 mg) were added, and shaking at 60° C. was continued for 16 h. The beads were centrifuged off, the supernatant was decanted and used for example 67 g, and the beads were treated with 10 μL of ethanolamine in 100 μL of DMF. The beads were washed 5 times with 1.5 mL of DMF, followed by washing 2 times with 1.5 mL of water. The beads have acquired a blue color, that can't be washed off.

Isolation of Non-Bead-Bound Polymeric Material

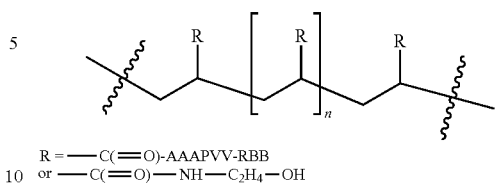

R = —C(═O)-AAAPVV-RBB
or —C(═O)—NH—C₂H₄—OH g) To the combined supernatants of e) and f) was added 120 μL of ethanolamine. The mixture was kept at 54° C. overnight. After pouring on 250 mL of diethylether, containing 1% formic acid, the insolubles were isolated by centrifugation, dissolved with 2 mL of DMF, and passed through a column of 6 g of Sephadex LH 20 with water-methanol (4-1). 2 mg of a blue high molecular weight fraction can be isolated.

Example 68. Polymer-Bound Dye with Hydrophobic Anchors and a Cleavage Site for Elastase

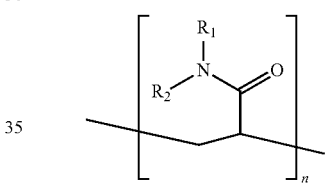

R₁=Ala-Ala-Ala-Pro-Val-RBB [SEQ ID NO: 34] and R₂=H or

R₁=n-octyl and R₂=H or

R₁=R₂=n-octyl a) H-AAAPV-RBB [SEQ ID NO: 34] (240 mg; Example 68c) and poly-(4-nitrophenyl)acrylate (103 mg) were combined and dissolved in DMF (5 mL). Triethylamine (600 μL) was added, and the mixture was agitated overnight. N,N-Dioctylamine (130 μL) was added and the mixture was kept at 54° C. with occasional shaking for 5 h. n-Octylamine (150 μL) was added, and the mixture was kept overnight at 54° C.

The mixture was poured into water (50 mL) containing 1% of formic acid. The precipitated material was collected by centrifugation and re-dissolved with warm methanol (10 mL). After a second precipitation with water (200 mL, with 0.5% of formic acid), a precipitate appeared and was isolated by filtration. The blue material was dried, re-dissolved with warm methanol (10 mL) and precipitated with diethyl ether. After filtration and drying, a blue powder remained. (Due to the polymeric nature of the materials, no specific characterization was possible).

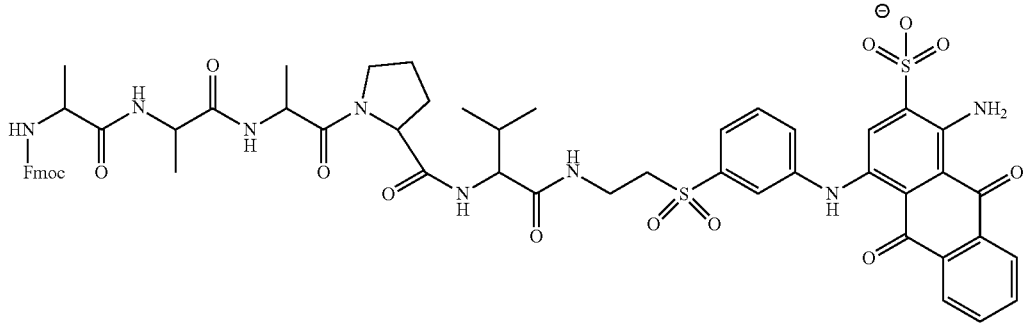

b) Synthesis of Fmoc-AAAPV-RBB [SEQ ID NO: 36]: A stirred mixture of tetrapeptide Fmoc-AAAP-OH [SEQ ID NO: 32] (740 mg) and HOBt·H2O (200 mg) in 10 ml of DMF was treated with DCC (198 mg) at ambient temperature for 15 min. H—V-RBB (680 mg; Example 42) was added in one portion and the reaction mixture was stirred at room temperature until reaction monitoring via ESI-MS (negative mode) indicated consumption of starting materials (~15 h, overnight). All volatiles were removed under reduced pressure. The solid residue was applied to 10 g of silica gel and chromatographed with a gradient of cyclohexane-ethyl acetate-methanol from 7-2-1 to 11-6-5 (each containing 0.1% of formic acid). Yield: 342 mg. ESI-MS (negative mode) [M−H]": 1131.

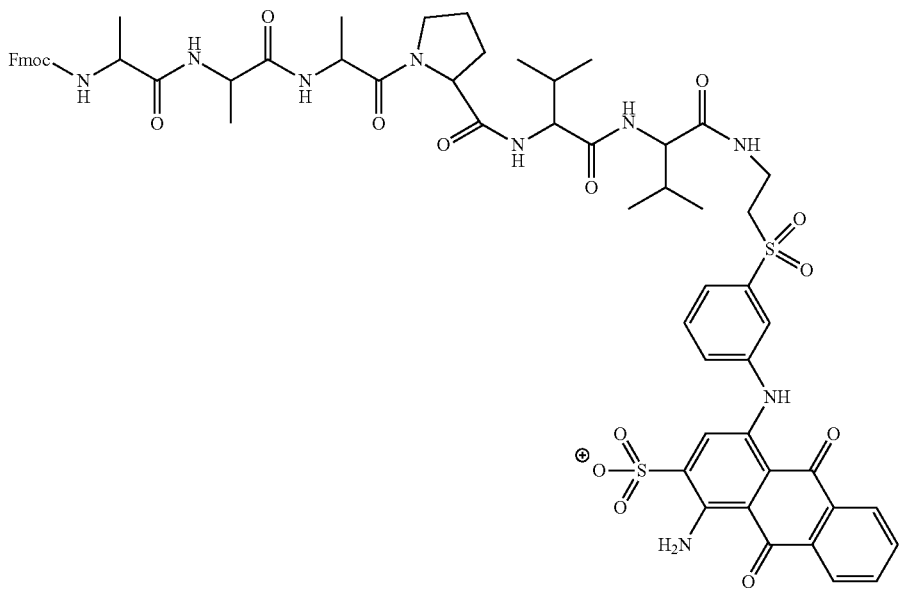

Fmoc-AAAPVV-RBB [SEQ ID NO: 37] was prepared using an analogous procedure as Example 68b starting from Fmoc-AAAPVV-OH [SEQ ID NO: 38]. ESI-MS (negative mode) [M−H]−: 1230.

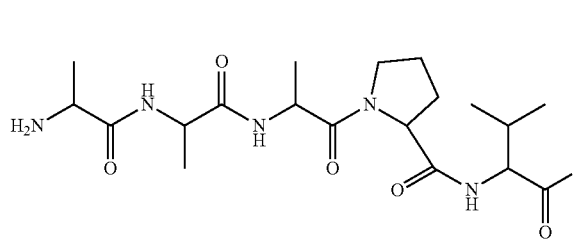
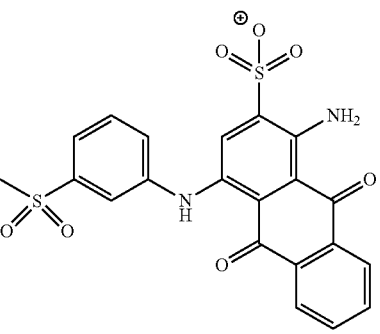

c) Synthesis of H-AAAPV-RBB [SEQ ID NO: 34]: Fmoc-AAAPV-RBB [SEQ ID NO: 36] (342 mg, example 68b) was dissolved with DMF (~12 mL). Piperidine (0.5 mL) was added. The mixture was stirred for 1 h at room temperature, until reaction monitoring with MS indicated consumption of the starting material (m/z=1131, negative mode) and formation of the product (m/z=909, negative mode). All volatiles were removed under reduced pressure, and the residue was stirred for 30 min with a mixture of DCM and methanol (5:1, 5 ml), and then precipitated by addition of diethyl ether (20 mL). The precipitate was isolated by filtration and treated for 60 min with diethylether (25 mL) with heavy stirring. After filtration by suction and drying at 54° C. for 3 h, 288 mg of an intense blue, fine powder was isolated. ESI-MS (negative mode) [M–H]–: 909.

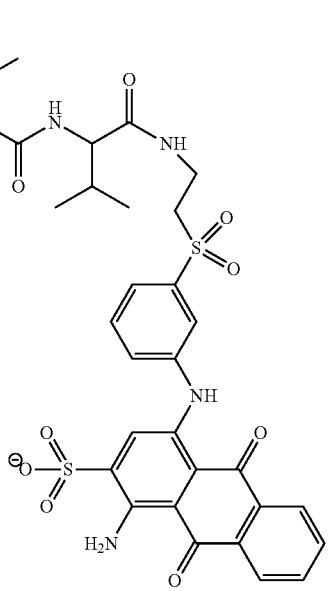

Synthesis of H-AAAPVV-RBB [SEQ ID NO: 35] was prepared using an analogous procedure as described in Example 68c. ESI-MS (negative mode) [M–H]−: 1008.

d) 40 mg of AAAPV-RBB [SEQ ID NO: 34] and 14 mg of poly-p-nitrophenyl acrylate were combined in 1 mL of DMF. When everything was dissolved, 100 µL of trimethylamine are added, and the mixture was agitated for 30 min. 20 µL of N,N-dioctylamine are added, and the mixture was agitated at RT overnight. The reaction mixture was passed through a column of 6 g of sephadex LH 20 with methanol-water mixture (1+3) twice to yield 13 mg of a dark blue polymeric powder. (Due to the polymeric nature of the materials, no specific characterization was possible. However, material passed through Sephadex is of high molecular weight and blue, thus proving attachment of the dye to the polymer).

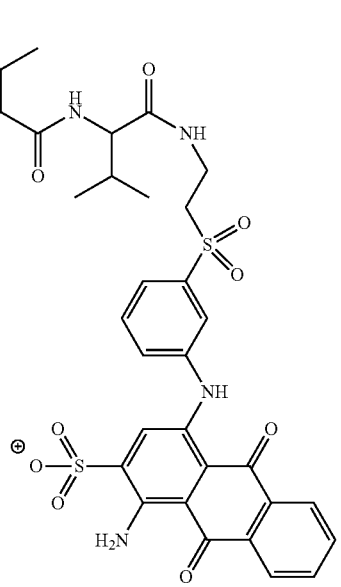

e) Synthesis of N-[(3-triethoxysilyl)propyl]-N'-[AAAPVV-RBB]urea [SEQ ID NO: 37] and subsequent binding of the compound to silica gel: H-AAAPVV-RBB [SEQ ID NO: 35] (49 mg; Example 68c) was dissolved with dry DMF (2 mL). (Isocyanatopropyl)triethoxysilane (80 µL as a 10% solution in dry DMF) was added and the mixture was stirred at ambient temperature. After 2 h, a second portion of (isocyanatopropyl)triethoxysilane (80 µL as a 10% solution in dry DMF) was added and the mixture was stirred overnight. When reaction monitoring by ESI-MS indicated complete conversion (negative mode) [M–H]⁺: 1255), 35 mg of silica gel (Reprosil 100, Dr. Maisch, 5 µm, pore size 100 Angström, spec. surface 280 m²/g) was combined with 100 µL of the reaction mixture and incubated overnight at 75° C. with shaking. The product was isolated by centrifugation and washed with DMF (5×1 mL) and water (2×1 mL). It comprised a dark blue powder, that did not leach any blue with water or DMF within 5 h.

Example 69. Fmoc-A-(N-phenylpiperazinyl)amide

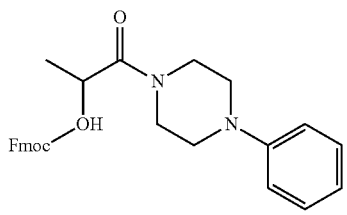

Fmoc-A-OH (1.69 g) and HOBt (1.2 g) were suspended in DCM (25 mL). 1-Ethyl-3-(3-dimethylaminopropyl)carbodiimide hydrochloride (EDCI) (1.12 g) was added and the mixture was stirred for 10 min. N-Phenylpiperazine (605 mg) was added and the mixture was stirred for an additional 60 min at room temperature. The mixture was extracted with 1 N aq. HCl and 1 N aq. K₂CO₃ (2× each), then with brine and dried over sodium sulfate. Evaporation yielded 1.3 g of sufficiently pure product. ESI-MS (positive) [M+H]=456.

Example 70. Bis-(4-dimethylaminophenyl)-(4-[4-N—(N-Fmoc-alanyl)]piperazinophenyl)-carbenium ion [Fmoc-A-(CV)] (a) and Bis-(4-dimethylaminophenyl)-(4-[N-piperazino]phenyl)-carbenium ion (CV) (b)

(a)

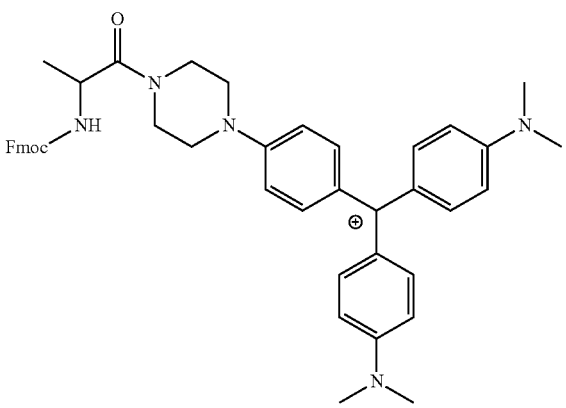

(b)

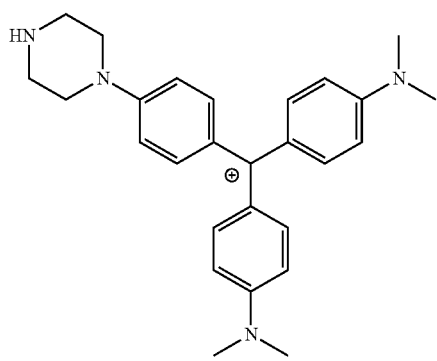

To a mixture of crude Fmoc-A-N-phenylpiperazine amide (2.52 g, example 69) and 4,4'-bis(N,N-dimethylamino)benzophenone (Michler's ketone, 1.92 g), was added phosphorous (V) oxichloride (1.6 mL), and the reagents were mixed until everything was homogenously wet. The mixture was heated to 100° C. for 2 h, left to cool and dissolved with a mixture of acetone and water (1:1). Silica gel (8 g) was applied to the blackish-blue solution, and the mixture was evaporated to dryness. Elution with a gradient of cyclohexane-ethyl acetate-methanol (8/1/1, containing 0.5% formic acid to 3/1/1, containing no acid; then 0/1/1, containing 3% triethylamine) provided 1.22 g of (a) (m/z=706) and 720 mg of (b) (m/z=413) as a salt. ESI-MS (positive) [M]=706 and 413, respectively.

Example 71. 4-([4-(H-Ala-Ala-Pro-Val-Ala) [SEQ ID NO: 28] amido N-piperazino]phenyl)-bis-(4-dimethyl-aminophenyl)-carbenium ion (H-AAPVA-CV) and 4-([4-(H-Ala-Ala-Pro-Val-Ala)amido N-piperazino]phenyl)-bis-(4-dimethyl-aminophenyl)-carbenium ion polyacrylamide C. Fmoc-AAP-OH (110 mg) was combined with HOBt (50 mg) and suspended in DMF (20 mL). EDCI (50 mg) was added, and the mixture was stirred for an additional 10 min. The intermediate from step B (110 mg) was added, and the mixture was stirred for an additional 2 h. Reaction monitoring with MS (m/z=1044) indicated the formation of expected product.

D. The reaction mixture was treated with piperidine (0.5 mL) and stirred overnight. MS indicated formation of the target compound (ESI-MS (positive) [M]=822). All volatiles were removed in vacuo at <30 mbar/50° C. Treatment of the material with elastase released A-CV, as found by MS-analysis (m/z=484, positive mode).

E. 579 mg of poly-p-nitrophenylacrylate are dissolved with 6 ml of DMF. The residue of D is added and the mixture is agitated for 72 h at RT. MS indicates disappearance of the

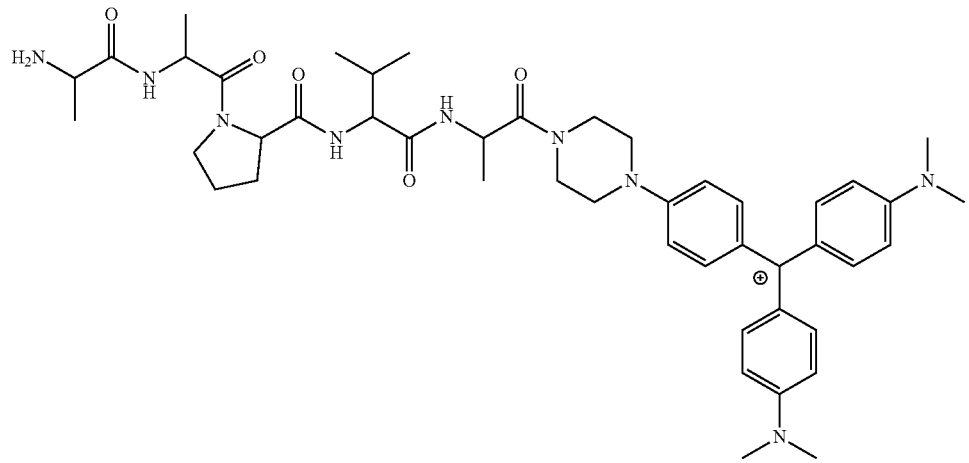 [SMILES: CC(N)C(=O)NC(C)C(=O)N1CCCC1C(=O)NC(C(=O)NC(C)C(=O)N1CCN(c2ccc(C(c3ccc(N(C)C)cc3)c3ccc(N(C)C)cc3)cc2)CC1)C(C)C]

A. Fmoc-A-CV (980 mg; Example 70a) was dissolved with DCM (40 mL). Excess piperidine (2 mL) was added, and the mixture was stirred overnight. All volatiles were removed in vacuo and residual piperidine was removed in vacuo at <30 mbar/50° C. The residue was washed cyclohexane (3×), dried and dissolved with DCM (10 mL). The product was identified by MS (m/z=484).

B. Fmoc-Val-Pfp (870 mg) was added, and the mixture was stirred for 15 min. All volatiles were removed in vacuo, and the residue was treated with piperidine (2 mL) in DCM (20 mL). All volatiles were removed, and the mixture was washed with cyclohexane (3×), and dried in vacuo at <30 mbar/50° C. The mixture was purified by HPLC to yield 110 mg of the desired intermediate.

peak at m/z=822. 500 µL of ethanolamine are added, and the mixture is agitated at RT for 7 h. The blue color of the CV-cation can be reestablished by acidic treatment. 1 mL of the preparation is passed through a column of Sephadex LH 20 (20 mL, water/methanol 2+1). The bluish-green fraction eluting at the front is collected and dried i.v. Treatment with porcine and human elastase releases A-CV, as proven by the appearance of a mass peak at m/z=484. (Due to the polymeric nature of the materials, no specific characterization was possible. However, material passed through Sephadex is of high molecular weight and blue, thus proving attachment of the dye to the polymer. Furthermore, the disappearance of the peak at m/z=822 in the mass spectrum during the reaction supports this).

Example 72. Bis-(4-dimethylaminophenyl)-(4-[4-N-{6-N-valinoyl)aminohexanoyl}]piperazinophenyl)-carbenium ion (Fmoc-Val-Aminohexyl-CV or Fmoc-V-Ahx-CV)

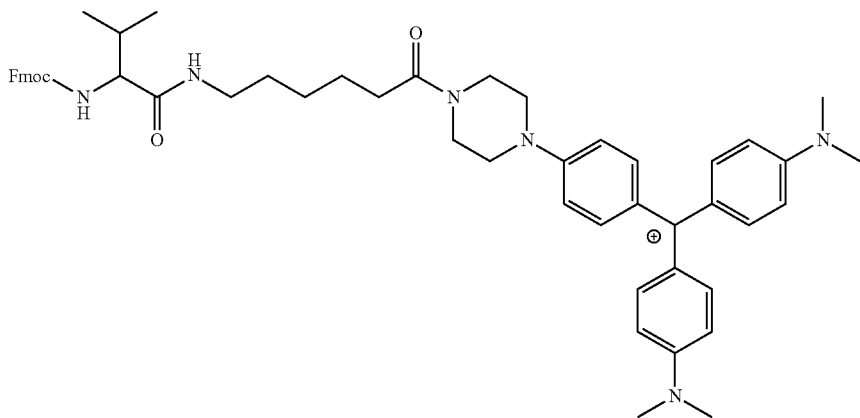

To a solution of C V (720 mg; Example 70b) in DCM (15 mL) was added Fmoc-6-aminohexanoic acid pentafluorophenyl ester (1.18 g). The mixture was stirred for 1 h prior to the addition of piperidine (1 mL). After stirring for 1 d, all volatiles were removed in vacuo, and the residue was extracted with cyclohexane (3×) and re-dissolved with DCM (15 mL). Fmoc-Val-Pfp (1.13 g) was added, and the mixture was stirred for 1 h. All volatiles were removed, and the residue was dissolved with a mixture of methanol (22 mL) and water (3 mL) (containing 3% formic acid). The preparation was precipitated with water with 3% of formic acid (50 mL) and centrifuged. The residue was separated by preparative FIPLC to yield 160 mg of a blackish-blue material. The material was dissolved with DCM (5 mL) and treated with piperidine (250 overnight. Concentration and purification with FIPLC yielded 40 mg of the desired product. ESI-MS (positive) [M]=847.

Example 73. H-AAPV-Ahx-CV [SEQ ID NO: 21]

Treatment of Fmoc-V-Ahx-C V (Example 71) as described in Example 42, Step D, produced H-AAPV-Ahx-CV [SEQ ID NO: 21]. ESI-MS (positive) [M]=864

Treatment of the product of Example 72 with elastase releases no Ahx-CV, as found by MS-analysis (no m/z=526, positive mode).

Example 74. Jeffamine EDR176-Modified Hypromellose

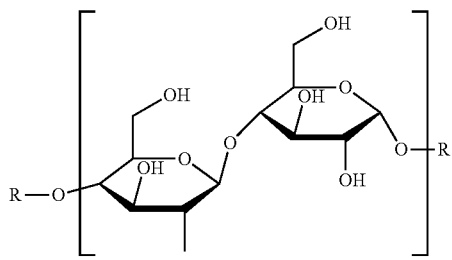

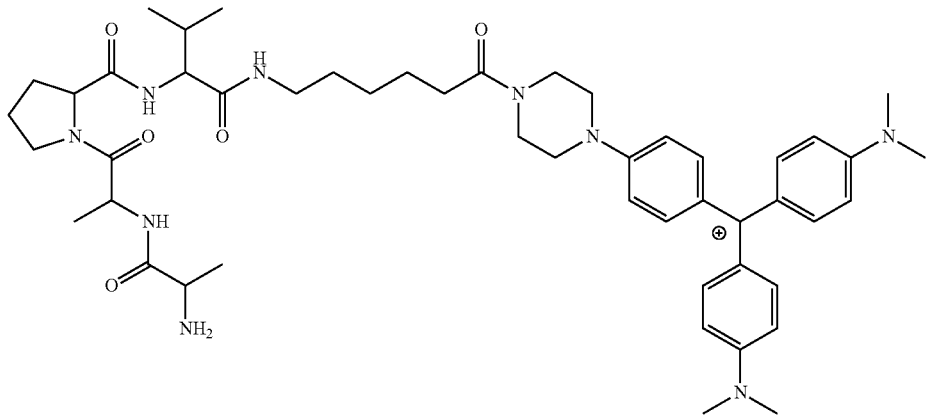 [SMILES: CC(N)C(=O)NC(C)C(=O)N1CCCC1C(=O)NC(C(=O)NCCCCCC(=O)N1CCN(c2ccc(C(c3ccc(N(C)C)cc3)c3ccc(N(C)C)cc3)cc2)CC1)C(C)C]

-continued

R = H or CH3 or

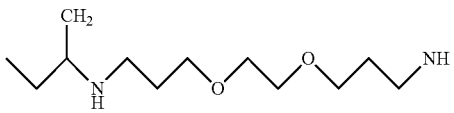

Hypromellose (89 kDa, 5 g) was dissolved in MP (150 mL). After dissolution, toluene (100 mL) was added. The mixture was refluxed with a dean-starck trap for 1 h to remove water by azeotropic distillation. The dry solution was cooled to 0° C. At this temperature, tosyl chloride (1.45 g) was added, followed by pyridine (30 mL). The mixture was kept at this temperature for 1 h. Finally Jeffamine EDR 176 (15 g) was added, and the mixture was stirred for 12 h at room temperature. Then the mixture was heated to 90° C. for 1 h. After the reaction was complete, the volatiles were removed by evaporation. The resulting solution was dialyzed against water (MWCO 10.000-20.000 Da). The solution was evaporated to dryness. The resulting product was dissolved in ethanol and precipitated with ethyl acetate/cyclohexane (3×). The product was a dark brown polymer film. Yield: 1.7 g; 0.34 mmol/g N.

Example 75. EDA Modified Hypromellose

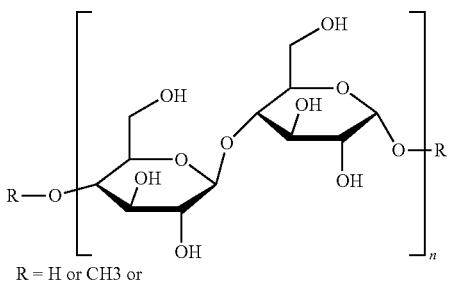

R = H or CH3 or

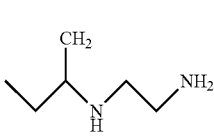

Hypromellose (89 kDa, 5 g) was dissolved in MP (120 mL). After dissolution, toluene (50 mL) was added. The mixture was refluxed with a dean-starck trap for 1 h to remove water by azeotropic distillation. The dry solution was cooled to 0° C. At this temperature, mesyl chloride (1.9 mL) was added, followed by pyridine (20 mL). The mixture was kept at this temperature for 1 h. Finally, ethylene diamine (EDA, 100 mL) was added, and the mixture was stirred for 12 h at room temperature. Then the mixture was heated to 90° C. for 1 h. After the reaction was complete, the volatiles were removed by evaporation. The resulting solution was dialyzed against water (MWCO 10.000-20.000 Da). The solution was evaporated to dryness and the resulting product was extracted with ethyl acetate (5×). Slightly yellow film. Yield: 2.9 g; 0.67 mmol/g N.

Example 76. EDA Modified Hydroxyethyl Cellulose

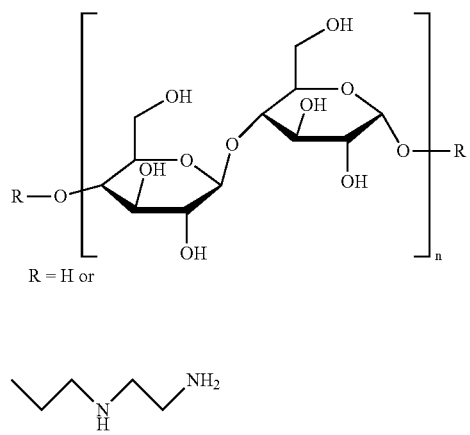

R = H or

Hydroxyethyl cellulose (90 kDa, 10 g) was dissolved in NMP (250 mL). After dissolution toluene (200 ml) was added. The mixture was refluxed with a dean-starck trap for 1 h to remove water by azeotropic distillation. The dry solution was cooled to 0° C. At this temperature tosyl chloride (8.8 g) was added, followed by pyridine (3.75 g). The mixture was kept at this temperature for 2 h and at room temperature for 5 h. Finally ethylene diamine (30 mL) was added, and the mixture was stirred for 12 h at room temperature. Then the mixture was heated to 90° C. for 2 h. After the reaction was complete, insoluble material was removed by filtration. Then the volatiles were removed by evaporation. The resulting solution was dialyzed against water (MWCO 10.000-20.000 Da). The solution was evaporated to dryness and the resulting product was extracted with ethyl acetate/ethanol (3:1, 3×). Yellow film. Yield: 3.85 g; 0.45 mmol/g N.

Example 77. Jeff Amine EDR 176 Modified Hydroxyethyl Cellulose

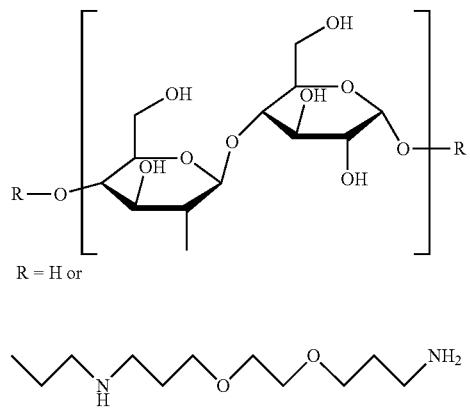

R = H or

Hydroxyethyl cellulose (250 kDa, 5 g) was dissolved in MP (160 mL). After dissolution, toluene (100 mL) was added. The mixture was refluxed with a dean-starck trap for 2 h to remove water by azeotropic distillation. The dry solution was cooled to 0° C. At this temperature, tosyl chloride (4.2 g) was added, followed by pyridine (1.75 g). The mixture was kept at this temperature for 2 h and at room temperature for 2 h. Finally, Jeffamine EDR 176 (20 mL) was added, and the mixture was stirred for 12 h at room temperature. Then the mixture was heated to 90° C. for 2 h. After the reaction was complete, insoluble material was removed by filtration. Then the volatiles were removed by evaporation. The resulting solution was dialyzed against water (MWCO 10.000-20.000 Da). The solution was evaporated to dryness and the resulting product was extracted with ethyl acetate (3×). Yellow film. Yield: 4.1 g, 0.99 mmol/g N in the high MW fraction.

Example 78. Trioxatridecandiamine modified Hydroxyethyl Cellulose

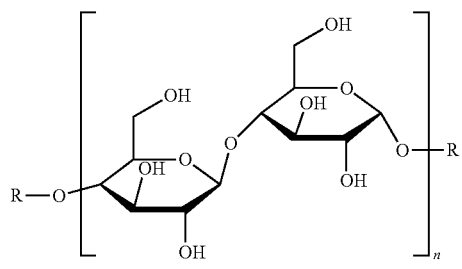

R = H or

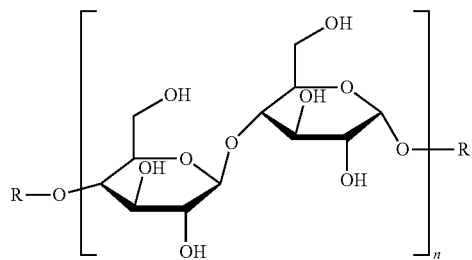

Hydroxyethyl cellulose (90 kDa, 5 g) was dissolved in NMP (200 mL). After dissolution, toluene (150 mL) was added. The mixture was refluxed with a dean-starck trap for 2 h to remove water by azeotropic distillation. The dry solution was cooled to 0° C. At this temperature, tosyl chloride (4.2 g) was added, followed by pyridine (1.75 g). The mixture was kept at this temperature for 3 h and at room temperature for 4 h. Finally, O,Oalbis(3-aminopropyl)diethylene glycol (50 g) was added and the mixture was stirred for 12 h at room temperature. Then the mixture was heated to 90° C. for 3 h. After the reaction was complete, insoluble material was removed by filtration. Then the volatiles were removed by evaporation. After adding water (100 mL), the resulting solution was dialyzed against water (MWCO 10.000-20.000 Da). The solution was evaporated to dryness and the resulting product was extracted with ethyl acetate (3×). The sticky brown mass was dried over P4010 and again extracted with ethyl acetate/ethanol (3:1). Dark brown film. Yield: 5.6 g; 0.98 mmol/g N in the high MW fraction.

Example 79. HEC-EDR176-N-Propionyl-AAPVA-RBB [SEQ ID NO: 26]

R = H or

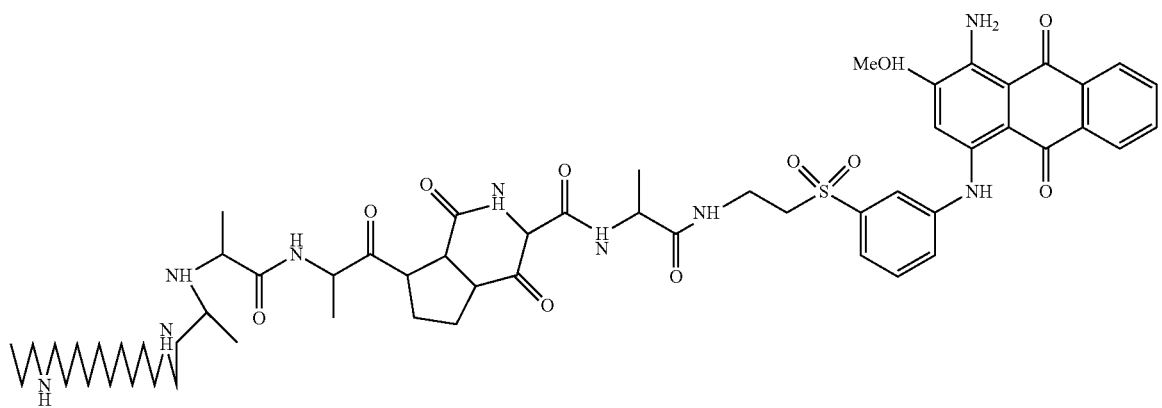

Jeffamine EDR 176 modified hydroxyethyl cellulose (0.05 g; Example 77) was dissolved in H₂O (10 mL) and MeOH (10 mL). To this solution, Acrylamido-AAPVA-RBB [SEQ ID NO: 26](Example 49) (21 mg) in MeOH (3 mL) was added. The mixture was adjusted to pH 8.0 with NaHCO₃ and stirred at room temperature for 18 h. A blue precipitate was formed. This mixture was dialyzed against NaHCO₃ and water (2×), (MWCO 12-14 kDa). After filtration, the light blue solution was evaporated to yield a blue colored film. Yield: 45 mg, blue color in the high MW fraction.

Example 80.
HEC-PEG200-N-propionyl-AAPF-RBB [SEQ ID NO: 12]

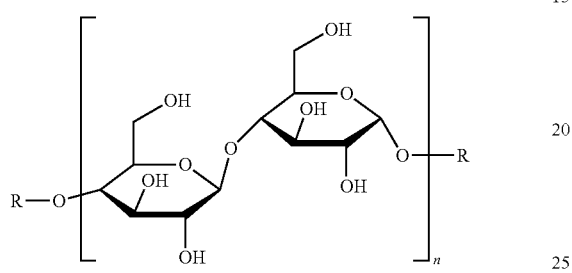

Trioxatridecandiamine modified hydroxyethyl cellulose (0.22 g; Example 78) was dissolved in H₂O (20 mL) and MeOH (10 mL). To this solution, Acrylamido-AAPF-RBB [SEQ ID NO: 12](example 47 0.085 g) in MeOH (5 mL) was added. The mixture was adjusted to pH 8.0 with NaHCO₃ and stirred at room temperature for 18 h. A blue precipitate was formed. This mixture was dialyzed against NaHCO₃ and water (2×). After filtration, the light blue solution was evaporated to yield a blue colored film. Yield: 137 mg, blue color in the high MW fraction.

Example 81. HEC-EDA-N-propionyl-AAPF-RBB [SEQ ID NO: 12]

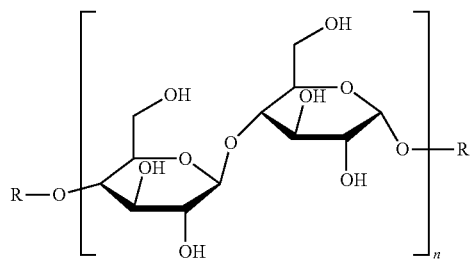

R = H or

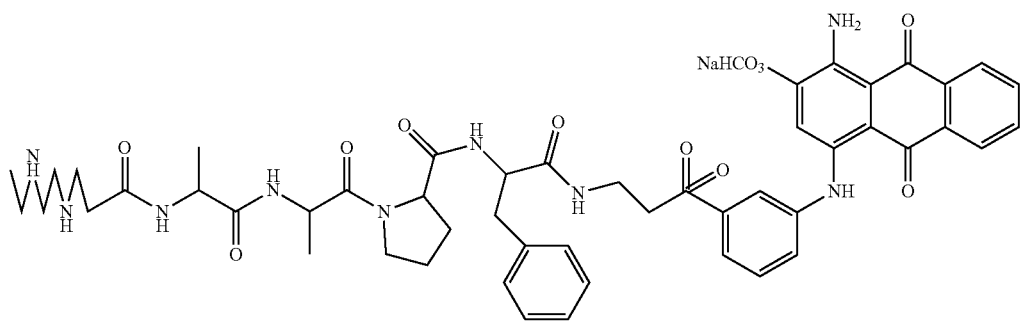

EDA modified hydroxyethyl cellulose (0.54 g; Example 76) was dissolved in H₂O (50 mL). To this solution, Acrylamido-AAPF-RBB [SEQ ID NO: 12] (example 47) (0.085 g) in ACN (30 mL) was added. The mixture was adjusted to pH 8.0 with NaHCO₃ and stirred at room temperature for 48 h. The solvent was evaporated under reduced pressure. A blue precipitate was formed. This mixture was dialyzed against NaHCO₃ and water. After filtration, the light blue solution was evaporated to yield a pale blue film that did not release color on washing. Yield: 400 mg.

Example 82. PEI-N-propionyl-AAPF-RBB [SEQ ID NO: 12]

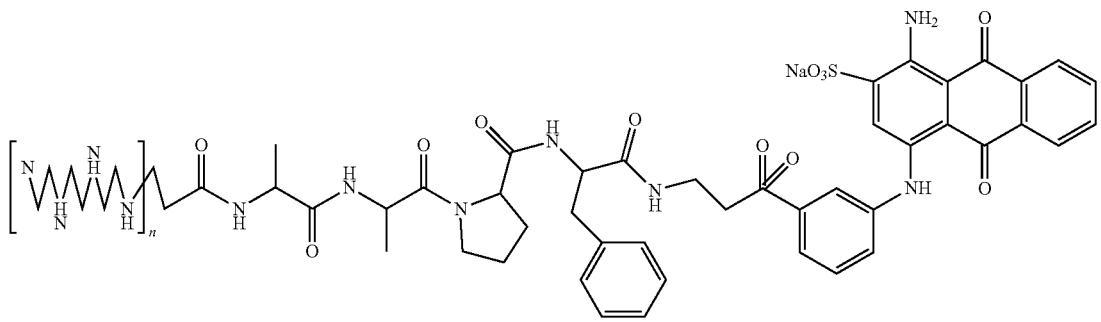

Polyethyleneimine (0.2 g; MW 60-75 kDa) was dissolved in H₂O (10 mL). To this solution, Acrylamido-AAPF-RBB [SEQ ID NO: 12] (15 mg) (Example 47) in ACN (1 mL) was added. The mixture was stirred for 18 h. Then the solution was dialyzed (MWCO 12-14 kDa) against NaHCO₃ and water. After filtration, the solvent was evaporated. A blue sticky residue was obtained. Yield: 140 mg.

Example 83. Acrylamido-AAPV-RBB [SEQ ID NO: 12]

Synthesis: 420 mg of H-AAPV-RBB [SEQ ID NO: 21] (example 44) and 200 mg of sodium bicarbonate are suspended in 25 mL of DMF. 45 µL of acryloyl chloride are added. After 2 h, further 40 µL of acryloyl chloride are added. After finishing the reaction overnight, the mixture is concentrated and chromatographed over silica gel with ethyl acetate to remove side products and impurities and then with methanol to elute the product. Yield 125 mg, ESI-MS (negative mode) [M−H]⁻: 892.

α,ω-Bis(N-Propionyl-AAPV-RBB)PEG$_{(24k)}$ [SEQ ID NO: 2]

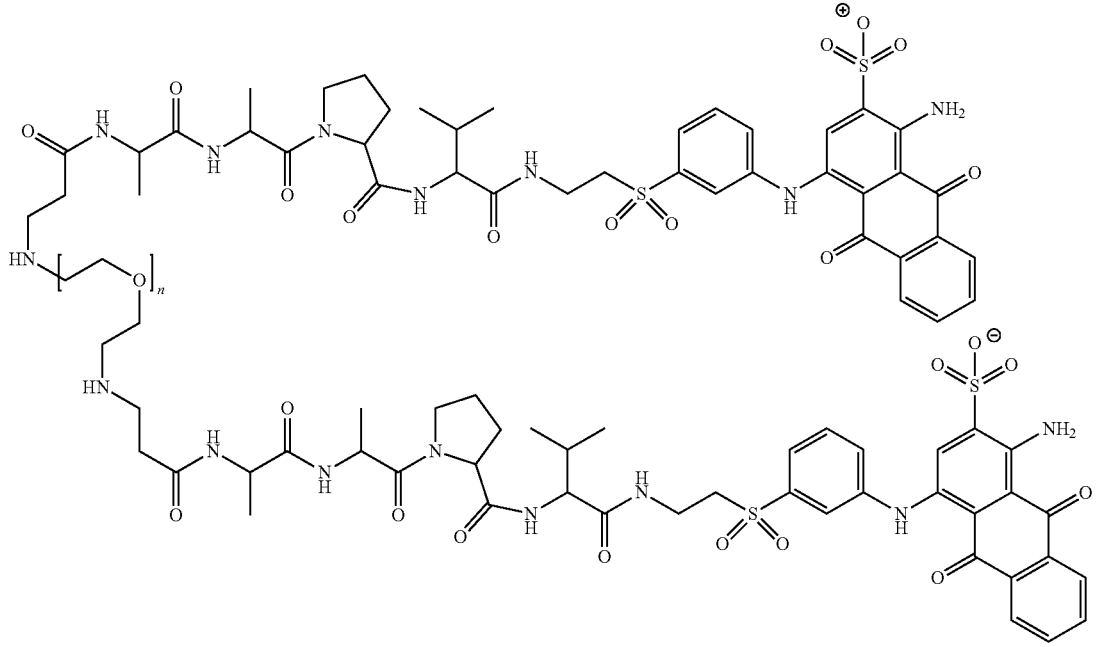

α,ω-Bis-amino PEG (0.3 g; MW 24 kDa, 0, 106 mmol/g N) was dissolved in H₂O (5 mL). To this solution, Acrylamido-AAPV-RBB (33 mg) [SEQ ID NO: 2] (example 83) in ACN (20 mL) was added. The mixture was stirred for 24 h at room temperature. Then the solution was dialyzed (MWCO 12-14 kDa) against NaHCO₃ in water/ethanol (9:1, 2×) and water (2×). After filtration, the solvent was evaporated. A blue water-soluble solid polymer was obtained wherein dye was associated with the high molecular weight fraction. Yield: 140 mg.

Example 85. α,ω-Bis(N-Propionyl-AAPV-RBB) PEG$_{(11k)}$ [SEQ ID NO: 2]

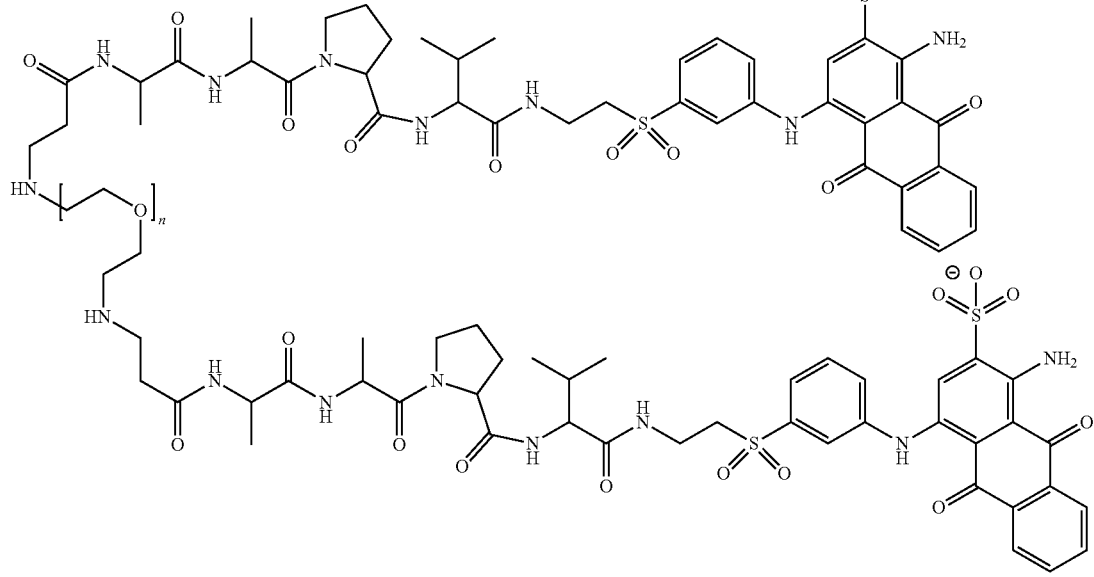

α,ω-Bis-amino PEG (0.25 g; MW 11.4 kDa, 0,190 mmol/g N) was dissolved in H₂O (5 mL). To this solution, Acrylamido-AAPV-RBB [SEQ ID NO: 2] (30 mg) (example 83) in ACN (20 mL) was added. The mixture was stirred for 48 h at room temperature. Then the solution was dialyzed (MWCO 12-14 kDa) against NaHCO₃ in water/ethanol (9:1, 2×) and water (2×). After filtration, the solvent was evaporated. A blue water-soluble solid was obtained in which blue color was associated with the high MW fraction. Yield: 120 mg.

Example 86. Propylamino Pullulan

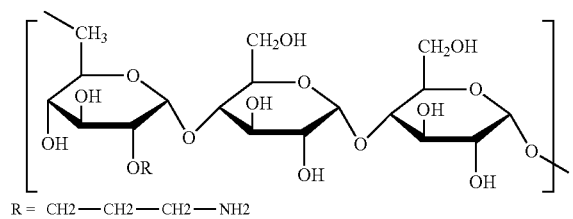

R = CH2—CH2—CH2—NH2

Cyanoethyl Pullulan (3.5 g) was dissolved in H₂O (200 mL). THF (200 mL) was added. To this solution 6.0 g of CoCl₂*6H₂O was added. The purple solution was cooled in an ice bath. At this temperature 6.8 g NaBH₄ was added over the course of 6 h. A black precipitate formed. The reaction mixture was stirred for an additional 12 h at room temperature. The mixture was acidified with acetic acid (10 mL). After 1 d the black precipitate was dissolved and the resulting purple solution was subjected to dialysis (MWCO 12-14 kDa, water 3×). A white, viscous suspension was formed. To isolate the product as free amine, NaOH (~2 g) was added. The less viscous product was dialyzed against water. After evaporation a brown solid formed, which was insoluble in water. Brown solid, 1.85 mmol/g N. Yield: 2.4 g.

Example 87. Propylamine HEC

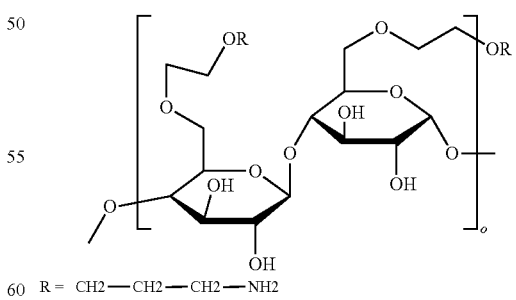

R = CH2—CH2—CH2—NH2

HEC (5.0 g; 90 kDa) was dissolved in H₂O (50 mL). NaOH (0.16 g) was added. To this solution, acrylonitrile (0.8 mL) was added within 4 h (in 0.2 ml portions) and stirred at room temperature for another 12 h. The yellow solution was dialyzed against water (MWCO 10-20 kDa, 2×). The resulting solution (150 mL) was diluted with THF (75 mL). CoCl$_2$·6 H$_2$O (6.3 g) was added. Reduction was achieved by adding NaBH$_4$ (6.8 g) within 4 h. A black precipitate was formed. The mixture was acidified with acetic acid (5 mL). After dissolution of the precipitate (2 d), the solution was dialyzed against water (MWCO 10-20 kDa, 2×). After evaporation, a yellow water-soluble solid was obtained. Yield: 3.5 g, 1.02 mmol/g N.

Example 88.
N-(Propionyl-AAPV-RBB)-Propylamino HEC
[SEQ ID NO: 2]

Hydroxyethyl cellulose (50 g; 90 kDa) was dissolved in H$_2$O (500 mL). NaOH (1.6 g) was added. To this solution, acrylonitrile (9.0 mL) was added within 6 h (in 2.0 ml portions) and stirred at room temperature for another 12 h. The mixture was diluted with water/THF (1:1; 200 mL) and additional acrylonitrile (2 mL) was added. After 1 h stirring at room temperature, the yellow solution was dialyzed against water (MWCO 10-20 kDa, 2×, 36 h). This solution (1160 mL) was diluted with THF (250 mL). CoCl$_2$·6H$_2$O (25 g) was added. Reduction was achieved by adding NaBH$_4$ (44 g) within 18 h at 0-5° C. A black precipitate was formed. The mixture was acidified with acetic acid (50 mL).

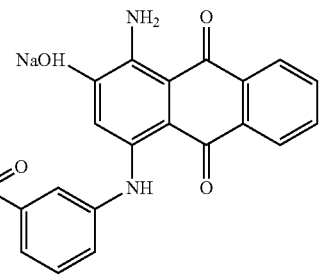

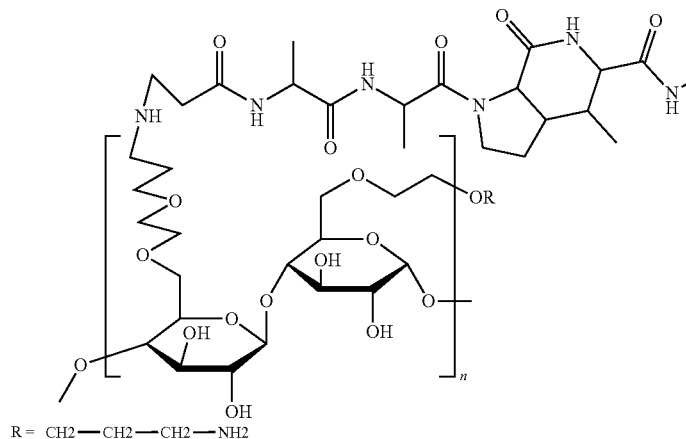

R = CH2—CH2—CH2—NH2

Propylamino HEC (500 mg; Example 87) was dissolved in H$_2$O (50 mL). Acrylamido-AAPV-RBB (75 mg) [SEQ ID NO: 2] (example 83) was dissolved in ACN (25 mL). The solutions were combined and stirred for 24 h. Then the reaction mixture was kept at 54° C. for 2 d. The resulting dark blue solution was dialyzed against NaHCO$_3$ in water/EtOH (9:1, 2×) and water (2×). After partial evaporation to 15 mL, a highly viscous blue solution was obtained. Under vigorous stirring, this solution was added to ACN (80 mL). The resulting blue precipitate was extracted with ACN until no more unreacted dye was detected in the supernatant. The product was stored in ACN and was a blue rubber-like solid, soluble in water/MeOH.

Example 89. Propylamine HEC (Scale-Up of Example 87 with Lower Concentration of Cobalt and Catalysts)

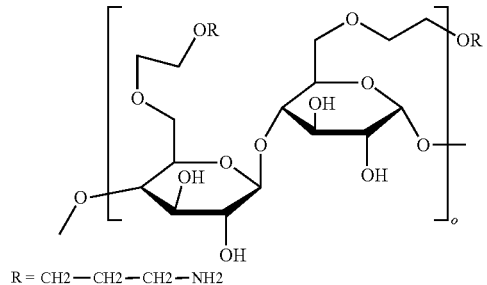

R = CH2—CH2—CH2—NH2

Within 3 d, the black precipitate was dissolved. After dissolution of the precipitate, the solution was dialyzed against water (MWCO 10-20 kDa, 2×). After partial evaporation of the solvent, a viscous yellow solution was obtained. Solid content: ~30 g. Yield: 30 g; 0.85 mmol/g N in dry matter.

Example 90. Acryloylated Long-Chain PEG(2000)-AAPV-RBB Linker. [SEQ ID NO: 2]

100 mg Bis-amino PEG 2000 was dissolved in DMF (10 mL). 12 mg acryloylated AAPV-RBB [SEQ ID NO: 2] (Example 83) in DMF (1 mL) was added and the mixture was stirred for 1 h. Then the reaction mixture was kept at 54° C. for 18 h. After evaporating the solvent, diethyl ether was added to extract excess bis-amino PEG and to precipitate the product. The precipitate was washed with ether (2×), dried and re-dissolved in ACN (25 mL). NaHCO$_3$ (50 mg) and acryloychloride (20 µL) were added and the mixture was stirred for 2 h. The mixture was filtered and evaporated to dryness. After extraction with ether, the residue was dissolved in water/ACN (1:1, 1 mL). The product, a dark violet solution, was used without further purification.

Example 91. [N-3-(triethyoxsilyl)propylaminocarbonyl]-AAPV-RBB [SEQ ID NO: 2]

211 mg of H-AAPV-RBB (Example 44) was dissolved in 10 mL of DMF. 63 of 3-(triethoxysilyl)propyl isocyanate was added in one portion and stirring was continued for 10 min. The solvent was removed and the product was precipitated with ether. After washing with ether, a dark violet powder was obtained. Yield: 120 mg; m/z=1085 (M−H).

Example 92. AAPV-RBB-Labelled Silica [SEQ ID NO: 2]

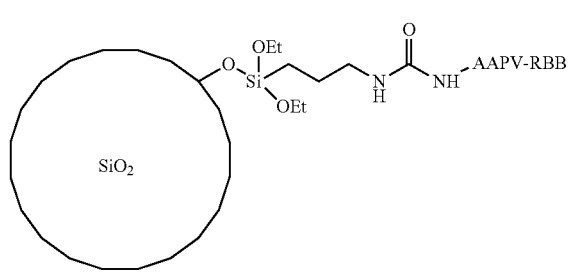

14 mg of [N-3-(triethyoxsilyl)propylaminocarbonyl]-AAPV-RBB [SEQ ID NO: 2] (example 91) was dissolved in 1.2 mL of DMF. 100 mg of Silica gel was dispersed in this solution. Then 1 µL. of sulfuric acid was added and the reaction mixture was heated to 75° C. The mixture was kept at this temperature for 2 days. The dark blue silica gel was transferred into a column and washed with acetonitrile (200 mL), water/acetonitrile (1:1; 500 mL), water/methanol (1:1; 500 mL), and water (500 mL). Results: 65 mg of dark blue powder (see enzyme assay for further characterization).

Example 93. Peptide-Labelled beadBALL Amine Microspheres with Long-Chain Linker

Acryloylated long-chain PEG(2000)-AAPV-RBB [SEQ ID NO: 2] linker (0.5 mL; Example 90) was added to a 1-ml beadBALL Amine microsphere dispersion. The reaction was performed at 60° C. for 2.5 d. The microspheres were then centrifuged and washed with water/ACN (1:1, 8×) and water (2×). The resulting pale violet precipitate was re-suspended in water (1 mL) to provide a pale violet dispersion.

Example 94. Amidation of Fmoc-AAPV with Dianisidine [SEQ ID NO: 2]

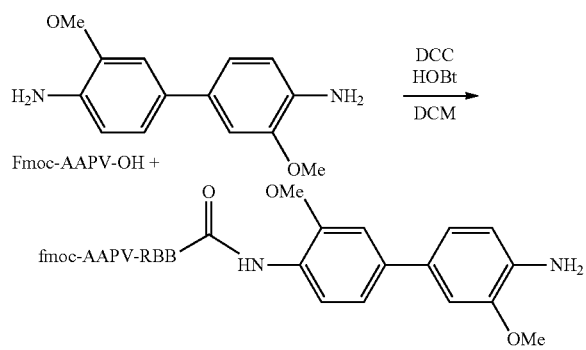

Fmoc-AAPV [SEQ ID NO: 9] (1 16 mg) and HOBt (40 mg) were dissolved in DCM (20 mL). The solution was placed in an ice bath and DCC (45 mg) was added. Stirring was continued for 30 min at 0° C. and an additional 30 min at room temperature. Then a five-fold excess of o-dianisidine (250 mg) was added. After a reaction time of 121 h, the product was observed by ESI-MS (positive mode) [M+H]⁺: 805, [M+Na]⁺: 827).

Example 95: Synthesis of O-allyl Chlorophenol Red

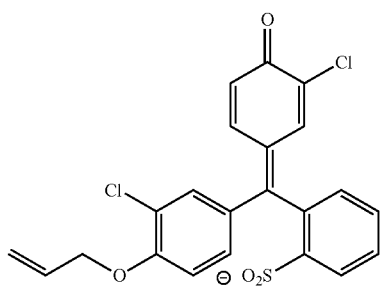

Chlorophenol red (2.76 g), allylbromide (1.29 mL), and potassium carbonate (1.8 g) were combined in dry acetone (50 mL) and heated for 96 h to reflux. After cooling to room temperature, all solids were filtered off and washed with acetone. The combined filtrates (~70 mL) were poured into diethyl ether (350 mL) with vigorous stirring. Stirring was continued for 20 min, then the precipitate was collected by filtration and re-dissolved (50 mL of acetone) and precipitated (400 mL of diethyl ether). After stirring for 30 min, the precipitate was collected by filtration and dried at 54° C. to yield 2.72 g. ESI-MS (negative mode) [M−H]": 461; the material no longer changed color with pH.

The same procedure with bromophenol red affords an analogous product. (ESI-MS (negative mode) [M−H]⁺: 551, isotopic pattern of 2 Br, 64%)

Example 96: Synthesis of C-allyl Chlorophenol Red

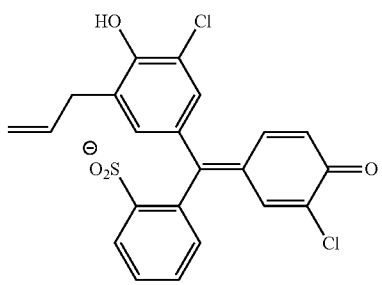

O-Allyl chlorophenol red (2 g, Example 95) was suspended in nitrobenzene (10 mL) and heated in an oil bath of 210° C. for 70 min. When TLC control (silica gel, Chloroform-methanol 10-3, 2% of formic acid) indicated complete conversion (educt: Rf=0.65, product: Rf=0.55, starting material does not change color upon exposure to ammonia, product changed color to dark violet upon exposure to ammonia), the reaction was left to cool to RT and then diluted with diethyl ether (50 mL). The precipitate was collected by decantation, re-dissolved with methanol (25 mL) and precipitated by pouring into vigorously stirred diethyl ether (300 mL). The solution-precipitation procedure was repeated until no smell of nitrobenzene was detected (2-3×). The product was dried at 54° C. to yield the target compound (1.39 g). ESI-MS (negative mode) [M−H]⁺: 461; the material changed color when treated with base to deep violet.

Example 97: Synthesis of C-allyl Bromophenol Red

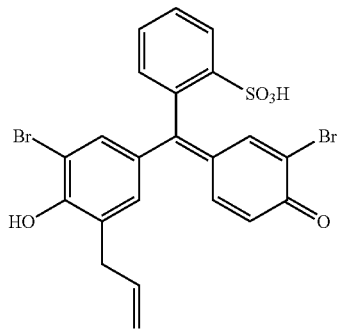 [SMILES: C=CCc1cc(/C(=C2\C=CC(=O)C(Br)=C2)c2ccccc2S(=O)(=O)O)cc(Br)c1O]

O-Allyl bromophenol red (690 mg, Example 95) was suspended in nitrobenzene (10 mL) and heated in an oil bath of 210° C. for 60 min. When TLC control (silica gel, Chloroform-methanol 10-3, 2% of formic acid) indicated complete conversion (educt: Rf=0.59, product: Rf=0.45, educt does not change color upon exposure to ammonia, product changed color to dark violet upon exposure to ammonia), the reaction was left to cool to RT and then diluted with diethyl ether (50 mL). The precipitate was chromatographed over siliga gel with chloroform-methanol-cyclohexane (6-1-4) to yield 210 mg of the target compound.
ESI-MS (negative mode) [M−H]$^+$: 551 (isotopic pattern of 2 Br); the color changed with ammonia to violet.

Example 98: Chemical Entity Containing a pH-Sensitive Moiety

| Ex. | Anchor | Polymer | Spacer | Recog-site | R-Group | Dye | Human Elastase Cleavage | Porcine Elatase Cleavage | Cathepsin Cleavage |
|---|---|---|---|---|---|---|---|---|---|
| 1 | Fmoc | — | — | AAPV | — | Indoxyl | +++ | n.t. | n.t. |
| 2 | Fmoc | — | — | AAPV | — | 5-Bromo-4-chloro-indoxyl | +++ | n.t. | n.t. |
| 3 | Fmoc | — | Ala | AAPV | — | Indoxyl | ++ | n.t. | n.t. |
| 4 | Fmoc | — | Ala | AAPV | — | — | ++ | n.t. | n.t. |
| 5 | Fmoc | — | Ala | AAPV | — | 1-H Indol-3-Amin | ++ | n.t. | n.t. |
| 6 | Fmoc | — | — | AAPV | — | MeO-napthol | + | + | 0 |
| 7 | Fmoc | — | — | AAPV | — | Napthol | + | + | 0 |
| 8 | Fmoc | — | — | AAPV | — | 2_Naphthol | + | ++ | 0 |
| 12 | Fmoc | — | — | AAPF | — | Indoxyl | + | + | 0 |
| 13 | Fmoc | — | — | AAA | — | Indoxyl | ++ | ++ | 0 |
| 14 | Fmoc | — | — | AAPA | — | Indoxyl | +++ | +++ | 0 |
| 15 | Fmoc | — | — | V | — | Indoxyl | 0 | 0 | 0 |
| 16 | Fmoc | — | — | AAAA | — | Indoxyl | 0 | 0 | 0 |
| 17 | Fmoc | — | — | APV | — | Indoxyl | + | + | 0 |
| 18 | Fmoc | — | — | Phe | — | Indoxyl | +++ | + | 0 |
| 19 | Ac | — | — | Phe | — | Indoxyl | +++ | + | 0 |
| 20 | Fmoc | — | — | F-V-T(BzI)-F | — | Indoxyl | 0 | 0 | 0 |
| 25 | Fmoc | — | — | AAPV | Ala-Val-1,2,3-triazolyl | RBB | n.t. | 0 | 0 |
| 26 | Fmoc | — | — | AAPV | 1,2,3-triazolyl | RBB | n.t. | 0 | n.t. |
| 27 | H | — | — | AAPV | Ala-Val-1,2,3-triazolyl | RBB | n.t. | 0 | n.t. |
| 28 | H | — | — | AAPV | 1,2,3-triazolyl | RBB | n.t. | 0 | n.t. |
| 33 | H | — | — | AAPV | Ala-Ala | RBB | n.t. | ++ | 0 |
| 37 | Fmoc | — | — | AAPF | Ala | RBB | n.t. | + | n.t. |
| 38 | H | — | — | AAPF | Ala | RBB | n.t. | +++ | 0 |
| 39 | Fmoc | — | — | AAPV | Ala | RBB | n.t. | +++ | n.t. |
| 40 | H | — | — | AAPV | Ala | RBB | n.t. | +++ | n.t. |
| 45 | Fmoc | — | — | AAPF | — | RBB | n.t. | ++ | n.t. |
| 46 | H | — | — | AAPF | — | RBB | n.t. | ++ | 0 |
| 53 | Fmoc | — | — | AAPF | — | Remazol Black-(N'-acetyl)-ethylamid | n.t. | + | 0 |
| 54 | — | CMC9M31F | — | AAPF | Ala | RBB | n.t. | ++ | ++ |
| 55 | — | CMC9M31F | — | AAPF | — | RBB | n.t. | ++ | ++ |
| 56 | — | paper | — | AAPV | — | RBB | n.t. | 0 | 0 |
| 59 | Fmoc | — | Ala | AAPM | — | RBB | n.t. | 0 | 0 |
| 60 | H | — | Ala | AAPM | — | RBB | + | 0 | 0 |
| 62a | Cys(TRT) | PAA | —C4H8—CH(NH)Boc))—C(=O)—O—CH2—C(=O)— | APPV | Ala | RBB | + | + | n.t. |

| Ex. | Anchor | Polymer | Spacer | Recog-site | R-Group | Dye | Human Elastase Cleavage | Porcine Elatase Cleavage | Cathepsin Cleavage |
|---|---|---|---|---|---|---|---|---|---|
| 62b | Cys(TRT) | PAA | —C4H8—CH(NH2)—C(=O)—O—CH2—C(=O)— | AAPV | Ala | RBB | ++ | + | n.t. |
| 63b | COOH | PAA | —C2H4-gly | AAPV | Ala | RBB | + | ++ | n.t. |
| 63c | dioctyl amine | PAA | —C3H6—O—C2—H4—O—C3—H6-gly | AAPV | — | RBB | + | +++ | n.t. |
| 63c | dioctyl amine | PAA | —C3H6—O—C2—H4—O—C3—H6-gly | AAPV | Val | RBB | + | +++ | n.t. |
| 67a | mercapto-ethyl | PAA | Ala | AAPV | — | RBB | ++ | n.t. | n.t. |
| 67a | mercapto-ethyl | PAA | Ala | AAPV | Val | RBB | +++ | n.t. | n.t. |
| 67b | mercapto-ethyl | PAA | Ala | AAPV | — | RBB | ++ | n.t. | n.t. |
| 67b | mercapto-ethyl | PAA | Ala | AAPV | Val | RBB | +++ | n.t. | n.t. |
| 67d | Sepabeads EP | — | —CH2—CH(OH)—CH2-Ala | AAPV | — | RBB | 0 | n.t. | n.t. |
| 67c | Sicore-amino-Beads | PAA | Ala | AAPV | Val | RBB | 0 | n.t. | n.t. |
| 67f | Sicore-amino-Beads | PAA | Ala | AAPV | Val | RBB | 0 | n.t. | n.t. |
| 67g | hydroxy ethyl | PAA | Ala | AAPV | Val | RBB | +++ | n.t. | n.t. |
| 68d | dioctyl amine | PAA | Ala | AAPV | — | RBB | ++ | n.t. | n.t. |
| 68d | dioctyl amine | PAA | Ala | AAPV | Val | RBB | +++ | n.t. | n.t. |
| 68e | Silica gel | — | Si—(CH2)3—NH—(C=O)-Ala | AAPV | Val | RBB | +++ | n.t. | n.t. |
| 71e | hydroxy ethyl | PAA | — | AAPV | Ala | CV | 0(+) | n.t. | n.t. |
| 79 | — | HEC | Si—(CH2)3—NH—(C=O)-Ala | AAPV | Ala | RBB | +++ | n.t. | n.t. |
| 80 | — | HEC | EDR176-N-Acrylamido | AAPF | — | RBB | n.t. | ++ | + |
| 81 | — | HEC | EDA-N-Acrylamido | AAPF | — | RBB | n.t. | +++ | + |
| 88 | — | HEC-Propyl-amino | — | AAPV | — | RBB | +++ | n.t. | n.t. |
| 92 | Silica gel | — | Si—(CH2)3—NH—(C=O)— | AAPV | — | RBB | ++ | n.t. | n.t. |
| 93 | Amino-PVC-beads | — | ECH-diamino-PEG(2000) | AAPV | — | RBB | 0 | n.t. | n.t. |

A chemical entity comprising a pH-sensitive moiety selected from bromothymol blue, phenol red, bromophenol red, chlorophenol red, thymol blue, bromocresol green, bromocresol purple; and other sulfophthalein dyes is linked to the anchor region using methods known in the art. For example the pH-sensitive moiety is linked to the anchor region (selected from a polystyrene bead, silica gel bead, polysaccharide bead, polyacrylamide bead, cellulose bead, polysaccharide, derivatized cellulose, polyacrylate, polyethyleneimine, polyacrylamide, UV-activatable group, and peptidoglycanderivative, and a combination thereof) via a single bond, an alkylene linker, an alkenylene linker, and alkynylene linker, an amide linker, or an amine linker.

Example 99: Testing of Enzyme Hydrolysis of ELA and CATG Substrates

The foregoing example substrates were tested for their rate of hydrolysis and utility in tests for ELA and CAT activity detection.

Elastase: Assays with pancreatic porcine elastase and human elastase from leucocytes were performed in a total volume of 25 NL, containing 1 U/mL enzyme, 1 mg/mL to 5 mg/mL substrate (depending on molecular weight and amount of loaded dye) in 100 mM potassium phosphate buffer, pH 7 (or alternatively a 500 mM NaCl, 100 mM sodiumacetate pH 7). Appearance of the assay mixture was either a clear solution, a suspension or a gel, depending on the properties of the enzyme substrate. Incubation was performed at 37° C. After 3 and 20 h, 10 μL samples were taken and the enzyme was denatured by addition of 10 μL MeOH to each sample. After mixing and incubation at −20° C. for 20 min the samples were centrifuged at 13.000 rpm for 10 min. Each assay included a control without enzyme, containing 1 mg/mL to 5 mg/mL substrate and analysis was performed in the same way and in parallel to the enzyme-containing assays. The supernatant after MeOH precipitation was analyzed via ion trap MS, either [M+H]+ or [M−H]−, depending on the properties of the molecule and the expected cleavage products.

Cathepsin: Assays with cathepsin G were performed in a total volume of 25 μL containing 0.5 U/mL and, if cleavage was observed—in an additional assay 0.1 U/mL enzyme, 1 mg/mL to 5 mg/mL substrate (depending on molecular weight and amount of loaded dye onto the immobile phase) in 100 mM Tris-HCl, pH 7 (or alternatively a 500 mM NaCl, 100 mM sodiumacetate mix pH 7). Appearance of the assay mixture was either a clear solution, a suspension or a gel, depending on the properties of the enzyme substrate. Incubation, control, sampling and analysis was as above.

The results of these studies are summarized in Table 2.

Table 2: Summary of the rate of cleavage of specific substrates by Elastase and Cathepsin G.

Example 100: Cross-Linked Trap

A quaternary amine polymer such as polyDADMAC was mixed with polyethyleneimine polymer at a ratio from 19:1 to 5:1 depending on the preparation. The solvent was a mixture of water and acetonitrile (1:1 V/V) and the final concentration of polyamine polymer is 20%. To this was added, depending on the preparation, a volume of epichlorohydrin corresponding to any of 3, 6, 9, or 12% VN. The mixture was allowed to react under reflux at 60C overnight. Thereafter the mixture is heated without condenser to remove unreacted epichlorohydrin. To this was added an excess of aqueous ammonia and further reacted to quench all uncreaded epoxides (this latter step may also be left out for reactive bound trap materials). The mixture was concentrated in vacuo to remove acetonitrile and epichlorhydrin (if not quenched) and evaporated water was replaced. The final mixture contained 10-40% polyamines W/V. Viscosity was proportional to the degree of cross-linking.

Example 101: UV Initiated Cationic Super Absorber as Water Sink or Dye Trap

A quaternary amine polymer such as polyDADMAC was mixed with monomers containing a quaternary ammonium group such as (3-acrylamidopropyl)trimethylammonium chloride, [2-(Acryloyloxy)ethyl]trimethylammonium chloride, or [2-(Acryloyloxy)ethyl]trimethylammonium chloride in a ration of 5:1, 7.5:1, 10:1 or 15:1. To this mixture was added a radical starter selected from benzophenone, phenanthrene quinone, or benzoylperoxide. Additionally a cross linker such as di(trimethylol)propane tetraacrylate was added at 1% of the molar equivalent of the choline acrylate monomer. The solution was diluted with up to 25% isopropanol. For a dye trap, approximately 1 μL of the solution was applied to an area of paper to a non-woven cloth of 15 mm2 using a rubber stamp. It was then irradiated under UV radiation at 254 nM for 20 minutes. Function was demonstrated using a solution of water containing Brilliant Black 0.5% W/V which was drawn along the paper or non-woven and was trapped in the quaternary amine groups.

As a water sink or as a super absorber, a thicker bed of polymer was formed. Dots or diameter 4 mm or 4 μL were deposited on a hydrophobic surface like glass, foam or paper. The deposits were UV hardened using a hand-held UV lamp at 254 nm for 30 minutes. They were then placed into a water suspension of brilliant black dye or bromophenol blue dye. The degree of expansion and dye binding indicated potential as a super absorber or as a dye trap. Superabsorbers are designated via the ability to absorb greater than 100-fold their dry weight in water.

Using the composition: 1 mL of choline acrylate (80% solution in water), 10 μL of di(trimethylolpropane) tetraacrylate, 50 μL of a solution (20% w/v) of benzophenone in 2-propanol, 60 μl. of a solution (50% w/v) of HEPES (4-(2-hydroxyethyl)piperazine-I-ethanesulfonic acid), and 0.3 mL of poly(diallyldimethylammonium chloride) (molecular weight 400,000-500,000, 20% in water), deposition on a glass surface and subsequent irradiation results in flat disks. Applying 4, 6, 10, 20 or 30 μL results in disks of approximately similar weight Water uptake was as indicated in the following table:

| Weight of sample (mg) | Weight at 15 minutes in water (mg) | Weight at 1440 minutes in water (mg) |
|---|---|---|
| 4.9 | 148 | 1480 |
| 6.1 | 293 | 1720 |
| 9.6 | 360 | 2800 |

Example 102: UV Initiated Cross-Linked Trap and Superabsorber

Synthesis of a Cationic Trap by Polymerization of Acrylates 1 mL of choline acrylate (80% solution in water), 70 μL of di(trimethylolpropane) tetraacrylate, 50 μL of a solution (20% w/v) of benzophenone in 2-propanol, 60 μL of a solution (50% w/v) of HEPES (4-(2-hydroxyethyl)piperazine-1-ethanesulfonic acid), and 1.77 mL of poly(diallyldimethylammonium chloride) (molecular weight 400,000-500,000, 20% in water) were combined and vigorously mixed. 1 μL of this mixture was applied to a solid carrier (glass plate, filter paper, nonwoven) and irradiated with light of 254 nm for 20 min.

1 mL of (acrylamido)propyl trimethyl ammonium chloride (75% solution in water), 70 μL of di(trimethylolpropane) tetraacrylate, 50 μL of a solution (20% w/v) of benzophenone in 2-propanol, 60 μL of a solution (50% w/v) of HEPES (4-(2-hydroxyethyl)piperazine-I-ethanesulfonic acid), and 1.77 mL of poly(diallyldimethylammonium chloride) (molecular weight 400,000-500,000, 20% in water) were combined and vigorously mixed. 1 μL of this mixture was applied to a solid carrier (glass plate, filter paper, nonwoven fabric) and irradiated with light of 254 nm for 20 min.

1 mL of choline acrylate (80% solution in water), 70 μL of di(trimethylolpropane) tetraacrylate, 50 μL of a solution (20% w/v) of benzophenone in 2-propanol, 60 μL of a solution (50% w/v) of HEPES (4-(2-hydroxyethyl)piperazine-I-ethanesulfonic acid), and 3.54 mL of poly(diallyldimethylammonium chloride) (molecular weight 400,000-500,000, 20% in water) were combined and vigorously mixed. 1 μL of this mixture was applied to a solid carrier (glass plate, filter paper, nonwoven fabric) and irradiated with light of 254 nm for 20 min.

1 mL of (acrylamido)propyl trimethylammonium chloride (75% solution in water), 70 µL of di(trimethylolpropane) tetraacrylate, 50 µL of a solution (20% w/v) of benzophenone in 2-propanol, 60 µl. of a solution (50% w/v) of HEPES (4-(2-hydroxyethyl)piperazine-1-ethanesulfonic acid), and 3.54 mL of poly(diallyldimethylammonium chloride) (molecular weight 400,000-500,000, 20% in water) were combined and vigorously mixed. 1 µl, of this mixture was applied to a solid carrier (glass plate, filter paper, nonwoven fabric) and irradiated with light of 254 nm for 20 min.

1 mL of choline acrylate (80% solution in water), 70 µL of di(trimethylolpropane) tetraacrylate, 50 µL of a solution (20% w/v) of benzophenone in 2-propanol, and 60 µL of a solution (50% w/v) of HEPES (4-(2-hydroxyethyl)piperazine-1-ethanesulfonic acid) were combined and vigorously mixed. 1 µl, of this mixture was applied to a solid carrier (glass plate, filter paper, nonwoven fabric) and irradiated with light of 254 nm for 20 min.

1 mL of (acrylamido)propyl trimethylammonium chloride (75% solution in water), 70 µL of di(trimethylolpropane) tetraacrylate, 50 µL of a solution (20% w/v) of benzophenone in 2-propanol, and 60 µL of a solution (50% w/v) of HEPES (4-(2-hydroxyethyl)piperazine-1-ethanesulfonic acid) were combined and vigorously mixed. 1 µL of this mixture was applied to a solid carrier (glass plate, filter paper, nonwoven fabric) and irradiated with light of 254 nm for 20 min.

1 mL of choline acrylate (80% solution in water), 120 µL glycerol 1,3-diglycerolate diacrylate, 50pE of a solution (20% w/v) of benzophenone in 2-propanol, 60 µL of a solution (50% w/v) of HEPES (4-(2-hydroxyethyl)piperazine-I-ethanesulfonic acid), and 1.77 mL of poly(diallyldimethylammonium chloride) (molecular weight 400,000-500,000, 20% in water) were combined and vigorously mixed. 1 µL of this mixture was applied to a solid carrier (glass plate, filter paper, nonwoven fabric) and irradiated with light of 254 nm for 20 min.

1 mL of (acrylamido)propyl trimethylammonium chloride (75% solution in water), 500 µL of trimethylolpropane ethoxylate triacrylate (average Mn –692), 200 µL of a solution (10% w/v) of 4,4'-dihydroxybenzophenone in 2-propanol, and 60 µL of a solution (50% w/v) of HEPES (4-(2-hydroxyethyl)piperazine-I-ethanesulfonic acid) were combined and vigorously mixed. 1 µL of this mixture was applied to a solid carrier (glass plate, filter paper, nonwoven fabric) and irradiated with light of 254 nm for 20 min.

1 mL of choline acrylate (80% solution in water), 150 µL of di(trimethylolpropane) tetraacrylate, 40 µL of a solution (20% w/v) of benzophenone in 2-propanol, and 30 mg of triethanolamine were combined, diluted with 350 µL of 2-propanol and vigorously mixed. 1 µL of this mixture was applied to a solid carrier (glass plate, filter paper, nonwoven fabric) and irradiated with light of 254 nm for 20 min.

1 mL of (acrylamido)propyl trimethyl ammonium chloride (75% solution in water), 300 µL of glycerol 1,3-diglycerolate diacrylate, 200 µL of a solution (10% w/v) of 4,4'-dihydroxybenzophenone in 2-propanol, and 90 µL of a solution (50% w/v) of HEPES (4-(2-hydroxyethyl)piperazine-I-ethanesulfonic acid) were combined and vigorously mixed. 1 µL of this mixture was applied to a solid carrier (glass plate, filter paper, nonwoven fabric) and irradiated with light of 254 nm for 20 min.

1 mL of (acrylamido)propyl trimethyl ammonium chloride (75% solution in water), 1 mL of trimethylolpropane ethoxylate triacrylate (average Mn –692), 200 µL of a solution (10% w/v) of 4,4'-dihydroxybenzophenone in 2-propanol, 150 µL of a solution (50% w/v) of HEPES (4-(2-hydroxyethyl)piperazine-1-ethanesulfonic acid), and 2 mL of poly(diallyldimethylammonium chloride) (molecular weight 400,000-500,000, 20% in water) were combined and vigorously mixed. 1 µL of this mixture was applied to a solid carrier (glass plate, filter paper, nonwoven fabric) and irradiated with light of 254 nm for 20 min.

As a dye trap, approximately 1 µL of the solutions described above was applied to an area of paper or a non-woven cloth of 15 mm2 using a rubber stamp. It was then irradiated under UV radiation at 254 nM for 20 minutes. Function was demonstrated using a solution of water containing Brilliant Black 0.5% W/V which was drawn along the paper or non-woven and was trapped in the quatemary amine groups.

Optimal trapping effect was obtained using a degree of deposition that was sufficient to trap visible amounts of compound while still allowing water or protein solutions to pass through the trap area. Using the composition 1 mL of choline acrylate (80% solution in water), 70 µL of di(trimethylolpropane) tetraacrylate, 50 µL of a solution (20% w/v) of benzophenone in 2-propanol, 60 µL of a solution (50% w/v) of HEPES (4-(2-hydoxyethyl)piperazine-I-ethanesulfonic acid), and 0.3 mL of poly(diallyldimethylammonium chloride) (molecular weight 400,000-500,000, 20% in water) is effective but tends to be overloaded. Dilution to 20 or 40% and deposition of 0.2 to 0.6 µL per 12 mm2 on a non-woven containing viscose followed by 30 minutes irradiation at 254 nm with a hand UV lamp resulted in adequate trapping with suitable fluid transfer. These quaternary amines are most ideally applied as a viscous printed solution. To this end they can be formulated as follows: 15 g of a 3.3% Exilva suspension were prepared in demineralized water. 12.5 g of a 4% PolyDADMAC solution in demineralized water was added stepwise to under continuous stirring. Then 10.0 g demineralized water was added stepwise under continuous stirring. Then, 50 g of an aqueous Aerosil 200 gel was prepared by hydration of Aerosil 200 in demineralized water (10% WAV). 5 g of a 4% PolyDADMAC solution in demineralized water was added to the Aerosil gel stepwise. The Aerosil/PolyDADMAC Gel was added in small aliquots to the Exilva/PolyDADMAC gel and mixed. Finally an additional 7.5 g of the 4% PolyDADMAC was added to the mixture. The resulting 100 g solution contained 5% Aerosil200, 0.5% Exilva and 1% PolyDADMAC. This ink formulation can be labelled with 0.002% Fluorescein WAV for revelation under UV254 nm.

Example 103. 5-(p-Aminomethyl)phenyl-4-chloro-3-Indoxyl-P-D-galactopyranoside

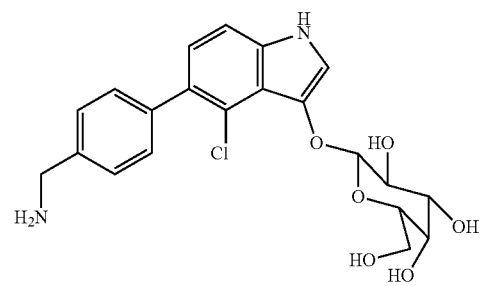 [SMILES: NCc1ccc(-c2ccc3[nH]cc(OC4OC(CO)C(O)C(O)C4O)c3c2Cl)cc1]

5-Bromo-4-chloro-3-Indoxyl-P-D-galactopyranoside (XGal, 100 mg, 0.25 mmol) was placed in a round-bottomed flask together with p-aminobenzyl boronic acid (38 mg, 0.25 mmol). The species were partially diluted in acetonitrile (3 mL) and water (~0.5 mL) at ambient temperature while stirring (magnetic stirrer, 300 rpm). Diisopropyl amine (DIPA, 78 yL, 0.55 mmol) was added, followed by palladium(II) acetate (Pd(OAc)$_2$ 3 mg, 0.0125 mmol) and triphenylphosphine species (TPPTS, 21.3 mg, 0.0375 mmol) while stirring. The system was heated to 80° C. and treatment was continued for 48 h. Reaction progress was monitored by ESI-MS. After cooling to room temperature any precipitates were filtered off (desired product stays in solution) and the reaction mixture was directly used for further treatment of co-bromo alkylated peptidoglycan derivative.

Example 104: 5-(p-Aminomethyl)phenyl-4-chloro-3-Indoxyl-P-D-galactopyranoside PG Adduct

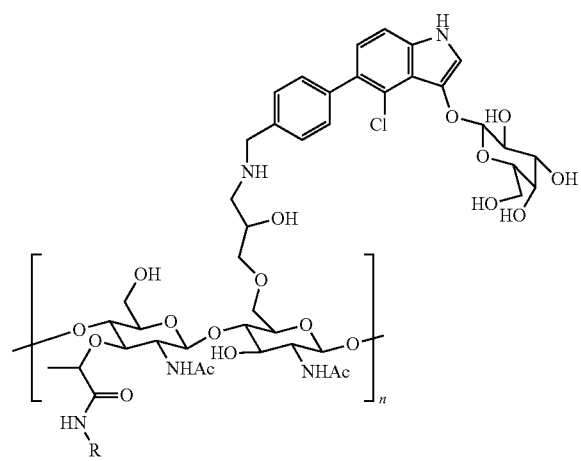

Dried co-bromo alkylated peptidoglycan (55 mg) was placed in a Eppendorf tube and was suspended in an acetonitrile/water (6:1) solution of 5-(p-aminomethyl-)phenyl-4-chloro-3-indoxyl-P-D-galactopyranoside (1.5 mL, excess) at ambient temperature. The reaction system was shaken for 72 h. Afterwards the precipitates were successively washed with water and ethanol followed by dialytic purification (water, 72 h) to ensure removal of small molecule XGal species. Upon dialysis the products were freeze dried to yield a yellow powder.

Example 105: 0-Alkylation of Peptidoglycan with Epibromohydrin

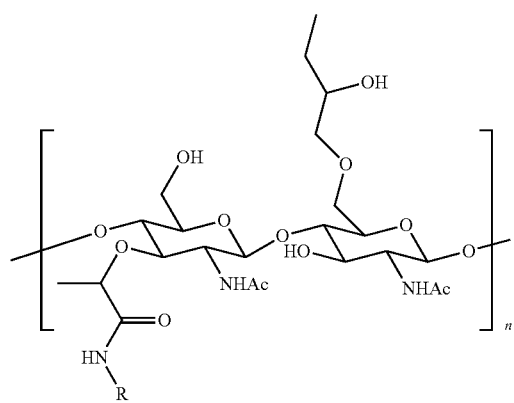

Dried Peptidoglycan (PG) (1.0 g) was placed in a 3 necked round bottom flask and was suspended in 1,4-dioxane (3 ml) at ambient temperature while slowly stirring (magnetic stirrer). Epibromohydrin (300 µL, 3.5 mmol) was added, followed by addition of perchloric acid 70% (30 µL). Treatment at ambient conditions was continued for 3 h. Afterwards the reaction mixture was poured into a paper filter and was subsequently washed with water, 1,4-dioxane and diethyl ether. Upon filtration alkylated PG was dried in vacuo and kept in refrigerator for further treatment. Yield: >1,06 g. (overall yield cannot precisely be determined).

Figure 7A:
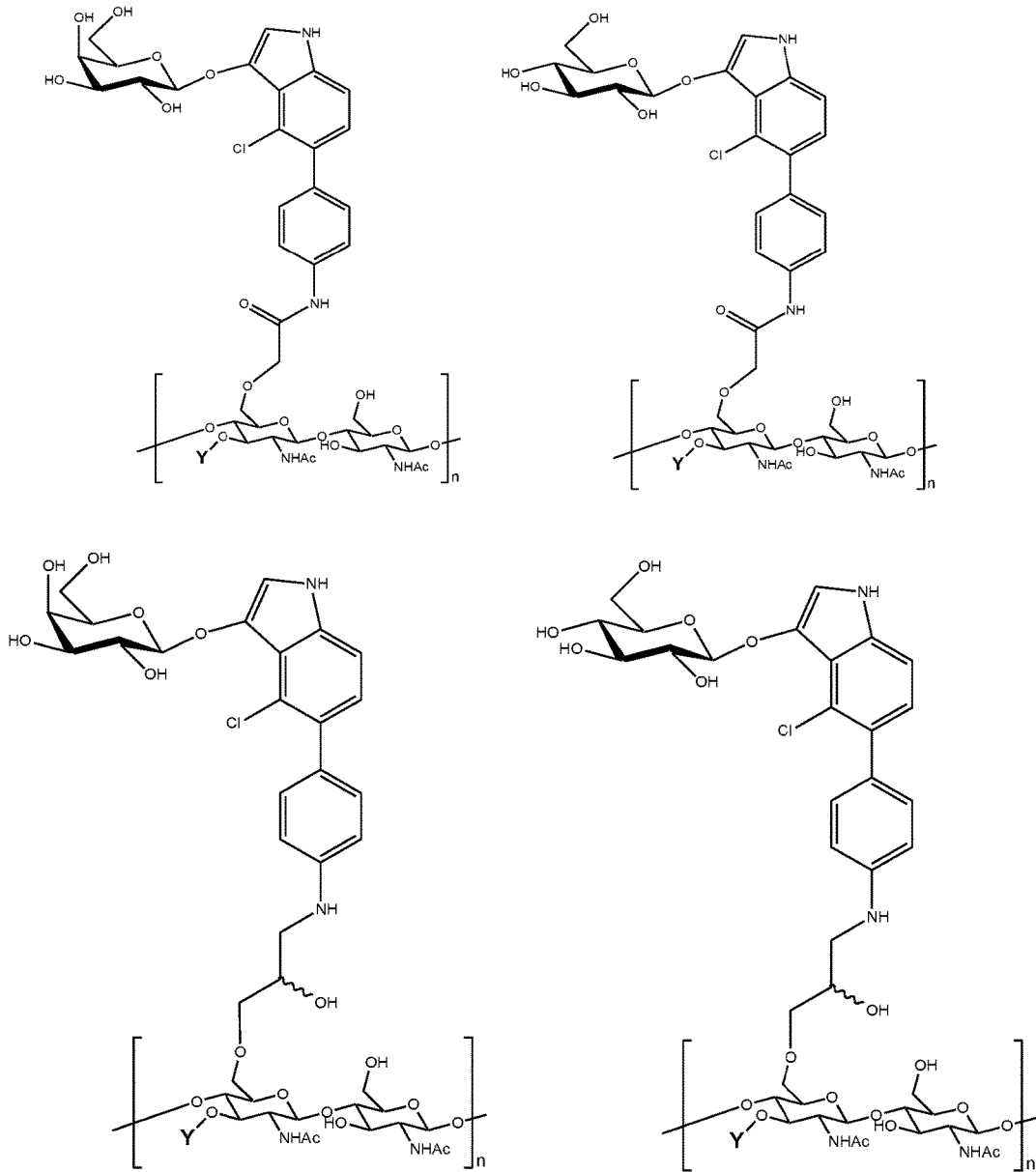
FIG. 7A: X-Gal, X-Gluc peptidoglycan and chitosan adducts formed via the methods of examples 103 and 104.
Figure 7B:
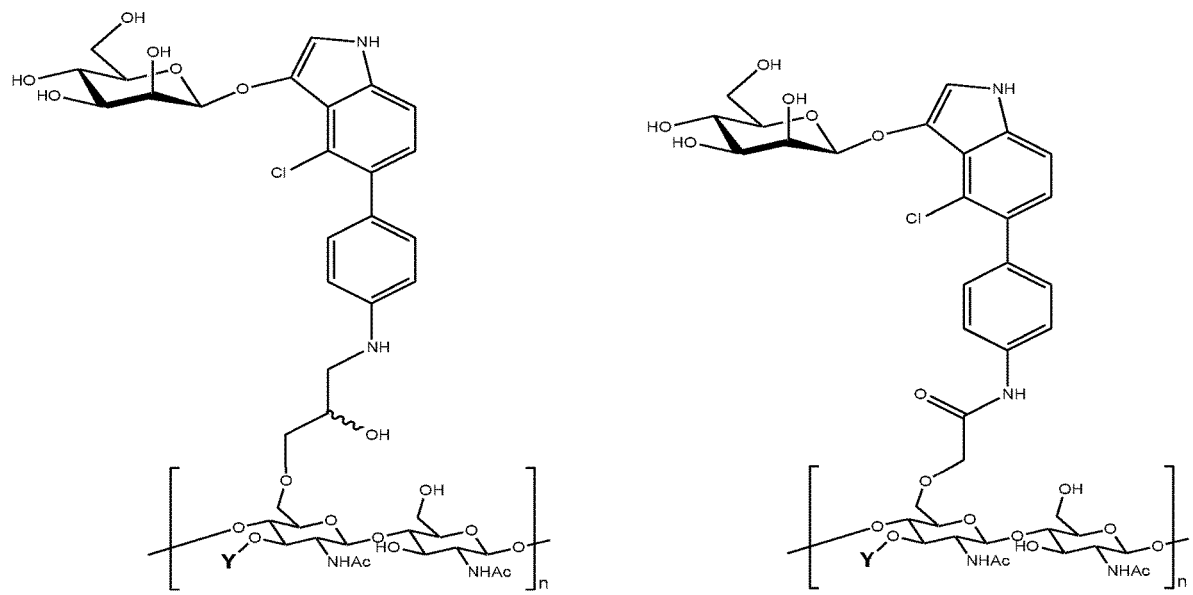
FIG. 7B: X-Man, peptidoglycan and chitosan adducts formed via the methods of examples 103 and 104.

Uses for the preparation include the immobilization of chromogenic substrates such as that in example 104 and FIG. 7A-C. Alternatively, the activated PG may be used to bind a secondary enzyme such as a glucosidase, galactosidase, mannosidase, esterase or phosphatase.

The general method for forming such materials is to take the freshly active product of PG and epibromhydrin and then wash it with several changes of water and buffer. Then it is mixed with a limiting amount of glucosidase, galactosidase, mannosidase, peroxidase, esterase or phosphatase and allowed to react under agitation. After reaction it is washed in an ammonium acetate buffer to quench the remaining Br groups and remove non-immobilised enzyme.

To perform the assay for lysozyme, PG containing a covalently bound substrate is mixed with a PG bound to the cognate accessory enzyme. On degradation by lysozyme, the accessory enzyme becomes available to activate the bound substrate which is also made more soluble by the action of lysozyme. Thus, PG-X-Gal conjugate is mixed with a PG bound to B-galactosidase.

Example 106: Formation of Chlorinated β-Lactam Precursor

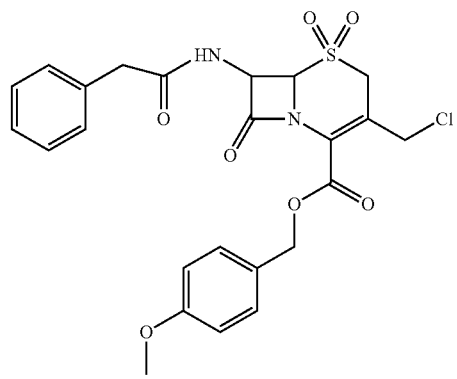 [SMILES: COc1ccc(COC(=O)C2=C(CCl)CS(=O)(=O)C3C(NC(=O)Cc4ccccc4)C(=O)N23)cc1]

3-Chloromethyl-7-(2-phenylacetamido)-3-cephem-4-carboxylate (1.04 g, 2.14 mmol) was suspended in DCM (dry, 40 mL) and m-chlorperbenzoic acid (77%, 1.09 g, 4.88 mmol) was added in one portion at RT. The mixture was stirred at RT over the weekend. The solid was filtered off and washed with DCM (30 mL); the filtrate was concentrated to dryness. The crude product was taken up in Et$_2$O (40 mL) and stirred in an ice-bath for 2 h. Then the solid was filtered off and washed with Et$_2$O (50 mL). The product (811 mg, 73%) was obtained as a white solid.

ESI-MS (positive): [M+Na]$^+$=541

Example 107: Formation of β-lactam indoxyl ether

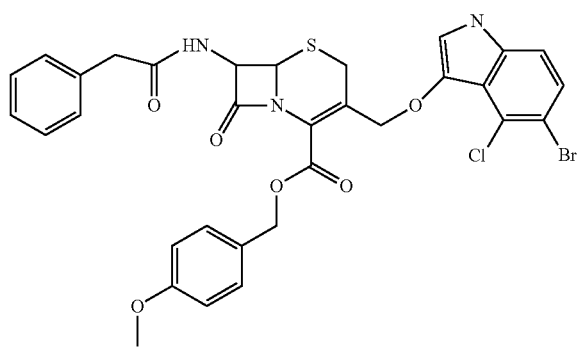 [SMILES: COc1ccc(COC(=O)C2=C(COc3c[nH]c4ccc(Br)c(Cl)c34)CSC3C(NC(=O)Cc4ccccc4)C(=O)N23)cc1]

3-Chloromethyl-7-(2-phenylacetamido)-3-cephem-4-carboxylate (488 mg, 2.00 mmol) was suspended in acetone (dry, 5 mL) at RT and the mixture was stirred at RT while streaming argon through it for 10 min. Then 5-bromo-4-chloro indoxyl (231 mg, 1mmol) was added in one portion at RT. Stirring with argon stream was continued for 5 min before potassium carbonate (278 mg, 2 mmol) was added at RT in one portion. The mixture was stirred at RT while passing argon through it for another 10 min. Then additional acetone (dry, 2 mL) was added. After two more minutes stirring at RT with argon stream the mixture was stirred under argon atmosphere at RT overnight. DCM (50 mL) and water (40 mL) were added; after extraction the whole mixture was filtered via a fluted filter. After filtration organic and aqueous phase were separated, the organic phase was dried ($Na_2SO_4$) and concentrated to dryness. The crude product was purified by column chromatography (silica gel, eluent: 2% MeOH in DCM). The fractions containing the product were collected to yield 228 mg of a deep brown solid.

ESI-MS (positive): $[M+Na]^+=718$

Example 108: Methoxy Aniline Derivative Salts

Figure 12:
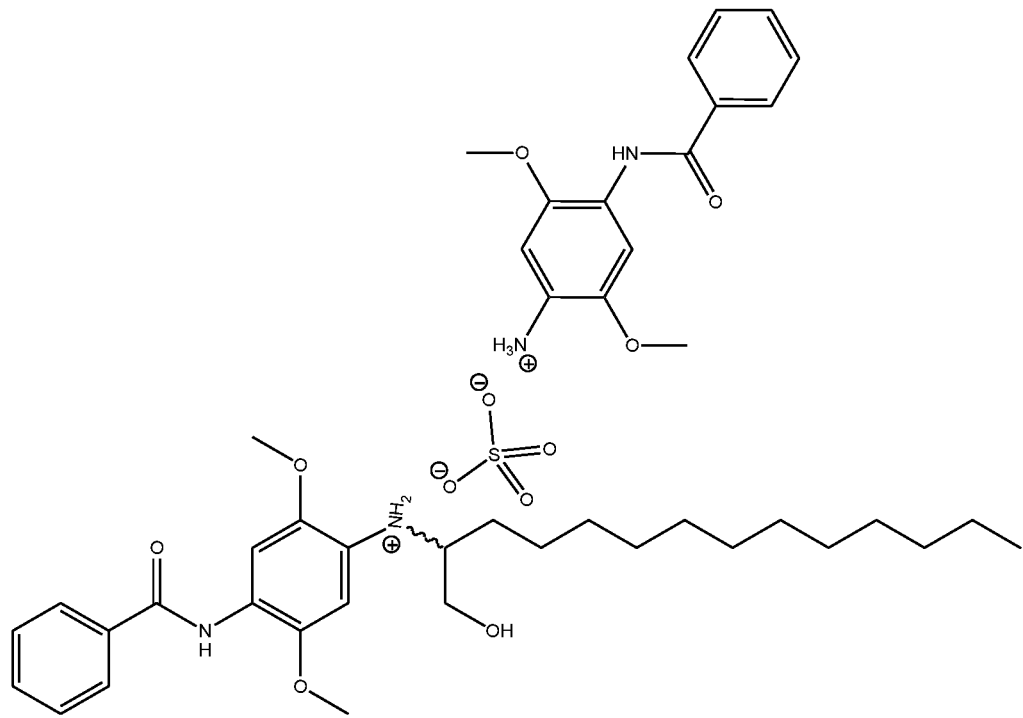
FIG. 12: The sulfate salt the product of example 10 and Fast Blue RR.

The substance of example 10 can be a direct substrate of MPO, however, it provides the most rapid reaction when it is formulated as an ion pair of the alkylated reaction product and a methoxy aniline and a divalent anion (see FIG. 12). The ideal ratio by mass is circa 2:8 aniline: product of example 10. The most efficient reaction occurs when the divalent anion is sulphuric acid, however, disulfonic substituted aromatic systems and phosphoric acid can also be used with diminished rate. HCl provides only limited reaction. On reaction, one of the products of MPO oxidation appears to be the dimer of the two aniline components (see FIG. 13).

A major requirement of such substrates is that they are not reactive with heme. Various methoxy anilines can be used as alternatives to Fast Blue, however, they (3,4-Dimethoxyaniline 2,5-Dimethoxyaniline) tend to react to a chromophore alone with heme and peroxide. To avoid this, deactivation via the amide is required. A variety of substituents are feasible. The alkyl anchoring moiety can be replaced by other similarly lipophilic groups either by direct alkylationor variants of the epoxidation reaction of Example 10. Similarly, the amide group can be varied Insert Markush Diagram—Fast Blue

Example 109: Preparation of Substrates on Solid Material Like Paper or Non-Woven Materials Elastase detection: Filter paper circles (6 mm) were impregnated with a impregnation dispersion mixture (0.25% (w/w) Nonidet, 2% (w/w) decanol in 0.05 M borate buffer pH 8 for 1-2 min. Thereafter the filter papers were placed on a glass plate and dried for 1-2 h at 54° C. After drying, elastase-substrate FmocAAPV Indoxyl ester from example 1 (20 mg/mL in methanol) was pipetted on the circles 2 times in 2µï. steps until a final amount of 80 µg per test circle (20 mm2) was applied.

Alternatively elastase substrate FmocAAPV Indoxyl ester [SEQ ID NO: 2] (example 1) can be mixed in methanol with 4-Diazo-3-methoxydiphenylaminsulfate and/or 2-Methoxy-4-morpholinobenzendiazonium salt with final concentrations of 10 mg/mL FmocAAPV Indoxyl ester, [SEQ ID NO: 2] and 5 to 10 mg/mL of the respective Diazonium salt (or a combination of both). The mixture was pipetted on the impregnated test circles 2 times in 2 µL steps.

MPO detection: Filter paper circles (diameter 6 mm) were impregnated by pipetting of 2 µL of a 40 mg/mL solution of the material of example 108 in DMSO Methanol (1 part DMSO, 2 parts MeOH) followed by a drying step (48 h, room temperature). To this are added 10 µg glucose and 3 µL of 0.1% glucose oxidase (3 µg) in water.

The positive control indicating moisture contact is a pH indicator based on a preparation of bromothymol blue in chitosan, containing glutaraldehyde. The mixture is pipetted in the reporter area, after drying leading to a dark yellow indicator system.

Alternatively a 0.1% bromocresol purple solution in Ethanol can be used, therefor 1.4 µL is pipetted on a filter paper disc (diameter 6 mm) and dried at 50°-60° C. for 1.5 h.

These various filter papers can be placed onto a stick to allow simultaneous assessment of bodily fluids at the point of care. We will refer to these as dipsticks.

Example 110: Clinical Assessment of Airway Aspirates

The dipsticks of Example 109 are maintained in an active state through appropriate storage and delivered to a clinical facility for testing. They may be used to assess the state of infection in airway aspirates. To test their ability to detect infection in these materials, the sticks are used to assess the aspirates of patients who are intubated as part of intensive care procedures. Aspirates are taken as part of routine care. After aspiration, the resulting material is placed in contact with the dipstick and allowed to react for up to 6 minutes. Depending on the degree of reaction, various cut-off values can be obtained that indicate the putative concentration of the biomarker enzymes. The presence of Elastase or MPO in the aspirate above background levels is an indicator of potential infection. To interpret the utility of these data, responses to the dipsticks were compared with what was known clinically about the samples. In some cases the samples were known to be taken from a patient being treated for an infection. In other cases the patient was considered not to have an airway infection. In certain cases, the samples were taken from a patient who subsequently developed an infection within two days. These samples were considered "non-infected" because that was the clinical diagnosis at the time they were taken. However, in future studies, we will classify samples from patients who go on to develop infections within two days as being "infected".

A total of 52 patients were assessed via 117 samples. The data can be tabulated according to the degree of reaction to each biomarker and the cut-off value used to indicate infection. These data were summarized in the following data sets.

Analysis of elaste response in all 117 patient samples.

| Elastase as a | Clinical diagnosis pneumonia | | | Sens (%) | Spec (%) | PPV (%) | NPV (%) | AUC |
|---|---|---|---|---|---|---|---|---|
| | Yes | No | Total | | | | | |
| | HNE | | | | | | | |
| Minute 6 | | | | | | | | |
| Cut-off 1, 2  Positive | 16 | 19 | 35 | 100.0 | 81.2 | 45.7 | 100.0 | 0.906 |
| Negative | 0 | 82 | 82 | | | | | |
| Cut-off 2, 3  Positive | 16 | 3 | 19 | 100.0 | 97.0 | 84.2 | 100.0 | 0.985 |
| Negative | 0 | 98 | 98 | | | | | |
| Total | 16 | 101 | 117 | | | | | |

Abbreviations:
HNE = Human Neutrophil Elastase;
MPO = MyeloPerOxidase;
Sens. = Sensitivity;
Spec. = Specificity;
PPV = Positive Predictive Value;
NPV = Negative Predictive Value;
AUC = Area Under the Curve.

Analysis of 52 patients using both biomarkers

| | | Clinical diagnosis pneumonia | | | Sens (%) | Spec (%) | PPV (%) | NPV (%) | AUC |
|---|---|---|---|---|---|---|---|---|---|
| | | Yes | No | Total | | | | | |
| HNE_6_2, 3 + | Positive | 9 | 4 | 13 | 100.0 | 90.7 | 69.2 | 100.0 | 0.953 |
| MPO_6_2, 3 | Negative | 0 | 39 | 39 | | | | | |
| HNE_6_2, 3 + | Positive | 9 | 3 | 12 | 100.0 | 93.0 | 75.0 | 100.0 | 0.965 |
| MPO_6_2, 3 | Negative | 0 | 40 | 40 | | | | | |
| | Total | 9 | 43 | 52 | | | | | |

Abbreviations:
HNE = Human Neutrophil Elastase;
MPO = MyeloPerOxidase;
Sens. = Sensitivity;
Spec. = Specificity;
PPV = Positive Predictive Value;
NPV = Negative Predictive Value;
AUC = Area Under the Curve.

Figure 10A:
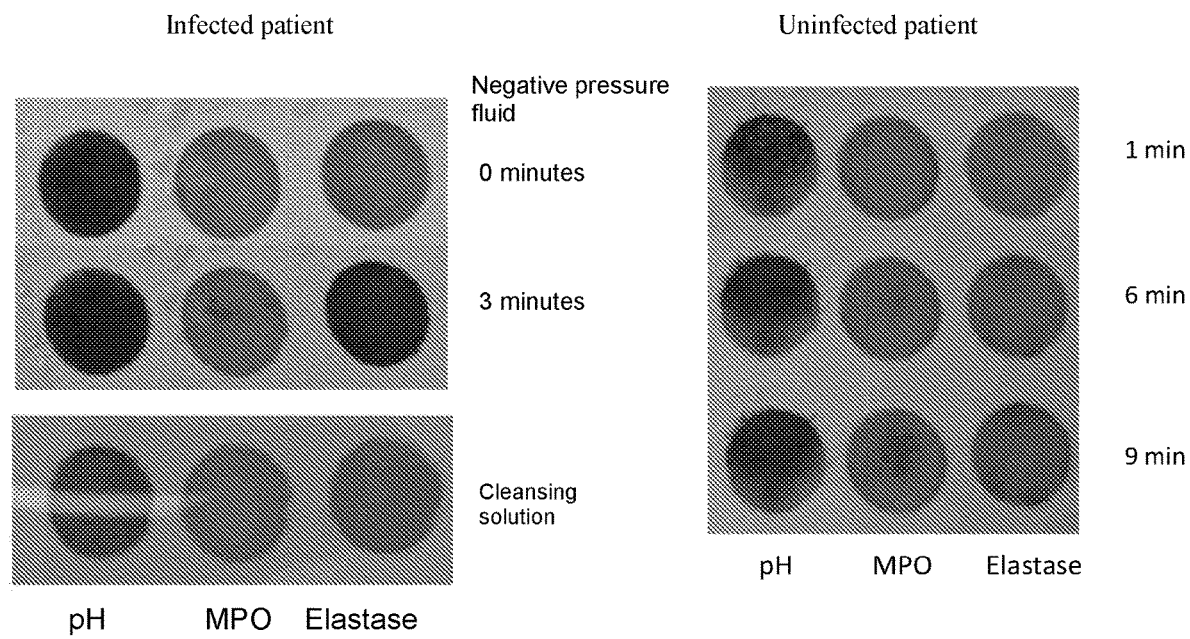
FIG. 10A: A stick containing indicator substrates from examples 10 and 18 can be used to detect the reaction of fluids derived from the negative pressure treatment of wounds.
Figure 10B:
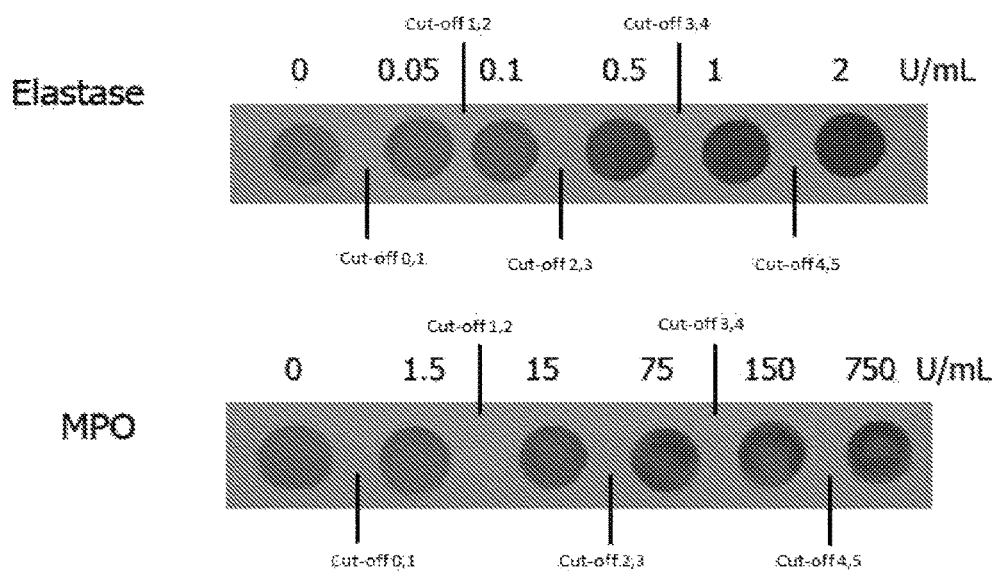
FIG. 10B: The same stick format can be used to monitor the aspirates of the airway or sputum to detect incipient infection. In this image the calibration of the sticks for the response to elastase or MPO is indicated.

These data are an analysis of the biomarker response in which the biomarker is reported with the time of reaction and the cut-off used. Thus, HNE 6 2,3 means that the reaction was watched for 6 minutes and degree of reaction in the $4^{th}$ spot of the example in FIG. 10B is used to indicate the presence of a positive sample. Using a higher cut-off for MPO (3,4) supports the finding.

Figure 14:
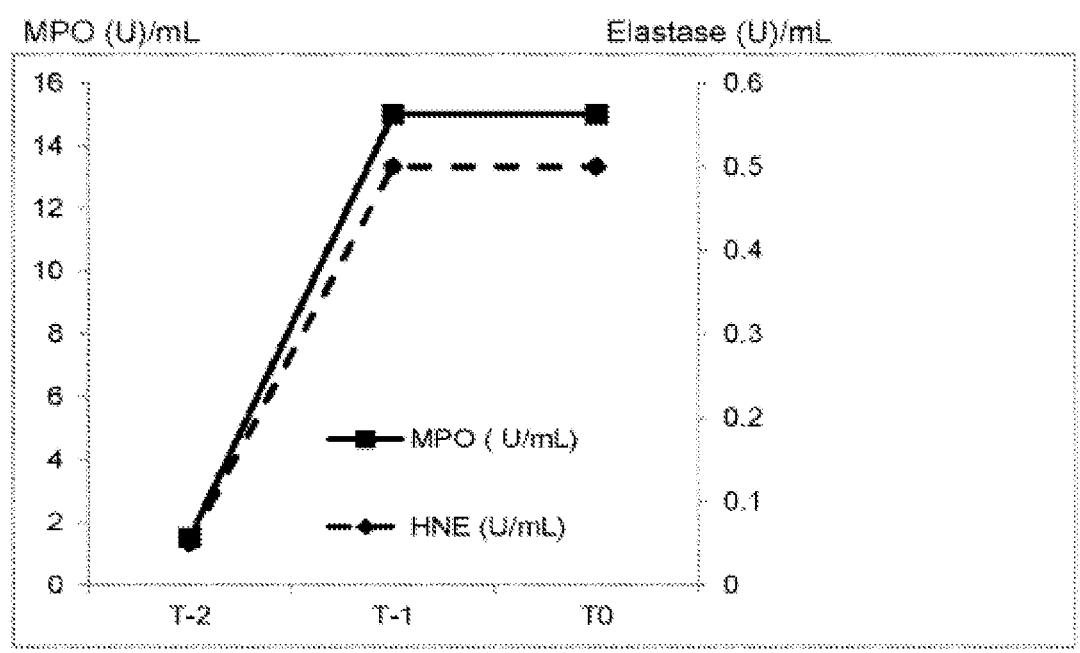
FIG. 14: A graph depicting biomarker response data for patients classified as "uninfected" who were sampled as an infectionwas developing.

However, a number of patients were sampled as an infection was developing and were classified as "uninfected". An example of this phenomenon is illustrated in FIG. 14. In the graph depicted in FIG. 14, the day on which a clinical infection was diagnosed is indicated as T0. T-1 and T-2 are the days of sampling prior to the infection being diagnosed clinically.

The data shown in FIG. 14 suggest that the response of the biomarkers can indicate the impending infection before it is clinically apparent to ICU staff. These data also suggest that the chromogenic substrates are able to usefully indicate abnormal levels of enzyme markers in an airway aspirate that is consistent with their infection status.

Example 111: Clinical Assessment of Negative Pressure Wound Therapy Fluids

Wound healing may be mediated by applying a vacume to the wound area. This may have many effects including drawing serous fluid from the body through the wound and thus bringing with it growth factors, immune cells and nutrients. It also may encourage or stimulate granulating tissue to proliferate. The fluids that emerge from the process are an indicator of the status of the wound bed. Assessing the presence of infection biomarkers may provide an indication if the wound is in good condition without removing the dressing or vacume sponge.

To assess the validity of this approach we took samples from such vacume acquired fluids and tested the response of the dipstick. The result is consistent with what is known about the wound and the observations made in example 110. Namely that there is a clear biomarker response in cases of diagnosed or suspected infection (See FIG. 10 A).

Example 112: Placement of the Indicator Materials in Tubing Used in Medical Devices In the previous two examples, the fluids were taken from the source and analysed using a dipstick system to estimate biomarker response. However, it is also possible to place materials containing the markers in situ in a medical device. These materials can be considered a form of monitoring system. For this application, the materials need to be suitable for sterilizing and they need to respond over the appropriate time-scale. For example, for many uses such as vacume treatment of wounds or ventilators, a period of 24 h would be sufficient to indicate a potential change in status. To this end, the rapid reaction of the dipstick is not required.

The format is also different. In FIG. 9, various formats are indicated. In FIG. 9B a format is shown that can accommodate the filter paper circles described in Example 109. The format may, however, be simpler in that tubing and cylindrical holders may be converted to hold paper or non-woven materials, polyolefins or celluloses of other inert materials that are carriers or solid supports for the reactive substrates (see FIGS. 9A, C and D).

To test this concept, we prepared hold paper or non-woven materials, polyolefins or celluloses treated with the materials described in Example 109 with some modification. In particular, the Elastase substrate was not printed or applied with the diazonium salt. This is because rapid reaction is not required in this setting. The conversion of indoxyl to a chromophore is usually via oxidation and the diazonium salts provide a direct reaction without the need for oxygen. In the monitoring setting, the reaction time is not critical. Similarly, for MPO oxygen is important and where this is limiting, the reaction rate is limited.

In this format, the passage of fluid gives rise to a wetting of the support material and conversion of the substrate. The converted substrate is then visible as a stripe. The presence of the stripe within a certain period of time serves as an indicator of the fact that the source of the fluid may have become infected. Such a color indicator could be place in a vacume line where it comes into contact with a body fluid. It may also be place in an aspiration line, or in a ventilator device.

Example 113: Electronic Monitoring of the Biomarkers

The color generating substrates are a means to allow an interpretation of biomarker response without use of a device. However, in certain circumstances, on-line monitoring, or quantitation may call for an electronic assessment. There are a range of modes that may be employed to this end.

Color sensing is one means in which a sensor can be placed to read the color of reflected light and thus the rate of change of the reagents. Color measurement using sensors, however, relies on the fluids having only limited background color or high contrast relative to the sample color. To achieve color sensing an electronic board is placed opposite the reagents on the dipstick or chip system. The board contains a source of light (e.g. small LEDs with red green and blue color) and a sensing chip. Signal change over time is recorded to estimate the activity in the sample.

Figure 11:
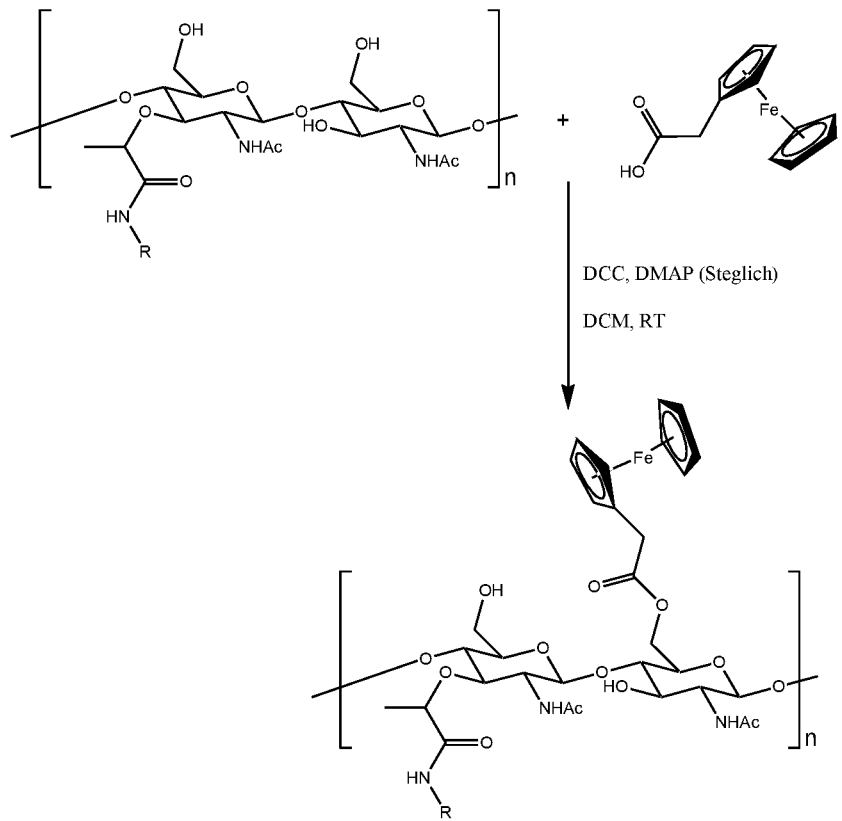
FIG. 11: A scheme for the production of a carboxy ferrocene peptidoglycan conjugate

Another mode is amperometric sensing. This is relevant to substrates that produce or consume a REDOX active product like indoxyl (lysozyme, elastase) or a peroxide (MPO). Oxidation of the substrate gives rise to a current that can be measured by appropriate electrodes. Examples of REDOX active agents released by the enzyme include indoxyl referred to many times herein, but also ferrocene as in FIG. 11.

Example 114: Solubility of Indicator Substrates

The ability of enzyme substrates to stay attached to solid phases such as paper is important to their function. To test the degree to which the dried substrate resists the re-solution into an aqueous phase, the substrates are applied to the solid phase using an appropriate solvent (Acetone, methanol, DMSO etc. see also Example 109) and allowed to dry at room temperature for up to 48 hours. Thereafter, the paper or non-woven material is incubated in 50 mL of either water or artificial wound fluid (2% bovine serum albumin in phosphate buffered saline containing potassium chloride, urea pH 7.2) for 2 minutes with gentle agitation by rotation, thereafter it is washed again using successive changes of fluid, for example, 4 changes of 50 mL. The solution or loss of the substrate is estimated by a number of methods. These include LCMSMS analysis of the solving solution or remnant analysis of the material on the solid phase by enzymatic reaction or direct analysis by LCUV or LCMSMS. The LCMS methods are as follows:

HPLC grade methanol, acetonitrile, water DMSO and THF were used to prepare stocks and as mobile phase. The quantifications were carried out on an Agilent 1260 series HPLC system with ABSciex API 4000 mass spectrometer as a detector. The column used was a ReproSil Pur Phenyl 3 μm 60×2 mm, operated at 45° C. The mobile phase was: water+0.1% formic acid and acetonitrile. The chromatographic run was a gradient the flow rate 500 μL/min. The injection volume was 5 μL The parent/fragment species detected were 694/561 for product of example 1, 485/467 for the product of example 10 and 273/258 for Fast Blue.

| Minutes | % Solvent A (Water + 0.1% FA) | % Solvent B (acetonitrile) |
| --- | --- | --- |
| 0 | 99 | 1 |
| 1 | 99 | 1 |
| 2 | 0 | 100 |
| 5 | 0 | 100 |
| 6 | 99 | 1 |
| 10 | 99 | 1 |

10 mg/ml stock standard solutions were prepared for each of the compounds in methanol, 1:3 mixture of DMSO Methanol and a 1:1 mixture of DMSO Methanol for each analyte respectively. The stock was dissolved 1:100 in THF and further 1:10 dilutions were prepared in THF for a calibration range of 0.1-10000 ng/mL.

Assay by enzymatic reaction is according to Example 109 in which the other required reagents are added to the material after the substrate has been rinsed and dried. Once the required accessory reagents (buffer, activators) are added, an excess of enzyme is added. Reaction is then compared with unwashed samples. Ideal substrates or substrate preparations resist 2 or more changes of 50 mL of water without substantial loss of reactivity.

This experimental system defines the "water resistance" of the substrate when dried on filter paper. Thus, a water resistance of 1 means that a signal is still visible after 1 change of 50 mL of artificial wound fluid. A water resistance of 2 means that the signal is still visible after 2 changes of 50 mL of artificial wound fluid and so on.

Example 115: Protease Substrates

Substrates for Cathepsin may be prepared using the methods of earlier examples for peptide indoxyl coupling. Sequence variation is used to vary enzyme selectivity.

Example 116: Protease Substrate Preparation

Peptide substrates such as those described here can be most efficiently prepared by coupling di-peptides. Preparation of the dipeptides AA and PV in protected form allows their subsequent direct coupling to form the desired AAPV product [SEQ ID NO: 5].

Example 117: Viral Protease Substrate Preparation

In certain instances, pathogens are not bacteria but virus. In the upper airway, the majority of infections are viral in nature. In certain instances, a viral infection resolves without invoking bacterial super infection. However, it is common that bacteria are also promoted in the context of a viral infection. This is because virus often suppress the immune system during infection and then promote inflammatory responses in order to better distribute (mucous, coughing and sneezing).

Virus either use self coded proteases, or host proteases. Virus types that encode their own proteases employ analogs of the 3C protease.

The consensus recognition motif for 3C protease is Leu-Glu-Val-Leu-Phe-Gln [SEQ ID NO: 40] motif or LEVLFQ [SEQ ID NO: 40]. Thus, one means to assess a sample of mucous for the presence of viral signals is to use a chromogenic substrate for a viral protease. One such example is the peptide LEVLFQ-Indoxyl in which the C-terminal is esterified to indoxyl.

In contrast, many virus types do not encode their own proteolytic functions but instead use the host functions. Common is the use of the furin protease by virus. The consensus furin cleavage site (-RRRR- [SEQ ID NO: 41] or -RRKR [SEQ ID NO: 42] or RLGR [SEQ ID NO: 43] or LLGR [SEQ ID NO: 44] or LLAR [SEQ ID NO: 45]) is highly basic. Chromogenic Furin substrates cannot be conveniently formed from poly arginine, and instead, lysine replacement is used. One example of a chromogenic substrate is LLAR-Indoxyl [SEQ ID NO: 45] or LLAL-Indoxyl [SEQ ID NO: 45]. Alternatively, arginine is left protected by the Tosyl groups which are the sterically least cumbersome of the protecting groups available for arginine.

While preferred embodiments of the disclosed technology have been shown and described herein, it will be obvious to those skilled in the art that such embodiments are provided by way of example only. Numerous variations, changes, and substitutions will now occur to those skilled in the art without departing from the disclosed technology. It should be understood that various alternatives to the embodiments of the disclosed technology described herein may be employed in practicing the disclosed technology. It is intended that the following claims define the scope of the disclosed technology and that methods and structures within the scope of these claims and their equivalents be covered thereby.

We claim:

1. A chemical entity comprising a compound of Formula I:

A-R-I    Formula I wherein
   A is an anchor;
   R is an enzyme recognition site; and
   I is an indicator region;
   wherein the enzyme recognition site (R) comprises a peptide of from four to eight amino acids, the peptide having an N-terminus and a carboxy terminus, the peptide having at least one enzyme-labile;
   wherein the anchor (A) comprises a fluorenylmethyloxycarbonyl group (Fmoc) linked to the N-terminus of the peptide; and
   wherein the indicator region (I) comprises an alcohol-containing or amine-containing chromophore or chromophore precursor linked via an amide or ester or carbonate bond to the carboxy terminus of the peptide.

2. The chemical entity of claim 1, wherein the enzyme recognition site (R) comprises a site for protease.

3. The chemical entity of claim 2, wherein the enzyme recognition site (R) comprises a site for elastase.

4. A chemical entity comprising a compound of Formula I:

A-R-I    Formula I wherein
   A is an anchor;
   R is an enzyme recognition site; and
   I is an indicator region;
   wherein the enzyme recognition site (R) comprises at least one enzyme-labile region;
   wherein the anchor (A) comprises a fluorenylmethyloxycarbonyl group (Fmoc)
   wherein R-I comprises the amino acid sequence (a) $X_y AAPX_y$-Z; (b) $X_y AAPX_y$-L-Z; (c) $X_y AAP(V/F/A)X_y$-Z or (d) $X_y AAP(V/F/A)X_y$-L-Z; wherein each X is, independently, any amino acid; y is, each, independently a number selected from 0 to 200; L is a linking moiety; and Z comprises a member selected from the group consisting of an indoxyl compound, an indole, a napthol, Fast Blue RR and Remazol Brilliant Blue.

5. The chemical entity of claim 2, wherein the enzyme recognition site (R) comprises a site for 3C protease.

6. The chemical entity of claim 2, wherein the enzyme recognition site (R) comprises a site for cathepsin G.

7. The chemical entity of claim 1, wherein the indicator region (I) comprises a dye containing a sulfonylethyl-hydrogensulphate-reactive-group or a dye containing a dichlortriazine reactive-group.

8. The chemical entity of claim 7, wherein the dye containing a sulfonylethyl-hydrogensulphate-reactive-group is reactive black 5, remazol brilliant blue, reactive violet 5 or reactive orange 16 or a combination thereof.

9. The chemical entity of claim 7, wherein the dye containing a dichlortriazine reactive-group is reactive blue 4, reactive red 120, reactive blue 2, reactive green 19, or reactive brown 10, or a combination thereof.

10. The chemical entity of claim 1, wherein the indicator region (I) comprises a detectable label selected from the group consisting of a luminescent molecule, a chemiluminescent molecule, a fluorochrome, a fluorescent quenching agent, a lipid, a colored molecule, a radioisotope, a scintillant, biotin, avidin, streptavidin, protein A, protein G, an antibody or a fragment thereof, a polyhistidine, Ni2+, a Flag tag, a myc tag, a heavy metal, and an enzyme.

11. The chemical entity of claim 1, wherein the enzyme recognition site (R) is provided via a bond between the anchor and the indicator.

12. The chemical entity of claim 11, wherein the enzyme recognition site (R) is specific for a lactamase.

13. The chemical entity of claim 11, wherein the enzyme recognition site (R) is specific for a glycosidase.

14. The chemical entity of claim 1, wherein the indicator region (I) comprises a detectable label selected from the group consisting of indoxyl and Fast Blue.

15. The chemical entity of claim 4, wherein y is, each, independently an integer from 1 to 50.

16. The chemical entity of claim 4, wherein y is, each, independently an integer from 1 to 10.

17. The chemical entity of claim 4, wherein each of amino acid sequence (a)-(d) is labile for elastase.

18. The chemical entity of claim 4, wherein the indicator region (I) comprises a detectable label selected from the group consisting of an indoxyl compound and Fast Blue RR.

19. The chemical entity of claim 5, wherein the 3C protease enzyme recognition site (R) comprises an amino acid sequence $X_y UUUU_y$-Z, wherein X is any amino acid; y is, each, independently, a number selected from 1 to 50; U is an amino acid selected from LEVLFQ, and Z is a label.

20. The chemical entity of claim 6, wherein the cathepsin G protease enzyme recognition site (R) comprises an amino acid sequence (a) $X_y N^4 N^3 N^2 N^1 X_y$-Z; or (b) $X_y N^4 N^3 N^2 N^1 X_y$-L-Z; wherein each X is independently any amino acid; each y is independently a number selected from 0 to 6; $N^4$ is selected from alanine, glycine, valine, and glutamine; $N^3$ is selected from alanine, glycine, proline, lysine, and serine; $N^2$ is selected from proline, alanine, and glycine; $N^1$ is selected from serine, lysine, phenylalanine, arginine, leucine, and methionine; L is a linking moiety, and Z is a label.

21. The chemical entity of claim 12, wherein the enzyme recognition site (R) comprises a lactam linkage comprising a conjugated lactone and amide.

22. The chemical entity of claim 13, wherein the glycosidase is β-lactamase.

23. The chemical entity of claim 18, wherein the indoxyl compound comprises an indoxyl ester.

\* \* \* \* \*

UNITED STATES PATENT AND TRADEMARK OFFICE
CERTIFICATE OF CORRECTION

PATENT NO. : 11,740,241 B2
APPLICATION NO. : 16/090075
DATED : August 29, 2023
INVENTOR(S) : Jan Hinrich Guse et al.

It is certified that error appears in the above-identified patent and that said Letters Patent is hereby corrected as shown below:

In the Claims

In Claim 1, at Column 179, Line 55, please replace --at least one enzyme-labile;-- with --at least one enzyme-labile region;--.

Signed and Sealed this
Twenty-sixth Day of September, 2023

Katherine Kelly Vidal
*Director of the United States Patent and Trademark Office*